United States Patent
Abu-Threideh et al.

(10) Patent No.: US 6,492,153 B2
(45) Date of Patent: Dec. 10, 2002

(54) ISOLATED HUMAN KINASE PROTEINS, NUCLEIC ACID MOLECULES ENCODING HUMAN KINASE PROTEINS, AND USES THEREOF

(75) Inventors: Jane Abu-Threideh, Germantown, MD (US); Fangcheng Gong, Germantown, MD (US); Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/759,359

(22) Filed: Jan. 16, 2001

(65) Prior Publication Data
US 2002/0094560 A1 Jul. 18, 2002

(51) Int. Cl.[7] .......................... C12N 9/12; C12N 1/21; C12N 15/54; C12N 5/00; C07H 21/04

(52) U.S. Cl. .................. 435/194; 435/252.3; 435/320.1; 435/325; 536/23.2

(58) Field of Search .............................. 435/194, 252.3, 435/320.1, 325; 536/23.2

(56) References Cited

PUBLICATIONS

Rohlfing et al., EMBL Database, Accession No. AC005070, Jun. 1998.*

* cited by examiner

*Primary Examiner*—Maryam Monshipouri
(74) *Attorney, Agent, or Firm*—Applera Corporation; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

9 Claims, 34 Drawing Sheets

```
   1 TCGGCGGAGC GAGTGGAGGC TGCAGCCCAG CTCGTCTCGG CGCCCGCGTC
  51 GCCGTCGCGA AGCCCCCGC CCCGCTTCCG CCGCGTCGGA ATGAGCTCCC
 101 GGAAAGTGCT GGCCATTCAG GCCCGAAAGC GGAGGCCGAA AAGAGAGAAA
 151 CATCCGAAAA AGCCGGAGCC TCAACAGAAA GCTCCTTTAG TTCCTCCTCC
 201 TCCACCGCCA CCACCACCAC CACCGCCACC TTTGCCAGAC CCCACACCCC
 251 CGGAGCCAGA GGAGGAGATC CTGGGATCAG ATGATGAGGA GCAAGAGGAC
 301 CCTGCGGACT ACTGCAAAGG TGGATATCAT CCAGTGAAAA TTGGAGACCT
 351 CTTCAATGGC CGGTATCATG TTATTAGAAA GCTTGGATGG GGCACTTCT
 401 CTACTGTCTG GCTGTGCTGG GATATGCAGG GGAAAAGATT TGTTGCAATG
 451 AAAGTTGTAA AAAGTGCCCA GCATTATACG GAGACAGCCT TGGATGAAAT
 501 AAAATTGCTC AAATGTGTTC GAGAAAGTGA TCCCAGTGAC CCAAACAAAG
 551 ACATGGTGGT CCAGCTCATT GACGACTTCA AGATTTCAGG CATGAATGGG
 601 ATACATGTCT GCATGGTCTT CGAAGTACTT GGCCACCATC TCCTCAAGTG
 651 GATCATCAAA TCCAACTATC AAGGCCTCCC AGTACGTTGT GTGAAGAGTA
 701 TCATTCGACA GGTCCTTCAA GGGTTAGATT ACTTACACAG TAAGTGCAAG
 751 ATCATTCATA CTGACATAAA GCCGGAAAAT ATCTTGATGT GTGTGGATGA
 801 TGCATATGTG AGAAGAATGG CAGCTGAGGC CACTGAGTGG CAGAAAGCAG
 851 GTGCTCCTCC TCCTTCAGGG TCTGCAGTGA GTACGGCTCC ACAGCAGAAA
 901 CCTATAGGAA AATATCTAA AAACAAAAG AAAAAACTGA AAAGAAACA
 951 GAAGAGGCAG GCTGAGTTAT TGGAGAAGCG CCTGCAGGAG ATAGAAGAAT
1001 TGGAGCGAGA AGCTGAAAGG AAAATAATAG AAGAAAACAT CACCTCAGCT
1051 GCACCTTCCA ATGACCAGGA TGGCGAATAC TGCCCAGAGG TGAAACTAAA
1101 AACAACAGGA TTAGAGGAGG CGGCTGAGGC AGAGACTGCA AAGGACAATG
1151 GTGAAGCTGA GGACCAGGAA GAGAAAGAAG ATGCTGAGAA AGAAAACATT
1201 GAAAAGATG AAGATGATGT AGATCAGGAA CTTGCGAACA TAGACCCTAC
1251 GTGGATAGAA TCACCTAAAA CCAATGGCCA TATTGAGAAT GGCCCATTCT
1301 CACTGGAGCA GCAACTGGAC GATGAAGATG ATGATGAAGA AGACTGCCCA
1351 AATCCTGAGG AATATAATCT TGATGAGCCA AATGCAGAAA GTGATTACAC
1401 ATATAGCAGC TCCTATGAAC AATTCAATGG TGAATTGCCA AATGGACGAC
1451 ATAAAATTCC CGAGTCACAG TTCCCAGAGT TTTCCACCTC GTTGTTCTCT
1501 GGATCCTTAG AACCTGTGGC CTGCGGCTCT GTGCTTTCTG AGGGATCACC
1551 ACTTACTGAG CAAGAGGAGA GCAGTCCATC CCATGACAGA AGCAGAACGG
1601 TTTCAGCCTC CAGTACTGGG GATTTGCCAA AAGCAAAAAC CCGGGCAGCT
1651 GACTTGTTGG TGAATCCCCT GGATCCGCGG AATGCAGATA AAATTAGAGT
1701 AAAAATTGCT GACCTGGGAA ATGCTTGTTG GGTGCATAAA CACTTCACGG
1751 AAGACATCCA GACGCGTCAG TACCGCTCCA TAGAGGTTTT AATAGGAGCG
1801 GGGTACAGCA CCCCTGCGGA CATCTGGAGC ACGGCGTGTA TGGCATTTGA
1851 GCTGGCAACG GGAGATTATT TGTTTGAACC ACATTCTGGG AAGACTATT
1901 CCAGAGACGA AGACCACATA GCCCACATCA TAGAGCTGCT AGGCAGTATT
1951 CCAAGGCACT TTGCTCTATC TGGAAAATAT TCTCGGGAAT TCTTCAATCG
2001 CAGAGGAGAA CTGCGACACA TCACCAAGCT GAAGCCCTGG AGCCTCTTTG
2051 ATGTACTTGT GGAAAAGTAT GGCTGGCCCC ATGAAGATGC TGCACAGTTT
2101 ACAGATTTCC TGATCCCGAT GTTAGAAATG GTTCCAGAAA ACGAGCCTC
2151 AGCTGGCGAA TGCCTCGGC ATCCTTGGTT GAATTCTTAG CAAATTCTAC
2201 CAATATTGCA TTCTGAGCTA GCAAATGTTC CCAGTACATT GGACCTAAAC
2251 GGTGACTCTC ATTCTTTAAC AGGATTACAA GTGAGCTGGC TTCATCCTCA
2301 GACCTTTATT TTGCTTTGAG GTACTGTTGT TTGACATTTT GCTTTTTGTG
2351 CACTGTGATC CTGGGGAAGG GTAGTCTTTT GTCTTCAGCT AAGTAGTTTA
2401 CTGACCATTT TCTTCTGAA ACAATAACAT GTCTCTAAGC ATTGTTTCTT
2451 GTGTTGTGTG ACATTCAAAT GTCATTTTTT TGAATGAAAA ATACTTTCCC
2501 CTTTGTGTTT TGGCAGGTTT TGTAACTATT TATGAAGAAA TATTTTAGCT
2551 GAGTACTATA TAATTTACAA TCTTAAGAAA TTATCAAGTT GGGAACCAAG
2601 AAAATAGCAA GGGAAATGTA CAATTTTATC TTCTGGCAAA GGGACATCAT
2651 TCCTGTATTA TAGTGTATGT AAATGCACCC TGTAAATGTT ACTTTGGATT
2701 AAATATGGGA GGGGGACTC AAATTTCAGA AAAGCTAAAA AAAAAAAAA
2751 AGTAATAAGG AAAATACTC TTATATTAAA ATACCCTTTC TTTGTTTTTT
2801 TGTTTTTCCT ATTTCATATT ATTAAATACA CTTAACGTTG CGAAAGCACT
2851 ATGAAAAAAT TAATACCATG AAAAGGATCA AAAATCATAA ATCAAACCC
2901 CACTATAGTC CAACGACAAT TCATTCTCGG CGGTCAACTT TTTAACATCT
2951 TATACTAGTA CCTGAGACTC TGGTGCTCAA TATTAATATT CTAAATCTAC
3001 CACCAAGTTA GGCCCGTAAT GTCGTCTCTC TCGTGAATCT GTCATACAAT
3051 ACATTTTTCT ATTTATTTAG TGGGTCTCGT TTATCTTTCG CCCACATCTT
3101 TGTTCACTAT TTTCTAGTTA CTCTTATCTT TGGGCTGATT AATCCTTCTC
```

FIGURE 1, page 1 of 2

```
3151  ATTATACTCA TATAAACTTC TGAATTTTTC ACATAAAACT ACTAGAGCTA
3201  CCTCACCATC TCTGTTTTTA ACGCGAGCAG TTACTATATA ATTACTATTT
3251  AAA
```

FEATURES:
5' UTR: 1-90
Start codon: 91
Stop codon: 2187
3' UTR: 2190-3253

Homologous proteins:
Top 10 BLAST Hits

|  | Score | E |
|---|---|---|
| gi\|3406050\|gb\|AAC29140.1\| (AC005070) serine kinase SRPK2 [Homo ... | 1415 | 0.0 |
| gi\|4507221\|ref\|NP_003129.1\| SFRS protein kinase 2 [Homo sapiens... | 1400 | 0.0 |
| gi\|3406051\|gb\|AAC29141.1\| (AC005070) serine kinase SRPK2-altern... | 1396 | 0.0 |
| gi\|6678135\|ref\|NP_033300.1\| serine/arginine-rich protein specif... | 1324 | 0.0 |
| gi\|7513813\|pir\|\|JC5929 serine/arginine-rich protein-specific ki... | 1320 | 0.0 |
| gi\|4507219\|ref\|NP_003128.1\| SFRS protein kinase 1 [Homo sapiens... | 792 | 0.0 |
| gi\|3135976\|emb\|CAB16202.1\| (Z99128) dJ422H11.1.2 (Serine Kinase... | 785 | 0.0 |
| gi\|7513812\|pir\|\|JC5930 serine/arginine-rich protein-specific ki... | 783 | 0.0 |
| gi\|7949139\|ref\|NP_058075.1\| serine/arginine-rich protein specif... | 781 | 0.0 |
| gi\|3135975\|emb\|CAB16201.1\| (Z99128) dJ422H11.1.1 (Serine Kinase... | 778 | 0.0 |

BLAST to dbEST:

|  |  | Score | E |
|---|---|---|---|
| dbj\|AU124932.1\|AU124932 | AU124932 NT2RM4 Homo sapiens cDNA c... | 1515 | 0.0 |
| gb\|AI038250.1\|AI038250 | oy85e06.x1 Soares_fetal_liver_spleen... | 1279 | 0.0 |
| gb\|AA553654.1\|AA553654 | nk79c03.s1 NCI_CGAP_Sch1 Homo sapien... | 1267 | 0.0 |
| gb\|AW149364.1\|AW149364 | xf36c05.x1 NCI_CGAP_Brn50 Homo sapie... | 1203 | 0.0 |
| emb\|AL045361.1\|AL045361 | DKFZp434C115_r1 434 (synonym: htes3... | 1144 | 0.0 |
| gb\|BE793406.1\|BE793406 | 601588440F1 NIH_MGC_7 Homo sapiens c... | 1084 | 0.0 |
| gb\|AW629710.1\|AW629710 | hh68h04.y1 NCI_CGAP_GU1 Homo sapiens... | 1084 | 0.0 |
| gb\|AI032748.1\|AI032748 | ox13f05.x1 Soares_fetal_liver_spleen... | 1076 | 0.0 |
| emb\|AL045362.1\|AL045362 | DKFZp434C115_s1 434 (synonym: htes3... | 1070 | 0.0 |
| gb\|AA573426.1\|AA573426 | nk99b04.s1 NCI_CGAP_Co3 Homo sapiens... | 1068 | 0.0 |
| gb\|AI830963.1\|AI830963 | wj80d11.x1 NCI_CGAP_Lym12 Homo sapie... | 995 | 0.0 |
| gb\|AI127471.1\|AI127471 | qb99f03.x1 Soares_fetal_heart_NbHH19... | 971 | 0.0 |
| gb\|AI199780.1\|AI199780 | qi60h04.x1 NCI_CGAP_Brn25 Homo sapie... | 948 | 0.0 |
| gb\|AI184192.1\|AI184192 | qf46g01.x1 Soares_testis_NHT Homo sa... | 948 | 0.0 |

EXPRESSION INFORMATION FOR MODULATORY USE:
library source:
Expression information from BLAST dbEST hits:

| | |
|---|---|
| dbj\|AU124932.1\|AU124932 | Neuronal precursor cells |
| gb\|AI038250.1\|AI038250 | Fetal liver spleen |
| gb\|AA553654.1\|AA553654 | Schwannoma tumors |
| gb\|AW149364.1\|AW149364 | Brain |
| emb\|AL045361.1\|AL045361 | Testis |
| gb\|BE793406.1\|BE793406 | Lung - small cell carcinoma |
| gb\|AW629710.1\|AW629710 | Genitourinary tract cell tumors |
| gb\|AI032748.1\|AI032748 | fetal liver spleen |
| emb\|AL045362.1\|AL045362 | Testis |
| gb\|AA573426.1\|AA573426 | Colon |
| gb\|AI830963.1\|AI830963 | Lymph |
| gb\|AI127471.1\|AI127471 | fetal heart |
| gb\|AI199780.1\|AI199780 | Brain |
| gb\|AI184192.1\|AI184192 | Testis |

Expression information from PCR-based tissue screening panels:
Whole brain

FIGURE 1, page 2 of 2

```
  1    MSSRKVLAIQ ARKRRPKREK HPKKPEPQQK APLVPPPPPP PPPPPPPLPD
 51    PTPPEPEEEI LGSDDEEQED PADYCKGGYH PVKIGDLFNG RYHVIRKLGW
101    GHFSTVWLCW DMQGKRFVAM KVVKSAQHYT ETALDEIKLL KCVRESDPSD
151    PNKDMVVQLI DDFKISGMNG IHVCMVFEVL GHHLLKWIIK SNYQGLPVRC
201    VKSIIRQVLQ GLDYLHSKCK IIHTDIKPEN ILMCVDDAYV RRMAAEATEW
251    QKAGAPPPSG SAVSTAPQQK PIGKISKNKK KKLKKKQKRQ AELLEKRLQE
301    IEELEREAER KIIEENITSA APSNDQDGEY CPEVKLKTTG LEEAAEAETA
351    KDNGEAEDQE EKEDAEKENI EKDEDDVDQE LANIDPTWIE SPKTNGHIEN
401    GPFSLEQQLD DEDDDEEDCP NPEEYNLDEP NAESDYTYSS SYEQFNGELP
451    NGRHKIPESQ FPEFSTSLFS GSLEPVACGS VLSEGSPLTE QEESSPSHDR
501    SRTVSASSTG DLPKAKTRAA DLLVNPLDPR NADKIRVKIA DLGNACWVHK
551    HFTEDIQTRQ YRSIEVLIGA GYSTPADIWS TACMAFELAT GDYLFEPHSG
601    EDYSRDEDHI AHIIELLGSI PRHFALSGKY SREFFNRRGE LRHITKLKPW
651    SLFDVLVEKY GWPHEDAAQF TDFLIPMLEM VPEKRASAGE CLRHPWLNS
```

FEATURES:

Membrane spanning structure and domains:

| Helix | Begin | End | Score | Certainty |
|---|---|---|---|---|
| 1 | 165 | 185 | 0.676 | Putative |
| 2 | 463 | 483 | 0.896 | Putative |
| 3 | 566 | 586 | 0.765 | Putative |

FIGURE 2, page 1 of 2

Hmmer search results (Pfam):

| Model | Description | Score | E-value | N |
|---|---|---|---|---|
| PF00069 | Eukaryotic protein kinase domain | 136.6 | 4.3e-37 | 3 |
| CE00022 | CE00022 MAGUK_subfamily_d | 7.5 | 0.04 | 2 |

Parsed for domains:

| Model | Domain | seq-f | seq-t | hmm-f | hmm-t | score | E-value |
|---|---|---|---|---|---|---|---|
| PF00069 | 1/3 | 92 | 232 .. | 1 | 123 [. | 90.1 | 6.6e-24 |
| CE00022 | 1/2 | 206 | 232 .. | 128 | 153 .. | 5.4 | 0.17 |
| PF00069 | 2/3 | 522 | 591 .. | 123 | 185 .. | 27.5 | 1.6e-06 |
| CE00022 | 2/2 | 677 | 697 .. | 263 | 283 .. | 2.1 | 1.6 |
| PF00069 | 3/3 | 670 | 697 .. | 248 | 278 .] | 19.6 | 0.00025 |

FIGURE 2, page 2 of 2

```
   1  TCTCAAACCT TTTCCTCCCG CTGGGGAAGT GGCAAACTAC TGAAGTTCCT
  51  TACTTGCCTC TCCTCCTTCA GAACTCTCTT TTGCCTGGGA CCATTCCACT
 101  TTCAGTAAGG GCACATGTGT TAAAAAGAAG CGAGCATTTA CATGGCTTCC
 151  AGAAGAATTC TTGTACTTCT TGGTAAGGCC CTGGTTGGGA AGTTTTGAAT
 201  GTATTCTGGA AGTGGTGTGT GTGTGTGTGT GTGTGTGTGT GTGTGTGTGT
 251  GTGTGTGTGT GTGTGTGAGA GAGAGAGAGA GAGAGAGAAT GAATATTATT
 301  CTCTTTCAGG GCTCTGTGAA GAGAATGGTT AACTTGGAGT GTTATCATCA
 351  CTACAATCCT GATGTCTGTT ACCCAGGGAG CTGTAACTGT TGAGTCTTCA
 401  TAAATTCCCA GAAAGCAGCA ATCAGTACAT TTTCAGCTTA TAAATATTCT
 451  TTAGTTGTCC TGCTAAAGAT ATTCATACCT TTGATTATTT GCCTTTAAGT
 501  TGACCTATTG TGTGTGATCC CCACCCCTTC CTCATGATGT CAGGTGTTTC
 551  TGCTGCCTTC TATTCCTACT CCTTCCTTCA GTTGTGGCCG TATGGGTTTT
 601  TTTGTTGGCA AGCCACATGC ATTAGTGGTG GTGTTGGAGG CTCTCAGATT
 651  GGGCAAGGAT TTAGAGGCCC AGTTTAGAAG AGGCAGTGGT TGAGGCAGCT
 701  CCTTTGGCCT GTCTCTTAGT GGCAGCTACA GATGAGCTTG CATTGCTAAG
 751  ACCCTGACCT TCTCAAGATT CCAGGGCTGA AGAGTGAGCT TTGACTGTAT
 801  GCCGCAGGCT GTGCTGCAGT GAGGAGAGAA AGGATCCAGA ATCGGCCTTC
 851  CACTGGGCAG AGAGCAACAG TGTTCCAAAA GGAAATCTAG CAATAACACC
 901  AAGATTCCAC CTGCTCTCAA CAACTAGGGC TTAGGTCTTT GAACTCTTCA
 951  TTGACAACGG CTATACCCTT AAAATAGGGC GCATGCTGGG TGACAGCAGG
1001  TGCATGGTGT GAGGAACTGG TGCTAAAGAA TTTTGCTGGA CCAGAACCAG
1051  ACCACAATAT GTTTGTCAAG CTTGTTCTTC TAGACGCAGC AGGCCTGAGG
1101  GCTGCCGTTG CAGAAATGCC CCAAGGAATG GCACTCACAT GTCGGGCAAC
1151  TGACCCTCAG AGCAACCTTT CCACAGCAGC CGTCATCTTC AGCGCACGCA
1201  TTCAGTGGTA GTTTTATTAG TGGGATAGCT TAAGGGAGAG ATGTGCTTCC
1251  GGCATCCAGA TTGAGACTGT AGGGTCCTAT TTCCCCGCAC TGGGGCATGG
1301  TTAGGAATAG TAAGTGAATC CCATTATGAA CCATTCTCCT CATAGAGCCC
1351  TGAAAGGGAA TAATCTCAAT CAATCAAACA CACACACACA CACCGCTTCC
1401  AGAATACATT CAAAACTTCG AACAGGCCTT ATAGAAGTAC AAGAATCTTT
1451  CTGGCAATCT TGTATATTTT AGCTACAGTG TATGTTAATC AGCTTTTATG
1501  AGTTATTGAA ACCTAACCTC ATTGCCACCT ATTTCTATGG GAAAAGAATT
1551  CTCATTTTCA GATAACAGGA AATAAGTGCT TTCAAAAGTT GAGTGCTGCT
1601  TGCGCCTGTC TTTTTATAAT CGTTGTGATG TTTTCTAACC AATAAGGCTA
1651  TATACCATGG AATACGCTTT CATTTCACTT AAATTTCCCA GAATTGGTAG
1701  GAGTTGAGTG GAGCGCACTG AAATTTCCTA ACATTGGTAG TTCTTGAAGC
1751  GCTAAGTGAA AAGATACCTA CAGAAAAAAA TTCCTTAGCT AATAAGGGCA
1801  GATTTTTTTT TTTTTTGGCC TGACTTATAT GTTGAAACAC TACTTGAATT
1851  CAACTAAAAT GGGTGAAGTG ACATTAAATG ACATTCTTC TTAGTATGTG
1901  ACAAGTTTTA TTTTTTCCCC CATATTAAGA AGTGCTCAAA TGCATCCATA
1951  ATGCAAGATG TACTTCTAAG TAAATAGCAA TTTTCTCTCT GCTCTTTCAG
2001  GCCGGAGCCT CAACAGAAAG CTCCTTTAGT TCCTCCTCCT CCACCGCCAC
2051  CACCACCACC ACCGCCACCT TTGCCAGACC CCACACCCCC GGAGCCAGAG
2101  GAGGAGATCC TGGGATCAGA TGATGAGGAG CAAGAGGACC CTGCGGACTA
2151  CTGCAAAGGT GATGTGCCAA GCATGGTGGT GTGGGGCTTG CCTTCCCCAT
2201  TGGGCTGTGT AGTAATTTGT TGGGGGAATG GACAAGGGGA GGAGGTAGTG
2251  ATGCAAATTG CTTGGTCTTC ATTAAATTAG CCTCCTTGTG TCATTATCAT
2301  TTTAAATTCT TAGGTCATTG TATAGAGACT GATATCAGAA AATATTAAGT
2351  GATATGAGAG AGAATTGTAA GACAAAATAC ATGTATTTGT ACATACATAT
2401  TCTAGGTACT TTCAGAAGGA CTTAAATCTG TTAGAATTAA AGGTAGTATA
2451  CAGCAGGACA GTTAGAGGAC ATAATAAACC ATCTAAAAGG AGCACTGGGC
2501  CAGTGCGGTG GCTGAAGCCT GTAATCCCAG CACTTTAGGA GGTCGAGGTG
2551  GGCAGATCGC TTGAGTTCAG GAATTCAAGA CCAGCCTGGG CAATGTGGTG
2601  AGACACTGTC TCTACAAAAA GTGCAAAAAA TTAGCTGGGC ATGGTGGTAA
2651  GTGCCTGTAG TTCCAGGCAC TTGGGGCGCT AAGGTGGGAG GAACACTTGA
2701  GCCCAGGAGG CAGAGGTTTC AGTGAGCTGA GATCGTGCTA CTGCAGTCCA
2751  GCCTGGGCGG CAGAACCAGA TCCTGCCTCC AAAAAATAAA GTACAATAAA
2801  AACATTAAAA TAATAAAAGA ACATAGAGAG GAGAAAGTGT ACCAGGCTCC
2851  TGAGGGAGC TAATTATAAC TCTTGTGCAC TGTATTTGAC TTTCTGTTTT
2901  CTGACTGCTA AGGCTAAAAG AAAACCATTC CTTTCTTTGT GTAGCATTGA
2951  ATTACATAGC GTTTATTGTC TGTGGGAAGC AAGCATGCAC ATTTGTTTAC
3001  AGAGAAAGAT TCTTTCCTGG CATTGTACTT AACGAAAAAG ACATTCTGTG
3051  GGGTTCTGCC ATTGTGTGAC ATAGTGGGTT ATGTTTTCAG CTATGATTTC
3101  ACGGAAGACA CAGAAACTAT TCAAGTGGAG TGTTCTTGTA TTGATGCTTT
```

FIGURE 3, page 1 of 30

```
3151  GTAAAGACCA AGAGTTAAAC TCCTAAAGGG CAAGCGTGTT GTGTGATGAA
3201  TATTAAGAAC AATATGATCT AGACACCATG CTTTGTGTGG ACCCAACTGA
3251  GAATCTAGGA GAAAGAGAAA TGACTATTCA GCTGCTTCTT TGTCACTTAA
3301  CTTACTGATT TGGACATTAA TTTTCTGGAA TTTGGAGCTC CTGAGCCAAA
3351  GTTGGTGAGA TGAATTTATT TGCTACAGAT TTTAAAAATT GTAAATCAGA
3401  TTCTATATAG CATTAGAATA AATGGCAGAA AATGCAGACA TGTTCAGAAC
3451  ATAAAGCATT AATGAATTTT GGGTTCCATA TGTCTTAATA ATTCATCATT
3501  TATCTAGTAG ATATAGATCA TTTGTATGTT GGTTCAGAAA CAGTGTACAT
3551  TTAATTACCT GCTAAGAGGA AGAGAAAGTT ACTGTACTAC AAAAGTGTAG
3601  GAACTAATCT ACTCTAACCT GATTCTTTCA TAGGTGCACG TACTTCCACA
3651  TAGAATCAGT GTGTTCCTTA GAAAAGAGTG TAGATCTTAC TTAGCATTTG
3701  TCTGAATAGT GGTTACAACC CCAAAGATCT ATGCAGTCTA GTAAAAGAAA
3751  AGATAGAGCC AGTTTGAAAG GTGACAAGAA GGTGTTTTCC ATCCTCCCTC
3801  TTACTCTTCA TTTCTTATAC TGTCTTCGAT TTTTCTGCTG AGGCCCAGCA
3851  TTAGGTTCAT CTGTAGGTGC CATTCTTTTT TCTTTTCTTG TTTTTTCTTT
3901  TTCTGAGACA GTCTTGTTCT GTTGCCCAGG CTGGAGTGCA ATGGCGTGAT
3951  CACAGCTCAC TGCAGCCTCA ACCTCCTGGG CCTGAGCAAT CCTCCCATCT
4001  CAGCCTCCTG AGTCCTGGGC TTGAGCAATC CTCCCATCTC AGCCTCCTGA
4051  GTCTTGGGCT TGAGCAGTCC TCCCACCTCA GCCTCCTGAG CAGTTGGAAC
4101  TGCAGGCATG TGTCACCACC CCTGGTTAAT GAAAAGTTTT TTTTTTTTTT
4151  CTTCTGGTAG CGACAGGGTC TGGCTAGAAC CATTCTTTAG GAGCTGTTTC
4201  CTTCAGCAAA TAGGTTCTAC CAAGCAGGAG TGAAAACTGT CTTGTTCATC
4251  TGGATCTTAA GTATGTGGGT CAGGAGATGT AACCAATACT CTCATCCCCT
4301  TACTATCTCT GGGAACCAGC ACAGTGGACA TCCAAACCCC AAATATAGGG
4351  CTAAGAATAA AGTATTCCAC AGCCGGGGCT GTTTCTAGGT AACATTCACT
4401  GAACTCTAAC CTTCACAGAG TATTAAAGTC AGCATCAGTA AGGTCATTAG
4451  AGATAGTAAG GTTCCCTCCT TATACCCGTG CCAGCCCCCC CCAAATTTGG
4501  TAAGTAACTT GTACCTTTAG TTAGCATTAC ATGTGACAGA TGCCCTACTT
4551  TGAATTTTGT GGTATATTCC ACAACAGTTT GTATAAGATT ACTGACATAT
4601  ACATATTCAG GGAGTCCAAG GAATTGATTT GGAATGTCTG GAATAAGACC
4651  TGTGGCCTTC TCATTTTTTG TTCTTGGATA AAGAGATAAA TCCCCTCACC
4701  CTCTGCCAGG ACTGGTTGAG CTAAAATTAC TAATATGGTG TTTTATCATC
4751  CCTGAATACT TTAGTACATT TTACCTACAA TCAAGTACAT TCTCCTATAT
4801  ATCAAAATAC AACCATCAAG ATCAGAAATT TAACACTGAT ACTTCACTAC
4851  TATTCAGACC TCGGGCTTAT CAGGTACTGC CAGTTGCCCA GTGTTGTCCA
4901  TTATGTGTAA TGAATCTGTG GCAGAAGCGC ATATTCTGTT TTCTTGTTTT
4951  TGTAATTTCT TTTAATTTGG AACAGTTCTC AGTGTTTTCC TGGCTTTCAT
5001  GTCCTTGACA TTTTTGAAGA TTGTAAACCG GTTATTTTAT ATAATGTTTC
5051  TCAATTTGGG ATGCCACAGT AGTGATGTTG TCTTTTTGCA TTAAATCCTT
5101  TCAGATGGTA CACAGGTTTG ATTTATTCCA TTGGAGTTGA TGCCTTCACT
5151  TGATCAAGAT TGTGTCTGCC AGATATCCCT GACAGCTGTT CTTTTCCCCT
5201  AGTAATAAGT ATTTTGTTGA GAGTTACTTT GAGACTACAT ATATAACCCA
5251  TTCAAATATT TATCCCTACC CCCGCCGCCA CCCCGGGCTG ACTTTCTGTC
5301  TCGGGTGGAC TGATAAATTC ATGGATCTCT GTTTTATTCA GTGGGTTATG
5351  ATCACTTACT CTCCTTATAT GTTTTGATGC TTAGATTATC CCAAATTTTG
5401  TTCTTAGGAG CCCCTTCAGA TTGGTTCTGT GTCCTTTTGA AATGCCTCAA
5451  TCGTTCTTTG ATCGTTTATT TTTTGTTTT GTTTGAGAT GGAGTCTCGC
5501  TCTGTCACCC AGGCTGTAGT GCAGTGGTGT GATCTCTGTT TCACTGCAAC
5551  CTCCACCTCC TGGGTTCAAG CAATTCTCGT GCCAGCCTCC TGAGTAGCTG
5601  AGACTACAGG CTCATGCCAC CACGCCTGGT TAACCTTTGT ATTTTTAGTA
5651  GAGATGGGGT TTCACCATGT TGGCCAGGCT GGTCTTGAAC TCCTGACCTC
5701  AAGTAATTCT CCTGCCTCAG CCTCCCAAAG TATTGGGATT ACCGGTGTGA
5751  ACCACCATGC CCGGTCCTTT GATCATTTCT TTACCTTCAA GTACAGTAGG
5801  ATATGCCAGG TTCATCTTGT GTTTTTCCTA TCCCAGCCCT GGAGTCTACT
5851  CTTTTCACAG AGAATCCTGC TTTTTTTTTT TTTTTTTTA AATTAAACAA
5901  TAATATTTAG AAAGCTAGAC CTGGGCATTA GGTGTGCTTA TTACTTTTGG
5951  CTTGTCACTT TCAGATCTCA GTACAGAGCT AGGAACACAA ACATATGCAC
6001  CTGCTTCCTT TATGTTTATA TTTATTTATA TATTTACATA TGTTTTGAAA
6051  TCCATGAGTT TATTAATCTG ATACCTCTAA TACCAGAAGA TTCAGCCTGG
6101  TGTTCTCCCT TTCCATCTTT GTGGTTTCTT TCTCTGATAG TAAGAGTCTG
6151  GGCTCTTCCC ATCCTCATTG CGTTGACTTA GTTGATTGAT TTCCCTGTAT
6201  GGTATGAATC ACCAGTCACC ATCACTATGT CTCTCCCTTC CCTTCTCACC
6251  TAACTCATGC TCTGACATCC TTTGTTGATT GGCCCTGCCT CATGGCTTGG
```

FIGURE 3, page 2 of 30

```
6301  GATTTAATGG TCCAGGATGG GAAGGGGAGA GAGCTTTCCC AGGCTGGTAG
6351  TGTGTGTTAT GTAATCTGAG GTATCATTTT TCTTCTGATA CTTCACCTCT
6401  TTCTCTTGCT TTTATTGACT TCATTCCTGG AGAGTCTCTG CCCTCAATTA
6451  CTTCTCAGTT TCCTCAAAAT ACAATTAAAA AAAAATTAAC AACAAAAGAC
6501  ATCACATGTA TTTCTTTTTA AAAATAAAAT TTGTTCATCA CAGGAAATGT
6551  AGACACTTGG GTTGGAGGGC AGAAGTCACC TGTGATCCCA CTACTCAGCA
6601  AGAGCTGCAG CAAGCCTTCA TCATTTATGA TCAGCTAGAT TACATCTTAA
6651  CTTTTTACCT CATCTTTACA AGTTTCCCTT ATTTAAAATG TATGAACCCT
6701  CAGCTGTTTT AATAAGAGGG TCCATATTTA AAGTTCTGAT ATTGCAAAAG
6751  CATTGTTCAT TGCTCTTGTG TACTTACTTG CCTTGGTATT CTCTCTGGAG
6801  TAGGACTCTT CATTTCCTGA CAGCCATGTT CCTACTCGCG TTATCTTAGA
6851  TCTCCAAGAG GATTATGGCA TTATTGACTG ATTCCTGACA CTTGGTTCAA
6901  AACCTGGCTG TGTTGCTTTG TAGCTCCGTC TTCTTGGACA AATTCCTTTC
6951  TCTTTAGGCT TTGGTTTTTC ATCTATGATA TGATAATTTA TATTATATTA
7001  ATGTTAATAC CTAAGATTTT TATGAGGATT TAAATGAAAT ATATGAAGTT
7051  CATGACACAG TATCTGATAC GAGGCTCATA AGAAATATGA GTTTCACTCT
7101  TCTTCTGTCT GTTCTATCAT TCTTCTTTCA TTGTGTTCTC ATCTGTACTT
7151  CATGCTGTCT ATACCCATCA GTGCTGGCTC CCTTAACTCC CTGACCGTGT
7201  CTCATGTTGG GTGTGTTTCC TTAACCTCTG GAGAGAGAGC TGTCAGCACT
7251  GCCTATCTTT TTTACATATC ACCTCTGGTC TGTTGTCTGG GCACAAGCTG
7301  TAGCAGTAGG CTGTGCAGTT TATTCAGATT CTGCTTCCAA GCCCTGGGGA
7351  TTACCAAGAT CAGGGGCAGG GTCAGCCTGT AAACAAACAC TGTCGGGAGG
7401  CCTTGTGTCA TACATGCTTG TTTCATGAGT TTGAGCAAAA AAAACCTGTG
7451  TCACAGCCAA ACCTCCTTTT GTGGGAAGAT TTGTGTTTCA TGTGGGGTTT
7501  TCAGAGGCAG TAGGGGGTGC CTGGTAAACA TTCCTAGGCT GCACTGTAAA
7551  CCCCTGAATT GGAATCCCTG AGAGTGGGAC TTAGGAATCC AAATATTTAA
7601  CAAATTCATC AGTGATTTTT CTGCACATTG AACACTAAAA TCTGCTCCAT
7651  TCTAAGGTCT GCATGTATCA TCCTTCTAAA ACTCCAAGGA TATAACCACA
7701  TGAAGGCACC CTTCATACTA TACGTGCAAT ATAAGCGGAA TCATTGCTTT
7751  GAACTACCTT ATGTTCCTAA CTTTTTCCAG AACCCTCGGT GTATACCTGC
7801  TACAAGGACA TACTAAATGG TGACTGTAGG AACATTGCCT TGCAATATCA
7851  GGCTGCCTGT AGTAGCTGTC CTCAGACATG AGTTTGTTG CTCTCTTAAA
7901  TCATTCTTAG ATAAGTTGGC ACCTTTGTAC AGTTTTCATC TCTTGAATTA
7951  TTTCTGGAGA CATCAACAGC TGTGGTCTGA CTTGGTATGA AAACATGTCA
8001  TTTCCTTAGA AATGCATTTA TTCGACCTCT AATCAGACCC TTTCCTTTAT
8051  TACCCACGGT ATTGTCCCCC GCATCCCCAA CTTATCATAG TGTGGAATTG
8101  TACATTTATT TCTGTGTTCA TGTATCTCCC CCTCTCTAGT CTGAAAGGTT
8151  CCCTTTGGTC AAGGCCCTGT AGTTGTTAA CTCCACTGCA TTTGAACCAT
8201  CCATAATGCA GTACGTATTT TGTTTGGATA AAGGCATTTT CTCTAGTGTT
8251  GGGTTGCAAG TACGGGATAG GCAGATGCT GATGTTCAGG TGGATCTGGG
8301  GAAGGCATGT CGGCATGAGC AGGCTGGCAT GCTGACTGGC AGATCAGAAT
8351  ATAGGGCCTT TGTTTCTGCC TCACGTTTTC TTAAAATCAT CCATAGTTCT
8401  CCGGAATACT TAACCTGTCA CACACATTTG AGTGACATAT ATTTCTTACC
8451  TGTAAAAACT TAGGGACATT ATTTTCTTCA AAATAGAGCA TAAAATATTA
8501  TAAGTATACA CACTAGAAGC ATGTCAGATG AGTTTCTTCC TATACACAAA
8551  TTGCCTTTAC CCATGTGTGT CTATTTTCCA TCTGTGAAAA CGGTAGACTG
8601  GTTGAATTTT AATAACTCAC AAAATTTACT GTTGGTGGCT ATTTGCTGTC
8651  ATTGGCATCC CTCCTCCCTT TCTCCTTCCC TCCCTGCCCC CCAACCCTCC
8701  GAGTCTATGA CTTTGATTTA TTTTATTTTA TTTTTTATGA GATGGAGTTT
8751  CACTCTTGTC ACCCAGGCTG GAGTGCAATG CTGCAATCTC CACTCACTGC
8801  CTCTACCTCC CGGGTACAAA CAATTCTCCT GCCTCAGCCT CCCGAGTAGC
8851  TTGGATTACA GGCATGCACC ACCATGCCCA GCTGATTTTT GTATTTTTAG
8901  TAGAGATGAG GTTTCACCAT GTTGGCCATG CTGGTCTCGA ACTCCTGACC
8951  TCAAGTGATC CGCCTGTCTC AGCCTCCCAA AGTGCAGGGA TTACAGGTGT
9001  GAGCCACTGT GCCCAATCTG TGTTGTTTTT TAAGGAAAAA AAAGCAAAGA
9051  ACCTTAAAGC TGCTTTAGAA TTGATATTTG TACAGTAAAA AGAATAACAA
9101  ACAAAAGAAA TATTTGTACA GCCAAGTAAT GTTGGCTGTG TTACATCAGA
9151  GGTTCTTCGC TGGGTGCGGT TTGACCCCT GGGAGTCCAT TTGTGAATGT
9201  TTGGAGACAT TGCTTGCCG TGACGGGCTG CTACTGGCAT CTCTTGGGCA
9251  GAGCCAGGGA TGCTGCTAAA GGTTCCACAG CGCACAGGAC AGTTACCCAT
9301  AACAGAAATT ACTCAGCTCC TAATGTCAGC AGTGCCCAGA TGGAAAATCT
9351  CTGCCATAGA AATGCCTGTT TTTGTCTATT AAAATGGTGT TGTGTGGCTG
9401  AAGTATTTTA TAGACGTGTG GTCTTTACTT TCTGTTCCTT TTGATAGAAA
```

FIGURE 3, page 3 of 30

```
 9451  GATAACCTTT CTTTATTCAC AGTTCTTTTA CTTAAAATCA TTAATGCTGC
 9501  ACAGATACTT AATTCACTAT GCTTTTCATT TATTAGTTGG CTTAATTTGG
 9551  CTTAATTCAA GCCTTAAAAA GAAACCCTGC CTATCTATGT GAACAAAGCA
 9601  ATAGATGCTC TTGAACCTAT TACATAAGGC CTCATTACAT TTCTTTTATG
 9651  GAGACCAAGG AGATTCTGAC TCCTGATCTG TTGGTGCTTT AAATTGACAA
 9701  GGATATTTAT GATACAAGCT TTAAATAGCA TGACAGGTGA GTTCATGGTT
 9751  TATTCATTGA GGCTTGATGA TGTGCAAAAC GTTGTACTTT ACTACAGGGC
 9801  ACATAGAGGT AAATGAGAAA CAGCCCTACT TTCTAGATTA TGGCCTCTTA
 9851  GACTTTGCCA CTAGAATGCC AGCTACTTAA GGGCAGAGCC TTGACCTGTC
 9901  TAGCTTCCCT GGCACCCCAG TAGAACAATC TGTGGCCTGC TGAATAGTGA
 9951  CTGAATGAAT AGACTGCTCA AATATCTTTT TTTTCATCTA AGTGTGGTTC
10001  GTTAATAATA AGTGAGAAAA GGGAAGATAT GTGAGGGCTA AAAGGAAGAA
10051  TGTTATATTT GAATAGAGGA CTCAGAAAAG ATGTTATAAA AAACTGAAAG
10101  GGACTTTGTC AGTAAAGAAT ATTTGGATGA TGTTGAGAGT ATGGGGCACT
10151  ACTCAGACTA AATCCTGGAG GCAGAACAAG GTGTAAGAAG CCCTAACTGC
10201  TTGTGTTTTC CTAACAAATG GGGAAACTAA AAATTGATGG TAGAAGATTA
10251  GGTTTAAAAG CAGTTTGGGA GCATCATGTA GAGGATAGAG ATGAGTGTGA
10301  GAAATTTGTG GTGAAGTAAC TTTAAAGCAT CACTTCAAAA TATTACCAAA
10351  AATCCCCACA GAAAACCGAA AGAAAGCAGA GTAGAAACAG AATCCTGGTG
10401  TTATAATCTC TCCTCTTTTT ACAAAACATA TTTAGCAGGC CGGGCATGGT
10451  GGCCCACGCC TGTAATCCCA GCACTTTGGG AGGCCGAGGT GGGCAGATCA
10501  CGAGGTCAGG AGATTGAGGC CATCCTGGCC AACATATCGA AGCCCTGTCT
10551  CTACTAAAGA TACAAAAAAT TAGCCGGGCA CGGTGGCACG CGCCTGTAGT
10601  CCCAGCTCCT CGGGAGGCGG AGGCAGGAGA ATCACTTCAA CGTGGGAGGC
10651  GGAGGTTGCA ATGAGTTGAG ATTGCGCCAC TGCACTCCAG CCTGGGCGAT
10701  AGAACGAGAC TCTGTCTCAA AAAATAAAA ACAAAAAATA AAAATATATT
10751  TAGCAAAAGA GCAGTGCCAA AATGTCAGCA GTATGTGGTA GGCCTGAGGT
10801  GTTTTTTTGA AATATACTTT TATCTTGTTG CTGCAGCACC ATTTATCGAG
10851  AAAGACTTGT TCCCCCACCT ATTCAGTTGC TTGCCTTTGT CCATCAGTAG
10901  ACAGAATGTA TGGGGGTTTG TTTGTGGACT CCATCTGCTC CATCCCTCTT
10951  TTGGTCAATG CTTGCTCTAA AGGTCTGGTT ACTATAGCTT TGTATAGCAT
11001  GCCTTGAATG GGTAGTGTCA GTCTTCCAGC TTTGTGCTTC TCTTCCAGGA
11051  TTGTTTTGAC CTGTCTCGAT CCTTTGCATT TTGTATAAAT TCAGAGTCAG
11101  CTTATACATA TAAATTTTAG ATACGCCTTA ATAATATTGA ATCTTCCAAC
11151  CCATTAACAT GGTATTGTGT CCGTTTATTT AGGTCTTTAT TGTTCTCAGA
11201  AATGTTTTGT AGTTTTTGGT GTGGTTTTGA TGGGTTATAG AAATGTAACT
11251  GATTCTTATG CACCAACCAC GTGGCCTGTA ACTATGCTGT TTGCTTATTT
11301  ATTAGTGTTT GTGCATGTGT AAATTTCTCT AGGTTTTCTC TACACACAAT
11351  CATTTCATCA TTTCAGGGCA AATGGAGGTT TTTCTTCTTC CTTATGATTC
11401  TTTATAAATT ATTATTCTTT TTTGCCTCAT TCTTTTATGC ATGAGGTTGA
11451  ATAGAAGTGG TAAGAATAGA CATCTCCCTT GTCTTGTTTC TAATCTTACA
11501  GTGAATATGT AGTTTTTTTT TAGATACCTT TATCAGGTTG AGATGGATCA
11551  TATATTTAAA TATAAAGTTA AAACTGTAAA GTTTCTAGCA AAAAGTAAGA
11601  GAATATCTTC ACAACCTTGG GAGTAGGGAA GGATTTATTA GAGAGCATAT
11651  AAGAAACATT AACTATAAAA TAAAAAATTA ATTAGACTTA ATCAAAATTA
11701  AAAACTGTTC CTGATTAAAA GACATTTTTA AAAATGAAAA GACCAGCTTC
11751  AGACTGGGAG AAGCTCTTTG CAATACATTT ACCTGACAAA GAATGTGACT
11801  GGGAGGGAAC TTCAAGTGTG AGATTTTGGA AAAATGTTCT GTATATTGAT
11851  TAGAGTATAT GTATTTGTCA AAAAGCAGGG AATCGTACAC ATAAAACCTT
11901  TGACTTTCAT TGCATGTAAA TATCTGAATT TTAAAAAACA TTGATAGTAG
11951  CTAGTTACAT CTGGATTGTA GGGTTTTGGT TTTTGTCTTC TTTACCTCTT
12001  TGTATTGGTT TTCTTTGTTT TCTGCATTGA GCATATATTT CTTTGTAAAT
12051  ACAGAAGAAT ATGTGCTTTT ACTGCTGAAA GAAATCATAG ACGACACAAA
12101  CAAATGGAAA CACATCCCAT GCTCATAGGT GGGTAGAATC AGTATTGCGA
12151  AAATGACCAT ACTGCCGAAA GCAGTCTACA AATTCGGTGC AATTCCCATC
12201  AAAGTACTAC CGTCATTCTT CACAGAACTA GAAAAAACCA TCCTAAAATT
12251  CACATGGAAC CGAAAAGAG TCTGCATAGT CAAAGCAAGA CTAAGCAAAA
12301  AGAGAAAATT TGAAGGCATC ACATTACCTG ATTTCAAACT GTACTGTAAG
12351  AGCACAGTCA CCAAAACAGC ATGGTACTGG TATAAAAATA GGCACATAGA
12401  CCAGTGGAAC AGAATAGAGA ACTGAGAAAT AAACCCAAAT ACTTACAGCC
12451  AACTGATCTT TGACAAAGCA AACAAAAAAG GAACAGACA CCCTATTCAA
12501  CAAATGGTGC TGGGAAAACT GGCAAGCCAT CTGTAAGAGA ATGAAACTGG
12551  ATCCTCATTT CATACCTTAA ACAAAATCA ACTCAAGATG GATCAAGGAC
```

FIGURE 3, page 4 of 30

```
12601 TTAAATCTAA GACCTGAAAC TATAAACATT ATTAGGAAGG TAACATCGGA
12651 AAAATCCTTC TAGACATTGG CTTAGGCAAG GATTTCATGA TCAAGAACCT
12701 AAATGCAAAT GTGATCAAAA CAAAGTTAAA TACCTGGAAC TTAATTAAAC
12751 TAAAGAGCTT TTACACAGCA AAAGGAAGAG TCAGCAGAGT AAACAGACAA
12801 CCGAAAGCGT AGGAGAAAAT CTTCACAATC TATACATCCG ACAAGGACTA
12851 ATATCCAGAA ACTACAATGA ACTCAAATTA GCAAGGAAAA AAAAATCCCA
12901 TGAAAAGTG GGCTAAGGAC ATGAATAGAC AGTTCTCCAA AGAAGATATA
12951 CAGATGGCCA ATAGACTATG AAAAAATGCT CAACATCACT AATGATCAGG
13001 GAAATGCAAA TCAAAATCAC AATGCAATAC CACTTTACTC CTGCAAGAAT
13051 GTCCATAATC AAAAAATCAA AAATAATAG ATGTTAGCAT GGATGCAGTG
13101 AAAAGGGAAC ACTTCTACAC TGCTGGTGGG AATGTACAGT AGTACAGCCA
13151 CTATGGAAAC CAGTGTGGAG ATTCCGTAAA GAACTAAAAG TAGAACTACC
13201 ATTGATCCAG CAATCCCACT AACTGAGTAT CTACCTAGAG GAAAATAAGT
13251 CGTTATATAA AAAGTTACT TGCTCATGCA TGTTTATAGC AGCACAATTC
13301 ACAATTGCAA AATGTGGAA CCAACCCAAA TGTCCCTCAA TAAATGAGTG
13351 GATAAAGAAA CTGTGGTGTG TGTGGAGTAC TTCTCAACCA TAAAAGTAA
13401 TGAATTTTGG AGCAACCTGG ATAGGATTGG AGACTCTATT ATTCTAATTG
13451 AAGTAACTCA GGAATGGAAG ACCAGACATC CTATGTTCTC TCACTCATAA
13501 GTGGGAGCTA AGCTATGAGG ATGCAAAGGC ATAAGAATGA CACTGTAGAC
13551 TTTGGGGACT CAGGGGAAA GGGTAGGAAA GGGATGAGGG ACAAAAGACT
13601 ACAGACTGGG TTCAGTGTAT ACTCTATCGG TGATGGGTGC ACCAAAATCT
13651 CACAAATCAC CACTAAAGAA CTTACTCATG TAACCAAACA CCACCTGTTC
13701 CCCCAAAACT TATGGAAATT AAAAAAAAAA AAAAAAGCAG AAGCAGAAGT
13751 GGAGCTTTTA AAAGGAATAA GTGGACCAGG CATGGTGGCT TACACCTGTA
13801 ATCCTAGCAC TCTGGGAGGC CAAGGCAGAA GATCATTTGA GCTCAGGAGT
13851 TCAAGACAGC CTGGGCAACA TATTAAGACT TTGTCTCTAT TTAAAAAAAA
13901 AAAAGTTTTT TTTGTTTTTT TTTACAAAAG GATAAAAAGA ACCAGTGTAG
13951 GTTTTAAAGA GGGAAGTGCT ATAATTAAGG AAGCTTAATT TGAAATCTTA
14001 GTTGATTGAC ATTAAAGAGA GAGAAGATAC AAGGAGAAGA CAAAAGCAAA
14051 CAATGTTATG GAGGTACCGT CTTTATTATT CAACAATCTG TTGAGTATGG
14101 AGGGCAGTGA CCAGAAAACC CCACACACTT CTAAGTCCTG GAATAATCAG
14151 AAGAATAGTA CCTTCTGGGC ATCATTTATT TTAGTGTACT CTGAATTATG
14201 AAACTGCTTT TCTTCCCCTT CCCCATAGAG ATAGAGTGTC TCATTCTATT
14251 GCGTAGGCTG GAAGGCAGTG GTGTGATCAC AGCTCACTAC TACTACAACC
14301 TCCCAGGCTC AAGCTATCCT CCTGAGTAGC TGGGACTACA GGTCTGCATC
14351 ACCATGCCTG GCTGATGTTT AAATTTTTTT GTAGAGACAG GATTCGCTAT
14401 GTTACCCAGG CTGTTCTTGA ACTCCTGAGC TCAAGGAATC TCCTCCTGTT
14451 TCTGCCTCCC AAAGTGCTAG GATTGTGGGC ATGAGTCACC ATGCCTGGCG
14501 GATTTTAAAA ATGTTGATAG AGACGGGGTC TCCCTATGTG TCTCAGGGTG
14551 GTTGTCATTT CTTTTTTGCA TTGGATATCG TTTGGCTATG AAAAAGCTCT
14601 GAGCCAAATG TGCAGCCCAC CTCTAACAAG TGAACAGTAA TTTATAGCAT
14651 GCATTCTGTA TCCTAACTTC ACTGTAGCAT TATTCTGTTT TACTTTTTCT
14701 GGGCTATTTT TTCTGTGCCC CAATTTCTTT CTAATTTTGT ATCTTATATT
14751 GTGGTTTTAT AAGCTGCCTC AATTCCTTAT AGAAAAAAAT AGTGTAACAT
14801 ATATTAAAAC ATCACATCAT ACCCCATACA TACAATTATG GCTTACTAAT
14851 TAAAAATAGC TTTTTAAACA AGGTGAAATA ATGTTGGCAT TATTAGTAGA
14901 AACAGTGAAG TCGCAGTTGG ATTGGGGAAG ATGTTGATGA GTTTGACTGT
14951 TGATGGAAAT ATCAAGAAGG TGGTTAGAAA TATGAATCGG AGAATCAGAA
15001 GTATCAGCAA GCAGGTGGTT TAGTAAAGAA TTTAACCTTG CCTAAAGAGA
15051 TATCTAGCCT TTGTCCTTGG AGCCTTCCAA GGGCATAGAG ATCTGGGTGC
15101 CTTGGGCCAC ACCTGATAGT CTAACAGTGT GGCACATTAT TGAACGTGAG
15151 GATGGTCTTT GGGACCCCCA AACTCTGTGA TTCATGTCAG AAGGGAAGGC
15201 AGTTGGTGGA CTGTTCCCAA ACCTTACACA GATATTATAG ATTTGATAGG
15251 TAAAACAGAT CATATAATGG TAAGTGGTTT AAAAAACAA ACAAAAAAG
15301 GATGCAGAGA GGCTGTTCAA TGACAAGCCT TTGAGAAATT TAATGGAATG
15351 CAAGAGGAAA AGGAACACGT ACAAGAAACA GACATAGCAG TCAAGGAGGT
15401 AGGAGAGCAA CCAAGATATG TGTTCATTTT GACCTAGAGT GGACTGAGAT
15451 GGCAGCCGTG GTGTTATTCT GAATGACACA TTCCTGAACA CATTCAGTTG
15501 TGTAACCCAA AGTTTATATT GTTTGAATAT AGATGGGCAG TCATACTTGC
15551 AGTCATTCCA GATGTCAGTG GCTCTTGTCC TCACTTGTCA GCCCCTGCAT
15601 AATCTGCCCT TTTGGATCTG GAAGTCGCCA GAGGGAGCGC AGGATCCAGA
15651 CCGGAGTCCC CATGTGTGAT CTGTTGTGAT CCTCCTTCCT GCTCCTGGCC
15701 TGCTCCTGCT GGTGCTGCCA TTACCCACTA AGAGAATGCT GTGGCGTTCT
```

```
15751  GCCACAAGGC TGTCCCCACT GTACTCAGTG CCAGAGCACA GTTGTGTGGC
15801  ATGGCAGTGG TGAGAGACCA GTTCATATGT CTGCAACAGC CCCATGCCAT
15851  CACGCCACAG CGTGCCCACC ACCCCTATAG CCAGTGGCCT CACCCACTGG
15901  TCCCTGGAGT CCAGTTTAAT TTTTTAAAAA TTTGTAAAAA GAGTTATAAA
15951  AGAACTTCTA GTCAAAAAGA CCAAAGCCCA TGCCATCATC ACACTCCTCA
16001  GATTCTTCTT TGTTTTTCCT TTTCTTTATC TTTTTCTTTT CGGAGACCGA
16051  GTCTGGCTCT GTCACCCAGT CACTGCAACC TCCGCCTCCC AGGTTCAAGT
16101  GATTCTTGTG CCTCAGCCTC CTGAGCAGCT GGGATTACAG GCATCCGCCA
16151  GCCCACCCAT CTAATTTTTG TATTTTTGGT GGAGACTGTG CTTTGCCATT
16201  TTGGCCAGGC TGGTCTAGAA CTCCTGGCTT CAAGTGATCT GCCCACCTCA
16251  GCCTCCCAAA GTGCTGGGAT TACAGGTGTG AGCCACTGCA TCCGGCCGAG
16301  ATTCTTTTTT CTTTGCTTAC ACTTCCTTCT CCTCAGCTGG AGCAGCTGCT
16351  CTGGACAGGG CAGGACCTAC TGTTGATGCA GCAGCAGCTG CTGGAGCAGG
16401  TCCACCAACC CCTACATTAG GATGAGTCTC TCGATGTCAC CATAGGCCAG
16451  GGCCTTTGCC AACAAACCAG GCCGAAAAGG TTCAACATTT ACACCACCTA
16501  CTTTAATTAG GGCCTTGATT TATCCTCTGT GACGGTCACC TCGTTCATAG
16551  TGAAGAATGA GGGTGGAGTA GATGCAGGCG AATTCAGGGG CTGTGGTGCG
16601  GGCGAGTGGC GGGGCTGGTG CTGCTGTTGG ATGCAGTGCA AGTTGCTGGA
16651  TGAAGTGAGG GCCTCTCCCC AGTGTGACTG TAGCTTTCCC AGAAGTACTG
16701  AGCCCCTTGG CAGCAGCTGA GGAAAGGGCT GGAGTCTGGG TTTAGAAAGT
16751  GTCGACAATT AACATGGTGG CTTCTTCTTA GCTCATTCTC TGTCCCTTCC
16801  TCCCTCCACC CCCTTTAGGC TCACTGTAGC ATAAGGGTTT TTTTCCTTTT
16851  ATGCTCCCAG CTAAAAGCTG GAACACTCTT GCAAGTCTTT TTGTTAGTTG
16901  GGGCTATCCA CCAATTCTCT TTAAGGGCCC AGGCATGTTT GATTCTTATT
16951  TGGGATCTAA GGTAGTATTC TAAAAACATT TACAAACAGA ACCTGTTACG
17001  AGTAATATCT TTTCTCTTTT ATTTCCCATT TGGTGCTAAT TTAAAAATGG
17051  ACTGTATTCT TAGAGTTCTT TATTCAGATT TCACTCCTTA ACATTGATGT
17101  TCTGGATTCA GTAGAATTGT TAAAATTTTT TCCTCTTTGT TTTGGATCCT
17151  GTTTTAACCT GGAATTGAAA AGAGTGAAAT GAAGTAATGG AGTTCCAGAT
17201  TTTGTTGGGG ATTTTTTGTC TGGTTTATGT TGACTAGGAA GCAGTAATTG
17251  AAAACATGCT ATTTTTTCCC TCATACATTT TAAAAAATTG AGATATAATT
17301  TGCAAACATA ACATTCTCTG CTTTAAAGGG TACAATTGTG TGGTTTTCAG
17351  TATATTCACA TAATTTTGCA ACTCACCACT TTAAAATTCC AGAACATTTT
17401  CATCATTCTC CAGAAGAAAT GACTGTCCAT TGACAGCCAG TCCCTATTCT
17451  CCTCCCCTCT ACAACCCTTA GCAATCACTA AGCTACTTTT TGTCTCTATT
17501  CTGGACATTT TCATATAAAC AAACACAATA CATCACTTTT TGTGTTTGGC
17551  TTCTTTTACT TATAATGTTT TAAAGATTCA TTCTTGTTAT ACCATGTATT
17601  TTATTCATTC ATTTCATGAT TAATATTTCA TTTTCTGGAT GTATCACAGC
17651  AGTTCATATA CATTTGGGTT GTTATCACTT TTGGCTATTG AGAATATGCT
17701  GCTGTGAACA TTTGTATATG AGTTAAAGTG TACATTTGTT TTCATTTCTT
17751  TGGTATGTAT CTAGGAGTGG AAGTGCTGGG TCATATGGTA ATCACTTAAG
17801  GAGCTGTCAG ATTATTTCCC CAGATGGCTG TGTCACTGTA TATTCCCACC
17851  AGCAATCCTA TCTTGGTTAT AATTTACTCA CCTTTGTCCC TTTTATGTTT
17901  ATTTTTCTTG TGACTTACTT GCTTCTGTAA TTCTATTATA ATGAATGAGT
17951  TTTACCTATT TTTTTAAAAA ACCTTTGATT GATCCTGTCA ATGGCCTCTT
18001  CAGCTCTGCT TACTACACCA CGCATATTCA CCATGAGACT TTAAACCTGA
18051  ACGTCTGGTC AGACACCCAC ACCAAAATCC TTCCCTTGGA CAATAGTAAT
18101  TTTGCCTGTG TTGGTAACAC ACTGAGATGG TGGTGGTCTT TCCAAGGCTA
18151  TATGGTCTGA GGTATAAAAA AAGAGTTTTC AAGACGGAAG GATTTAATAA
18201  TAGCATTTAG TTTAAGCTAA ATTTCAGTTT CAGGAAGGTA AAAGCTGACA
18251  GGAACAGTGA ACTACCTGTG GGGAATTCTC TAGAGACTCA TGTGTGGGGC
18301  CAGTGATGAG TCAGGCAGAT GTCAAGGTGA GGATATATTA GCAAAGCATA
18351  GCAGATTATT CGGTGAAATT TAGCAATGAA ATGATTGTAG CTTCTAGGGA
18401  GTGGGGTCAG ATTTGTGCAA GAAAAAGCAT TTATTTTAGT GTGACATATC
18451  TGGGCATATT TCTAGGCAGA AGAGATAAGG TTTGAGTAGA GTTGAAAGGC
18501  CAGCAACAAA GGAATTAAAT GAGTGATTTT TGGAGCTAGT TGATCAGTCT
18551  TTTAAAGATT GAAGGCACAT CTTACCTGCA GAACCGAGGA GGAGGTTTTG
18601  CATAGCTGTT GTGGTGAGCA GAATAAAGAC CGTTGTGATT ATTGTTGTAT
18651  AATAAATTAT CCTCAAACTT AGCCTTAAAC CCCTTTTTAA TTTTGTTCAT
18701  GATTTTATGT ATCAAGAATT TAGAAAAGAC AAAGCTGGGA TGGCTTGCCC
18751  ATTGCTTCAC GGTATCTGGG GCCTCAACTG AGACATCTCA AGGGCTTGAT
18801  GTGGCTTCAT GGCTGGGGAC TAGAATTAAC TGAAAGCTTA CATCTGGCCC
18851  CTGGGCTAGA AAGATAAACA ACTAGGACAG CCTTATGGAG CACCTATCCA
```

FIGURE 3, page 6 of 30

| | | | | |
|---|---|---|---|---|
| 18901 | TGCCCTTTGC | ATATGGCTTG | GCTTTCTCAG | AGCATGGTGG | CCTCAGAGCA |
| 18951 | GTCATACTTC | CTACCTGGCA | ACTTAGAGTT | CCCAAAGGTA | ACACACACCT |
| 19001 | TCCAGAGTGG | AAGCTGTGTT | CCTTTTATGA | CCTAGCCTCA | AAAGTCACAC |
| 19051 | AGTCTCATCC | ACTATATTCT | TTTTGGTTAG | AAGCACATCA | GACGCTCATT |
| 19101 | CAGTTTCATG | ATTAGAGTCC | ATTTCTTGAT | AGTAGAACAT | CAGAGTAGAA |
| 19151 | GGGATAGTAG | AAGAGCAGGT | AGTTGGGGAG | ATACTGTTTC | GGCCTTTGTT |
| 19201 | GAAGAACACA | GTCCGTCAGA | ATACAGCAAC | AAGAAATCAA | TAAAGCAGCC |
| 19251 | ATAGAGAATG | AAATGATTTC | CTTTGCAGCA | ACATGGATGA | AGCTGGAGGC |
| 19301 | CATTATTTTA | AGTGAAAAAA | CTTAGAAACT | GAAAATCAGC | TACTGCATGT |
| 19351 | TCTTTCTTGT | AAGTGGGAAC | TAAACAATGG | GCACACATGG | ACTTAAAGAT |
| 19401 | GGAAACAATA | GACACTGAGG | ACTCCAAAAG | GGGCAAAGTT | GGGAGGGTGG |
| 19451 | TGTGGCTTGA | TAATTACCTA | TTGGGTATAA | TGGTCACTAT | TTGGTTGATG |
| 19501 | GGTATACCGG | AAGCCCAAAC | CCCACCATTG | TGTAATATAT | ACACATAACA |
| 19551 | AACCTGCACA | TGTACTCCCT | GAATCTAAAA | TAAAATTTAA | AAAGTAAAAA |
| 19601 | CCTATAAGCA | AGGGCATTCT | TCCTACTGTC | AAATGATACA | ACATTCATAG |
| 19651 | AAATAGAGAT | TTGTGTAGTT | TGAAAATACC | TTATATAAAT | CAAGATGAAA |
| 19701 | CCTTTATTTT | GCAGACATTA | AACCTAAAGT | TGACTGATAA | AGACATATTC |
| 19751 | GTCCCATAGC | CCAGAACATT | CTAGGGGAAT | AAAATCTATA | AAAAGATGCA |
| 19801 | GACTTCCAAA | TATATGTAGT | TATAGTTATG | TAGGTACAGT | AAACTAACCC |
| 19851 | CCTTTTTAG | GACATGTATT | TATCTAATTC | TCTTTTTGTC | TGGCATGGAT |
| 19901 | TATAAGCCTT | CTAAGCCTAG | AGTCTACTAA | GTATGTCTAA | ATTGCTATGT |
| 19951 | TGGGTGCCTA | ACAAAGGAGT | ATGTACAAGT | TGGTGCATGA | GTTAGACTTT |
| 20001 | TTGATGGTGA | TTAAACTGGA | AAGCATGAAT | TATTCTTGGA | TTATAAAACT |
| 20051 | AGGTGGGGCT | TTCGAGTGAG | GCTCAAAAAT | CAGTTTTGTT | TTCCACATAG |
| 20101 | AGACCTTTTA | CTTATTCTTT | TTGTAGTCAG | TTTGTCTCTA | AGACCTTTTT |
| 20151 | TCTCTTTCTC | ATTTTTTAGA | ATAATTAAGA | ATTTCATTAG | AGTAGTTTAG |
| 20201 | AATTTAGATT | ATTTACAGTG | TATTATTATT | ATTATTTTTT | GACAAGAGAA |
| 20251 | CGTAACATAC | ACCTGGGAAC | ATGTCTTCAG | TTATGAGTCA | GACATGGATA |
| 20301 | TGTGCTATAA | TATATACCCT | TGCACTCCAT | GAACAGCAGG | AGCCTGAAAT |
| 20351 | AGGTCCTAAC | CTTTGGAAGG | AACTTAATTT | TTTAGTTATA | TTTTGAGGTT |
| 20401 | GGAATGTGGA | TAATGAGGGC | TTTTAGTTTT | AAACAGCCAG | AGAGCTGTTT |
| 20451 | TCTGAGTTAT | TTTAATTGTT | AAATTTTTTT | AGTTACTAAG | AATTTTTTCT |
| 20501 | TTTAGATATA | AATCTTATTT | CTTTTTCTCT | TTTTTAATT | TTTTCTTTTA |
| 20551 | AAAGAAATCT | CATGTCTTAA | GTGGATTCTG | ATTTCTGAAT | TCTACTTTGA |
| 20601 | CTCAGCTAAG | ACTTTCTCAT | TCTAAGATCA | GTTATGTTTC | TTCAGTTCAT |
| 20651 | AATTCAATAT | ATTATACATT | TATTTATCTG | AAACATAATT | AAGAACCGAG |
| 20701 | AAATGAGCCC | AAAGTTTTTG | AACAGATACA | AACAATGTCC | AAGTTCACGT |
| 20751 | ACTAAAGTTC | ATGTACTCAA | GCTCATGTTC | TTTATTCTGG | AGGAAAGTCC |
| 20801 | TTTTAATGAT | CTCATAGAAT | GTCTACTCCT | CCTTTGCCCA | TGAAACAAGG |
| 20851 | AGAAGGTTAA | GAATAAGAAG | GAATTAGAAA | TAATATATAA | AAACTATCAT |
| 20901 | AAAGTCCCAA | TAAACATTGC | AGCCTAGATA | AGTGGTAAA | ATTCTTAGAT |
| 20951 | GGAAAGACCA | CATGACTTAT | TAGGGGATAA | CCAGATTGTT | ATTAAGTATT |
| 21001 | TTTGCAGCAA | AATGTTAGGC | CAGAAGACAC | TAGAGAAGTA | CATTTAACAT |
| 21051 | ACTCAAGGAA | AGAAAATGTC | AGTCAAATAT | TTTACATCCA | GCCAAACTGA |
| 21101 | CCTTCATTAT | ACAAATCTCA | TACAAACTGT | TATATACATT | TAAGCACTGA |
| 21151 | GGGAATATTG | TTCTTTTGAA | CACTGAAGTT | AAAAGCTTCT | AGCAACCTAA |
| 21201 | ATCAAGGAAG | AGGCCTGTAT | AGACATACAG | ACTGCTTTCA | TTAAAATACA |
| 21251 | AAGTATACCT | GAAAAATCAA | ATCTGTAGCA | TTCCTCTGGG | ACACTTAGCT |
| 21301 | TATAGAATAC | TATTAAGCGT | CTTAACTAGA | CAGTTAAATG | GACTTGAAAG |
| 21351 | ATCGTGTATT | TGGTTTCCAT | AGAAATTTAA | GGGTAAATTT | TATAACAACA |
| 21401 | TATATTTTGT | AACAGTGGTT | TGGATTATTC | TGTCAAGGTA | TCCTAAGAGA |
| 21451 | GAAATAGCTG | TGTCTGGCAT | TATGTATGTA | AGAAATAAAG | GAAAAATATT |
| 21501 | AGTAATAGAC | CAGGTGTGGT | GGCTCACTCC | TATAATCCCA | GCACTTTGAG |
| 21551 | AGGCCAAGGT | GGGCAGATCA | TTTGAGGTCA | GGAGTTCGAG | ACCAGCCTGA |
| 21601 | CCAACATAGT | AAAACCCCGT | CTCTACTAAA | AATACAAAAA | AAATTAGCCA |
| 21651 | GGTGTGGTGG | CACATTCCTG | TACTCCCAGC | TACTCCGGAG | GCTGAGGCAG |
| 21701 | GAGAATGGCT | TGAACCTGGG | AGGCGGAGGT | TGCAGTGAGC | TGGGATCATG |
| 21751 | CCACTACACT | CCAGCCTGCA | CAACAGAGAG | ACTCCATCTC | AAAAAAAAAA |
| 21801 | AAAAAAAAAA | AATTGGTAAT | AGTGTACGTT | AACTCTTTTT | AGTTATGGAA |
| 21851 | TCTGAGATTT | ACAGGGTATC | AGTATACTTA | AAATACATTC | AGCGAAGTTG |
| 21901 | AACACTTAGT | TGTATTTGTG | TGTATGAGAA | AAAACAGCTT | GTTTCCCAAA |
| 21951 | TTACAGAGTC | AAGTAAATCT | CTAGACATGG | CCTCTTAAAA | ACAGCCACGC |
| 22001 | AGGGCGTGGT | GGCTCACACC | TGTAACCCTA | GCAGTTTGGG | AGGCCAAGGT |

```
22051 GGGCAGATCA TTTGAGGTCA GGAATTGTAG ACCAGCCTGA CTAACATGGT
22101 GAAAACCCCA TCTTTACTAA AAATACAAAA AAATTAGCCA GGTGTGGTGG
22151 CACATGCCTG TACTCCTAGC TACTCTGGAG GCTGAGGCAG GATAATGGCT
22201 TGAACCTAGG AGGTGGAGAT TGCAGTGATC TGGGATCATG CCACTGCACT
22251 CCAGCCTGGG CAACAGAGTG AGACTCTGTC TCAAAAAAAC AAAAATAGAC
22301 AAACAAACAA ACAAAAAAAA CCCGCTAGCC ATTTACGATC TGATATGTTA
22351 ACCATTGTGC AGTTGTAGGA TTCCTGCTGA TCCCCAAGTG CATTTAAAAT
22401 TGTGTTCTAA AGTACTCTTG GTATTGAGAC ATGGTTCTGG AGTGTTCTAG
22451 ACTAGAATGT AGATTAGGAT TTTAGTTATT GGCTTGTATA GTAATGTGAC
22501 TTTGCATTGT GAGCTCTTAT TCTCTAGGGT TTTTTCTGAA AAATCAGTAT
22551 CAGTATATTG AAGAAAATTT TTTACACAGC TACAAACTTA TAGCACTAAA
22601 ATGACAAAAA AAGATGATTA GTCATAAAAA CATAAGAGAT CCTTATTTGT
22651 ATTTAAATAA TTTTCTTTGT CTAGAATTTG ATTCCAGCTT TGTAAATGTA
22701 TGGAGCTTTT AGTGAACTTT AACTTCATAA ATGTTGTGG ATCCCGTGAT
22751 AGCTTGGCTC AGGATCTTGT AAATACTATC ACAGCTCAGT CTTTCTTACT
22801 AGTTTGCCTT GAGTACTACA CATTTTAATT TTACATTGTA ATAGAAATAT
22851 GATTTTTTTT TCCCCTATAC AGTTGTCTTC GTAGTGTTTT ATATGATACT
22901 ACTTGGGATA TATTTAGATT AGTAGTTTAC TTTCCCTCCT TCTGGTCATA
22951 AGAGATAAGG GGAAATCTTC TAATAAATAC TTTGTTAATT TTTTCCTTAC
23001 AAGTAACAAA GTCAAAACTT GCCAGGCACT GTGGCTCACG CCTGTAATCC
23051 CAGCACTTTG GGAGGCCAAG GCAGGTGGAT TGCTTGAGGC TAGGAGTTTG
23101 AGACCAGCCT GGCCAACATG GCCAAATCCC ATCTCTACTT AAAAATAAAT
23151 AAATAAAAAA CACAAAAATT AGCCGGGCAT GTTGGTGCAC ATCTGTAATT
23201 CCAGCTACTT GGGAGACTGA GACACAAGAG TTGCTTGAAC CCAGGAGGTG
23251 GAGGTTGCAG TGAGCTGAGA TTGTGCCGCT GCACTTCAGT CTGGGCAGCA
23301 GGGTGAGACT CCATCTCAAA AAAAAAAAAA AAAGGCGGGG GGGGAAACAA
23351 AGTCACAAGT TTTGCACAAA TCTCAAGGCT CTTCAAAGTC TGATTCAATG
23401 TACCATTCTT GTTTTCTTTC TCAGCCTCAA ACATAGTTAA TTTATTTCAC
23451 CTTAAACTGC TGTGCTTGTC GTCATGCTAT CCTTTTTTAC GTCAGGGCTT
23501 TCCTCTTTTT TGCTGTTAGA GTATACGGTT GAATTTTTTT TTTTTTTTTT
23551 TTTTTGAGAC AGAGTCTTGC ACTTGTTGCC CAGGCTGGAG TGCAGTGGTG
23601 TGATCTTGGC TCACTGCAAC CTCCACCTCC TGGGTTCAAG CGATTCTCCT
23651 GCCTCAGCCT CCTGAATAGC TGGGATTACA GGTGCCTGCC ACCACGCTTG
23701 GCTAATTTTT TTGTATTTTT AGTAGAGTTG GGGTTTCATC ATGCTGGCCA
23751 GGCTGGTCTT GAACTCCTGA CCTCAAGTGA TCCACCCGCC TTGGCCCCCG
23801 AAAGTGCTGG GATTACAGGC GTGAGCCCCC GCGCCTGGCC ATCTCAGTTG
23851 AATTTTAGCC TACATTTGGT TTTTGTGTGT GTGTTTTCTG TTTTTTTTTT
23901 TTTTTACTTT TATCTTAGGT TCAGGGGTAC ATGTATGTGC ACATGTGTTA
23951 TGTAGGTAAA CTGTGTGTCA CGGGGATTTG GTGTATAGAT TATTTCATCA
24001 CCCAGGTAAT AAGCATAGTG CCCTATAGAT GTTTTTTCTA ATTCTCTCTG
24051 TTCTTCCACC CTCCATCCTC AAGATGCCCC CAGTGTCTGT TGTTCCCCTC
24101 TTTGTGTCTT TGTGTTCTCA TTGTTTACTT CCCACTTATA CATGGGAACA
24151 TGAGGTATTT GGTTTCTGCT CCTGTGTTAG TTTGCCAAGG GTAATGAATG
24201 GCCTCCAGCT CCATCCATGT TCCTGCAGCG GACATGATCT TGTTCTTTTT
24251 TTATAGCTAC ATAGTATTCC ATGGTATATG TGTACCACGG TTTCTTTATC
24301 CAGTCTACTG TTGATGAGCA TTGCTTCCAT GCCTTTGTCA TTGGGAATAG
24351 TGTCGCAGTG AACATACACG TGCGTGCGTG TGTCTTTACA GTAGAACAGT
24401 TTATATTCCT TTCGGTGTAT ACACAATAAG GAATTGCTGG GTCGAATGAT
24451 AACTCTGTTT AAATTTCCTT GAGGAATTGC CATACTGATT TCCACAATGG
24501 CTGAACTAAT TTACACTCCC ACCTGCAGAG TATAAGCATT CCCTTTTCTC
24551 CACAACCTTG ACAACATCTG TTAATTTGT GACTTTTTAG TAGCCATTCT
24601 GACTGGTGTG AGATGGTGTT TCATCGTGGT TTCAATTTGC ATTTCTCTAA
24651 TGATTAGTGA TGTTGAGCAG GTTTTTATAT GCTTATTGGC CGCATGTACG
24701 TCTTCTTTTG AAAATGTCTA TTCATGTCCT TGCACACTC TTTAATGGGG
24751 TGGTTTTTTG CTTGTATATG TGTTTAAGTT CTGTGTAGAT TCTGGATATT
24801 ATACCTTTGT CAGATGCTTT GTTTGTAAAT ATTTCTGCCA TCCTGTAGGT
24851 TGTTTACTCT GTTGATAGTT TATTTTGCTG TTCAGGAAGT TCTTAGGTTC
24901 CCTTTGTCAG TTTTTGGTTT TGTTGCAATT GCTTTTGACA TTTTCATCAT
24951 GAAATCTTTG CCAGGTCCTA TGTCCAGAAT GGTATTTCCT AGATTATCTT
25001 CCAGGCTTTT ATTTTTTCTT GTTGTTGTTG AGACAAAGTC TTGCTGTGTC
25051 ACCCAGGCTG GAGTGCAGTG GCACCATCTC GGCTCACTGC AACCTTCATC
25101 TCCCGGGTTA AAGTGATTCT CCTGCCTCAG CCTCCCAGT AGCTGGGATT
25151 AAAGGCATGC GCCACCACAC CTGGCTAATT TTTGTATTTT TTTAGTAGAG
```

```
25201  ACAGGGTTTC ACCATGTTGG CCAGACTGGT CTCGAACTCC CAACCTCAAG
25251  TGATCTGCCT GCCTTGGTCC CCCAAAGTGT TAGGATTAGA GACGTGAGCC
25301  ACTGCACCCA GCCTTTCCAG GGTTTTTATA GTTTTAGGTT GTACATTTAA
25351  CTCTTAATCC ATCTTGATTT TTGTATATGG TGTAAGGAAG GGGTGCGGTT
25401  TCAGTCTTCT GCATATGGCT AGCAAGTAAT TCTAGCACCA CTTATGGACT
25451  AGGAAGTCCA TTCCCCATTG CTTGTTTCTG TCAGCTTTGT CAAAGATCAG
25501  CGGTTGTAGG TGTGTGGCAT TATTTTTGGG CTCTCTACTC TGTTCCATTG
25551  GTCTTTGTGT TTGTTTTTGC ATCAGTGCCA TGCTGTTTTG GTTACTGTCA
25601  CCTTTTAGTA TACTTTGACA TCAGGTAACG TGATTCTTCC TGCTTTGTTC
25651  TTTTTGCTTA GGATTGCCTT GGCTATTTGG GCTTTTTTGG TTCCTTATGG
25701  ACTTTAAGAT CTTTCTAATT CTGTGAAGAA TGCCATTTAT AGTTTGATAG
25751  GAATAGCATT GAATCTGTAA ATTGTTTCAG GCAGTATAGC TGTTTTAACA
25801  ATATTGATTT TTCCTGTCCA TGGGCATGGA CTGTTTTTCC ATTTGTATCA
25851  TCTCTGATTT CTTTGAGAGT GTTTTGTAAT TCTTATTGTA GGATCTTTCA
25901  CTTCCCTGGT TAGCTGTACT CCAAGATATT TTATTCTTTT TTTTTTTTTT
25951  TTTTTTTTTT GAGATGGACT CTTACTGTGT TGCCCAGGCT GGAGTGCAAT
26001  GGCGCAATCT CAGCTCACTG CAACCTCTGC CTCCTGGGTT CAAGTGATTC
26051  TCCTGCCTCA GCCTCCCCAG TAGCTAGGAT TAAAGGCATG CGCCACCACA
26101  CCCGGCTAAT CTTTGTATTT TTAGTGGAGA TGCGGTTTCA CCATGATGGC
26151  CAGGCTGGTC TCAAACTCCT GACCTCAAGG GATCCGCCTG CCTCAGCCTC
26201  CCAAAGTGCT CGGATTACAG ACATTAGCCA CCATCCCTGG TCTTTTAATT
26251  TTTTAAGTGA CATTTACCAG CTGTAAATTA TCATACCTGA ATTGCTATTT
26301  GGGCTACTGT AGTGAATCGG ATTATGCTTT GGGCCAGTTA GTTTTACAGT
26351  TTTAAATAGC CATAGACAAT ACTCTTAACT CTGACCTGCT CATTTGTTAA
26401  TCTGTCATTA GTCACAGTGG GTTAGAGTAC TGGCAGAACA GTAAACACTA
26451  ACGTGGCACA TAATATATAC CCAGGTATAG TTTTGAGTGA GGTAGCTGGG
26501  GCAAGTGCTG ACACAGGTTA AGTAACTGGC TTAATGTTAT AGTAGTAAAT
26551  GCCAATGCTG ATATTCAAAT CGACATCCCT GAATTCAAGC ATAAATATCT
26601  GTTAAGTAAT TGGTAGTAGG CAGGGGTTTA GAATTATGTG TTGGCCTTGA
26651  CATGAACATT TTAGGTATTC AGGGTTGCTC AATCAACGGA CTGACCTTTA
26701  ATCTGTGTGA TTTCACTGCA AAAATGGTTT CTGAATCCAT TTATATTTTT
26751  ATATTTTATA AAAGAAAAC ACTATTTTCC TTATTAGTAA TTTAAAGCAC
26801  AATTTACATT CACCACAGCA TAATTTTTGA TAGTATTATT ATTATTAGTG
26851  TTTCTTCTGT GGTGAATGTA ATTTAAATTG TGGTTTAAAT TACTAATGAG
26901  GAAAATAGTG TTTTCATTTA TATTTATCTT ACCCTTAAGT AATTTTTGTT
26951  GTTACTTGTT TTTTTGTTT TGTTTTGAGA GAGGGCCTTA CTTTGTCTCC
27001  CAGGTTGGAG TGCAGTGGTG TCATCACTAC TCATTGCAGC TTCGACCTCC
27051  TGGACCCAAG TGATCCTTCG GAGTAGCTGG GATCATACGC ATGCGCCACC
27101  ATGCCCAGCA AAATTTTTA AATTTTGGAA TGATGGGGGA CTCTCACTCT
27151  TTTGCCCAGG CTAGTCTCGA ACTCCTGGCT TCAAGTGATC CTCCTGCCTC
27201  ATGTGTGATT ATCAGCGGCG TGAGCCACCA TGCCCAGCCT GTTGTTACTT
27251  TTTTAGGTTG TAGATAAGTA GGAATCCTCC CGTGTCTTTT GGAATATTAG
27301  CCTTTGCTCT GGTTTTTCCT CTAGAGCAGT CTCCCATTCA TTACTGTTAT
27351  AGGAAATATT TGACTGTAAT AACAGAGATT GACTTGTATT CAAGAGTTCT
27401  TAAATAACAA TGGCTTCTCT GATTGACTGC TTTTGAATTT CTTCCAGTTT
27451  CAAGGGAGTT TAATGGTTGT GCCAGAGGCT TCATTATTGT TTATATTTTT
27501  GGTTGCTACT AAGTGCTTTT AAAAACGTCC TTAGTCTTGA TGCTTTTTTT
27551  ATATTTAGTA TTATTATTAT TAGTGTTTTT GCTGTGGTGA ATGTAATTTA
27601  AATTGTGCTT TAAATTACTG ATGAGGAAAG TAGTGTTTTC TTAGATTGAA
27651  ACATTTTTAT TGATATCACC TACAGGCATT TCTTCACAG CTCAGGGAAT
27701  GTGACTGTCA AATCTTAGGA AGAATGTGTT GTGAATTTTT TTTTTTTTTT
27751  TTTTTTGAGA CGGAGTCTCG CTCAGTCGCC CAGGCTGGAG TGCAGTGGTG
27801  CGATCTCAGC TCACTGCAAG CTCCACCTTC CGGGTTCACG CCGTTCTCCT
27851  GCCTCAGCCT CCCGAGTAGC TGGGACTACA GGCGCCCGCC ACTATGCCCA
27901  CCTGGCTAAT TTTTTTTTGT ATTTTTAGTA GAGATGAGGT TTCACCGTGT
27951  TAGCCAGGGT GGTCTCGATC TCCTGATCTT GTGATCCGCC CGTCTCGGCC
28001  TCCCAAAGTG CTAGGATTAC AGGCGTGAGC CACCCGTGCC TAGCCTGTTT
28051  TTTCTGTTTT TGTTTTTGTT TTTTAAGAG CAGTTTTAGG TTCACTGCAA
28101  AAATTGAAAG CACAGTGATA ACCTATGAAC TCCCTGCCCT GACGCATGCA
28151  TAGCCGCCCC CAGGATGAGC ATCCTCCTTC AGAGTAGTAC ATTTGTTAGA
28201  ATTGGTAAAC CTCCATTGAC ACATCATTTG TACTGTTTTT AAAAACTTAC
28251  ATTTTAACTC TTTTATGTTG AAAATCTTGG TTTTTAAATG ACATTTACCT
28301  ATTTGTTTTA TCTTGTAAAT GAGATATTTC AATAATATTC ATAAGAACAT
```

```
28351  CATTGACAAC AAATATGCTA AGGTTTTAAG ATTTTCTTGC AGTCCTTTGT
28401  GTCCTTACAT TGTATCACAC ATCTTAATAA TCTAAAGATA TCCTTTCATT
28451  GAAGTAAAAA GATTGGTTGC ATATGTTCTA AATAATTTTT TTTTCAGTGA
28501  AGAAAAGTGG TGGTTAGTGC ATACATAATA GCAAGTCATG CCGTCTATTC
28551  TCAGTGCTTT TAAAAAAAGC AAGTCATCAA AAGGTTTCAT TGATATCTCT
28601  GCATATCATG TTTTTATTTT CACTTTACCA GCTCTTTTTT ATGTGTTTTT
28651  TTTTCCTGAT TTAATCACTT TCCTGACAAT TACCAGGTAC TTTTTGGAAG
28701  TGGTTAATAT TAGCGGAATT GCAGCATGTA TAACCAAGAA GGTATTAACA
28751  TGTATACGGA ATATCTACAG TGATAAGAAA ATGACAGTCC ATTAGAAAAG
28801  TGATCAAAAT CATTGAACAG ATTCTTACTT CACTCAAGAA AATATATGAC
28851  TAGGCAGGGC ATGATGGCTT GCGCCTGTAA TCCCAGCACT TTGGGAGGCC
28901  GGGGCAGGCG GATCACCTGA GGTCAAGAGT TCAAGACAG CCTGGCCAAC
28951  ATGGTGAAAC CCTGTCTCTA CTAAAAATAC AAAAATTAGC CAGGCGTGGT
29001  ATATATATAT ATACACACAC ACACACACAC ACACATATAC ACACATACAT
29051  ACATACATAC ACACACACAC ACATACACAT ACATATATAT GTACACACAC
29101  ACATGCATAC ATCTATATAT ATGTATGTAA AACCATATGC CACTGTGCAT
29151  ATATATATAT ATATACACAC ACGTATATAC ACACACACAC ACACACATAT
29201  ATACATACAC ACACACACAC ACACACACAT ATATGCAAAA CCACATACAT
29251  CTCTGTGGCT TGTCTGTGAA TAAAGATAAA TTTTATTTCT TTTTTTTCCA
29301  GCAGTGATGC CTTTTTATTT ATTTTGCATG ACTGTACTAG TTAGAGCTTC
29351  CAAAACAGCA GACTAGAAAT GGGGAGAGCA GACATCCTTA TCTTGTTTCT
29401  GATATTAGGG GGAAAGCATT TGGTCTTTAA TAGTTAAATC TGATGTTATC
29451  TGTGGGCTTT TCATTGATGT TCCTCTATTC CTGCTTCATT GAGAATTGTG
29501  ATCAAGAATG AATGTTTCAT ATTGTCAGAT GATTTTCTGT GTCTGATGTG
29551  CTCATCATAT AGATTTTCTT TTTTAGCATA TTAATTATGA TGAATTACAT
29601  CAGTTGGATT TTGAATACTG ACCCAAGTTT GTGTTCCTGG AATAAACCCC
29651  ATTTGATCAT GATGTTTTAT CCTTTTGATA TATTATTTGA TTTGATTTGT
29701  TGAACGTTTG TCTGGAACGT TTGTATCCAC ATTATGAGGA AAATTGGTCT
29751  GCAGTTTTCT TATAATGTCT TTGCCTGGCT TTGGAATAAA AAATGCTGGC
29801  TTCATAGGAT CAAAACTGGA AGTATTTCCT CTTTTTTTAC TTTTTAGGAG
29851  GAATTTGTAG TATTTTTTTC ATAATATCAA GATAAAAATAT ACCAATGCAT
29901  TTTTTATGGG AAGATTTTGA ACAATAAATT CATTTTTTAA AATAGATACA
29951  TGGTTTTTCA GATTTTTTTT TCTGTTTGGA CCTTGAGTGG TTTGTGACTT
30001  TTCAGGTATT TGTCCATTTT ATCTAAGTTT TCACATGTAT AGGTATAACA
30051  TGATAATATT CCCTTCTATC TTTTTAATAC CTCAAAAATA CATAGTGACA
30101  TTACCTCACT CATTGCTCAT GATGGTAATT TGTGTTTTCT CTCACTGCCC
30151  AATCTGCCTG GCCCGAAATT TGTTAATTGC TTTTATTTTC TTAAAGAACC
30201  AGCTTTTGTT TTCACTGATT TTCTCGACTG TTCTTATGCT TTTTTGTTTT
30251  ACTTATTTAT AGTTCATATT ATTATTATAT TTTCATTCTT CCGTTTGCTT
30301  TGGGTTAAGT TTGCTATTTT TTTAGTTTTC TAAGGTGGAA ACTAAGATTA
30351  CTTTTTTGAG ATCTTTTCTG GTATAGGCAT TTAGTGCTAT AAATTTCCCT
30401  CTGAGTTTGC TTTAACAGCA TTTCATAGAT TCTGATATAT TAAGTTTTCA
30451  TTTTCACTTA ATGTAAGAAA TACTTGCTAT TTTCTTTTTG ATTTCTTCTT
30501  TATCCCATGG GTTATTTTTG AATTGTGTTA CTTAGTTTCC AAATTTCTGA
30551  GTATTTTCTC TTCTTGGTTT GTAATTTAAT TCTGTTATGG TCTGAGGACA
30601  TACTTTGTGT GATTTGAATC CTCTTCTTTC TTTCTTTTTT TTTTTTTGAA
30651  ACGGAGTTTA ACTCTGTGGC CCAGGCTGCA GTGCAGTGGT GTGATCTCGA
30701  CTCCGCAACC TCTGCCTCCT GGGTTCAAGA GATTCTGCCT CATCATCCCA
30751  AATAGCTGGG ACTACAGGCG TGCACCACCA CGCCCAGCTA ATTTTTGTAT
30801  TTTTAGTAAG AGAGGCGTTT TTGTCACATT AGCCAGGCTG GCCTTGAATT
30851  CCTGACTTCA GGTGATCCAC CTGCCTCGGC CTCCCAAATT GTTGTGATTA
30901  CAGGCATGAG CCACCATGCC CAGCCGAATC CTCTTATTTC TATTGAGACT
30951  TGTTTTATGG TCTAGTACAT TATATATCTT GGTAAATGTT TTGTGTGCCC
31001  TTGAAAAGAG TATTTGTTGT TGAGTGTAGT GATCTATAAA TGGTAATTAG
31051  GTCAAGCTGG TTGATAGTGT GTTCAAATCT TCCATATCCT TACTGATTTT
31101  ATGTCTGCTT GCTTTTATCA GTTTTGGGGG AAGGAAATAT TAAAATCTTC
31151  AGTGACACAG AATGTGTCTT TATGTTATGT TACTGTGAAC AAATTTCTTT
31201  TTTCCACCCC TTCCTTTTTT TAATCATTGT GTGTGTTGGG GGTGATTCTC
31251  AGCTTTCCCT AGTCCTTTGA AAGTTTTCAG TGGTTATGTA GAGAAACCCC
31301  ACAATCAGAG GGCTGAGAAA GCATTCTCAG CGGAACTCAG GTAATACTTA
31351  ATATTATCTT TATTAAGAAA ATAAAGAGAC TTTGTTGAAA ATACTTCCAG
31401  AACATTGTCA TGGAGTTCTG AACTTCTGGT TAACTCCATA AATAGAATCT
31451  ATTTTTGCTA GGCAAGGAAA AGGGAACCTT TATCTTTGGC CAGTAAGTCT
```

FIGURE 3, page 10 of 30

```
31501  CCCAAATAGG TAAAAAGGAG AGTTTTAAAA TTTTCTTCTT TGGAGTCTTC
31551  TTATTAGCAT AGGTAGAGTT TTAGTTACAG AAATCTTGGC TGTGCTAGAG
31601  GCATGGAAGT AGAAGAAACC AGAGCAATGA ATTTAATGGT TACTTAACAG
31651  TTTGTTCTTG TTCTCTTTGT GTTTGTAATC CGATAAGAGT TTTTTTTTTT
31701  TTTTATTAGA GACAGGGTCT CACTGTACTG CCCAGGCTGG TGTCGAACTC
31751  TTGGGCTCAA ACAATCCACC TGCCTCAGCC TTCCAAAGTG CTAGGATTAC
31801  AGGTGTGAGC CACTGCACCC GGCTAAGATT TGTTTTTTTA AGCAGCCAAA
31851  AAAAAAAAAA AAAACACCAA CACACAACTA TTTGATAAAT GCATGGTTTT
31901  TATATTAAAT AGTACAAATA GTGAAGTGTA CAGGTGTTAT CAACCAAACT
31951  CTTAAGTCAT GGTGATCTTC AAGTGCCTGA GGCTTTCTGG CACCCTGCCT
32001  AATGCTATTA GCAGGGTCCA TAGCAGTGTT ATTGTCCCAT ACTCCTTTTC
32051  TGTTCTCTGG TGAAGCAGCA AACTGAATAA AGTTTGAGTC TTTGTCTAGT
32101  GACTGTACTT GTTTCTTGT GTGCTGGGCA ATGTGGTAGA CCATGGGGTT
32151  CCATTGCTAA TAGCCATTAT GGTGCACATA GTTAACTAAG CCCAGGGAAT
32201  TGGGGTCATT TCTGGTGGAG TTACTGGAGT GTTCATTTTT TCAGATTCCC
32251  TGGGTATTAG GTTAGTGTGG TCTGGTGCAC GGGGACAGAG ACCACTCTTC
32301  TGGCAGCATG GGTGTTAGAG GAGATGCCCT GTGAGCAAGG CTGCCATTCT
32351  GTGAGAAGGG AATGAAAAAT GAATGGTCAG AAGATACTTG ATTGTGTAGG
32401  AAACCAGGAG TTACAATATG AGAATATACA TAGACTTGAA ATTGTGTATA
32451  TCACGTTTTC AAAATAGAAG TAAGTTAAGT GCGTTATACT TTCAGTTGTT
32501  TTAAAAATAC TATTACTAGC CAGGCATGGT GGCATGTACT TCTTGGAGGC
32551  TGAGTTGAGA AGATTGCTTG AACCCAGGAG TTCAAGGATG TAGTAAGCCC
32601  TGTTCGTGCT GCTCTACTGC ACTCCAGCCT GGGTGACAGA GCTAGCCCGC
32651  ATCTCTTTAA AAAAAAATG CCCCTCTTGT GTAATTTGCC TTTTTATAGA
32701  GATAATATTT TTAGCTAGAC TGAGGGCTTC AGGGATACTT TACTCCAGTA
32751  GTAATTTGT TGTTGTTAGC TTTCAAAGCC CTTGAGAAAA GGAGCTGCTA
32801  TGCTTACACT GTGATTACAT TGGAAATAGT GCTCTTCTGT TTTTGCTCAC
32851  ATGTATACAC TTCGGCTAAT TGAGAATTTG AATCTGAAAC ATATACTAGT
32901  GATACAGGTT TCTTTTTATG CATAAATTAT TTTTAAATTT AGTGACAAAT
32951  ATTAGCAATA ATGTACGTTT AAGTAGTATA TAGATTTTAA TTAAGACATC
33001  CCATGTTTTC TGTGTACTAA GACCAGGAAG CAGTCCTCTA GTTATTAAAA
33051  TTGGAGTGTA TTTCTTACTA GTTGATAAAA CATGGGTTTT GGAGTCATAC
33101  CTAGTTTCCA GCCGTGAACC TAGTACTTCA TAATCTATGA TACTTGGTGT
33151  TCTCTGTAGC ATTGTAGAAA TAATACCATC TACTTTGTAT GGTGGTTTCA
33201  AGAATTATGG TAGATCAGTC TTTCCTAAAT ACTTGTGTTA TAAAATGTAA
33251  CTAGGTCTCT GAAGAAATAA TTCCATGAAC ACGTATGTCA GGAATATGCA
33301  GCATTTTCTG TTCTCTTAAA GGTTCTCACT CTGTATTAAA ACATTAGGCC
33351  TATGGTCAAG AAATCTGCTT TTCTTTGTTC AACACTGCGT TTCTCAAACA
33401  GAACTTCTCC CTTCTTCCTT CCTACTCCCC TGCTCCTCTA TTGAACACCT
33451  GCAGTATATT ATAGTTTATT TTTGTTTCAT GGAACATAGT TTTGAAAATA
33501  AAGTGCCTCG CACAGTGTTC CTAATTATAC TGGATAAACT GTTTCATTTC
33551  CTGCTTTGAA TGTTAATTTT AATGGTTTGA AAACTGTATT GTAGGCTGGG
33601  CGCAGTGGCT CATGCCTGTA ATCCCAGCAT TTGGGAGGC CAAGGTGGGT
33651  GGATCACCTG AGGTCAAGAG TTAGAGACCA GCCTGACCAA CATGGCAAAA
33701  CCCTGTCTCT ACTAAAAACG CAAAAATTAG CCAGGTGTGG TGGTGCAAGC
33751  CTGTAATCCC AGCTACATGG GAGGCTGAGG CAGGAGAATG GCTTGAACCC
33801  AGGAGGTGGA GGTTGCAGTG AGCCGAGATG CCAGTGCAC TCTAGCCTGG
33851  GTAACAGCGA AACTCGGTCT CAAAAAATAT AAATAAATAA ATAAATAAAT
33901  AACTGTATTA TAAACTCAGA GCTCATTTCT TTTAATTAAT TTTAGTTTAA
33951  TCTTCTAAGT AGTAAGCCAT TTAATAATTT GCTACATTTT ATTCCTAATT
34001  CACTATCATT TAGTTCATAT ATTTAGCCCA AAATGTTGTC ATACACCTTG
34051  AGATTCAAAT CCAGGACAAG CAAGTGCAGA GGCAGTAGAA GGGTAAGAAT
34101  CTCACGAACT CAGTATCTGG TCAGATTCCT GCTTCACTAA TCCAACACAA
34151  TTTAAATGTT CAGAAATATA TTCTTGAAGT ATTATTGAGA GCCCTCTGGG
34201  AATATATTGA AGGATCTGGT TAGATACTTC CTATAACTGC TCTAGAGCTC
34251  TTAAGACTAG GCACAAGCCA TCCACATCTT TATTGAGTAA TTTGTAAGAA
34301  TTCTGCAGAT TAAAAAGAA ATAACATCTT TACAATAAAA AAGCAAATGT
34351  TAAAAGAATG AAAAATCTGT TTCCAAAGTA AAAAAGTAGT AAAATATTGT
34401  TTTAGAAAAA TTGAAGAAAT TGAAAAAGCA TAGATAAAAA GAATAAAATG
34451  TAGATAAAGA GACTTAAGAG TAATTTTATA CCCAGGAATG TCCATTCCTA
34501  ACATCTTATC CTCCGTATTT CACAAAAAGT GTACCATATT ATCCATGCTA
34551  GTTTGTAGCT TGCTTATTCT GCTTAAAAAT GCGAAGTGAA GAACTTCTCA
34601  TGCCAGATAT CAGTGAGGCA CCCTACTTGC CCTCAAGAAT CTACCTTAAT
```

```
34651  AGGGTGCCCT CTATAGCTGA TTTCTTCCTC TCCCTTCCCG TCCCCTCCCC
34701  TCCCCTCCCC TTTCTTTCTT TTCTTTTTTC TTTTCCTTGC CTGCCTTTCC
34751  TTCCTTCCTT CCTTCCTTCC TCTCTTTCTT TCTTTCTTTC TCTTTCTTTC
34801  TTTCTTTCTC TTTCTTTCTT TCTTTCTTTC TTTCTTTCTT TCTTTCTTTC
34851  TTTCTTTCCT TTTTCTTTTT CTTTCTCCTT TCTTTCTTTC TTTCTTTCTT
34901  TCTTTCTTTC TTTCTTTCTT TCTTTCTTTC TTTCTTTCTT CCTTTCTTTC
34951  TCTTTCTCTC CCTCTTTCTC TTTCTCTCCC TCTCTCTCTC CCTCCCTCCC
35001  TCCCTCCCTC CCGTCCTTCC TTCCTTCCTT CCTTCCTTCC TTCCTTCCTC
35051  CCTTTCTTCC CTTTCTTTCC TTTTCTTTCT TTCTTGTCTT TCTTGTCTTT
35101  CTTGGTGGAG TCTCACTCTG TAACCCAGGC TGGAGTGCAG TGGCTTGATC
35151  TTGGCTCACT GTAACCTCTG CTTCCTGGGT TCAAGCAATT CTTCTTCATC
35201  AGCCTCCCGA GTAGCTGGGA TTACAGGAGT TCGCCAGCAC ACCTGACTAA
35251  TTTTTTGTAT TTTTAGTAGA GATGGGGTTT CACCGTGTTG GCCAGGCTGG
35301  TCTTGAACTC CAGACCTCAG GTGATCTGTC CGCCTTGGCC TCCCAAAGTG
35351  CTGGGATTAC AGGTGTGAGC CACCGTGCCC GGCCTCATTT CTTCATTTGT
35401  GAGGAATGTT TCCGGGCAGG AGTTAGGAGT TGGCAGAAGA GTGATGAGAG
35451  GAACAAGCCC TGTTAGAGGG TAAATTAAGA CATCATTGTA CAGTTTCTAG
35501  TTATTAATAA ACCATTAATG TATGCAGAAT TATACAGAGT AAACATTGTT
35551  TATTTGGTC AGTTTTCTTG CACATATCCA AAAAGATTTG AATTTAACTT
35601  GTTTAGGAGA AAAAAAGTCT TTAAATACCA AGAGCTGGTA TGTGCATAAC
35651  GTACACACCT AGATTGAAAT ACAGAACCTT GGCCAGGTGT GGTGGCTCAT
35701  GCCTATAATC CCAGCACTTT GGGAGGGGAG ATGTGCGGAT TGTTTGAGCC
35751  TAGGAGTTCA AGACCAACCT GGGTAATGTG GTGAAACCCT GTCCCTACAA
35801  AAAATACAAA AATTAGCTGG GCATGGGTGG TGTGTGCCTG TAGTTCCAGC
35851  TACCTGGGAG GCTGAGGTGG GAGGACCTCT TCAGCCTGGG AATCAGAGGT
35901  TGCATTGAGC TGAGATCATG CCATTGCACT CCAGTCCTAGA CAACAGAGTG
35951  AGACCCTGTC TTAAAAATAA ATAAGTAAAT AGAGAACCTC AAGTTATCAT
36001  TACGGTGTGC TAGATGGTTC ATTGCCTCTT TAAATTAAAT TAAAACAAGA
36051  AGTCTAATAG GAATTCATAG AACACTTTTT GGTCAGGCTG TCTGGATTGC
36101  AGTCGCACAC TTTTCACTCA GGCTCATTGC AGCCTCCACC TCCCAGTTTC
36151  AAGTGATTCT CTCCCCTCAG CCTCCTAAGT AGCTGGGATT ACAGGTGCTC
36201  GCCACCATGC CCTGCTGATT TTTGTATTTT TCGTAGAGAC TGGATTTCAC
36251  CATGTTGGCC AGGCTGGTCT CGTACTCCTG ATCTGAAATG ATCCACCTGC
36301  CTTGGCCTCC CAAAGTGCTG AGATTACAGG TGTAAGCCAC CACATCCAGC
36351  CAACACTTTT TCTTGTTGAA AGATATTCCT GAAAAAAATG TTGTATTATT
36401  AAACATGTTT TAGTCTGCAT GTATTATGTA GAGCTTTCTT TAATGACATC
36451  AAGAATGACA AAAGAGATGA AATGTTTATT ACTACTTTTC GAATATTTTG
36501  AATTTTTTTC TTTCTTTCTT GTTTTTTAAG GTGGATATCA TCCAGTGAAA
36551  ATTGGAGACC TCTTCAATGG CCGGTATCAT GTTATTAGAA AGCTTGGATG
36601  GGGGCACTTC TCTACTGTCT GGCTGTGCTG GGATATGCAG TAAGTGTTCT
36651  TTGTCATTTG TGCATTTGTT TCCTGGAGTA GTTCAACATC TGTGTTCTAA
36701  GAAGGTATGG CTGAGGGTCA CCACTGCTTT GTTGAGGTAT GTGAAGTGCT
36751  TAGCACAGGC CTGCCTCAGC TGGCTAGATT CCTTCCTGCC CCCTGCCTTA
36801  GTTTGAAGTT CATTTGAAAT CTTAAAATAT TACTTGCTTC CAGCTTTATT
36851  TCAAAGTTAA TTCATTGAAA TTGTTTTACA CTGGGATTAT ATTATTTTTC
36901  TAGTAATTCA TCCATATCAG ACAAACATAA TGTATAGTAT AGGCGTTTCA
36951  AATCAGTCAT TTTTAACTTT TCAAAGCCAT GACCCATAGT AAGAAACTTC
37001  ATTGCTACTC CATACACACA CACACACACA CACACACACA CACACACACA
37051  CACACACACA TTTGGTGCGT GTGTGTGTGT GTGTACTG AAACAAAGTG
37101  TTAAAGAGA ATGGTTTCA CTATTAGGTT GGTGTGTAAT ATTCGTGATA
37151  ACTCTGATGT TTATCTAGTC TTATTTAAT TAGGGAAAAA ACAAAACAAA
37201  ACATAAAAGA GATTGTCTTG ACCCATACTA CTATTTAATG TGGCCCCACC
37251  ATTTGAAAAG TACTATTTA AAGGAAAGCT TATGTTTCTG TGTATTGGAT
37301  AGATCTCATT ACAAGTTGAA TATCCCTTAT CTGAAATGCT TTGAGACCAG
37351  AAGTGTTTTG GATTTTGGAA TATTTGTGTA TATACACAAT GACCTATCTT
37401  GGAGATGTGA CCCAGATCTA AACACAAAAT TCATTATATT TCATATACAC
37451  CATATACACA TACCCTGAAG GCAATTTTAT ACGATATTTT AAATAATCTT
37501  GTGCAACATG CAAATCTTTT ACTGAGTTTT GATTGCAGTC AGAGGTGGAA
37551  TTTTACACTG TGGCATCGTG TTGACACACT CATAATGTTT TAGGTTTTGG
37601  CGCATTTTGG ATTTTACATT TTCCAATTAG GGATGCTCAA CCTGGATACC
37651  AGTGATTCTT TCTACTGATA ATATAGATAA ATAGACTCTT TTTTTGTTTT
37701  TTCTTTTAGG GGGAAAAGAT TGTTGCAAT GAAAGTTGTA AAAGTGCCC
37751  AGCATTATAC GGAGACAGCC TTGGATGAAA TAAAATTGCT CAAATGTGTA
```

FIGURE 3, page 12 of 30

```
37801  AGTACTTTAA AAATGTGAAT GATATAAGAA AACTTAATGA CTTAAAATTT
37851  TACAGAAAGA TTTTTCTGGG TAATACTAAA TTAAAGTCAA GTTTGGCTGG
37901  GCACGGTGGC TCATGCCTAT AATCTCAGCA CTTTGGGAGG CCAAAGCGAG
37951  CAGATCACTT GAGGTCAAGA GTTCGAGACC AGCCTGGCAA ACACGGTGAA
38001  ACCCCATCTC TGCTAAAAAT ATAAAAAATA GCCAGGCATG GTGGTGGGCA
38051  CCTGTAATCT CAGCTCCTTG GGAGGCTGAG GCATGAGTAT CACTTGAACC
38101  TGGGAGGCAG AGGTTGCAGT GAGCCGAGAT CGTACCACTG CACTCCAGAC
38151  TGGGCGATAG AGCAAGACTC TGTCTCAAAA AATAAATAAA TAAATAAATA
38201  AATAAAGTTT ATTTTTTATA ACTTTGTGAT GAATTTTTTA TTTTAAAATA
38251  TACTTTATTT AAACAGTATT GGTGTTATAA TGGGAAAACA TGCTTTGTCT
38301  CAAACTCCTG TGTTCTTGCA TTCATTTTTC TTGGCATAGG TTCGAGAAAG
38351  TGATCCCAGT GACCCAAACA AAGACATGGT GGTCCAGCTC ATTGACGACT
38401  TCAAGATTTC AGGCATGAAT GGGATACGTA TCCTTTACTT CCTGATTTAT
38451  TTGTATTTTT ACCTTTTAAA AATGAAAAT ATTTCAAGCT CCTATAATCT
38501  CTGTTACTG CTGTATCACC TTCAACATAA ACACTCTAGG AACATTGTCA
38551  AGTATTATGA AGTGGTCCAC CTAGAATAGT TTTCATGGCT TTTTGGGGTG
38601  TTTGGTAGAG TAGCATCTTA GAAACTTATT TTTAACACAA CAACTTGACT
38651  TAATTTTGGT GTGGAATTAA TTATTGATCT CTTCCCATTA ATAGTGGTAA
38701  AGTTTTTTTT GTGGTGGTAG ATAAAAGCAT ACATCAGCAC CACTTCTTTG
38751  TGTTTAAAC TTTCTAAAAC CAGTGCATAA GGACAATCTG TGTGTGCCCC
38801  AGTGGCTGCA AAGCACCATG TGAAAATGGA GCATTGGTTA AGATAAAAGG
38851  AAAAATGCTC TGTAAATGTC CACATCCCAA GGTGGCGCTT GACTGCTCTT
38901  AGTTCTGAAT AGTACTAATA ATTGCCAAAT TCTTTTTCCA AAATGATACA
38951  ACTGAGCCTT TCAAATAATT GTCCTGCAGA GGCTCATCTT TCTGTCAGGT
39001  GAGTATGGAA ACATTTTGGT TTTCTTGATT TTATTCCTGG TTATCTATAT
39051  TGCAAAAGTT AAGGAAAAGT AAAATGATGC ATTTTCTATA CTCTGCATTT
39101  TCTATACTCC TTGATAAATC TGACATAAGC CAGTGCTTGA TCGAAAATAC
39151  CTTTATTGTT TTTCTTTACA AACTTATTGG GAGAAATTTC AAACATATAA
39201  GAAAGAGATC ATACTACAGT AAATTGTTGT AAATTCGTCA CTCAAGTTTA
39251  ATAATTGTCA TGGTCTGGCC ATAATTGATC CATCTATCTT TTCTTGCTGA
39301  ATTATTATAG AGCAAATCCT AGAAGTCATG TCCTTTTACT TCTGTGTCAT
39351  TGTGAATCTT TGAAAAAAAT ATGAACTTTT AAACATAACC TTAAAACTCA
39401  CCAAAGACAT TAACGGGTTC TTGATATCTC GTCAGATATC GTTGGTATTG
39451  GAGACTTCTT AATACAGATT TCCTTGGTAT TGCAAAAATG AACTTTTAAA
39501  GACATATTTG AATCATTTTT AACAATATTG TTTACTCCTA AGTCTGTATT
39551  CACTTACTTT AGTTGTTCAG TTTCAGATTA ATTTGCTCAA TTTACATTTT
39601  TCTGTTTCTT GTTAGACTAT GATCCACAGA GTATTTAAAT TATCCTGACA
39651  GAAAGTTAGT GATTCTTAAC AGAGGAAAGT GTTTCTTGGT CAGCTATAAG
39701  TGTAGGTGTT TCTCATGTTT TTTAAAAGGA TGGATGGCCT TAGTCGTAAT
39751  GTGTCCGTTT CCTTCTGGTG GGTTCTTGGT CTCACTGACT TCAAGAATGA
39801  AGCTGCGGAC CTTGCAGTGA GTGTTACAGC TCTTAAAGGT GGCGCATCCA
39851  GAGTTGTTTG TTCCTCCCGG TGGGTTCGTG GTCTCGCTGA CTTCAGGAAT
39901  GAAGCCACAG ACCCTCATGG TGAGTGTTAC AGCTCTTAAA GTTGGTGTGG
39951  ACCCAAAAAG TGAGCAGCAA CAAGATTTAT TTTGAAGAGT GAAAGAACAA
40001  AGCTTCCACA GCATGGAAGG GGACCCAAGC AGGTTGCTGC TGCTGGTTCG
40051  GGTGGCCAGC TTTTATTCCC TCATTTGTCC GTGCCCACGT TGGAGAAATG
40101  GACCTGCCGA TTGGTCCATT TTACAGAGTG CTGATTGGTG CATTTACAAT
40151  CCTTTAGGTA GACACAGTGC TGATTAGTGT GTTTTACAG ATTGCTGATT
40201  GGTGCATTTA CAATCCTTTA GACACAGACC ACTGGTCAGT GCGTTTTTAC
40251  AGAGTGCTGA TTGGTGCATT TACAATCCTT TAGCTAGACA CAGAGCACTG
40301  ATTGGTGCAT TTACAATCTT TAGATAGACA CAGAGCACTG ATTGGTGCAT
40351  TTACAGTCCT CTAGCTAGAC AGAAAAGTTT TCAAAGTCCC CACTCGACCC
40401  AGGAAGTCCA GCTGGCTTCA CCTCTCACTA ATACTAGTTA TCTTTGGAAG
40451  TGTGTCTAGG AAGAAGACAA GCAAAGGTGT CCCTTGACTT TCCTTTCTTT
40501  TTTGAGAATA TCAGTTTTGA CCATGCTACT AAGTTATGTG GATGCTTGTT
40551  GGTTTTGATG GGGACTCAGG AGGAAGTGAA TTAGGATTGT AGAAAGGGTT
40601  GGCATGTTAT CCTTATCCTT CCTCTACCTG AGGAGTTGGC AAAGGGTAGC
40651  TCCAGGGAGA AGTGACAGAG AGCAAAGTAT CCCAAAACCT GTAGCTCAGA
40701  GAAGAAAGCA AAAATGAAGA AAGAGATGA TGCCTTCAGT GTCATGAGTA
40751  CTTTTTCTTT ATGTGGGTGT TGGATCCTCT GAGATAGCCC TTTGTGTGCC
40801  TGGAGTAGGC AGTACTTTCA TTTTCCAAGG TTCAAGAAAA TCGGACCACT
40851  TTACTCAGAG GCACATGACT GATGGGTGCT AGGTTGTGTC AGTAGCTGTG
40901  GTCTTCTGGC TTCTTCAGA TTTTTTGCTC TTTATATCAT GTTTGGAACA
```

FIGURE 3, page 13 of 30

```
40951  GATCCACCAT TTTGATATTT TACTTTCACA AATGTCAGAA GCCTAAGGAT
41001  AAGGCTTTTT CCCAGATTTA AACTCCAAAA TGACATCCAG TTTATGCATC
41051  TACTAAGTCA TGATCAACTA GGGAAGCATT TCCTTCACTC TATATATTTG
41101  AGAAGGTTTT TATACAAGGG AATGTCACCA TGTTCATAGA AAAACTAGAT
41151  TAAAAGACAA AAATAAAGAA TATAAACTTT ATTTCTCACA TAAGTTTCAT
41201  CAAGTTCAAG ACACTTTTGT AAACAATCAT ATCAGCCATT TAGTTGCTCC
41251  CCAAAGAACC AGGGGTCTTA GGAATTTAAC CATGTCAGTG AAATCTTTTT
41301  TACATTATTA ACTGAAGAAA AATGGGTGCC CTTTTTAAGA TTAAGAAACA
41351  AAAATTAGGA GTAGCCAAAT AAGGATAATA AGGTGGATGT CTAATGAGTT
41401  TCCACTGAAA CTCTTCACAA AATTGCCCTC GTTTGATGAG AGGAATGAAC
41451  AGGAACATTT ACATGGTGGA GAAGGACTCC TTGGTGAAGT TTTCTGAGGT
41501  ATTTTCCTGC TAAAGCATTC ACTGACTTTC TCAAAATTAG CTCTCATAAT
41551  AAGCAGGTGT TATCATTCTT TGGTTCTCCA TAAAGTCAAC AAGCAAAATG
41601  CCTCAGCATC CCAAAAAACG GTTGCAGTGA CCTTTCCTCT TCACTAGTTC
41651  ACTAGTGCTT TGACTGGACC ACTGCCACCT CTTGGTAGTT ATTGCTTTGA
41701  TTGTGCTTTG TCTTCAGGAT CATACTGTAG AACCATGTTT TATGTCCTGT
41751  TACAGTCCTT TGAAGAAATG CCTCAGGATC TCGATCGTAC CTGTTTAAAA
41801  TTTCCGTTGA AAGCTCTGCT CTTGTCTTGA TCTGGGAACA ATGGTTTTGG
41851  CACCCATTGA GTGGAAAGTT TGCTCAACTT CAGTTTTCAA TTGGAATTGC
41901  ATAAGTTGAA CCAGTCGTGA AGTCTGTGGT GTTGGCTGTT GTTTGTGCTG
41951  TCATCTGTCC TCTTCAATTA GGGTGCAAAC TTTTTTTTTC TTTGAGATGG
42001  AATTTTGCTC TTGTTGCGCA GGCTGGAGTG CAATGGTGCA GTCACGGCTC
42051  AGCACAACCT CCGCCTCCCG GGTTCAAGAG ATTCTCCTGC CTCAGCCTCC
42101  TGAGTAGCTG GGATTACAGG CATGTGCCAC CACGCCCAGC TAATTTTGTA
42151  TTTATTTTTT ATTTTTTATT TTTTTAGAGA CGGGATTTCT CCATGTGGGT
42201  CAGGCTGGTC TCGAATTCCC GACCTCAGGT GATCTGCCCG CCTCAGCTTC
42251  CCAAAGTGCT GGGATTACAG GTGTGAGCCA CCATGCCCGG CCGCAAACTT
42301  TTTTTCCACA CAAATTGATG CAAATGGTCT GCCGCTGCAG GCTTCATCTT
42351  CAACATTATC TCATCCCTTC TTAAAACCGG TTATTCATTT GTAAACTGCC
42401  GATTTATTTG CGGTATTGTC CCCTTAAACT TACCATAAAG CATCAGTGAT
42451  TTCACCATTT TTTCACCCAA GCTTCATCAT AAATTTGATG TTTGTTATTG
42501  CTTTGATTTT AGAATTCATG TTGCTCTGTT AGAGGCTTTT TTCAAACTGA
42551  TGTCTTATCT TGCGAGTGCC TCAAACTAGA TCCTGTTCAG ATACTTTAAC
42601  AAACTAGTAT GAGTTTATTT TGGTGCAAAA AAATTTTTGA AATCTATGCA
42651  TAGTGTTTTC AAAATACACA TTTTCCATAG ACTTTTGAA AATCCCTCAT
42701  ATTTCTTTTA GAAATTCATC TTGAGTATAC TAGGAAGTAC CAGTGGCTGC
42751  TAATGTTACC TCGTCCTTTT TCTCCAGTTA ATTTCTGCTA ACTGCTGAGT
42801  ATATTTTTCC CTTTGGATAG ATAAATCAGT AAGCAGATAG CGGCAGAGCA
42851  CTCACTTCTT CTGTGTCCGA CTTGCAAGGT CCTTCTTGGG ACAGCTAATA
42901  GAACATTTCT TTGGAGAAAC TACTTAATCC GTGGGTAAAT AGAGGTTTTT
42951  GAAATATACG TTCTAGTGGG TATTTTTACT GTTAAGCAAA ATGCGAAGTA
43001  ATCATCATAT CCAGATATGC CAGTGCTTTG AGAAGACTTA GGTTATGTTT
43051  GGGATATCCT GGGCCTCGCC CTATGCCTGC TGCTAAATGT AGTCCTTAAA
43101  TAATCTGCCG TTTTGTAAT GAGCCTGGGA AATAGTAAGA AACTTCTGGC
43151  TTTAGATTAT CTGCGCATAA ATCTGTAGTG CTTACATTCT TAAACAGTAT
43201  AGAAAGATTT TTCTTTTTTT CACTAAAAAT ATTTAAAATA ATATTGTTTT
43251  AATATAGCAT ATTCAGTTAT TATAGTTGAT TAAATCAACT ACTTTTTTTG
43301  ATTCTAAAGT CAAATGTAAG CCTCCAGGGA TGAATAAAAT GTTCTCAAAG
43351  GGTTTCAGAG CCATTTGTAA TCTTCCTGTA TGAATGACAT GAATATATAA
43401  TGAAATTGGA GGTATCATAG TTGTGAAGGC TGAAATACCT ATTTTAAAAA
43451  AAAATTAAGT TGGGGCCAGG TGTGGTGGCT CATGCCTGTA ATCCCAGCAC
43501  TTTGGGAGAC CAAGGTGTGT GGATCACTTG AGATTAGGAG TTTGAGACCA
43551  GCCTGGCCAA CATGGTGAAA CCCTGTCTCT ACTAAAACTG GAAAAATCAA
43601  CTGGGCATAG TGGCACACGC CTGTAATCCC AGCTATTTGG GAGGCCGAGG
43651  TAGGAGAATC GCTTGAACCC AGGAGGTGGA GGTTGCAGTG AGCTGAGATC
43701  GTGCCACTGC ACTCCAGCCT GGGTGACAGA ACAAGACTGT GTCTCAAAAA
43751  AAAATTAAGC TGGGCATGGT GGTTTTCACC TGTAGTACTG ACTACTTGGG
43801  AATCTAAGGC AAGAGAGTAT CTTTAGCCCA GGAGTTCTAG TCCACCTGGC
43851  ACAGCGTAGT GAGACCCTGT CTTTTTAAG AAAAGAAAAT CCAGATTCCT
43901  GAGATGTTGT TACTATAGAT TAAGTCTTAA TACCATGTCT TAAATGGTGA
43951  TCATACATTC TTAACACCTG CCTATAGTAT TAAAATTGAT CTAGTTGTAT
44001  AATGTAAGAT ATTATTCAAG GAAAGATTA AATAGGTCTT AACTGTGTTT
44051  ACTAAATTTT TATTTTATAA TGTGTTTTAT GTAGCTTATC AAGTAGAAAT
```

FIGURE 3, page 14 of 30

```
44101  TTAGGCAGGC AGTTAGGACA CTTGAGATAC TGGAGCTCTG TATTTGTTTC
44151  ATGTCAGTTC CTAGGAGGTT TCAGTCTTGC CTGTTTCATC AGGCTGATTT
44201  CCAGGGAGTG TGCTGAGATG GGTGAGAGTG CAGCTCAGTG TAGGCTTGAG
44251  TAGTGGCTCA GCCACCTGGC ACTTCTAAG TGCACTCTAC ACCTAGAAAG
44301  TGCCATGTCC TCATGCCTAC AGTGGGGTTA ATTACATTAT TGCCTAAGGT
44351  TGTTTGGAGT ACACGTGAAA TAATATATGG CACAGAGTAA GTACACTTAG
44401  CCCTTTTTTA TCTGCTGGTT CCCCATTCAT AGATTAATA AACGTTGGAT
44451  GAAAAATATT TGGGAAACAC CAGTAAAAAG TAGTAGAAAT TAAGAAATAG
44501  AGTATAACAA CTATTTACAT AGCATATACA TTGTATTAGG TATTATAAGT
44551  AATCTAGACA TGATTTAAAT AAAGTATATG GGCTGGGCAC GGTGGCTCAT
44601  GCCTGTAATC CCAGCACTTT GGGAGCCCAA GGCGGGTGGA TCATGAGGTC
44651  AGGAGATCGA GACCATCCTG GCTAACATGG TGAAACCCTG TCTCTACTAA
44701  AATTACAAAA AATTAGCCGA GCGTGGTGGC GGGCACCTGT AGTTTCAGCT
44751  GCTCGGGAGG CTGAGGCAGG AGAATGGTGT GAACCCAGAA AGCAGAGCTT
44801  GCAGTGAGCC AAGATCACAC CACTGCACTC CTGGGCGACA GAGCAAGACT
44851  CCGTCTCAAA AAAAAATAAA AATAAAGTAT ATGGAAGGAT GTGAATAGGT
44901  TATGTATATA CTACACCAGT TTACTGAAGA GGCGAGCATA TGTACATTTT
44951  GGTATCTGAG AGCGGTCCTG GAACCAATCT CCTGAGATAC TGGGAAACAC
45001  CTGTATTTAG TAATGTCAGT TCTTGTTATT TAAGTGAGAT ACAACATTTT
45051  CTCACTTTTG GTATTACTGA TAGGGTTGAT GTTGTATTTT ATAAAGTAAT
45101  AAGTGCTTTG CAAGTGACAC AATGGTGCTG CTTTCAATAA CTGCCTCACT
45151  CCAGGCAGTG CATCCACAAA CGATCCTTAA CTGTGTCCCA GATGTCTGCA
45201  TGGTCTTCGA AGTACTTGGC CACCATCTCC TCAAGTGGAT CATCAAATCC
45251  AACTATCAAG GCCTCCCAGT ACGTTGTGTG AAGAGTATCA TTCGACAGGT
45301  GAGACTTTTG ACAGCAGCCC CTAGGCCCTA GTACCTAATT GGTTAGGCTT
45351  TCAACATGAA TGCTGTTTAC AAATATGTAT ATGTATTACA TATGTATCAG
45401  TGCATAATGT ATATATGTTA TGTATGTTAC ATATGTATCA GTGCATAACA
45451  TTTTGAACTC TTATTAAGTC AGTATTTAAT GATATTTGT GTTGTGAAGG
45501  GAACAACATG TAATTGTCAG GCATACGTTT TTGCCTGTC GTTTTTTTTT
45551  TTAAGGTATG TGACATGGTA CAATTACATT GTTTTGTTC AGTATCTACT
45601  ATAAAACATC CACTTAGTTC ATTAGGAAGT AATTTAGAAG AAATAACTTA
45651  CTGGGTTTAT TTACTAAGTA TCCTTGGATG GAGATTAAAT AATAGATAAT
45701  TGAAGAGTTG TGTACAAAGT TTCAGTTATA ACGTGGTTAA ATTCTGCAGA
45751  TCTAATAGAC AGCATGATGA CTATAGTTAA CATTATTGTG TACTTGGAAT
45801  TTGTTAACAG AGTAGACTTG AATGTTCTCA TCATGTACAC ACACACAGAG
45851  TCTATATGTC ATACTGGGTT AGGTTAATTA GCTGTTTTGT GCTAATCATT
45901  TCACAGTGTA CACATATTTC AAGACATGTA CACTACTAAT ATATTCAGTT
45951  TTTATTGTCA GTTGTACCTC AGTAAAGCTG GGGAAAAAAA TGGAAATGTT
46001  TAACTCATAT AGAAATTACT GTATTAGATG TGTGTTTTGT TCAGTTGCCC
46051  TGCCAGAAGA AAACCCTCAG CTAGGGTCAG GCTTAGAGAT GATGCTCTAG
46101  TAAACATCTG TAGAATGAAA GTATGCGTAG ATGGAAGAAC TCCTCCTAAT
46151  TAGCAGTGTT TGCCCATTCC AGTGTTCTGC ATGGAATCAG TATGTATTCT
46201  ACTCATTGCC TGTAAAAAGT TTGAAGTTTA AATTTGTGTA GTAAAAGCAT
46251  CTTTGATATT TCTGTTGAAT TTGTGTGCAG ATAACTTTGT TTAGCCTGCC
46301  TGTGTGTTCA TCTCTTCTTC CTTTTGTACG GGTTTTTTTT TTTTTTTTTT
46351  TTTTTTTGGA GACGGAGTCT CGCTCTGTCA CCCAGGCTGG AGTGAAGTGG
46401  TGCAATCTCA GCTCATTGCA GCCTCCTGAG CAGCTGGGAC TATAGGTGCT
46451  TGGTACCACA CCCAGCTAAT TTTTGTATTT TTAGTAGAGA CAGGGTTTCA
46501  CCGTGTTGCC CAGGGTGGTC TCAAACTCCT AAGCTCAGGC AGTCTGCCTG
46551  CCTCTGCCTT CCAAAGTGCT GGGATTACAG GTGTGAACCA CTGCACCCAG
46601  CCTTGTATGG AAAATTGGCA GCTTATTCTG TAACATGACA GATGTTACTT
46651  GAGAAGAGGG GCTGGAGAGG GAAAAGTTCA CTACATTGTC TTCTATATCA
46701  GTTGAATTGA GGTGTTTCTA TGTAGTATTA TGCTAGGTAT ACATGTGGGC
46751  CTAGATTTAT GGCTAACTTT TGTTCAGTAC TGTATCTGTT TGCCCTTAGC
46801  TTTCAAATAG TAGCATTTTT ATTCATTATT TCGACAGGCT GATATCTCAA
46851  ATGAACAACT TTAATGTAGA AGAGGTTATG TGGTGAGGGC AGAAATTAGT
46901  ATGTTAAGTG GAATTATTTG ATCCCCAAAT AAGACTAGTG TATTATTTGT
46951  AACATTTAGC AGCAACTCTA AAGTCTTTAA AAAAAAAAAA AAACACAAAA
47001  AAACACAAAA AAATAAAGCC ATATTGTTAA AACTTGGGAA GAATCTCCTA
47051  ATTATTTTTG ATAAATCTTG AAAATATTAA AGGAATTACA CATTCTAACA
47101  AATACTGAAT AATTTCGAAA ATAGCTGCCT GCATGTATTT CCCGCAGGCT
47151  CCATCATTTC CCAGAACCTC ATGCTTTCAG AGGGGCTTGC TGTTGCCTTA
47201  AGTGACTGAC CACACCACCA CCCTTTAGGC TTAGTGTGTA AGAAGGTGAA
```

```
47251  TTTGGCCAGG CGCAGTGGCT CACGCTTGTA ATCCCAGCAC TTTGGGCGGC
47301  CAAGGCGGGT GGATCACGAG GTCAGGAGAT TGAGACCAGC CTGGCCAGCA
47351  TGGTGAAACC CCATCTCTAC TAAAAACACA AAAATTAGCC AGGCGTGGTG
47401  GCACACGCCT GTAATCCCAG CTACTCTGCC AGCTGAGGCA GGAGAATTAC
47451  TTGAACCCGG GAGGTGGAGG TTGCAGTGAG CTGAGATCAT GCCACTGCAC
47501  TCCAGCCTGG GCAACAGAAC AAGACTCCAT CTCAGGGAAA AAAAAAAAAA
47551  GGTGAATTCA CAGATGAGCC ATTGACATTT ATTTTATCTT CTAGAGAAGA
47601  AAATATAGCC TTAGCAAGTT GAAGGAGTCT GTAAGTTGAA AGATGAAAAT
47651  CTGAGGTTCA GTGGAACCTC AGTGCATCCT TGTTGAATGA ACCGAAGATT
47701  AAATAAGTTA ACCTGTGTTC TTCATTTTGT TTTTGTTTTT TGAGACAGGG
47751  TCTTCCTCTG TTACCCAGGC TGGAGTGCAC TGGTCAGTCA CAGCTCACTG
47801  CAGCCTTGGC CTCCTGGGCT CTAGTGATCC TCCCACCTCA GCCTCCCTAG
47851  TAGCTGGGAC TGCAGGCATG CACCACCGTG CTAGCTAATT TTTATTTTTT
47901  TGTAGAGACG GGGTCTCACT GTGTTGCTCA GGCTGGTCTC TTTGTCTCCT
47951  GGACTCAAGC AGTCTTCCCA TCTCAGCCTC CCAAAGTTGC TAGGATTATA
48001  CCACACCTGG CCAATGCGTG TGTTATCCTC ACTGTAATTC ATGTACCCTG
48051  TTTTTGGTGG AAACTTAGAA AGAGCTCTTA TATTATTTCT TTAGTTCAGA
48101  GAAATTCAAG CTGAAAATTT GATTGTGTCA TGTGGTCTGC ACTTTGTTCT
48151  TATATGCAGT GTTAATGGAA TTTTGGTTTG GTTTTGGTTT TGTGTGTGTG
48201  AACCCATCTT TCTTTAAGAA AAATATTATC ATGGAATCTG GATTTTTCC
48251  CCCTAAGCTT ACGCAGAACT TTCAGTGTAG TAAGTTGTTC AAGAAATTAC
48301  ATACTCCAGT TAATAATCTA CTTACCTGAG GTTTCCCTTC AACCCCTTTG
48351  ATTCAGCCTA TGTTTTCAGT ATTTCTTTCT CCCGGGTAGT ACTAGGAAGA
48401  TTTTTTATTG CAGACTGACA CAGTTATATC ATTTCCCAGA ACAAGCCAGA
48451  GCAGACCAAT TTTCTTAGTA TTTTCTTAGT ATCCTTTCAC TGTAGACCTT
48501  CTTCTTAAGA GTCATGGATA ACCGACCATG TTCCAGTCAT TCTCCTTACT
48551  CTATCACTTG CTGTGCTTCC CCAGGAACCC GCCTGTTGAA CTCTCCTTTG
48601  CCATGTCTTT TACTCTTGAT GTTCTTTGTA TTTCTGTTGC TGTCCTCTTT
48651  AGTTCAGGCC CTTATCACCT CCAGCTAGTA CCTTTTCACA GGCTTTTCTT
48701  GGCTCTCTGT GCATACAGCC CATCCAATTC CCGGTCCCTT TTCCAGTTTA
48751  TTCTCCTTTC TATTGCAAGT AAAACCTTGC TTTAATGACT CATATTCCCA
48801  TTGAGAATTC TTTAGTGGCT TCCCATTGCC TGTTTGCTGA AGCTTTATGT
48851  TCTTGGCCTT CATGAAGCAA TATATGGAGT TGTTAAGAGC TTGGGTTTGG
48901  CATCAAATAT ACCCTACTTT CACCAAAGGG CTTTGGCCAA GTTACCTAAC
48951  TTCTGCAAAC CACAATTTCA TCATCAATAA AAGTGGGGAA AATAATGATA
49001  CCAGCCAGGC GTGGTGGCTC ATGCCTGTAA TCCCAGCACT TTGGAAGGTT
49051  GAGGTGGGAG GATTTCTTGA GACCAGGAGT TCAAGACCAA CCTGGGCAAC
49101  ATCGCAAGAC CGTGTCTCTA CCAAACAAAA TTTAAAAATT AGCCAGGTAT
49151  GATGGCATGC ACCTGTGGTC CCAGCTACCT GGGAGGCTGA GGTCGGAGGA
49201  TCACTTGAGC CCAAGGGGTC AAGGCTGCAG TGAGCCATGA TGGTGCCACT
49251  GCACTCTAGC CTGTGTGACA GAACAAGACT GTCTCTTTAA AAACAAAAAA
49301  CAAACAAAAA TGATACCTTC CTCATTAGTT TATTGTAAAG ATGTAATGAG
49351  AGATAGTAAT GCTAATAGTA GCAAATAGTT AATTCAGTGC TTACTATGTG
49401  CCAGGTATAA TTTGAGTACT TTGCATAGTT GAGTTCCTCA CAATAACCCT
49451  GTGAAATGGG TATTATTACT TTCCTGATTT CATCAAGAGG AAACAGAAGC
49501  CCAGAGAGGT TAAGTAACTT GCCCCTAGTT AGGAAGTCGC TTAAAAAGTG
49551  CTAAGTGGTG AAGCAGGAAT TCAAACCCAG ATAGTCTGGC TTCAGAGCTC
49601  ATGGGTTTAC CATTTTGGCC GTTATATAAT GGGTTTTATA TAATAAACTT
49651  ATTATGAGCC TGTAATAAGT TTGGAATTGT ACTGGGCCTA TGTCCAGTAG
49701  AAGTTAAGTC ACTTTCTGGG AACCTGTTTA AGATTTTCTA TCATCTGGTG
49751  TCAGCCTGTA TTTCCCCTTG CAGACAAAAA GTGATGTCCC TCAGGTACCC
49801  TATTTCCCTC TGGAATCTAC CAGCTTACGT TTTTTATGAA TGTTCAAAGA
49851  TGTCCCAAAC ATTTATAATG TGCAGATTTA CCAGAATTTT CATTCATGAA
49901  TGTTTACTGG TTTTATTTTG TAGGTAGTTT AGAGAAAGTA CTCACTGGTA
49951  ATCATCTTGA CCCCTAAGGG CACCTTTCCG TTTTTTATCT CCACATCTTT
50001  GATCATCTCT TTTGTTCTAG GCTGCCAGAA ATGCCATCCT TGTCTACCCA
50051  CATTTTTAAG ACTCAACGAA AATCCCACCA TTGTGACAAA GGCTTCTCAC
50101  AGTACCCAAT TAAGAGGATG CCTTCCCTTC TTGAAATGCC TTCAGCTCAC
50151  ATTTGGTCCC ATAACTACGT GTAGGCCCCA TCTCAACCCT AGGGCTGCTG
50201  GCACTTCAGA CCAGATAGGA TGTTTAGCAG CGTCCCTGGC ATCTACCCCT
50251  CAGAGCCAGT ATCAGCTGTC ACCATCCCTG ATTGTGGCAA TTAGAAATAT
50301  CTCTGAACTT TGCCAGTTTT CCTCTCACTG AGAACCACTG GGATAAGAGA
50351  AAGTGTAAGG TGTATTGTGC TTTGGTGACA GACTTGATTT AACATCATAG
```

```
50401  CTTTGGCACT TCTATCTTGT ACTCCTGATC AGTTACTTAG CCTCTGTGAG
50451  TCTGTTTCCT CATTTGTAAA CTCGAAATAG TAATGCATAA TTTGTAGTTT
50501  GATTGTGGAG ATTAAGAATA AGGGGGCTGG GTGCAGTGGC TCACGCCTGT
50551  AATCCCTGCA CTTTGGGAGG TTGAGGTGGG TGTATCACCT GAAGTCAGGA
50601  GTTCAAGACC AGCCTGGCCA ACATAGTGAA ACCTTGTCTC TACTAAAAAT
50651  ATAAAAAATT AGCTGGGAGT GGTGGCACAT ACATATAGTT CCAGCTACTT
50701  GGGAGGCTGC GGCAAGAGAA TCACTTGGAC TTGGGAGGCG GAGGCTGCAG
50751  TGAGCCGAGA TCGTGCCATT GCACTCCAGC CTGGGTGACA ATAGCGAAAT
50801  TCTGACTCAA ACAGACAAAC AAGAATAAGG GTGGGCCAGG TGCGGTGGCT
50851  CACACCTGTA ATCCCAGCAC TTTGGGAGGC CAAGGCGGGC AGATCATGAG
50901  GTCAGGAGTT CTAGACCAGC CTGACCAATA TGGTGAAACC CCATCTCTAC
50951  TAAAAATACA AAAATTAGCT GGGTGTGGTG GCACGTGCTT GTAGTCCCAG
51001  CTACTCGGGA GGCTGAGGCA GGAATTGCTT GAACCCAGGA TACGGAGGTT
51051  GCAGTGAGCC GAGATTGTGT CACTGCTGCT CTTCAGCCTG GGTGACAGAC
51101  TCTGTCTCCA AACAAACAAA AAAAGTATAG CCATTAGATT TTATGAAGTA
51151  GATATTATAA TATGTAACCA GATGAGACCT TTAAAACCCA ATGTTTTTCC
51201  AGACTTCTCC CTTTGGGGTG CAACCCTCTA GTATGCCGAG AGCCACGGTG
51251  GTGCCCCGCA GGTCCTCTCA CCTGTATCAT TGGCTGATTT TGTCTCTCTA
51301  CACTTAGTAT TTATTTACCA TTGTAATTCT TTCAGTGGCC CTGTTTATCA
51351  GTAAATTTTG TTATGACTGA ACCAGTATTG TTCAAGTTCA GACCAGAAGC
51401  TTTCATGTCA ATTTGGTAAA CATTTTGATA TTACTGGGTT TGTTCAGCAT
51451  GGTAGTGCAC ACGATGCTGT ATTGACTTGG AATTCTCCTC AGGATGTTGA
51501  GCCCTTGACT CAGGAAATGT GGTGAGGTGG CTCTGTTTCA AGGGACTAAG
51551  CTGCTTTCCT GAGCCATTGC TTTGTGCAGT CCCAGTGCTG GGCACAGCAG
51601  CTTTAACTTT CTTCCTGATG ACATTCAGAA GTACAGCTGC TGGCTTTTCT
51651  CATTAATTCT CACCAGTTAG AGATGAAAGA AAAAGGAGCA GAGGCTATTT
51701  CAGGACAATG TGGGTAAGGA CGCCGTCCCC TGGATTTTTG GTTTGAGCGT
51751  GTCTCTGGCT CTTGTCCTCT TTTATTGTTA ACAGGTATTT CCAAGCTCCT
51801  CCATTGAGTT TAACATCTTG GTTTTCACAG GCAGTTGGTG GGACCTGCCT
51851  TGTGTGTTTC ACTGTGGAAG GGAAATCTAG TGGAACCCTC AGTGTTTCCA
51901  GCAGGAAACT TCTAGGCTTG CGGAGAACCC CTCTGGTGTC CCGCACGCCC
51951  ACAAGTAATT AATATTCTCA ATGAAGAACT CCTGCTTGGG GTCGCCTCCT
52001  TCCTCTGCCA GCCCATCTGG CTGCCCACGT GGGTTTCTCT GGGTGCTTCA
52051  TTAGGTTCTG TTACCCACAG AGTAGGAGGA GACAGAGTCT CCCTGCTCTG
52101  TGTCCTTTGT TCAGGTGTGG GAGGAAGAAA GTCCACCGCT TATCACCAGT
52151  AGCAGAGCAT AATTTGGAAA GTTGCTCTCA TTCTATTTCT TTTTACAGTT
52201  CAGAATTTTG GGGGAAGCTT TGCACTCTGG GCTGTGAGCA AGGCCAGGGA
52251  GACAGTCTTT AGAGGAGTCT CCACATTATG CTTGACTGTT CCCCGACTTA
52301  TCTACAAGAT TACAGGACCT ATTTCAATCA AGTTGTGGTG GAGAGGAGCA
52351  GATTTGTGTT GCGAAGACCA GTAATAGATG GTATCTGACA CAAATGTTGA
52401  TGTACAGAAA GAAAGCTTTG AGACCATTTT AACCAAGCCC CTTATTTTGA
52451  AGATGAATTT GAGGTTCAAG GAAAAGAAGG AACTTTCTCT GAACCTGTAG
52501  CTAGTTAATT TGGAATGGGA CTCGGGGCTT CTAGCTCCCA GCCCTAGACT
52551  TAGCCTTCTT TTCCGCACTG CTGCTGAACT CAAAGTCTGA CTTTACCCAG
52601  AGAAACCTGG CACTTGTTCC TCATGTGTGT GAAATGGCTC CCTGAGTGGG
52651  ATGATTGAGA GTCACGTCCC TGGCTCGTCT GGGCTTAGGT TGATCTCAGC
52701  TTCCCTGGCA GCCAAAGGAT CTCTGCTGCC TCCTGCTGCT AGCACCAAGT
52751  ATTAAGGTTT TTTGTTTGTT TTTGAGACGG AATCTTGCTC TGTCACCAGG
52801  CTGGAGTGCA GTGGCGCGAT CTCGGCTCAC TGCAACCTCC GCCTCCTGAG
52851  TTCAAGCAAT TCTTGTGCCT CAGACTCCTG AATAGCTGGG ATTACAGGCA
52901  TGCACCACCA CACCCAGCTA ATTTTTGTAT TTTTAGTAGA GATGGGGTTT
52951  CACCATGTTG GCCAGGATGG TCTGGATCTC CTGACCTTGT GATCCGCCCA
53001  TTTCGGCCTC CCAAAGTGCT GGGATTACAG GCGTGAGTCA CCGCGCCCAG
53051  CCGTATTAAG GTTTTTAGGC AAGAAAGATG AACATACTGT GATTTGACAA
53101  GTAAAAGCAA CAGAGGAAAG AATTAGTAAA GACTTAACTC TGTCAGATTT
53151  TGCAAGGGGA GATCTATCCC ATGGGGATGA ACATGATTC CTTTTGGTTT
53201  GTGTTTTTGT TTTTCCCATT GTCACAGTTA TCCTGTATAA ATAATTGTAG
53251  GAGTTCTCGT CAATGTTGGT TGATTCTGGG GTGCATTATT ACTTAAAACT
53301  TCACTGGAAA GACAAATGTT ATTTTTGAAA ATAAAACCAT TTAAAAATAG
53351  TAGTTCTGGC CAGGCATGGT GGCTCACGCC TGTAATCCTA GCACTTTGGG
53401  AGGCCGAAAT GTGTAGATCA CCTGAGGTCA GGAGTTTGAG ACCAGCCTGG
53451  CCAACATGGC GAAACCCCG TCTCTACTAA AATACAAAAA GTAGCTGGGC
53501  ATGGTGACAT GTGCCTGTAA TCCCAGCTAC TAGGGAGGCT GAGGCAGGAG
```

```
53551  AATTGCTTGA ACCCAGTAGG TGGAGGTTGC AGTGAGCCAA GATCGTGCCA
53601  CTGCACTCCA GCCTGGGTGA TAGAGTGAGA CTCCATCTCA AAAAAAGAAA
53651  AAAGTAGTTC AAAATTAAAT TATGGAATCA AAGTTTTGTT GCTGGGATGT
53701  ACCATACGGG TTATCAAGTA TAGTCCTTTT ATATTAGAAA TGGAAACAAC
53751  TGAGACCCAG ATAATTTTTT TTTTTTTTTT TTTGAGACAG AACCTCACTC
53801  TGTTGCCCAT ACTGGAGTGT GGTGACACGA TCTCAGCTCA CTGCAACCAC
53851  CGCTTTCTGG GTTCAAGTGA TTCTCCTGCC TCAACCTCCT GATAGCAGCG
53901  ATTACAGGCA TGCACCACCA TGCCTGGCTT ATTTTTGTAT TTTTAGTAGA
53951  GAGGGGGTTT CACCGTGTTG GCCAGGCTGG TCTTGAACTC CAGACCTCAG
54001  GTGATCCACC TGCCTTGACC TCCCAAAGTG CTGGGATTAC AGGTGTGAGC
54051  CATCGTGCCA GCCAACCCAG AGAACTTTAA TAAGTGACTT AGGAAGCTGG
54101  ATGTGGTGGC TCACACCTGT AATCCCAGCC ACTTGGGAGG CTGAAGCAAG
54151  AGGATCACTT GAGGCCAGAA GCTTGAGGCT TCAGTGTGCT TTACTTACAC
54201  CTCTGAATAG CCACTGCACT CCAGCCTGGG AACATAGCGG GATCCCATCT
54251  CTAAAAGAA ATTAATTTTT AAAAGTGAT GAAAATCAT AATTCAATAA
54301  GTCAATATCA GTACAAGTCT TCTGACTTAG ATACGTTTTA CCATTTAAGT
54351  TTCTTGTGTG CTAGACTTTG TTTTTGTGAG TTTTCCGTAG ATTATTTCTA
54401  AAGCTTATTG CTACATTTGT GTGTAACAGG TGTTTCCCCC TCCCATAGAT
54451  GAGAATGAAA GCTCAAACAG CTTAAACAGC TTGCCCAGGG GTAACACAAT
54501  GAGTAAATGG TTGAGCAGTA ATTTAAGAGC AGTCTGAATC CAAGGTCATG
54551  TTTTTAACGC TGCCCTGTTG CCATTTCCTT TAATGGTTTC AATTATCTTA
54601  ACTAACTTTA TTTGTCCCAG TGGCAAAGTA TTTTTCTTGT GTTTATTGCC
54651  CATTGCTGTT TTAGGAAAGT TAGCCTAGTT GAGTGCAATA GCCAATTTTT
54701  TTTAAAAAAA ATCTGGAACT TTAAGTTTTT ACTGAGATCA CTTCTTGCTT
54751  GTCATGAGGT GCATCATTGT CATTGGGACC TCATGTGAAC ACATTTGCAC
54801  ACTGAGGCAC ATTAACTCTT AACTGTGCAG CCTCCCGCAC AGTGAATCAA
54851  CCTTTGAACT GTGAAAGAAG CCAAGGTGGA AGATAGGAC AACTCTCGTG
54901  CATGAGAAAA TGGTCAAATA TATTTAGGA AAGAAAGATA CTGACATTTT
54951  TACCTTGAGA TAGTATTTGA TACCGAAATA CAATTTTAGT TGGAAAACGA
55001  TTTTTCAAAA ATCGTATTCC TTTGACCTCT ATGGGCTGGA CATCATCAAT
55051  GTGCCTATCC ATTAATTTCT TGTACTTTTC AGAATCTCTT TTGTTGTTCA
55101  GATATAGAAC TCCACATATT ATTCAGTTTG CACCAGGAAG ATGCATGAAT
55151  GTCGTTGAAT AACATGAGCC CATTGGATTG TGTTTCCTTC AAAAGTATAA
55201  CCATGTTCTC CATGGAAATA TTTTACATCA TGTTATCTTT CTTACTATTG
55251  GTCCTTTGAC ATTTTATTTG CTTTTTTTCT TTTTTCCTTT TAGACAGAGT
55301  TTTATTCTGT CGCCTAGGTT GGAGTGCAGT GCCATGATCT CAGCTCACTG
55351  TGACCTCCGC CTTGTGCCTC AGCCTCTTGA GTAGCTGGGA TTACAGGCGT
55401  GTGCTACCTT GCCTGTGCCA CTATGCCTGT GCAGTTTTTT TGTGTTTTTA
55451  GTAGAGACAG GGTTTCGCCA TGTTGGCCAG GCTGGTCTCG CACTCCTGGC
55501  CTCAAGTGAT CTGCCTGCCT CGGCTTCCCG AAGGGCTGGG ATTACAAGGC
55551  AAGGCTGAGC CCGGCCTTGA CATTTTAAAT GTAATTTAAA CATATCCTAA
55601  TTGCAGTATT ATCCAAAACA GTAAATATTC TAAGGCAAAA AATGTCTTAA
55651  AATCTTATCC TAGTTTTATC TACTTCACTG GTACTTACTA GGAACTTGTC
55701  AGTATCTTAT TAAATCATAT TTGCCATGCC CATGATTCAT CTTGGTTTTT
55751  TTTTTGGCCA ATTACCCCAC CCGTCATACT CATTTCCTGT CCTGAATTGG
55801  TAACCTCTGT GAGGATATGA GGACTGTAAG CAACATGAAG CCTGGGAGCT
55851  TTTATATATC AAACACCTGG AATAATGGCA TGTGATAGGA GCTCAGGCGA
55901  TGCACATTCA GTGAATTTAT GTAAAAATAC TCTGTAAGGT AAAGTTGTTT
55951  TAAATGTTTG TAGGGATTTT GATCGTTTTT AAGAGGTATT CCTGTTTTCA
56001  TTTTCCTTGT AAAATCTTTG TTCCCTCTCA CTTCATAATG CTACTTTAAC
56051  TTCTACTAAC AGTAGGCTAA CTACTAATAG CTTACTGTTG ATCAGATGCC
56101  TTCCACTGTC GATTAAACTG GAATATTTC AGTGTTGGAT TGAAGGAGTG
56151  GCCTGCCCCT CCACACCTGT GGGTATTTCT AGTCGGGTGG GACGAGAGAC
56201  TGAGAAAAGA AATAAGACAC AGAGACAAAG TATAGAGAAA CAACAGTGGG
56251  CCCAGGGGAC TGGCGCCCAG CATACCAAGG ACCTGCACCG GCACCGGTCT
56301  CTGAGTTCCC TCAGTTTTTA TTGATTATTA TCTTCATTAT TTCAGCAAAA
56351  AGGAATGTAG TAGGAGGGCA GGGTGATAAT AAGGAGAAGG TCAGCAACAA
56401  ACACGTGAGC AATAGAATCT ATGTCATAAT TAAGTTCAAG GGAAGGTACT
56451  ATGACTGGAC GTGCACGTAC ACCAGATTTA TGTTTCTCTC CACCCAAACA
56501  TCTTAGTGGA GTAAAGAATA ACAAGGCAGC ATTACTGCAA ACATGTCTCA
56551  CCTCCCACCA TAGGGCGGTT TTTCTCTCAT CTGAGAATTG AACAAATGTA
56601  TAATCGGGTT TTATACCGAG ACATTCAGTT CCCAGGGGCA GGCAGGAGAC
56651  AGTGGCCTTC CTCTATCTCA ACTGCAAGAG CTTTCCTCT TTTACTAATC
```

```
56701  CATCTCAGCA CAGACCCTTT ATGGGTGTTG GGCTGGGGGA CGGTCAGGTC
56751  TTTCTCATCC CACGAGGCCA TATTTCAGAC TATCACATGG GGAGAAACCT
56801  TGGACAATAC CCAGCTTTCA AGGGCAGAGG TCCCTGCAGC TTTCCACAGT
56851  GCATTGTGCC CCTGGTTTAT TGAGACTAGA GAATGGCGAT GACTTTTACC
56901  AAGTATACTG CTTGTAAACA TTTTGTTAAC AAGGCATGTC CTGCAGAGCC
56951  CTGGATCCCT TAAACCTTGA TTTCATATAA CACATGTTTT TGTGAGCTCC
57001  AGGTTGGGTC AAAGTGGCTG GAGCAAAGTG GCTGGGGCAA AGCTACAAAT
57051  TAACAACATC TCAGCAAAGC AGTTGTTTAA AGTACAGGTC TTTTTCAAAA
57101  TGGAGTCTCT TATGTCTTTC CTTTCTACAT AGACACAGTA ACAGTCGGAT
57151  CTCTCTTTTC CCTACATTGG ATGATGTGAA ACATATAACA CTTCCTGTCT
57201  CTTGTGAACA AAATGCCTAT TCAATTCATT GTTTGAATGG TCATTGATGT
57251  AATATTTGCT TAACATTTGG AATTTCTAAT GCTTATATGA AACATGATC
57301  TGTTTTGTAA AAATAAATTT TGTTTATGGA AATAATTGAA AAAATTATTC
57351  TCCAGTGGAA ATAATTATAG AAAAACACTG ACCTTGTATT TAGGTCACTG
57401  ACACTGTAAG TTTTTGATTG TTTTAATATG AGAAATATGA ATATCTTGGT
57451  TCATCACTTT CTTTTAGTAT AATGCTGTAG GGTTGTCTAG ATACCAAGGC
57501  TATTTTCTAT TTAAATCAAG CCCCCCTTCT CTTGCAGTGT TAAAAATGTA
57551  TGGACATCAT TAGCCATCAG GGAAATGTAG ATCAAAACTA CAACAAGATA
57601  CTTCATATCC ACTTGGGTGG ATAAAGTAAA AAACGATAGT AAGTGTTGTT
57651  CAGGGCGAAG AATTGGAACC CTCATACATT GGTGATAGGA ATGTAAAATG
57701  GTGCAGCCAC TGTGGAAGAC ACTTTGGCAG TTCATCAAAA AGCTAAATAT
57751  AGAGGCACCA TATGACCTAA GTACGGTAAC TCCTAGGTAT ATACCTCCCC
57801  TCAAAAAAAG TATGTTCACA CAAAAATGTA TACACGGAGT GTGAATAGCA
57851  GTATTATTTT TATAGCCCCT AAAGTGAAAA TAACCCAAAT GTTCATGAGG
57901  TGAAGGGATA AACACAATGT TGTATCTCCA TACAGTGGAA TACTGTTTGC
57951  CAATAAGAAT AAGCGAAGTA CTAATACATG CTGCACAAGA GTCAAACTTG
58001  AAAACATTAT GCCAGTTACA AAAAAATACT TTATATGATT CCATTTATAG
58051  GAAATGTCCA GAATCAGCAA GTAGATTAGT GGTTGCTAAG GGTTAGAAGG
58101  GGTAGGAGAG AGATGGGAAG TGAATGCTGA TGAATATGTT GTTTCTTTTT
58151  GGAGCAATGA AAATGTTGTC ATTTAAATAG TGGTGGTAGT TGCCGTGTGT
58201  GGTGGCTCAC GCCTGTAATC CCAGTACTTT GGGAGGTCGA GACAGGTGGA
58251  TCACAAGGTC AGGAGTTCGA GACCACTGGC CAATATGGTA AAACCCCGTC
58301  TCTACTAAAA ATACAAAAAA AATTAGCCAG GCGTGGTGGC ATACGCCTGT
58351  AATCCCAGCT GCTTGGGAGG CTGAGGCAGG AGAATTGCTT GAACCTGGGA
58401  GGCGGAGGTT GCAGTGAGCC AAGATTGTGC CACTGCACTC CAGCCTGGGT
58451  GACAGAGCGA GACTCTGTCT CAAAAAATAA ATACATAAAA AATTTAAAAA
58501  ATAAATAGTA ATGATAGTCG CACATCTAAA ATCCATTGAA TTGTATACCT
58551  AAAGGGGTCA ATTGTATGAT ACATGAATTA CTAGCCTACT GTTGATCAGA
58601  ATCCTTAATG ATCACATGAC CAATTAACAT GTATTTTGTA TGTGTGTTAT
58651  ATAGCATATT TTTACAACAA AGTAAGCTAG AGAAAAGAAT GTTAAGACAA
58701  TCATAAAGAA GAGAAAATAT ACTTACTATT CATTAAGTGG ATAGATCATA
58751  TGAAGTAGAT GATCATAAAG GTCTTCATCC TCATTATCTT CGCGTTGAGT
58801  AGGCTGAGGG GTTGGTCTTG CTGTCTCAGG AGTGGCAGAG GTGGAAGACA
58851  ATCTGTGTAT AAGGGAACCC ATGCAGTTCA AACCTGTGTT GTTCAAGGTT
58901  CAACTGTATG TAGATGCATT TGCTTCCATG AGCATAAATA ATCTCTGAAA
58951  TTATACACAC TGGTTGCTTA TGGAAAGGAG AGCTGGATTC CAATGTGGGT
59001  AGGCATGGGA GGGAGATTTT TACTAAATAT CCTTTTGTGT TTATCAAACT
59051  TTGTACCCTG GCATTGTATT ACATGTTTTT CAAATAAATA AAAGTTATAT
59101  AATGAGATAT TAATAGCTTA TCTTCTCTCT TGATTTTACT ATATCCAGGT
59151  CCTTCAAGGG TTAGATTACT TACACAGTAA GTGCAAGATC ATTCATACTG
59201  ACATAAAGCC GGAAAATATC TTGATGTGTG TGGATGATGC ATATGTGAGA
59251  AGAATGGCAG CTGAGGCCAC TGAGTGGCAG AAAGCAGGTG CTCCTCCTCC
59301  TTCAGGGTCT GCAGGTGAGG GAGCTGAGCC AGCTTCATTT CAGTGTGGGG
59351  GCATTGGGAG CTTGCAAAGT TGCAGTTGTT GAAGGTATCT GAATCAAACG
59401  TTACACATAA GGAAGATTTT GGAAAGTTT AATTGCTGGA ATAACTGCA
59451  CCCTTGAAAT GGAAAATGCC CCAGCTACAT TATATTTTAA TATTGGAAGT
59501  ATTTACTTTT GTCCCCCTTT AAAAGGCCAT TTAAATTTGT AGTTGCTGCT
59551  TCATCTATAT TTGAACAGTT TTTTCTGTTG CCAGCTTCTC TGCAGAGGAG
59601  AACATAGTAA CAGCTTTCCT GTAGCTGACC TTTAGTCATC AGAATATTTT
59651  TCTGGCTTCA ATTTTGTGTA CATAAATTCT TGTTGTCCAT TTAGCATAGC
59701  TATGTCAATC TGAGTTGTAT CAACAGATTT GGAGTTAGTT AGAAAAGGCC
59751  TGATGGTGGG GGAAGAAGAT CAAGTGACCT GAGTATTGGG ATATCTTTAT
59801  TTCTGGGGCG GGTCGGGGA GGTGGTGCAG TGAAGTGTGG ACTGTGCTTC
```

FIGURE 3, page 19 of 30

```
59851  TCACTCTTCG ACACCATGAT CTGTGCCTTT GTGTGTTGTC AGGCAAGCAT
59901  GGATACTAAA GGGCTGAGGC TCCTGGGACT GCCTGGGGCT CTCTTCACAT
59951  CTCCTTTACT GCCATCAGGG TGTTGTTTAG ATCATGGACC CAGCCTGTTA
60001  AGCTTTTGAC CCTGGTGTAG GGGTTTAATC ATGTGATTCC TAGACTATTT
60051  GCTGCATACC AACTGCAGTA TTTGATTTAA ATTATAGAAA GCTTGCAAAA
60101  TAGATTCCAA ATATCGATGT ACATCTACAT TGTTCATTTC ATTATATTTT
60151  AAACAAATTT GGTTTAATGA CTGTGATATG TATTCTTTTC CATTTTCTTA
60201  AGTGATCTGT TGGTGCTTGA GCTTGACTGT GTTTGAGATG TATTAGTATT
60251  TCATTTTAGA TAAATAAGAG AAATGGCTCA GTATGAGTAA CTTCTGCTGT
60301  GACTTCAGGA GTCACTCATT TGTTTCAGTG GCATAAACTT ACTCTAGATC
60351  CTTGTGATTA AGAAGCTCTG ATTAATAGTT TTTGAAGTTG GATAGCCATT
60401  AAAAGACAAT AATTATTTCA CTTTGCAATT CGAATGACCT ACATGAAGGC
60451  ATGTGTCTGT TTTCTGCTAA ATACAGATTT TGTTTGATTT TATTTTAGTG
60501  AGTACGGCTC CACAGCAGAA ACCTGTAAGT ACTTACGCAT ATTACTTTAT
60551  ATGCACCATG TTAAAAGAGA CCGTTTATTA TTGAGTTGTT CAAATTATAA
60601  AAAAGTTGTG TATTTAAAGG GTAGACACAT TTATAAAAGC TGTGTATCCT
60651  CAAATAGGTA AGACTTAATG TCTTGTTAAT TTTTTTTTTT TTTTTTTGA
60701  AAACTGAGTT TCACTCTGTT GCTCAGGCTG GAGTGCAAGT GGTGCGATCT
60751  CGGCTCACTG CAACCTCCCC CTCCCTGGTT CAAACGATTC TTGTGCCTCA
60801  GCCTCCCGAG TAGCTGGGAT TACAGGCACC TGCCACCGCA CCCAACTAAT
60851  TTTTGTATTT TTAGTAGAGA GGGGTTTCAC CATGTTGGCC AGACTGGTCT
60901  CGAACTCTTA ACCTCAAGTT ATCTGCCTGC CTCGGCCTCC CAAATTTCTG
60951  GGATTACAGG TGTGAACCAC CACGCCCAGC CTGTCTTGTT AAGTTTTAAT
61001  GATCTGTGCA GAGTTGGGAT AGTTAGAGCC TTTCAAAAAT TGTCTTCTTT
61051  ATGCATTTTC TGGACTATGG TGGCCAAGTT TAGTGAAATG TGAGGTGATG
61101  GAGTTGAAGT ATTTTTATTT CAAAACCACT TTACATTATT TCTGATTGGC
61151  TGCTAAGTTA CCTGTTTTTC TGAAGCTGTT GTTCTAATTT TTTCCATGCG
61201  GATGTTAAAT AAGAAAGAGA CTGATCTATT TTGTGGTCCT GTCAAAACAC
61251  TATGTCCTTA TTAGATACTG GGTGTGGTGA CTCACGCCTG TAATCCCTGC
61301  ACTTTGGGAG GCTGAGGCCA CTAGATCACT TGAAGTCAGG AATTCAAGAC
61351  CAGCCTGGCC AACATGGTGA AATCCTGTCT CTACCAAAAA TGCAAAAACT
61401  AGCTGAGTGT GCTGGTGGAC GTCTGTAATC CCGGCTACTC AGGAGGCTAA
61451  GGCAGTAGAA TCACTTGAGC CCAGGAGGTA ACGGTTGCAG TGAGCTGAGA
61501  TCACGCCACT GCACTCCAGC CTGGGCGACA GAGTGAGACT CCATCTCAAA
61551  AAAAAAAAAA AAAATTAGCC GGGTGTGATG GTGTGCACCT GTAGTCCTAG
61601  CTACATGGGA GGCTGAGGCA TGAGAATCAC TTGAACTCAA GAAGTGGAGG
61651  TTGCAGTCAG CTGAGATCAC GCCACTGCAC TCCAGCCTGG GCAACAGAGA
61701  CTCTGTCTCA AAGAAAACAA CAACAACAAC AACAAAACAC TATTTTTACT
61751  GAGACAGCTC TTGATTTGGA ATGTAAGTTC TGGAACAAGA GGGAGCTTTA
61801  ATAATTAAGC TTCCTGGCCT GCTGAGAAGC TCAAGTTGTT TCCCATAGTT
61851  CTTCCCTGGC TTGAGCTGCT TGAATTTACT GATTGATTGA AAGGTTGGAG
61901  GCTGTCATTG CCAGTGCTTT GCAAGTCAGG TAACCATGAC GGGAGGCAGA
61951  CAAAAGCTGT AGCTTTTTCT TTTTTCCCTT TGCAGCATAG GCTTATCTCT
62001  TACAGTTCAT GTTGTCTTGG CTGCTAAGAG CTTCATATGT GAGACCCAAA
62051  CACACAGTGA CATACACCTG CTCGGGCACC TGTTTCATTT TTGGCATTGA
62101  GGAGCTGGGA TGTTGTTACT TTGTATATAG ACAGCAGCAA ATAAAACTTG
62151  CAAGAGGAGC TTCTCCTTTA AGGCCAAGAG AATTTCGAAC TTCAGTTCTC
62201  TTAGAGTTTG AATGGTGAAG ACTTACTGGA TTTAAGCTAT ATCCCTCTGA
62251  GGGCAGGACC TGGTAGTAGA CCTAGTACGT GATATCAGTC AGCACTGCTT
62301  TCCCTTTGAT TTTATCGTAA GCCTTACCAC AAAGTGGATC TGTCTGGGTT
62351  TGGGATTTTA ATAGAATATG GCATGAGAAA GCAGAGTTTA TTGCTATTTG
62401  CCATGCTGCT AGTCGTTATA CTATCGTGGT GCTTTAAAAA GAAGAATACT
62451  GACCTGTGGT CTTTCCTTAA CATAGATAGG AAAAATATCT AAAAACAAAA
62501  AGAAAAACT  GAAAAGAAA  CAGAAGAGGC AGGCTGAGTT ATTGGAGAAG
62551  CGCCTGCAGG AGATAGAAGA ATTGGAGCGA GAAGCTGAAA GGAAAATAAT
62601  AGAAGAAAAC ATCACCTCAG CTGCACCTTC CAATGACCAG GATGGCGAAT
62651  ACTGCCCAGA GGTGAAACTA AAAACAACAG GATTAGAGGA GGCGGCTGAG
62701  GCAGAGACTG CAAAGGACAA TGGTCAGTGG GGCCTGGAAC CTGGGCTGCA
62751  TGGGGTTCTC AGAGCTCCAT TAGTAGGGTT CTGCCAGGTC AACATGGGGG
62801  CTGATTTGTG CTGCTGCTGC AGATGACAAG GATGATTCTC TCCAACTCCC
62851  TATTGGGAAA TATGGGAAAT AGCCTCGTAC TTCATTTGTG AACTGTATGC
62901  CAGAAATATG TTAACATTTC AAAATAGTTT TTAAAAATGT AAAATAATTG
62951  AGAAATTCCA TGTTTCTATC ATGCTAATGA TGGTGCTTTA TTTTGTCATT
```

```
63001  AACTTTTTAC CTAACTGTAA TGCACCACAA GTCTGTTTCT GAAGATTATA
63051  GAGGGTAGAA ATGGAAGTGC AACTTTATTT AGAAAGAGTT ATTTTCCCTT
63101  AAAGCTAACT TTTTCTTATA AGAGCAGGCC AATTACTAAA TGAATGAAAA
63151  ATGAGATTTA GAAACCTGA AGGTTTTACC CCAAAAGCCA AGAGGTGTTT
63201  ACCAGGTGGT ACATAAGCAT ATTCAAAATG TATTTTATTG ATGGAGATAA
63251  GTACTTAATG AGGCTGTATT AAGGAGAGTA ACAAGTTCTA ATTCTTGACC
63301  CATCAAATTC TTAAGGTGAA GCTGAGGACC AGGAAGAGAA AGAAGATGCT
63351  GAGAAAGAAA ACATTGAAAA AGATGAAGAT GATGTAGATC AGGAACTTGC
63401  GAACATAGAC CCTACGTGGA TAGAATCACC TAAAACCAAT GGCCATATTG
63451  AGAATGGCCC ATTCTCACTG GAGCAGCAAC TGGACGATGA AGATGATGAT
63501  GAAGAAGACT GCCCAAATCC TGAGGAATAT AATCTTGATG AGCCAAATGC
63551  AGAAAGTGAT TACACATATA GCAGCTCCTA TGAACAATTC AATGGTGAAT
63601  TGCCAAATGG ACGACATAAA ATTCCCGAGT CACAGTTCCC AGAGTTTTCC
63651  ACCTCGTTGT TCTCTGGATC CTTAGAACCT GTGGCCTGCG GCTCTGTGCT
63701  TTCTGAGGGA TCACCACTTA CTGAGCAAGA GGAGAGCAGT CCATCCCATG
63751  ACAGAAGCAG AACGGTTTCA GCCTCCAGTA CTGGGGATTT GCCAAAAGGT
63801  AAGTGTTTCT TCCCATCAAC TGTCTGCCAT CGCTGACTCC AGGGACGTGC
63851  CTTTAACAAA TGCTGTGAAG GAATTGGCTG GAAGTGGCCA AGCCCTGTGT
63901  GTGTGTACTG ATCAGTTTTA TTACTTTTAT ACTCCTGAAG AAGTAATGTG
63951  ATTTAAATAA ATTTTCTATG CCATTAGGCT ATTTCTTGCT CTCTGCATAC
64001  CAAATCTTAT TTCTGACCAG TTTTCATTTT TAATATATTT AGTCAGCAGC
64051  ATCATTTGCA AAAACCTTCC AGTTTTAGCA ACTTACACCT TTCTAGAATG
64101  TGTAGTTTAG TTTAAAATTC GTATCTTCTT CCATCTAATG TCATTATATT
64151  TAGTTTAGTT TAGTTTTGTT TTGTTTCTAT TCAAGAAAAT TATGCCTCCT
64201  CTTTGACTCT ATTGAGAAAG AAGTGTCATA TTGTCTTTTG ATAGTTGTTC
64251  CTGATTATAG GACCCTACTA TTGGTAACTG GCCCAGGATT GTAATTTTCA
64301  AGGAATTGGC ATGGATTTAA ATGTGATGAC AGATTATAGA TTGGCTCTTG
64351  TGTTCTTGTC TACCTAAGAA GGCTTGACTT ATTCAAAGCC TTATTTTGGG
64401  AGTGAATGCC AAGTGACTCT AGTAAGTGAA AACTGGGTAA CACAGCTGGT
64451  TTCCATACTG GCTTATGGGG GAAAAGCTCT GAAACCTCCC TCTGCTCCCT
64501  CTACTGACAA GACTGTTTAA CACACAGCGA GTAAAATTGA TGAGCCAGCC
64551  CTGCAAACAG CCCGACATTC TGCAGCCCCT TTGGTTCCAG CAGTCTGGAA
64601  TTGCACGCCG AGTAAGCTGG CTTTGTTACG CACTGGCTAT GATGAATCCT
64651  CCTAAGGATT TGCTTTCTTT ACTTGGCTGG ACGTGGTCAG CTCCTGTTCC
64701  CCTTTCCAGG GAGTGTTTGA AGGTGCTTAC ATAGAATGTA GGTTAATTTC
64751  TGGGAAAGGG CAGTAGTGAG AGGTACCTTA TCCAGACTTA TTGTTGCTGT
64801  TGCAGTTCAA TTTTTCTCTT ACTTGAAGTT TCTTTTTTTT TTTATGAGAT
64851  TGAGTCTTGC TCTGTCACCC AGGCTGTAGT GCAGTGGCGC GATCTCGGCT
64901  CACTGCAACC TCTGCCTCCC GGGTTCAAGC GATTCTCCCG CCCCAGCCTC
64951  CTGAGTAGCT GGGATTATAG GCGCGTGCCA CCATGCCCGG CTAATTTTTG
65001  TATTTTTAGT AGAGACAGGG TTTCACCATG TTGGTCAGGC TGGTCTCAAA
65051  TTCCTGACCT CGTGATCCAC CCGCCTCAGC TTCCCAAAGT GCTGGGATTA
65101  CAGGCGTGAG CCACCGCGCC CGGCTGAAGT TTCATATAGA AAGTAATTTA
65151  CAAAGTACCT TTTTAATTAT TTCTATTTTA TTCATTCATT TATTTATTTA
65201  TTTTTTGAGA CAGTCTCACT CTAGTTGCCC AGGCTGGAGT GCAGTGGTGC
65251  AATCTCAGCT CACTGCAACC TCCGCCTCCT GAACTCAAGC AATTCTCCTG
65301  CCTCAGTCTC CCGAGCAGCT GGGATTACAG GCGCCCGTCA CCATGCCCGG
65351  CTAATTTTTA TATTTTTAGT ATAGACAGAG CTTCACCATG TTGGCCAGGC
65401  TGGTCTCCAG TGCCTGACCT CAGGTGATCT GCCCTCCCCA GCCTCCCAAA
65451  GTGCTGGGAT TACGAGCCTG AGCCACCATG ACCAGCTCAA AGTACCTTTT
65501  TTATTCATAC TTATTTTGCA AGTATTAGCT GGGCTGCAG TGGCTTCAAG
65551  TACAGTCAGC CCTCCATATC CATGGGTTTT ACATCTTTGG ATTTCCCATC
65601  CATGTGTTCA GCTAACTTCA GGTGGGAAAT AGTTGGAGGG GAAAAAAAAC
65651  TGTGTCTTTA TTGAACATGT ACAGATTTTT CCCCCCTTGT CATTACTCCC
65701  TAAACAATAC AGTATAACAA CTATTTACAT ACCATTTACA TTGTAGCAGG
65751  TATTATAAAT AACTAGAGAT CAACTAAAGT GTATAGGAAG ATATATGTAG
65801  GTTATATGCA AACACTACAC CGTTTTATAT CAGACATTTG AGCATCTGTG
65851  GATTTTGGTA TCCTCAGGAT GTCCTGGAAC CAGTTCCCCT GCAGACACCG
65901  AGAGGCACCT GCATATCAGA TTAAACCCCA GCTCAAAACT TAATAACTGT
65951  GGAACTTTGG TTTCTTACCC TGTCTGAGCC TTGGTTCATT CCTCTATCAA
66001  AAGAAAGAAA TGGCTACCTC TAAGGTTGTT AGTAGCACTG AATTAAATAA
66051  AACAGGTCAA TGGCAAAGGT ACATAAATAA CATATAATAA TAATATATTG
66101  AAAAATTTCC CATTGAATGT AAGTTGCCTT GGTCATCACA ATCCATGTAA
```

```
66151  AGGAGCAGAA  TTGCTGCTTG  TTACCACATG  GTCATCATTG  GAGGCCCAGG
66201  CAAGTCATAA  GACTTATCCT  ATTGTTTACA  TGACAGCTCC  ATCTCTGTGT
66251  CACAGGAAAC  TTCAAACCTT  ACATGTCCAA  AACCAGAATA  CAACTTTCCC
66301  TGCCAACCTG  CTACACATAC  TGTATTTCCT  ACACTTGTTG  CCACCATTTC
66351  TTGTTGCTCC  AGTGAGAAAC  TTGATCATCA  GGATGTCTTC  TTTTTTTCTC
66401  TCATGTCCAG  TAAATCATCT  CATTTTGCCA  GTCATACCTC  CTAAGTAGGG
66451  GTCCCCCTTG  CCTTGTCCCT  AAAGTGGGCA  GTGTCATTGC  TTGCCTCTCC
66501  TATTATGGAG  GTTCCTTACT  GGTGTCTTGG  CTTTGTGTTC  TCTCCAGCTT
66551  TTCTCCCCAC  CTGCCTTTCA  GCATGCCCTT  CCATGGTGCT  GCTAGAGTGT
66601  CTTTGCAGTA  TGCTCACCCG  ATCAGTGTAT  TCCCCTGCTC  ACAGTTTCCA
66651  CAGCTCCCCA  TCATCTACAG  CAGTGGTCTC  CACAGTGGAG  AGTGTACATC
66701  CCTGCATAAC  CAGCACCATC  CAGGAAGGTG  CAGGAAGGAA  TTATTAGAGC
66751  ATCTGTGTAT  TTTTTTATTT  TGAAAGAATA  GTACAATAAA  CAACTGTATA
66801  TCCTCCACAT  AGATTGAGCA  ATTCACATTT  TGCCGCATTG  CATATACTTT
66851  GTGTACACAG  ACACTGCATG  CTACACATAT  TAGGATACTT  CACTCCTAAA
66901  TACTTAAGCA  TTCATCTTCT  GAGAGATGAA  TTAGAACGTC  CTCCATTGTA
66951  ACAATAATAC  TATTACAACG  TGTAAGAATA  GCACTAATTT  TATATTATTA
67001  TTATTTGAG   ACAGGATCTT  GCTCTATCGC  CCAGGCTGGA  GTGCAGTGGC
67051  GTGATCTCGG  TTCACTGCAA  CCTCTGCTTT  CTGGCTCAAG  TGATCCTCCC
67101  ACCTCAGCCC  CCAAGTAGCT  GGGACTACAG  TTGGCACTAC  CATGTCTGGT
67151  CAACTTTTAT  ATTTTTGGTA  GAGAAAGTAG  GGTTTTACCA  TGTTGCCCAT
67201  GCCAGTCCTG  AACTCATGGG  CTCGAGTGAT  CTGCCTACCT  TGGCTTCCCA
67251  AAATGCTGGG  ATTAAAGGCG  TGAGCCATCA  CACCTGGCCT  AATATCATCT
67301  ATTATTTATT  CCATATTCAA  ATTTCCTCAA  TAATTCTAAA  ATTTTCTTTT
67351  TAAATTTTCC  TGATCTAGGA  TATGATCCAA  CACAGTAGCC  TGCCTCCTGG
67401  GTGAGGGCTT  CCTGTATCCC  CAGCAGGCTT  ACTTCTCTTT  CCCCTCTGCT
67451  CCTGCTGGCC  ATGCTTGTCT  TAGTTGTATG  GGCAGTGCTC  ATTGTCACTG
67501  TCTGTCTTCT  CATTAGAATG  TGAACTCTTG  GAGAGTGCAG  TGTGTTTTTA
67551  TCTTTGCATC  CTCAGCATCT  GATTCAGTGC  TAAGATAAAT  ATTTATTGAA
67601  TAACGAACAA  ACAAATGAGT  GATACCTTTT  TACATTCTTC  TTCTCTTTCC
67651  TTTCTCCCGC  TTTTTTCCAT  TTATAGTCAC  AATTTTACTG  TGTCCAACAC
67701  ACATACCATC  CCCAATACCT  GTTGCATCAG  GTAGAAACTG  GAGGTCTTGA
67751  AGAGCATTTT  AATATTGGCA  AATTCTAGGG  ATGTACCAGG  GACAGGATCT
67801  CCTTTGTTTG  GAAGCACTCA  GTTTTCGCCC  GCAGCTTGGC  CATTTGATAA
67851  GCAAGAGCAG  CCTCCCCCAT  GGGAGGTGTG  TTTTGTTTTC  TGCATGGGAA
67901  GGGGTATAAG  CCTAGAGTCT  TGCACTTGAC  CACACGGTAC  TTCGTGAATT
67951  TGAGGCAAGA  GAAACAATGA  AGAGTTTGTG  TAGATCCTGA  CTTTAGGGCA
68001  GAATGTACAT  GTTAGGGCAT  AGTAGAAGAA  AGACTGGGGC  CAGTTTGAGG
68051  AACTTGAAGA  AACCTAAATG  CCAGGCTAAA  GAAGGTACAC  TTTTTTCCTA
68101  GAGTAATTTG  GCAGCCATTG  AAGGTTGAGA  AGAGGATGGT  CCCTCTTAGA
68151  TGATCAGCTG  CCAGAGCCTT  AGTGTGTATC  TTGGCTCAAC  ACATCTGAAG
68201  GACAAAGGCC  CTGGAACAGG  GTGGTTTTGT  TGGTCTTACC  TGTGGGCTAT
68251  TTCTGGAATC  CTTTCTGTGT  CACTCGATGG  GGACCCACAC  CACTGTCAGT
68301  CCTTGCTAGG  CTACTGTTAA  CACAGCCTCC  GTGCTCCTAT  CACTTGAGCT
68351  TTTGCTCCCC  AGTCTGTCTC  TGTCTGGCAG  TCCAGAGAGA  ACTGTTTAAG
68401  GCTTAACTTC  TTCCCCCTTA  CCCACCCTCG  CCTCACCAAC  ATGATCTCCA
68451  TTGTGTTTCC  CATGTAGAGT  AGTGATGCCC  TGAGTTGTCC  TTCACTGAAG
68501  CTGACAAACT  CTCCAGTGTG  TTCCCTGGCA  GGTCTCTGTT  GGTGCCTGCT
68551  CCAGACCCAT  TCTCTGTTTC  CCTAATTCAT  TCTACACCGT  TCACACTGGC
68601  TTCTTTCTAA  AGTTTCTCAA  AGTTGCAAGC  CTGTTTCTGC  CTTAGGATTT
68651  TTGTACTTCC  CGTGTCCTTT  GCCTCAAACT  TCTCTTACTT  TCATGCCTGC
68701  CTTTGTTCAG  ACCTCTCCTG  AATGTCACCT  TCTCAGAAAA  GATCTCCCCT
68751  GAACAGCCTT  GGCATTATCC  ATCTCCTTTC  TCTGCTTTGT  TTTTCTTCAT
68801  AGCCTGTTTA  GCTACCTGAC  AGGATGTGTG  GATTCCTCGT  TTATTTGCCT
68851  TATTGCCCAT  ATTTTCAACC  AGTACACGAG  TTTCCTAATT  TAGCTTGTGT
68901  TTTTTTCTTA  CAGTGTTCCC  AGTACCAAGA  CCATGCTTAG  CACACAGAAG
68951  GTACTCAGTA  AATATTTGTT  GCACGAATGG  TTGAGGTGGC  AACATTAAAT
69001  CTCTTAGTTC  CACTACTTCC  TTGGGCCTCA  TAGTGAACCT  CCTCCATATA
69051  GAGGGATAT   TCTTGTCGTC  CTTGTAAGGA  CCCCTTATGA  TGTAAAGAGT
69101  CAGTGTGTGC  CTAGCTCCAT  GTGTTATGTG  CGTGTGACAG  CAGCTGTCTC
69151  ATTATGCTGA  GGCACTGTTG  GCTACCATCT  AATAGTTCCT  AGGATAGCTT
69201  CTTGTGGAAT  GAGTGACCAC  AGTGTCACCC  AAAGACTAGC  GTATCAGAAG
69251  GTGACTTAAG  GGGCCCAGTT  CTTCCCGAAG  TGAAAGCTTT  CCACTCATTC
```

FIGURE 3, page 22 of 30

```
69301  CCCTCTTAGT GGAAGCAGAG TGCAATTGCA AGCTTTTCAT TTTGGAAGGA
69351  AGACAGCTCC AGTTTGTCCT TTGTGTCACC ATTATCTGTA AGAAGGAAAC
69401  CGTGTGACAG GTCACTACTG TGGTGACTCA GTCAGAGGAG GTGTGACAAA
69451  AGCATTCCAG TTGGGTTTCA GTGGACTTCT TGGGAATGTA GCAGTCTGGT
69501  ACCTTAGTTC AGGAACTATC ATACTGAGAA AAGAAAGAAA AGCAAAATCT
69551  CTTTTACCTC CTGTTGTGTT TTTATACAAT TAAGTTATTG AGATACATTA
69601  CCTAGCATCA TTTGGAACGC ATCAGAAGCT AAGTAACTGT TTACAAACCC
69651  GAACCAGGAG GATAACAGCA TGTCACCAAA GAGATTCTGT TCAGTGAACC
69701  TTAATGAGGG ATATTAAGTA CAAGAAACAC CCTGAATTT AGGCCAGGTG
69751  CGGTGGCTTA TGCCTGTAAT CCTGGCACTT TGGGAGGCCA AGGTGGGCAG
69801  ATCACTTGAT GTCAGGAGTT CGAGACCAGC CTGGCCAACA TGGTGAAACC
69851  CCGTCTCTAC TAAAAATACA AAAATTAATC GGGCATGGTT TCAGGCGCCT
69901  GTAATCCCAG CTACTCGGGA GGCTGAGGCA GGAGAATTGC TTGAATCTAG
69951  GAGGTGGAGG CTGCAGTGAG CCGAGATCGC GCCACTGCAC TCCAGCCTAG
70001  GCGACAGAGT GAGACTCTGT CTCAAAAAAA AAAAAAAAAA TTCCCTGCAT
70051  TTAAATGTGA GGTGATGGGT CTTTGAAAGT ATATTTCTTC TAGCGTGATT
70101  GAATTAAGCA GCTCCTGAGA AATGTTTTTA AAAACAACAT CTCAGAGTGG
70151  TGGCAGATTA CAGATCATCT CCTTCCACTT GAGTGCCCTC AGATAACAGC
70201  CAACTCGGCT ACTGTTCTCA TGGAGAAAAA GAAATCACAT CGTTCTGTGG
70251  CTCAGGAGGA CCACAATATG TCTAACCGGG CTTCGCCCTC TTCTCATTAG
70301  ACCTATGATT TGAGTTGTTT GTGGGGGCGG AACTTGCTCT TGGGCCTCCC
70351  CTTCCCTCTG CTGCTGCTCT CTGGTCCCTC ACTGACCAGT TGGGAGCCTC
70401  TGCCCCAGAC GATGGTTCAG CTGGTCACAG CAGAGGGAAG CCCCTGCGTC
70451  TGGCCAGGCG CCCAGATGCT GTCCTGACTC TCCTGTGTTT GGGTTTTTAG
70501  TGTCTTCGGT GGGGAAGGGG TGGTCCCTTC CGATTCTTCT TTTCCTGAAC
70551  ACCAAGCCTC ATAGAGTTTA AGTCATTTGC CAGTCTTACA ACTTGTAGAT
70601  ATTGAAACTT AGATTTGAAT CCAATTTTTC AAACCTCAAA TTCCATTTTC
70651  CTTCTTGCTG ATTCTTCTTG ATTAAATGAC ATACGGGCA TTCATCTAGT
70701  CATGTCTAGT GTTGTTCATC TACCCATTGG GTCAGCATTT TTATATTTAT
70751  CCTGGACCTC TGTTCTCAGC CCCAGGTGAA TCAGTGTATA TTCATTTTGC
70801  CTTCTTTTTT GGTCTTTGTG CTGCTTTCTT TCTGAATTTT TGCTGAGTTC
70851  TGGTGTTTCT TTTCCTGAGC TCATACCTGG CCTTTGGTGA GGCTGTGCAG
70901  AATCCTTATA AGAAGGAAA CAGGCATATG GAAGGTAGCA AGCAGGGAAT
70951  ATCTGTACCT GGCTGGCTCA TTTGATTAAC ATGCTAGAGG AACAGGTCTT
71001  GAGGGTTAAG ATACTGGTCA GAATTCTCTT GGCGTCCTCT GGAGCCCCCC
71051  TAGGGAGCTG TGTGGGCACC CTAGGTCCTG AGGCCCTTGC CTGTTCACTG
71101  CCTTACGGCA AGTTGCAAGG CTGGCCCTCC TTCCTCTTAT GGGGCTTGCT
71151  GAAGAATCAG AGCCTCCCCA AGCACCCTGG TTTCACAGCT CGTATGTACC
71201  CCAACAGAGG TTTAGTTCAT TTCAGCAGTG CCCAGCTTCA AGGAAACAAA
71251  GGGGCTCTCC TAGGTAGGTG TTTATATTAG TCTGTTCTCA CATTGCTGTA
71301  AAAAATACCG GAAACCCGGT AGTTATAAA GAAAACAGGT TTAATTGGCT
71351  CACAGTTCCA CAGGCTGTAC AGGAAGCATG GCTGGGGAGG CCTTAGGAAA
71401  CTTTCAAATA TGGTAGAAGG GGAAGCAGGC ATCTTACATG GCTGGAGCAG
71451  GAGGAGGAGA GAAGGGGGAC GTGCTACACA CTTTTAAACA ACCAGATCTC
71501  GTGAGAACTC ACTCAGTATC ACGAGAACAG CAACGTGGAA ATCTGCCCCC
71551  ATGATCCAGT CACCTCTCAC CAGGCCCCTC TTCTAACACT AGGGATTACA
71601  ATTCGACATG AGTTATGGGC AGGGACACAA ACCCGAATCA TATCAGTGTT
71651  TAATGTTCTA CATTGAACAG GCTTTCTGC TTGGTTTTTA AATACCATTT
71701  CAAAATTTAC TTATACAGTA AATAAAAGTC CTGGTTTTAT TTCATCTTTA
71751  CCAGAAATCT GATCTTGTAG GTCAGTCTGA GGTTGGTGA TGAAGATGCT
71801  GACTTTAAGG ACTATTTTTC TGGGCCTCAC CAGATTATTT TTGTTTGTCA
71851  CTTGCCCCTT GGTTAACTCT GCTTGATACA GGCATGATCT GAACTTGTTT
71901  GAGAAGATCT GGCCCCAGAA TCTCTGGGAA GCTGGCCCTA TACCTGCCTT
71951  TGAGATTCCC TGGAGTCATC CTGGAATTTA GAATGACTGC TCATGTACAT
72001  GACAAGTTCA TGACTGACCT CAGAGGTTGC CTTTATGGCC CAGGCCATCT
72051  CAGGAGACCT CTGTCTGGGA CCTTCCTTGT CTAAAACAAA ACCAGAATAG
72101  TTTAGTCCCT GCCTTTAATC TGTGTTTGTT AATCAACAGT CATCTACCCC
72151  TTGAGATCTG TGTGTGCTCA GCCCAAGCAG TGGGAACTGT AGGGGATGAT
72201  GTGGGTGTGA GGTGTCGGTG CCAGGGACCC TGATGTCTTG TGGCGTCCAA
72251  GGAACTGTGT GTCACTGAGA GTGATCGGCC CCCACAGCAG TGTTCTTTCT
72301  ACCTTCATGT TCCTTGTAAT AATGCATCAG CAAGCTCGAT CTGGGCCGTG
72351  AAGGGATGGA TTGACACCAT GAAGAGCCGC CACAAAGCTG CAGACAGGGG
72401  GACAGCAAGG CTGGCTTGTT CTAGGGCTGA CCTGGACCCG AAGAAACTGG
```

FIGURE 3, page 23 of 30

```
72451  GGATAAAAAG AGAAAGGTCA AGGCAGTGCC CTTGGCGTCC TGTGGGCAGC
72501  CCAGTTTGCT CTTTTCTGGA GTATTTTCCA GAGGTGGAGA ACAAGCAATT
72551  TTAGTTCTGT CAAGTTTAAT TTACAGTATT CCAGGCCTAA GTGATCATTC
72601  CACTACTCTT GAGGAAAGGA GACTGACCCT GGCAAACACT GTGCTCACAC
72651  ATGCAAACCA CCTATCCCGA TCACTAACTG TCCTGCTGTT TGCTCATGCC
72701  AGCAAAAACC CGGGCAGCTG ACTTGTTGGT GAATCCCCTG GATCCGCGGA
72751  ATGCAGATAA AATTAGAGTA AAAATTGCTG ACCTGGGAAA TGCTTGTTGG
72801  GTGGTAAGTA GAGTTTTCTT TCTAAAACCT TTGGTCTTGA TTCTGTGTGC
72851  GAAGACACTT TTTGAATGTC TGTGTTGCTC CGTGGTAATG CAGCCTGTTC
72901  CCTTCCAGCA TAAACACTTC ACGGAAGACA TCCCAGACGC GTCAGTACCG
72951  CTCCCATAGA GGTTTTAATA GGAGCGGGGT ACAGCACCCC TGCGGACATC
73001  TGGAGCACGG CGTGTATGGT AAGGACGGCT GTGCCCTTTG CTGCCATGGG
73051  AATTGGCTCG TTCCTTTCAC ACTCTGGATG GGGCTGAGTC TCTCTGAGGC
73101  ATGCGACCTC AGTTTTTCTG ACTGTAAGGG TCATCCACCG TGGGCTGGGT
73151  GAGGGGAAGG TTGCTGCCGC AGGCATCTTA AGAAGTGGAA GGATCCTCCT
73201  CAGGCGGGCC CTGGGTGTTT GGTGTGGTTG TGGGCTTGTG AGAGAGACAT
73251  GGTCTCTTCT TAAGGCCCTG CACAGCCCAC AGCCCCATGA ATCAGACTCA
73301  GTTGTTGTGA CACAGTGACT TCACTTGTGG TCCCTGAAAA TGTGCAGGGT
73351  ATAGGGAGCT TTTCCCTTCA CTCACACTGT GGAGGAAGAT GAGGTAGCAT
73401  CTCCAGGGGA AGACTGCCTA AGGCGGGCAG GTGGGAGCCC CTCCAGGTAA
73451  GCCTCTGCCT GGTCAACCAG ACATGCAGGG TTCCTCACCT TTCCAGACTG
73501  GAAGGGATTT CCCCAGATGC CAATGCATAA TCTCTCTTCC CTTATAAAGC
73551  AAGAGCTAGC AGATATTCTG GCTTATTCTA GGATGTCTAG CCCCTTCTGA
73601  AACAGTGGCA GCAACGCCCA CTCCCTCTGA CAGAGTCTGT TCCCAGAGTG
73651  GTTGAGATGA CGGCTTCCAC AGGGCGGCAG AAGCCTCTTC TTCTATCTGT
73701  CAGGCCTGTT TTGCTGCTGG TTTTGTGCTG CACAGTTGCA TTGTCTGTAA
73751  ACTCCCCTGG CCCTGCCTGG CATCGTTTGG TCATTGACCC TGAACCTGTG
73801  AGTTGGTGAA CACAAAGGGC CCTGCATTTG CGAGCCAGTT CCTGGTTCTC
73851  TTCCTCTGCC CTGTTTCCTG GCCCATTCAG CAGCTTTTTC TCAGTGGTAT
73901  TTACTTAGGC GTTCCGTGTT GGGAAGGTG GGTTGCTTGC TGTTGGGTTT
73951  CATGCTTTTC CTATTCCATA CTGCTTTTTA TCCATATTCT TCCAATATTT
74001  AAAAGAAAAG ATTGTGTGCA AGGCTTAGCA TTTTTCTTCT CACTGAAAAA
74051  AGGAATGCAG AATAAATATA TTAATTTTCT GTTATTCAGA GGTTAATTTA
74101  ACAATTTTCT TGAATTTACT GTGTTTTACC TCCTCTAATG CTCAAGTAAA
74151  AGCATTGTTG AGCAGATAGT GCCAGCTGAT AGGAGAAAAA GAGGGTGCTT
74201  TCTGTCTTTC AGCTTTGACT CAGCATGATC TGAGTCAGCA CATGGCCAGA
74251  TAGGTCCTGA AACACCAGGC CTTTCTATTC CCTCGTTGCT CTTAAGGATA
74301  ATACCAGACA ATAACGTTTA AATTATTAAA GGTATTAAAG TTCTTCCATA
74351  TCAAAAACCA AGTCCCTGCC TTAGCTAGGT ATAGAAAAGA ACGGTTAAAA
74401  GAACCGGTGG CCAATGATGG TCACTTTGAA TTTAGAGAGT GCTGTGTGGA
74451  GAGGCATTTG ACCCTCTCTG TGTGACCCCA GCAGGCAGAC TGAGACGTGG
74501  GAGTTAGTGT AACGGGAGCT GCGGAGACAC TGAGTGGGAG TCGGGGAGCA
74551  GGGGCCATTT CAGGATGTGG GGAGGTTAGA CCACAATGGC CACTAGCAGC
74601  AGGGCTGCCC CGAATTAGGC GCTAAGTACT CTTTGAACTC TGAAATGCTG
74651  TGCTTCTAAT TTGGGGTATT AAGTTGGTG ATATAACCAG AAAAATAGGA
74701  CGCAGTCACG GATGTAGTGG GTTAATGGAG CTTTCAGCAC AATTTTATAC
74751  CAGGTTATCT GACCTGCCTT CCATTAGATG AACGTTGTC CCTCCATACA
74801  ATTTCCCTGT CCTGCTTACT TCTTGAAATG CTATTGCTGT GAACAGTGGC
74851  ATAAATATCA ATAACAGATT CCCAAGGAAA AGCCTTTCTG TCTTCTCACC
74901  TGCCCCCTTC CCAAGAATTA AGCATAAGCT CCCTCAGTGC TGTCAGGACG
74951  GCTTATGAGG TTTGCTTTTT CAGTTGGTTG TCATAAGGGA GGTTTTTTTT
75001  TTTTTGAAA GGGGCAGGCC CTCATTCACT GCTTGCCCCA CCCCCCAAAA
75051  GTCATGGCTT TAGAGGTTTC TTTTGTTCCT CCTAGAGAAC CTAGGAGCAA
75101  TGAGGCAGTT TTTCTTACCT CATCGTTCTG TTGTAGTGTA AAAATAGGAC
75151  ATTTAATATA TTAAATTTGA CCTCATAATA CCAAGCTGTC ATAAGGCCAC
75201  AGATGGTTCT TGGTGGTAAA GCCTATATAT AGTCTTTGAG GGTTTTGTTT
75251  GTTTGTTTGG AGACAAGGTC TTGCTCTGTT CCCCAAGCTG AAGTGCAGTG
75301  GCAGGACTAT AGTTCACTGC AGACTCCACT TCCCAAGCTC AAGTGATCCT
75351  CCCACCTCAG CCTCTGGTGT AGCTGGGACT ACAGGCACAT GCCACCACGC
75401  CTGGCTAATT TTTGTATTTT TTGTAGAGAT GGAGTTTGTC ACGTTGTCTA
75451  GGCTGGTCTT GATCTCCTGA GCTCAAGTGA TCCACCCGCC CTGGTCTCCC
75501  ATAGTGCTGG GATTACAGGG ATGTGACACT GTGCCCGGCT GTCTTTGAGA
75551  TTTATAAATA GCATCAAATC TCACAGAGAC TCTGTTGGGA ATGAGAGCTG
```

FIGURE 3, page 24 of 30

```
75601  ACGGGTGGTA GCCATTGGCT ATTGTCAGGG AGGACAGCTT TAGGCTCTGC
75651  AGCTGGAGAA GCACAACAGA ATGAGGGACC ACAGCAAGGG TATGTTGGGT
75701  TTGGATCTGT TTTACTTTTC TTGAGTTTTA CTTTTTTTTT GAGCTTTACA
75751  CCTTCCAGTG TAAGTACATA TAATCTGAAA CTTCTTTGTG GCTGAAGCAT
75801  TGGTTTCTCT GCATTATGT ATTAGAGTCT CTGATAGGAC TTTTTATGAA
75851  CTCCATGGTG AGTCCTGGTT AGTGCCATAG AAACAAGAAA AGCCATTCCA
75901  ACAAACTTCA CCAGACTTCT TCGGCACTGG TCACATTACA GAACAAATAC
75951  GTGATCTTAT TTGTTCAGAA TCGGGATACT TCAGCATAGG AGAATGTTTT
76001  AGGAGAGAGG TAGTTGGTCT CCCAAGAATC TGGAAACAAG TAGGTCCAGG
76051  GAAGAGCCCT TTGAGGGGAT TGAGCCAAGT AGAGAAGAAT CCGGAGTTCC
76101  CAGGTATTAA AAATAATAAT AAAGATTATA CTTAGGCCCA GCGAGGTGAT
76151  GCACACCTGT AATCCCAGCA CTTTGGGAGG CCAAGGCAGG CAGATCACTT
76201  GAGGCCAGGA GTTTGAGACC AGCCTGGCCA ACATGGCAAA ACCCCATCTC
76251  TACTGAAAAT ACAAAAATTA GCTGGGCATG GTGGCACGTG CCTATAGTCC
76301  TAGCTACTCA GGTGGCTGAG GCAGGAGAAT CGCTTGAACC CAGGAGGCAG
76351  AGGTTGTAGT GAGCCAAAAT TGTGCCGCTG CACTCAGCCT GGGCAATAGA
76401  AGGTTATACT GGGAGTAACT GAGTTGAAGG CAGAGTTTTT TTCATTGTAA
76451  TGTGCATTTG CCCTGTTGTA CATGTTGTAT TGTTAAGAGA ATCTTGCCAC
76501  TCTCCAAAGA ATCAAAAATG GGTAGCATTA CAGCCTTCAT CTTCCTTGTT
76551  CCTTTAAAAA AAAAGAAAAT TATTTGGCCG GGCTTGGTGG CTCACGCCTG
76601  TAATCCCAGC ACTTTGGGAG GCCGAGGCAG GCGGGTCACG AGGTCAGGCT
76651  AACATGGTGA AATCCCGTCT CTACAAAAAA TTAGCCGGGC GTGGTGGCGG
76701  GCGCCTGTAG TCCCAGCTAC TCAGGAGGCT GAGGCAAGGA GAATGGTGTG
76751  AGCTTGCAGT GAGCTGAGAT TGATTGTGCC ACTGCACTCC AGCCTGGGCG
76801  ACAGAGCGAG ACTCCGTCTC AAAAAAAAAT TATTTCATTG GTTGGCTTCT
76851  ATACATGTTT TCTTGGGAAT ATGTGGGTGC TAATCAAAAT GATGATTTTT
76901  TTCAAAGAAT ACATACCTGA CATATTTTGG CAGTAAGAAA TATGTACAAA
76951  GCTGGGTGCA GTGTAGTGCG CCTGTAGTCC CAGCTTCTCT GGAGGCTGAG
77001  AGAGGATCAC TGGAGCCCAA GAGGTTGAGT CCAGCCTGGA CAACATAGCG
77051  AGGTCCCTTC TCTAAAAAAT ATGAAAGAAA AAGAAATATA TGCAACCAGA
77101  TTGAAGTCAT TTTGAAAATT AATTAAAAGA GTTAGTTAGC ATAGGGCTCA
77151  AGGCAGGGGT TGAAAAGCAG CTTGGAACTT GATCCAGGCT TTTCAAGTCC
77201  TCGTTGTCCC ATTAGAGTTT TCAGATTTTT CTCTTAGCTT GTAAGATACT
77251  GAATTGATTG TTTCCCAGGC TAGAAGGACT CTCCTGGCCA TTGAGTGTGT
77301  AATCTAGTTG TTCCACTTGG ATTTGGGGCC AGTTATGAGG TTTTCCTGCC
77351  CTCATCTGGG ATTGGCCCAA CTGTCTTCTT TGTTTATTGG GTGGAAAGGA
77401  GAGGCCCTAC ATAAGGGCTT TCCTGGGTTT TCTGCTGGTG CCTTCGTGCA
77451  TCCACAGTGC TGGGACCACC AGCTCACCAT GCTGAGATGT GACATGTCCG
77501  TGTCTTGCTC AGACCTATGC CAGGTTCAGG GCAGGGATCC TGAGTTCATA
77551  AATTAATGCT TATCGCTCGG TCAGCTGGAA GCCATCTTGT CACCATCCTT
77601  CCTTCCTTCA AGTGATTGAC AGGCAGTCTT TTTTTTTAAA AAAGGTGAAA
77651  AGATGTGGTC CTGGGCTGAC TGCACTCACT CTTGGTTTGT TAAAGACAGT
77701  GCCAGGAGAG GTGGCCCCTC ACCCAGGCAG GTGAGCCTTC CCTTAAAGGT
77751  GCCTTTCCAG CACTGTGTGG TCATTGAAAG AAAAAGAAGG TAGGTTGATG
77801  CAGTGAAGTT TCCCCAGTAT TGGCTCCTTG GGGCGGGAAT GGGGAGGGCA
77851  GTCACAGATC CACAGGCATC AGTGATTGGG CCTCTGAGCA CCTTTTGGGA
77901  CAGCAAGATC CGTTCAGAAT AGAAGCAGCT ATGAGAAAAA CCAGAAATGG
77951  GATTTAGCTT ATTCTTTTTT TCTCTTTTAA AACATTCTCT TTGATCAGCA
78001  GAGCAGTAGC AGTTGCCATT TTTGTATATT GTTACTAGCT TAAACTCATG
78051  TTTTTGAGGG TTTTTTTGTG AGCAAGGGAA ATGGGAACAA ATGGTGTTCC
78101  CTACATGCTG GCATGCTGAG GGACAGCCAG TGGCCACCCA GGAAGCCAGT
78151  GCTCCGTGAC ATCCACAAAA GGGTCTGCAA GACCATCTGC TTCCTCTGGC
78201  CCTGGGACA AAGAGGGTCT TTTTTGTTTC CAGGTTTTCC TTTGGTTGAA
78251  TCAGAAATGA ATGAAATGCT GATGAAATG GTTGATGAGA TACTGAAAAT
78301  AGTCCTTGGT TACTAAAACA TGAAGGTCTT CGCCTAAAAG ACGCAGCAGT
78351  GTCTGCTATA CAGAGGCCAA GGCTATTATA GTGGTTGAGG CAGGTGCTGG
78401  AGTCAGACGG GCCTTGTTGA GTCCTGGGTT GAACTCTCGT TCTACCATTT
78451  ATAGAGTGCA TACCGCGCTC TGGCCAGGCC TGCATGCAGG TGCGGCTGAC
78501  TCACTGACGT TTTTGGTTTT GCTTCCTGCA AAATGAAGAG AATACATAGC
78551  TCTTATATCT TTCCTTAGAA ATGTAAAAAT ACTTCTGAAA CTTCTTTGAA
78601  TGTGGAAGAA AGAAAAAAAT TAGTATTGAG CACTTTCAGG AGGCTATTTT
78651  GTTTGATTCA GATCTTCATA AAGTGGCGGT CTCTTCTATA AGGAGAAAAA
78701  GCTGTTGACT TGGGGGCCAG TCTCTGAAGT GCTTAGCATG TCGTCTGTTG
```

FIGURE 3, page 25 of 30

```
78751  TATCCTAGGC ATTTGAGCTG GCAACGGGAG ATTATTTGTT TGAACCACAT
78801  TCTGGGGAAG ACTATTCCAG AGACGAAGGT GAGTATTGGT GCCTGCTGAA
78851  TACCTCGGTC TAGGTCTTCT GCCAGCCCTG AACTTCTGTA GAGTACTGTA
78901  TTTTTGTACT GAAATAGAGC CATGTGTTTG GTTTCAAAC ACCAAATTCA
78951  GATGCTTTTC CTTTGAGTTT GATGCCCCCT CAGTCTCAGT GAATGGGCAG
79001  AGCCTGCCTA GCACAGGCAG CACTCCAGCG AGCCCTCAGG GGCCCTACAC
79051  CAGCGGCTCT TCCTGGCCTT GCACAGGGCA GGAACCCAGC TGGCTGAGAG
79101  AAGACAGATG ATACAGACCT GAAGCCTCTA TGTGGTCCTT TTGACCATTG
79151  ATGTGCTGCC CATTTCTCTG TCCTGTTTGG GAGCTGAGTT GAAAACCCAG
79201  GAATTCTGGC TTGAATGCCA TCTGTAAACC TGACCATCTC CATGCTTATT
79251  TGCTTGCGAT GCTGGGGTGG CCTGGGGTGA GCTGGCCTCA GTCACTGTTA
79301  CTGCTCCAGG TGGTGCCTGA GGCCTGCCAT TCCCACAAGC CTCTGCATGG
79351  ATGTGCTGCA GACACTGTTG ATTTGAATCT ATTTCTGATT TTTTACTAAT
79401  TTCAATTTTT CCCTCTTCTT TTATCCCATC CTTCCCTTTG CCCCTCCCAT
79451  TCCCATATCC TTTTTTTCTC TCCTCCATAG ACCACATAGC CACATCATA
79501  GAGCTGCTAG GCAGTATTCC AAGGCACTTT GCTCTATCTG GAAAATATTC
79551  TCGGGAATTC TTCAATCGCA GAGGTAGTAC CTCTTCTTTT TGAAAAGCGC
79601  CACGATGCAG ACAGAAACTG AAGAGCAGCT GCTGATTTTA GCATTAATGG
79651  TGACAAAGGC ATTTCTCCTA AATTCGAAAC GCAACCCAGC AGAATTCCTA
79701  TGCTGATAGA AAAATTGTCA GGGAAGACCA CATTTAGCCC TGTGCTGCGG
79751  TCACCCTGTT CACCAGCCCC TCTCCTGTGC CCTCCAGCTC TGGATCCTGA
79801  ATCCAGCAAC GCGAGGAAGG CCTGTACTTT TGGTCATTCA AGTTGCGCTC
79851  TGTTTCTGTC TGCGCGGGCG GTGGTAGTGT CTGCATGCAG TGTACTGATT
79901  AAACTGTCGT GTGTTTCTGT TTTGCTGGCA ATGTTTCCCA ATGCAGATCA
79951  CATAGCATTG ATCATTGAAC TGCTGGGGAA AGTCCCTCGA AAATACGCTA
80001  TGTTGGGGAA ATACTCCAAG GAGTTTTTCA CCAGAAAAGG TAACGGTATT
80051  TATGCAACAC TAATTTTCAG CATAGTCTTC TCCCAAAAGG AGAAATTGTG
80101  CATTCGTGAT TGGGCAGTGG AGAAAGATCT GGAGTTTCAC AACTGGGGAA
80151  TTCTTCCGAA GAAAGCTCTC AAGAAATAAA CCTGACCCAT CTGATACCTG
80201  GAGTAAGAAT TTTGTAAGAG AACAGCCTTC CTAACAGCAT TTTTTCCTCC
80251  TCCGCTTCTC TCTTTTACTC CAAGTTACCA ATCTGTATAT TATTTATAAA
80301  AAGGAGTTTA GGTGATTGTT AAAAGCCAGC TAGACTTATC TTTCCATTTC
80351  ATGGACTCTC TGTAGTAGAA CAGAGGTGGC CTAGAGACTG GACTTAGGGA
80401  ACGTCCAGGG ACATTGCTTT TGGTCTGCCT GGGTTATTTC TGTAGTGGGT
80451  GTAGGCCTGT GAAATGCTGC GTACCTCACA TTCTTAAAAA TGACATCCTA
80501  CATTCCCATT GTGTTATGCC ACACTGTATT AAGGTGATTA TTTTCATGTT
80551  GTAGTTCTTA CTGATCTTCC AACTGTTTAT TTGCCCAGTA TAGTCCCCAG
80601  TTAGTAATTT ATAAAAACAC CAAGAGCCC TAGGAGTATT TTTAAAGAA
80651  CTCCTTCTAA GTGCTATATT CTTTTTTTTT TTTTTTTTT TGAGATGGAG
80701  TCTTGCTCTG TTGCCCAGGC TGGAGTGGAG TGGCGCAATC TTAGCTCACT
80751  GCAACCTGTG CCTCCCAGGT TCAAGCAATT CTCCTGCCGC AGCCTCCCAT
80801  GTAGCTGGGA TTACAGGCAC ACCACCACGC CCAGCTAATT TTTGTATTTT
80851  TAGTAGAGAC AGGGTTTCAC TGTGTTGGCC AGGCTGGTCT CAAACTCCTG
80901  ACCTCAAGTG ATCCACCCGC CTTAGCCTTC CAAAGTGCTG GGATTACAGG
80951  CATGAGCCAC TGCGCCCAGC CTGCTGTACT TTTTTGTGAT GAGTGTAGTT
81001  GGTCCTTCAT ATTTTTCAGG TTAGATTTTT TTTTTGGATG TGACAGCCCT
81051  TAATAAAGAA CTTTTAAAGT TGATGTGAGT AGGACATGGA CTTTTAGAAA
81101  TTTCTGAAAG TCCCAGATGC TCTGTCTACC TTACTTAGCT AAATTTGGAG
81151  AACCACATTG ATTTTTTTTT TTTTTTTTT TTTTTTTTT AGATGGAGTT
81201  TTGCTCTTGT TGTCCAGGCT GGAGTGCAGT GGCGCAATCT TGGCTCACTG
81251  CAACTTCCGC CTCCCAGGCT CAAGTGATTC TCCTGCCTCA ACTTCACAAG
81301  AAGCCGGGAT TACAGGCACC TGCCACCACG CCCGGCTAAT TTTTGTATTT
81351  TTAGTAGAGA GAGGTTTTCA CCATGTTGGC CAGGCTGGTC TCGAACTCCT
81401  GACCTAAGGT GATCCACCCA CCTCGGCCTC CCAATTGCTG GGATTACAGG
81451  TGTGAGCCAC TGCGCCTGGC TGTGCATTTA TTTGTCTTTG TTAATCGTCT
81501  GTCTGTTGAG GGGATCGAGG ACTCCATACT GTGCACAGCG GAAGGAAGG
81551  AAAGAGGGAC AGAAAGAGAG GCCTTGAATG ATCAAGTGAA GTCACTGAGT
81601  TGTTGGAAGG CAGGGCCTGT CAGCGGCCTG CAGGCATGGA GCTGGTTGCA
81651  GGCATCTGCT CTTGGGCTGT CACTCCTGTG ATGGTTCCTT TCAGTGAGAG
81701  CGGCCTGCGT GTGGCCATAA ATGGCTGGAA GGCAGCTTCC ACGTGGGCCT
81751  GTCAGCAACC TTGCTCCCTG AGACAGCTTG TGGATGTGTA CTCCAGGTT
81801  ACTGCCATCA TCACCACGTA TACTTAGGAC TTACGTGATC GAGTTCTTTT
81851  TGAGCAGCTT ATTTGAAGGT AACCTGCAGA GTTAAAATGC ATTTGGCATC
```

```
81901  CTTCCTAATG AGAGACCAAA AATATTTTCA CTTGGTGTTC CTGTGGTACC
81951  TCGAGTTCTT TTTTCCTGTT TTTGGATATA AGAGACCGTT TGTGACTAGG
82001  TGAGAAATCC CCTGAAATGA CTGGGAATTG GGACTTCAGT TCTTTCCTGA
82051  TTATTATTTC TAATGGCAGT AGAGATCAGA AGGGATTTAG GGTTTTTACA
82101  GAAGTCACAG GATAACATTA TGAGGAATGA GGGCCGGTCA TGGAAATAGA
82151  TTTCACCGTT GTCTCTTAGG ATGAGGGGAA TGGCTTGCTG CGTGAAACAT
82201  GTGTTTTGGC ATGTTCCCAT AAGTAATATA GGGGAAATTC CATAATTTCC
82251  ATAATTTTGG AAATAATGGA ATCTTAAAAA TATCCATTTA AATTTTTTTT
82301  CCTAAAATAG CTAAAATACT TTGTGCTAGA ACTGATAACA AAATTTAAAA
82351  CAGCTGTTGA TATGCCGTAT CACTTTTGAA AGCAGTTACT GATGGAGAGT
82401  GCCTTCCCAG GAGGTTTTCC CGCTCTTTCT CCTCTGGGTC AGAGGCAGAT
82451  TTTCATCCTT GCCACGCAGC CAGAGAAGAG TGGGGTCTGT GTGTTAAGGT
82501  TGAACATCAA ATGCAGCTCA TTTGTCTCCT CTCCTTGCGT ATAATTTAAG
82551  AAGTCATGAT CATTACTAGT TTGAATCATT CCTTGGCCAG AAAGTTAAAA
82601  ATTGAGCTGT ATTTTTGGTC AGGGAATGTA ATTACAGCTC TCACCCTCTT
82651  AAGGTTAATT TGCTGGACAT GAGCCACCAA AAAGCATTAA GAAACTACTG
82701  TGTTGATAGG TGGTCCAATA GAAATCAGCA CGTCCATGAA TTTTTTCCCT
82751  GTCCTGTCTT CAAGAAGTGG GTGGTCCCCA GAAGCTTTCC AGCCCTCAGA
82801  TCATGGTAGG AAAAACGGTG CAGCCAGGAG CAGACCTCAC TGGGCTGGTC
82851  ACCAGGAATT TTTCTGACCA TTCAGCAGGC ATATTTAGT AAAAATTGCT
82901  GCGTGGATAA TGGGATTATC AAATGAGACA GTTTACTTAA AAAAAAAAAA
82951  CTGGTCTCTA GATGACAGCA TCGAGTGTGT TGGGATAAAA GAGAGTGATT
83001  GTGTGCATGT GTGCGCGCGC GTGTGTGTAT GTGTGTGTGT CAGACTACAG
83051  ACCTTAAATA CAATTGAAAA TTTCAAAAGC AAGAAGCTTC TGTGCAGCAG
83101  CATAAAATCC ACGTTTCCCT GAGTCAGGGA CAACATCAAG AGAAATGTGA
83151  GAACTGAGGG CTAAAACCCA GGAGCTGAGT TTTAAAAAGA GATACTGTAT
83201  TCTGTATTTT TAATATTTAG TGTCTGAGCT GAACTTGTCA CAGTGTTTTA
83251  AAATTATCTC CTGAATACCT AAAAGCAAC AGATTCTTTT GATGCTGTAA
83301  AGAGCAAAGA AAGCTCTTTC GTGGGCATTT GACAGCTACA CAGGCTGGGC
83351  GTTGTCACTG CCACTCCTCT TGTTTATCCC TCCATCAGAT GATGGGCGTT
83401  TGGTTTTCCC CCACTTTTTG GCTATTATGA ATGATGCTAC TATGATCATT
83451  AATGTACAAG TTTGTGTGGG CAGATGTTTC CGTTCTCTT GAATACACAT
83501  GTGAAAGTTT AAGTATAAAT TTTTAAATTT TGATGAAGTC CAATTTATAT
83551  ACATTTTACA ATTTGTGCTT TTGATGTCAC ATCTAATAAA TCATTGCCTA
83601  CTTCAAGGTC ATGAAGATTT ACTTTCTAG GAATTGTTTA GTTTTAGCTC
83651  TGAGGCATAT GACCTATTTT GAGTTGATTT TTGTATGGGA TGTGAGGTAG
83701  GGTTTATACA CATTTTAAAC TCCAATATTT ACCTACATTT GGTTGTCTAC
83751  TTGTGTAAGA ATTCATTCAG ATCTCTTCAT TGTCTCTTGC TTTGTATTGG
83801  TATTTCTTGG TAGGTTTACT TTCTACGTGT ACACAATTGA TGCTCATCAG
83851  TTTTATATCA TGGTTTGCTT TGTAATTACC AGTGTTCATG TAAATATAGT
83901  CCAGGATTTG CCTTTAGAGT CCTCCCACAT GTAGTGTGGA ACCTCATGGG
83951  CTTCTTTATT TAATTCTGGA ATATGACAAT TCATGGATA AAATAATGTA
84001  TTTTCCTTCA CAAACCACTT TAAGATTCAA GAGAAGTATA ATAGAACTTC
84051  CCTGTTTCCT TAGAAGGACT CTGCAAGTCC AGGACTGGCC AGTACAGTTG
84101  CTGTCACAAA GCCTTTACTC TGCAGGAGGA ACCCTTCCTC AGAGCCTGCT
84151  TCCTGTTGGT TTTCCTTGGC TCTTTCAAGC TGTTTCTCAG AGCAAATTCA
84201  GAAGCCTAAG GGGCTCTTGG GGACCACACA ATTGGCTGCC AGGCTCATGT
84251  TTGCTTGTGT GTGTGTGAGT TGATACTGAG ATTGACAGCT GATAGTCACA
84301  GGAAGGGTGA AGTGATATTC CACATTCTTT AAGGAGGACA GGCTAGAAAT
84351  GGAACTTTAA GAAACTAAAA TTGTCACAGT TGTCTAGTTA TTTGCAAAAC
84401  TTGTTTCAGT GAAACACATC TTCATATATT TTCTTTTCTC TCTCTTTTTT
84451  TTTTTTTACG TCTTCATATA TTTTCTTTTT TCCTTTTTTT GAGACAGAGT
84501  CTCACTCTGT TGCCTAGGCT GGAGTGTAGT GATGCTATCT CGGCTCATTG
84551  CAACCTCTGC CTCCTGGGTT CAAACGATTT TTGTGCCTCA GCCTCCCAAG
84601  TAGCTGGGAT TACAGGTGTG CACCACCACG CCTGGCCAAT TTGTATTTA
84651  TTAGAGATCG GGTTTCACCA TGTTGGCCAG GTTGGTCTCG AACTCCTGAC
84701  CTCAGGTGAT CTTCCTGCCT TGGCCTCCCA GAGTGCTGGA ATTACAGTCA
84751  TGAGCCACCG TGCCCGGCCG ATGACATTTC TTTAACTTGT TAGGGTGCTA
84801  CTTTTATAGT AAGAGCAAAT GGTGAAAATG TGTTTTTAAA ATATGCTTTC
84851  CCCTCTTATT CTTAATTATC ATTCTAAGTG ATGGAGGTGG CTACATTTCT
84901  TGGGCATCAT CTGCAGGGCT GGAGCTGGCT CATGGACTCG AGACCCTCAC
84951  TCATTCAGTG AGCCCACTCT TGTTGTGTCT CCTAGCAATA GATACAGAGT
85001  TGGGGGCTTG GGCTTTGTGT TTAAGTAACC TTATCAACTA TTTCCAGGGC
```

```
85051  AAGGTTACTT CTTATACTGA GCTTAAGGGT TTGCACACAT AATCATTATA
85101  GCATCTGGGT GAGTTGATTT TCCTTTGCAT TATATTATAA ACTTTTTCCA
85151  CAAAAAAAGT CCACACATTT TTTTTTTTTT TAGAGGCGGT TCAGTGTTTT
85201  GTTATATTGC AGTGCTGCTC TGTGCTCAGG ACCATAGGTG TTTAGGACTC
85251  TCCTGCATAT ACTGTTGTTT ATAGACTGCT TCTTTGCACA GTCTTTACCT
85301  TGTTAAAAGT AGTTAGATAT TTTACTGCTC CTTGCGAATA TTTTTACCAG
85351  TTTATAGTAT GCCTAGTTAT GGATGAATAG TTTCTCATGG CCTTTCACTA
85401  TTATATTGTT TTGCTCACTG TTACTATGCA GCTGTTAAGC ATTTATAGTG
85451  GTAAAACTTC TCTTTTCATG GAAGATTGTA CTTAAAAGAT GCCTTGTTGA
85501  TGGATCTTAG TTTAACACCT GGCGCCTCAG AAATAGGTTC CTTTACTATT
85551  CTCAGCACAC AGTGCTTCTC TGTAGTTACC TATATTTGCA AACCTGGAGA
85601  GTATTTTTTC TGAGATAGAA TAGATTCATG TCATAAAAGT TCGCTCCCTT
85651  TCCCAGAGAA CTTGGTTTAG TCACATGTGA GCTTTCTTAG TTTGCTTTAA
85701  CTGTTGCTGT GGTGAGATCA ACAGTCTAAA TCAATATAGT CATATTACAG
85751  AAAATGTGGA AATTGAAATA ACCTACTAAC AAAAGCTGAT GTTTTGATTC
85801  AGTTGATTTC CATCTTAATG AGCATTTTAA TAATCTTGTG ATTATCTGTA
85851  GGACATAGTT TGACTGTTCT TTTACTGCCT AATGTTGTAC CATGATCTTC
85901  TCCCATGTTG TTAAGTAATA TTAAATACTA TTAAGTGAAT CTACCTTGGT
85951  TTTCTTTTAA CCACCATTTT ACTATTACTG GCTCTTCGTA ATTTTGCGAG
86001  TACATATAAT TTTGTGCCAG CATATATTAG GCATGAATTT GGGGTGGTGC
86051  AACCAGGGTT TATCTCCTTG GGCTGGATTC CTAGAGCCGG AATTTCAGGC
86101  TTAGAGGGAT AAACCTGCAG TCTCTGTTCA GACTTTGTTT TTATGGAGAC
86151  TGTGTTTCCT TCAACAGGAG ATCCTTTCCC GCCTCTAATA TTACAGGTTC
86201  ATTTCTTCAT CAACACAGAC CTGATGTCTA GTCTGGATGC GATGCTTTAC
86251  TCTAGCTCCA GTCCTCATAT TGGAAACAGA AGCTTATTTT ACATCTCAGC
86301  CCCTTTAGCA AGCAGCCCTC TTAAAGATTC TTTATACGGA ACCCTGTGCA
86351  CAGCATGATT GCAACTTTGT AGACATACTA GTGTGTAAGA ACACTCTTCA
86401  CAATAGACAC AAAAGAAGAG CAGTTGTGGG TAGGATTGTA GGCTACTTCC
86451  CCTTTTGTTC TTATACTTTT CTGTAATGCT CTTTCCTTTT CATTGTGTTT
86501  TTAAACGGGA GGGCTTTTCC AAGTTGACTC GAATAAATGG GTGAAACAGA
86551  ACAAGCCTCC TGAGAACACC TTTGTGAGCA GAGCACTGAT TATCTATTGA
86601  TGCATCTCAT GAAAAAAATG TACCTTGTTT AAATTAAAGC AGTTGAAAGG
86651  GGAGAGAAGT CAGTCCTTGC ATGAAGTGTG CCCTGCAGGT GCTTGAATGC
86701  CTCTCTCCCC CCACCGAGAC CTGGCTGCTC TGAGGTGTGG GCACAGGGGG
86751  GTGTTTCCTC TGCAGAAGCT GCTCAGGATG CACTGAGGGG CACCTAAGGA
86801  GGTCTGTGGG CAGGGGTGGG ATGTCCTATG AAAACTTCAA ACAGGCAGAG
86851  AAAACGAGTT ATTCACAGTG AAATTATCTG GAGCTTTTGA CAGTTTATTG
86901  CCTTTTTGAA AAGGTTATGG GGAGACAGGG TTTCGCTTGC TCTGTCCCAG
86951  GATGGAGTGC AGTGGCATGA CCTTGACTCA CTGCAGCCTT GACCTCCTGG
87001  ACTCAAGCAA TGCTCCTGCC TCAGCCTCCT GAGTAGCTGG GATGTACCAC
87051  CGTGCCCAGC TACTTTTTTT CTTTTTAAGT AGAGACAGGG TCTGGTCTAT
87101  GTTACCCAGG CTGGTCTGAA ACTCATGGGC TCAAGGGATC CTCCTGCCTC
87151  AGCCTCCCAA ACGGCTAGGA TTGCAGGAGT GAGCCACTGC CCTCAGCCCT
87201  TTATTGCAGT TTTGACTTAA AAATAACCTT TTTTTTCTCT TATGAAATGA
87251  CCATTACAGC TCGTAGGCCA TTTACTAGCT TGTTAGTCAT TCTGTTATGT
87301  CAACCAAAGC TGCCTGTAAC CGACACTTTT CATACTGCAG CTAGCACAGT
87351  TTGTGAAGTA TAACTTCAAG GTTTACAAAT TAATGTCCTA GGATCTTAGA
87401  TCTTACAACA AATGCGTAGA CATGAATGGT GTTTGATTTG GGTTGGCCTC
87451  AAGTTTGCAA ATTTTACGGA AGATCCCAGG TTGAAATGAG AGTGGCTTGC
87501  TTCAACCTTT GGAAAAGAAA ACACTCTGGG CAAACTGAGC CCACTCCACT
87551  TACTTAAAGA AGCTTAGAAC TAATGTGAAT GAACTATTAA TTAACCTCTA
87601  TTTAGATCCA CCAGGCTTAC TTGAAATATG CCTTGGTCAT ATGTACATGT
87651  AATGATTATT GCTTAGTGGG GAAAAGCTGG TGTTCTTTGT TGTTGCTGTA
87701  CAAGTGTTGA GCAGGTGGTT GTCCGCTTCA CTGAAAAGAA CCTGACTGGA
87751  CCAACAATGG GGAATGCAGA TTTGGAGCTT TCTTGACATT GGCCTGTTTT
87801  TTCCCCTGTA GGAGAACTGC GACACATCAC CAAGCTGAAG CCCTGGAGCC
87851  TCTTTGATGT ACTTGTGGAA AAGTATGGCT GGCCCCATGA AGATGCTGCA
87901  CAGTTTACAG ATTTCCTGAT CCGATGTTA GAAATGGTTC CAGAAAAACG
87951  AGCCTCAGCT GGCGAATGCC TTCGGCATCC TTGGTTGAAT TCTTAGCAAA
88001  TTCTACCAAT ATTGCATTCT GAGCTAGCAA ATGTTCCCAG TACATTGGAC
88051  CTAAACGGTG ACTCTCATTC TTTAACAGGA TTACAAGTGA GCTGGCTTCA
88101  TCCTCAGACC TTTATTTTGC TTTGAGGTAC TGTTGTTTGA CATTTTGCTT
88151  TTTGTGCACT GTGATCCTGG GGAAGGGTAG TCTTTTGTGT CTTCAGCTAA
```

FIGURE 3, page 28 of 30

```
88201  GTAGTTTACT GACCATTTTC TTCCTGGAAA CAATAACATG TCTCTAAGCA
88251  TTGTTTCTTG TGTTGTGTGA CATTCAAATG TCATTTTTTT GAATGAAAAA
88301  TACTTTCCCC TTTGTGTTTT GGCAGGTTTT GTAACTATTT ATGAAGAAAT
88351  ATTTTAGCTG AGTACTATAT AATTTACAAT CTTAAGAAAT TATCAAGTTG
88401  GAACCAAGAA ATAGCAAGGA AATGTACAAT TTTATCTTCT GGCAAAGGGA
88451  CATCATTCCT GTATTATAGT GTATGTAAAT GCACCCTGTA AATGTTACTT
88501  TCCATTAAAT ATGGGAGGGG GACTCAAATT TCAGAAAAGC TACCAAGTCT
88551  TGAGTGCTTT GTAGCCTATG TTGCATGTAG CGGACTTTAA CTGCTCCAAG
88601  GAGTTGTGCA AACTTTTCAT TCCATAACAG TCTTTTCACA TTGGATTTTA
88651  AACAAAGTGG CTCTGGGTTA TAAGATGTCA TTCTCTATAT GGCACTTTAA
88701  AGGAAGAAAA GATATGTTTC TCATTCTAAA ATATGCATTA TAATTTAGCA
88751  GTCCCATTTG TGATTTTGCA TATTTTTAAA AGTACTTTTA AAGAAGAGCA
88801  ATTTCCCTTT AAAAATGTGA TGGCTCAGTA CCATGTCATG TTGCCTCCTC
88851  TGGGCGCTGT AAGTTAAGCT CTACATAGAT TAAATTGGAG AAACGTGTTA
88901  ATTGTGTGGA ATGAAAAAAT ACATATATTT TTGGAAAAGC ATGATCATGC
88951  TTGTCTAGAA CACAAGGTAT GGTATATACA ATTTGCAGTG CAGTGGGCAG
89001  AATACTTCTC ACAGCTCAAA GATAACAGTG ATCACATTCA TTCCATAGGT
89051  AGCTTTACGT GTGGCTACAA CAAATTTTAC TAGCTTTTTC ATTGTCTTTC
89101  CATGAAACGA AGTTGAGAAA ATGATTTTCC CTTTGCAGGT TGCACACAGT
89151  TTTGTTTATG CATTTCCTTA AAATTAATTG TAGACTCCAG GATACAAACC
89201  ATAGTAGGCA ATACAATTTT AGAATGTAAT ATATAGAGGT ATATTTAGCC
89251  TCTTTTAGAA GTCAGTGGAT TGAATGTCTT TTTATTTTAA ATTTTACATT
89301  CATTAAGGTG CCTCGTTTTT GACTTTGTCC ATTAACATTT ATCCATATGC
89351  CTTTGCAATA ACTAGATTGT GAAAAGCTAA CAAGTGTTGT AACAATAATC
89401  CATTGTTTGA GGTGCTTGCA GTTGTCTTAA AAATTAAAGT GTTTTGGTTT
89451  TTTTTTTTCC AGACATTGCC TTGGTCATTG CCCTATAAAT GATAGAATCA
89501  ATGAACATTT GCTATCAGAG TAGTGTCACT AAAACTAAAT ACCAGCATTC
89551  CTGTTGCAGC AGATGTAGTT GTAGAACATG CATTGAGGCG TATTATAAGG
89601  AAATCATTTA TTGTTTTTTA AGGGCAGAAG GGATTTAGGA GAAAAGCTAC
89651  AGTATAGATT GATTCTCTAG AATATCAATG ATCCCTTTTC ATCCATGGTT
89701  CATCAAAAAC ATACTAACTG CATTTGTTTG ATCATTGCAA ATTTAAAACA
89751  AAACAGCATT TGCTGTTAGG AAACAAGACA CATAATCCTC TTAGGAATTA
89801  CCATTATATC ACATTACCAC TGTGAGGTAG AATGGATCAT TCATTAATTT
89851  CTTTATGAAA TTTGCATGCT AAGTTTTCT AATGAGGCTG TAGGTTTCCA
89901  TGTAAATTCT GTGATAGATA GTGGCTGTAG ACTGGTGATG CTATCCGTGA
89951  TTTCTATGAG AAACATCCTT ACAAGAACCA TAGGGCATAA TTTATATCTT
90001  CCCTAAGTGT AAAAGGATTT TTATCAGGGT GATAGTATAC TTGAATGAAA
90051  TTTGTCTAAT GCAGTTTTTG CTTATGTTGG AAAATAAACT AGATTATGAA
90101  TTTTTACAGG TGTGTCCCTT ATGATAAAAC AGCCTAACTA GTTTATAATA
90151  CAGAAACGGT TGTTCTAGAA GGAATATACA TTTGTATTAG CATAATATG
90201  GCTTTATCAG ATTCTTGGCG GCTTGTTGAT AAAGAATGCA CAAAAACTAA
90251  ATGAGAACCA CTGGTTATGC TAAACATTAT AACTAGCTCT CTGACTTCAA
90301  TTGAATGTCC TATCTATCTT TTCCTTTCTG TAGTCCATGT GAAATCTTCA
90351  TGGAAAATGA CAAGCAGTGG ATCACATATG TGTTTATAGC AGATACAGGA
90401  GCTGGCTATC TAGAAGTTGG CAGACAGAAC TGCCCAAAGG CAGAGAAAAG
90451  GTGGATATAA GATCTTCCGA GTCATAAACT TCTTAGGTGA AAACCGATTT
90501  ACTAACTTGC TTCTTCCCAT ACCTGGACCA TACATAACTA G
```

FEATURES:

| | | |
|---|---|---|
| 1999 | 2158 | Exon |
| 2159 | 36530 | Intron |
| 36531 | 36639 | Exon |
| 36640 | 37709 | Intron |
| 37710 | 37797 | Exon |
| 37798 | 38339 | Intron |
| 38340 | 38427 | Exon |
| 38428 | 45191 | Intron |
| 45192 | 45298 | Exon |
| 45299 | 59148 | Intron |
| 59149 | 59314 | Exon |
| 59315 | 60498 | Intron |
| 60499 | 60524 | Exon |
| 60525 | 62475 | Intron |

FIGURE 3, page 29 of 30

```
62476  62722  Exon
62723  63315  Intron
63316  63798  Exon
63799  72702  Intron
72703  72803  Exon
72804  72908  Intron
72909  72944  Exon
72950  87993  Intron
72950  73018  Exon
73019  78758  Intron
78759  78828  Exon
78829  79480  Intron
79481  79573  Exon
79574  87811  Intron
87812  87993  Exon
```

CHROMOSOME MAP POSITION:
Chromosome 7

FIGURE 3, page 30 of 30

ISOLATED HUMAN KINASE PROTEINS, NUCLEIC ACID MOLECULES ENCODING HUMAN KINASE PROTEINS, AND USES THEREOF

FIELD OF THE INVENTION

The present invention is in the field of kinase proteins that are related to the SRPK subfamily, recombinant DNA molecules, and protein production. The present invention specifically provides a novel SRPK2 alternative splice form that effects protein phosphorylation and nucleic acid molecules encoding the novel SRPK2 alternative splice form, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I-IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

SR-Protein-Specific Kinases (SRPK)

The novel human protein, and encoding gene, provided by the present invention is a novel alternative splice form of SR protein-specific kinase 2 (SRPK2), also referred to as SFRSK2. SRPK2 may play a role in autosomal recessive neurosensory deafness and neutrophil chemotactic response, which have both been mapped to chromosome 7 in the vicinity of SRPK2.

Mouse WBP6 (WW domain binding protein 6; WBP6/SRPK-1) supports the existence of an alternatively spliced SRPK2 gene product or an SRPK2-related gene. An SRPK-related sequence is also found on chromosome 8; this sequence is likely an intronless SRPK2 pseudogene with many inframe stop codons (Wang et al, *Genomics* 57 (2), 310–315 (1999)).

SRPK proteins phosphorylate the serine- and arginine-rich (SR) family of splicing factors, which are important for both constitutive and alternative pre-mRNA splicing (Wang et al., Genomics 57 (2), 310–315 (1999)); this SRPK-mediated phosphorylation regulates the functioning of SR splicing factors. SRPKs are important for spliceosome assembly and for regulating the trafficking of splicing factors (Wang et al, *J Cell Biol* Feb. 23, 1998; 140(4):737–50). SRPKs may also be important for tissue-specific regulation of SR protein disassembly (Kuroyanagi et al., *Biochem Biophys Res Commun* Jan. 14, 1998; 242(2):357–64). SRPK2 contains a proline-rich sequence at the NH2 terminus that can interact with WW domain proteins (Wang et al., *J Cell Biol* Feb. 23, 1998; 140(4):737–50). WW domains are found in a wide variety of proteins and modulate protein-protein interactions through binding of proline-rich ligand domains (Bedford et al., *EMBO J.* 16 (9), 2376–2383 (1997). SRPK2 is highly expressed in the brain, in contrast to SRPK1, which is highly expressed in pancreas. Different SRPK family members may regulate splicing in different tissues, different developmental stages, or in response to different signals (Wang et al., *J Cell Biol* Feb. 23, 1998; 140(4):737–50).

Kinase proteins, particularly members of the SRPK subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the SRPK subfamily.

SUMMARY OF THE INVENTION

The present invention is based in part on the identification of amino acid sequences of human kinase peptides and proteins that are related to the SRPK subfamily, as well as allelic variants and other mammalian orthologs thereof. Specifically, the present invention provides a novel alternative splice form of SRPK2. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart.

DESCRIPTION OF THE FIGURE SHEETS

FIG. 1 provides the nucleotide sequence of a cDNA molecule that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart.

FIG. 2 provides the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the SRPK subfamily. Utilizing these sequences, additional genomic sequences were assembled and transcript and/or CDNA sequences were isolated and characterized. Based on this analysis, the present invention provides amino acid sequences of human kinase peptides and proteins that are related to the SRPK subfamily, nucleic acid sequences in the form of transcript sequences, CDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention. The present invention specifically provides a novel alternative splice form of SRPK2

In addition to being previously unknown, the peptides that are provided in the present invention are selected based on their ability to be used for the development of commercially important products and services. Specifically, the present peptides are selected based on homology and/or structural relatedness to known kinase proteins of the SRPK subfamily and the expression pattern observed. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known SRPK family or subfamily of kinase proteins.

SPECIFIC EMBODIMENTS

Peptide Molecules

The present invention provides nucleic acid sequences that encode protein molecules that have been identified as being members of the kinase family of proteins and are related to the SRPK subfamily (protein sequences are provided in FIG. 2, transcript/cDNA sequences are provided in FIG. 1 and genomic sequences are provided in FIG. 3). Specifically, the present invention provides a novel alternative splice form of SRPK2. The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/ cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/ cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score 100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. The gene encoding the novel kinase protein of the present invention is located on a genome component that has been mapped to human chromosome 7 (as indicated in FIG. 3), which is supported by multiple lines of evidence, such as STS and BAC map data.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. The gene encoding the novel kinase protein of the present invention is located on a genome component that has been mapped to human chromosome 7 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y Acad Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that the kinase proteins of the present invention are expressed in humans in neuronal precursor cells, fetal liver/spleen, schwannoma tumors, brain, testis, lung small cell carcinomas, genitourinary tract cell tumors, colon, lymph, and fetal heart, as indicated by virtual northern blot analysis. PCR-based tissue screening panels also indicate expression in the brain. A large percentage of pharmaceutical agents are being developed that modulate the activity of kinase proteins, particularly members of the SRPK subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart. Such uses can readily be determined using the information provided herein, that which is known in the art, and routine experimentation.

The proteins of the present invention (including variants and fragments that may have been disclosed prior to the present invention) are useful for biological assays related to kinases that are related to members of the SRPK subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that the kinase proteins of the present invention are expressed in humans in neuronal precursor cells, fetal liver/spleen, schwannoma tumors, brain, testis, lung small cell carcinomas, genitourinary tract cell tumors, colon, lymph, and fetal heart, as indicated by virtual northern blot analysis. PCR-based tissue screening panels also indicate expression in the brain.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that the kinase proteins of the present invention are expressed in humans in neuronal precursor cells, fetal liver/spleen, schwannoma tumors, brain, testis, lung small cell carcinomas, genitourinary tract cell tumors, colon, lymph, and fetal heart, as indicated by virtual northern blot analysis. PCR-based tissue screening panels also indicate expression in the brain.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the kinase proteins of the present invention are expressed in humans in neuronal precursor cells, fetal liver/spleen, schwannoma tumors, brain, testis, lung small cell carcinomas, genitourinary tract cell tumors, colon, lymph, and fetal heart, as indicated by virtual northern blot analysis. PCR-based tissue screening panels also indicate expression in the brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel kinase protein of the present invention is located on a genome component that has been mapped to human chromosome 7 (as indicated in FIG. 3), which is supported by multiple lines of evidence, such as STS and BAC map data.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel kinase protein of the present invention is located on a genome component that has been mapped to human chromosome 7 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the kinase proteins of the present invention are expressed in humans in neuronal precursor cells, fetal liver/spleen, schwannoma tumors, brain, testis, lung small cell carcinomas, genitourinary tract cell tumors, colon, lymph, and fetal heart, as indicated by virtual northern blot analysis. PCR-based tissue screening panels also indicate expression in the brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that the kinase proteins of the present invention are expressed in humans in neuronal precursor cells, fetal liver/spleen, schwannoma tumors, brain, testis, lung small cell carcinomas, genitourinary tract cell tumors, colon, lymph, and fetal heart, as indicated by virtual northern blot analysis. PCR-based tissue screening panels also indicate expression in the brain.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that the kinase proteins of the present invention are expressed in humans in neuronal precursor cells, fetal liver/spleen, schwannoma tumors, brain, testis, lung small cell carcinomas, genitourinary tract cell tumors, colon, lymph, and fetal heart, as indicated by virtual northern blot analysis. PCR-based tissue screening panels also indicate expression in the brain. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in humans in neuronal precursor cells, fetal liver/spleen, schwannoma tumors, brain, testis, lung small cell carcinomas, genitourinary tract cell tumors, colon, lymph, and fetal heart.

The nucleic acid molecules are also useful for monitoring the effectiveness of modulating compounds on the expression or activity of the kinase (gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. The gene encoding the novel kinase protein of the present invention is located on a genome component that has been mapped to human chromosome 7 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077–1080 (1988); and Nakazawa et al., PNAS 91:360–364 (1994)), the latter of which can be particularly useful for detecting point mutations in the gene (see Abravaya et al., Nucleic Acids Res. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al, *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that the kinase proteins of the present invention are expressed in humans in neuronal precursor cells, fetal liver/spleen, schwannoma tumors, brain, testis, lung small cell carcinomas, genitourinary tract cell tumors, colon, lymph, and fetal heart, as indicated by virtual northern blot analysis. PCR-based tissue screening panels also indicate expression in the brain. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et a.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sanbrook et al, *Molecular Cloning. A Laboratory Manual.* 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli,* Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed, *Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., *Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P 1. For a description of the cre/loxP recombinase system, see, e.g., Lakso et al. *PNAS* 89:6232–6236 (1992).

Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a polypeptide comprising the amino acid sequence of SEQ ID NO:2;
   (b) a nucleotide sequence consisting of SEQ ID NO:1;
   (c) a nucleotide sequence consisting of SEQ ID NO:3; and
   (d) a nucleotide sequence that is completely complementary to a nucleotide sequence of (a)–(c).

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering said polypeptide from the host cell culture.

5. An isolated polynucleotide consisting of a nucleotide sequence set forth in SEQ ID NO:1.

6. An isolated polynucleotide consisting of a nucleotide sequence set forth in SEQ ID NO:3.

7. A vector according to claim 2, wherein said vector is selected from the group consisting of a plasmid, a virus a, and bacteriophage.

8. A vector according to claim 2, wherein said isolated nucleic acid molecule is inserted into said vector in proper orientation and correct reading frame such that the protein of SEQ ID NO:2 may be expressed by a cell transformed with said vector.

9. A vector according to claim 8, wherein said isolated nucleic acid molecule is operatively linked to a promoter sequence.

* * * * *

SEQUENCE LISTING

<160> NUMBER OF SEQ ID NOS: 3

<210> SEQ ID NO 1
<211> LENGTH: 3253
<212> TYPE: DNA
<213> ORGANISM: Human

<400> SEQUENCE: 1

-continued

| | | | | |
|---|---|---|---|---|
| tcggcggagc | gagtggaggc | tgcagcccag | ctcgtctcgg | cgcccgcgtc gccgtcgcga | 60 |
| agccccccgc | ccgcttccg | ccgcgtcgga | atgagctccc | ggaaagtgct ggccattcag | 120 |
| gcccgaaagc | ggaggccgaa | aagagagaaa | catccgaaaa | agccggagcc tcaacagaaa | 180 |
| gctcctttag | ttcctcctcc | tccaccgcca | ccaccaccac | caccgccacc tttgccagac | 240 |
| cccacacccc | cggagccaga | ggaggagatc | ctgggatcag | atgatgagga gcaagaggac | 300 |
| cctgcggact | actgcaaagg | tggatatcat | ccagtgaaaa | ttggagacct cttcaatggc | 360 |
| cggtatcatg | ttattagaaa | gcttggatgg | gggcacttct | ctactgtctg gctgtgctgg | 420 |
| gatatgcagg | ggaaaagatt | tgttgcaatg | aaagttgtaa | aaagtgccca gcattatacg | 480 |
| gagacagcct | tggatgaaat | aaaattgctc | aaatgtgttc | gagaaagtga tcccagtgac | 540 |
| ccaaacaaag | acatggtggt | ccagctcatt | gacgacttca | agatttcagg catgaatggg | 600 |
| atacatgtct | gcatggtctt | cgaagtactt | ggccaccatc | tcctcaagtg gatcatcaaa | 660 |
| tccaactatc | aaggcctccc | agtacgttgt | gtgaagagta | tcattcgaca ggtccttcaa | 720 |
| gggttagatt | acttacacag | taagtgcaag | atcattcata | ctgacataaa gccggaaaat | 780 |
| atcttgatgt | gtgtggatga | tgcatatgtg | agaagaatgg | cagctgaggc cactgagtgg | 840 |
| cagaaagcag | gtgctcctcc | tccttcaggg | tctgcagtga | gtacggctcc acagcagaaa | 900 |
| cctataggaa | aaatatctaa | aaacaaaaag | aaaaaactga | aaagaaaca gaagaggcag | 960 |
| gctgagttat | tggagaagcg | cctgcaggag | atagaagaat | tggagcgaga agctgaaagg | 1020 |
| aaaataatag | aagaaaacat | cacctcagct | gcaccttcca | atgaccagga tggcgaatac | 1080 |
| tgcccagagg | tgaaactaaa | aacaacagga | ttagaggagg | cggctgaggc agagactgca | 1140 |
| aaggacaatg | tgaagctga | ggaccaggaa | gagaaagaag | atgctgagaa agaaaacatt | 1200 |
| gaaaaagatg | aagatgatgt | agatcaggaa | cttgcgaaca | tagaccctac gtggatagaa | 1260 |
| tcacctaaaa | ccaatggcca | tattgagaat | ggcccattct | cactggagca gcaactggac | 1320 |
| gatgaagatg | atgatgaaga | agactgccca | aatcctgagg | aatataatct tgatgagcca | 1380 |
| aatgcagaaa | gtgattacac | atatagcagc | tcctatgaac | aattcaatgg tgaattgcca | 1440 |
| aatggacgac | ataaaattcc | cgagtcacag | ttcccagagt | tttccacctc gttgttctct | 1500 |
| ggatccttag | aacctgtggc | ctgcggctct | gtgctttctg | agggatcacc acttactgag | 1560 |
| caagaggaga | gcagtccatc | ccatgacaga | agcagaacgg | tttcagcctc cagtactggg | 1620 |
| gatttgccaa | aagcaaaaac | ccgggcagct | gacttgttgg | tgaatcccct ggatccgcgg | 1680 |
| aatgcagata | aaattagagt | aaaaattgct | gacctgggaa | atgcttgttg ggtgcataaa | 1740 |
| cacttcacgg | aagacatcca | gacgcgtcag | taccgctcca | tagaggtttt aataggagcg | 1800 |
| gggtacagca | cccctgcgga | catctggagc | acggcgtgta | tggcatttga gctggcaacg | 1860 |
| ggagattatt | tgtttgaacc | acattctggg | gaagactatt | ccagagacga agaccacata | 1920 |
| gcccacatca | tagagctgct | aggcagtatt | ccaaggcact | ttgctctatc tggaaaatat | 1980 |
| tctcgggaat | tcttcaatcg | cagaggagaa | ctgcgcacaca | tcaccaagct gaagccctgg | 2040 |
| agcctctttg | atgtacttgt | ggaaaagtat | ggctggcccc | atgaagatgc tgcacagttt | 2100 |
| acagatttcc | tgatcccgat | gttagaaatg | gttccagaaa | aacgagcctc agctggcgaa | 2160 |
| tgccttcggc | atccttggtt | gaattcttag | caaattctac | caatattgca ttctgagcta | 2220 |
| gcaaatgttc | ccagtacatt | ggacctaaac | ggtgactctc | attctttaac aggattacaa | 2280 |
| gtgagctggc | ttcatcctca | gacctttatt | ttgctttgag | gtactgttgt ttgacatttt | 2340 |
| gcttttgtg | cactgtgatc | ctggggaagg | gtagtctttt | gtcttcagct aagtagttta | 2400 |

-continued

```
ctgaccattt tcttctggaa acaataacat gtctctaagc attgtttctt gtgttgtgtg    2460
acattcaaat gtcattttt tgaatgaaaa atactttccc ctttgtgttt tggcaggttt    2520
tgtaactatt tatgaagaaa tattttagct gagtactata taatttacaa tcttaagaaa    2580
ttatcaagtt gggaaccaag aaaatagcaa gggaaatgta caattttatc ttctggcaaa    2640
gggacatcat tcctgtatta tagtgtatgt aaatgcaccc tgtaaatgtt actttggatt    2700
aaatatggga gggggactc aaatttcaga aaagctaaaa aaaaaaaaaa agtaataagg    2760
aaaaatactc ttatattaaa atacccttc tttgtttttt tgttttcct atttcatatt    2820 attaaataca cttaacgttt cgaaagcact atgaaaaaat taataccatg aaaaggatca    2880
aaaatcataa atcaaaaccc cactatagtc caacgacaat tcattctcgg cggtcaactt    2940
tttaacatct tatactagta cctgagactc tggtgctcaa tattaatatt ctaaatctac    3000
caccaagtta ggcccgtaat gtcgtctctc tcgtgaatct gtcatacaat acattttct    3060 atttatttag tgggtctcgt ttatctttcg cccacatctt tgttcactat tttctagtta    3120
ctcttatctt tgggctgatt aatccttctc attatactca tataaacttc tgaattttc    3180 acataaaact actagagcta cctcaccatc tctgttttta acgcgagcag ttactatata    3240
attactattt aaa                                                       3253
```

<210> SEQ ID NO 2
<211> LENGTH: 699
<212> TYPE: PRT
<213> ORGANISM: Human

<400> SEQUENCE: 2

```
Met Ser Ser Arg Lys Val Leu Ala Ile Gln Ala Arg Lys Arg Arg Pro
  1               5                  10                  15

Lys Arg Glu Lys His Pro Lys Leu Pro Glu Pro Gln Gln Lys Ala Pro
             20                  25                  30

Leu Val Pro Pro Pro Pro Pro Pro Pro Pro Pro Pro Pro Pro Pro Leu
         35                  40                  45

Pro Asp Pro Thr Pro Pro Glu Pro Glu Glu Ile Leu Gly Ser Asp
     50                  55                  60

Asp Glu Glu Gln Glu Asp Pro Ala Asp Tyr Cys Lys Gly Gly Tyr His
 65                  70                  75                  80

Pro Val Lys Ile Gly Asp Leu Phe Asn Gly Arg Tyr His Val Ile Arg
                 85                  90                  95

Lys Leu Gly Trp Gly His Phe Ser Thr Val Trp Leu Cys Trp Asp Met
            100                 105                 110

Gln Gly Lys Arg Phe Val Ala Met Lys Val Val Lys Ser Ala Gln His
        115                 120                 125

Tyr Thr Glu Thr Ala Leu Asp Glu Ile Lys Leu Leu Lys Cys Val Arg
    130                 135                 140

Glu Ser Asp Pro Ser Asp Pro Asn Lys Asp Met Val Val Gln Leu Ile
145                 150                 155                 160

Asp Asp Phe Lys Ile Ser Gly Met Asn Gly Ile His Val Cys Met Val
                165                 170                 175

Phe Glu Val Leu Gly His His Leu Leu Lys Trp Ile Ile Lys Ser Asn
            180                 185                 190

Tyr Gln Gly Leu Pro Val Arg Cys Val Lys Ser Ile Ile Arg Gln Val
        195                 200                 205

Leu Gln Gly Leu Asp Tyr Leu His Ser Lys Cys Lys Ile Ile His Thr
```

```
            210                 215                 220
Asp Ile Lys Pro Glu Asn Ile Leu Met Cys Val Asp Asp Ala Tyr Val
225                 230                 235                 240

Arg Arg Met Ala Ala Glu Ala Thr Glu Trp Gln Lys Ala Gly Ala Pro
            245                 250                 255

Pro Pro Ser Gly Ser Ala Val Ser Thr Ala Pro Gln Gln Lys Pro Ile
            260                 265                 270

Gly Lys Ile Ser Lys Asn Lys Lys Lys Leu Lys Lys Lys Gln Lys
            275                 280                 285

Arg Gln Ala Glu Leu Leu Glu Lys Arg Leu Gln Glu Ile Glu Glu Leu
290                 295                 300

Glu Arg Glu Ala Glu Arg Lys Ile Ile Glu Glu Asn Ile Thr Ser Ala
305                 310                 315                 320

Ala Pro Ser Asn Asp Gln Asp Gly Glu Tyr Cys Pro Glu Val Lys Leu
            325                 330                 335

Lys Thr Thr Gly Leu Glu Glu Ala Ala Glu Ala Glu Thr Ala Lys Asp
            340                 345                 350

Asn Gly Glu Ala Glu Asp Gln Glu Glu Lys Glu Asp Ala Glu Lys Glu
            355                 360                 365

Asn Ile Glu Lys Asp Glu Asp Val Asp Gln Glu Leu Ala Asn Ile
370                 375                 380

Asp Pro Thr Trp Ile Glu Ser Pro Lys Thr Asn Gly His Ile Glu Asn
385                 390                 395                 400

Gly Pro Phe Ser Leu Glu Gln Gln Leu Asp Asp Glu Asp Asp Asp Glu
            405                 410                 415

Glu Asp Cys Pro Asn Pro Glu Gly Tyr Asn Leu Asp Glu Pro Asn Ala
            420                 425                 430

Glu Ser Asp Tyr Thr Tyr Ser Ser Tyr Glu Gln Phe Asn Gly Glu
            435                 440                 445

Leu Pro Asn Gly Arg His Lys Ile Pro Glu Ser Gln Phe Pro Glu Phe
            450                 455                 460

Ser Thr Ser Leu Phe Ser Gly Ser Leu Glu Pro Val Ala Cys Gly Ser
465                 470                 475                 480

Val Leu Ser Glu Gly Ser Pro Leu Thr Glu Gln Glu Glu Ser Ser Pro
            485                 490                 495

Ser His Asp Arg Ser Arg Thr Val Ser Ala Ser Ser Thr Gly Asp Leu
            500                 505                 510

Pro Lys Ala Lys Thr Arg Ala Ala Asp Leu Leu Val Asn Pro Leu Asp
            515                 520                 525

Pro Arg Asn Ala Asp Lys Ile Arg Val Lys Ile Ala Asp Leu Gly Asn
            530                 535                 540

Ala Cys Trp Val His Lys His Phe Thr Glu Asp Ile Gln Thr Arg Gln
545                 550                 555                 560

Tyr Arg Ser Ile Glu Val Leu Ile Gly Ala Gly Tyr Ser Thr Pro Ala
            565                 570                 575

Asp Ile Trp Ser Thr Ala Cys Met Ala Phe Glu Leu Ala Thr Gly Asp
            580                 585                 590

Tyr Leu Phe Glu Pro His Ser Gly Glu Asp Tyr Ser Arg Asp Glu Asp
            595                 600                 605

His Ile Ala His Ile Ile Glu Leu Leu Gly Ser Ile Pro Arg His Phe
            610                 615                 620

Ala Leu Ser Gly Lys Tyr Ser Arg Glu Phe Phe Asn Arg Arg Gly Glu
625                 630                 635                 640
```

```
Leu Arg His Ile Thr Lys Leu Lys Pro Trp Ser Leu Phe Asp Val Leu
                645                 650                 655

Val Glu Lys Tyr Gly Trp Pro His Glu Asp Ala Ala Gln Phe Thr Asp
            660                 665                 670

Phe Leu Ile Pro Met Leu Glu Met Val Pro Glu Lys Arg Ala Ser Ala
        675                 680                 685

Gly Glu Cys Leu Arg His Pro Trp Leu Asn Ser
    690                 695

<210> SEQ ID NO 3
<211> LENGTH: 90541
<212> TYPE: DNA
<213> ORGANISM: Human

<400> SEQUENCE: 3
```

| | | | | | |
|---|---|---|---|---|---|
| tctcaaacct | tttcctcccg | ctggggaagt | ggcaaactac | tgaagttcct | tacttgcctc | 60 |
| tcctccttca | gaactctctt | tgcctgggga | ccattccact | ttcagtaagg | gcacatgtgt | 120 |
| taaaaagaag | cgagcattta | catggcttcc | agaagaattc | ttgtacttct | tggtaaggcc | 180 |
| ctggttggga | agttttgaat | gtattctgga | agtggtgtgt | gtgtgtgtgt | gtgtgtgtgt | 240 |
| gtgtgtgtgt | gtgtgtgtgt | gtgtgtgaga | gagagagaga | gagagagaat | gaatattatt | 300 |
| ctctttcagg | gctctgtgaa | gagaatggtt | aacttggagt | gttatcatca | ctacaatcct | 360 |
| gatgtctgtt | acccagggag | ctgtaactgt | tgagtcttca | taaattccca | gaaagcagca | 420 |
| atcagtacat | tttcagctta | taaatattct | ttagttgtcc | tgctaaagat | attcatacct | 480 |
| ttgattattt | gcctttaagt | tgacctattg | tgtgtgatcc | ccaccccttc | ctcatgatgt | 540 |
| caggtgtttc | tgctgccttc | tattcctact | ccttccttca | gttgtggccg | tatgggtttt | 600 |
| tttgttggca | agccacatgc | attagtggtg | gtgttggagg | ctctcagatt | gggcaaggat | 660 |
| ttagaggccc | agtttagaag | aggcagtggt | tgaggcagct | cctttggcct | gtctcttagt | 720 |
| ggcagctaca | gatgagcttg | cattgctaag | accctgacct | tctcaagatt | ccagggctga | 780 |
| agagtgagct | ttgactgtat | gccgcaggct | gtgctgcagt | gaggagagaa | aggatccaga | 840 |
| atcggccttc | cactgggcag | agagcaacag | tgttccaaaa | ggaaatctag | caataacacc | 900 |
| aagattccac | ctgctctcaa | caactagggc | ttaggtcttt | gaactcttca | ttgacaacgg | 960 |
| ctataccctt | aaaatagggc | gcatgctggg | tgacagcagg | tgcatggtgt | gaggaactgg | 1020 |
| tgctaaagaa | ttttgctgga | ccagaaccag | accacaatat | gtttgtcaag | cttgttcttc | 1080 |
| tagacgcagc | aggcctgagg | gctgccgttg | cagaaatgcc | ccaaggaatg | gcactcacat | 1140 |
| gtcgggcaac | tgaccctcag | agcaaccttt | ccacagcagc | cgtcatcttc | agcgcacgca | 1200 |
| ttcagtggta | gttttattag | tgggatagct | taagggagag | atgtgcttcc | ggcatccaga | 1260 |
| ttgagactgt | agggtcctat | ttccccgcac | tggggcatgg | ttaggaatag | taagtgaatc | 1320 |
| ccattatgaa | ccattctcct | catagagccc | tgaagggaa | taatctcaat | caatcaaaca | 1380 |
| cacacacaca | caccgcttcc | agaatacatt | caaaacttcg | aacaggcctt | atagaagtac | 1440 |
| aagaatcttt | ctggcaatct | tgtatatttt | agctacagtg | tatgttaatc | agcttttatg | 1500 |
| agttattgaa | acctaacctc | attgccacct | atttctatgg | gaaagaatt | ctcattttca | 1560 |
| gataacagga | aataagtgct | ttcaaaagtt | gagtgctgct | tgcgcctgtc | tttttataat | 1620 |
| cgttgtgatg | ttttctaacc | aataaggcta | tataccatgg | aatacgcttt | catttcactt | 1680 |
| aaatttccca | gaattggtag | gagttgagtg | gagcgcactg | aaatttccta | acattggtag | 1740 |

-continued

```
ttcttgaagc gctaagtgaa aagataccta cagaaaaaaa ttccttagct aataagggca    1800 gattttttt tttttttggcc tgacttatat gttgaaacac tacttgaatt caactaaaat    1860
gggtgaagtg acattaaatg acatttcttc ttagtatgtg acaagtttta ttttttcccc    1920
catattaaga agtgctcaaa tgcatccata atgcaagatg tacttctaag taaatagcaa    1980
ttttctctct gctcttcag gccggagcct aacagaaag ctcctttagt tcctcctcct     2040
ccaccgccac caccaccacc accgccacct tgccagacc ccacaccccc ggagccagag     2100
gaggagatcc tgggatcaga tgatgaggag caagaggacc ctgcggacta ctgcaaaggt    2160
gatgtgccaa gcatggtggt gtggggcttg ccttccccat tgggctgtgt agtaatttgt    2220
tgggggaatg gacaagggga ggaggtagtg atgcaaattg cttggtcttc attaaattag    2280
cctccttgtg tcattatcat tttaaattct taggtcattg tatagagact gatatcagaa    2340
aatattaagt gatatgagag agaattgtaa gacaaaatac atgtatttgt acatacatat    2400
tctaggtact ttcagaagga cttaaatctg ttagaattaa aggtagtata cagcaggaca    2460
gttagaggac ataataaacc atctaaaagg agcactgggc cagtgcggtg gctgaagcct    2520
gtaatcccag cactttagga ggtcgaggtg ggcagatcgc ttgagttcag gaattcaaga    2580
ccagcctggg caatgtggtg agacactgtc tctacaaaaa gtgcaaaaaa ttagctgggc    2640
atggtggtaa gtgcctgtag ttccaggcac ttggggcgct aaggtgggag gaacacttga    2700
gcccaggagg cagaggtttc agtgagctga gatcgtgcta ctgcagtcca gcctgggcgg    2760
cagaaccaga tcctgcctcc aaaaaataaa gtacaataaa aacattaaaa taataaaga    2820 acatagagag gagaaagtgt accaggctcc tgaggggagc taattataac tcttgtgcac    2880
tgtatttgac tttctgtttt ctgactgcta aggctaaaag aaaaccattc ctttctttgt    2940
gtagcattga attacatagc gtttattgtc tgtgggaagc aagcatgcac atttgtttac    3000
agagaaagat tctttcctgg cattgtactt aacgaaaaag acattctgtg gggttctgcc    3060
attgtgtgac atagtgggtt atgttttcag ctatgatttc acggaagaca cagaaactat    3120
tcaagtggag tgttcttgta ttgatgcttt gtaaagacca agagttaaac tcctaaaggg    3180
caagcgtgtt gtgtgatgaa tattaagaac aatatgatct agacaccatg ctttgtgtgg    3240
acccaactga gaatctagga gaaagagaaa tgactattca gctgcttctt tgtcacttaa    3300
cttactgatt tggacattaa ttttctggaa tttggagctc ctgagccaaa gttggtgaga    3360
tgaatttatt tgctacagat tttaaaaatt gtaaatcaga ttctatatag cattagaata    3420
aatggcagaa aatgcagaca tgttcagaac ataaagcatt aatgaatttt gggttccata    3480
tgtcttaata attcatcatt tatctagtag atatagatca tttgtatgtt ggttcagaaa    3540
cagtgtacat ttaattacct gctaagagga agagaaagtt actgtactac aaaagtgtag    3600
gaactaatct actctaacct gattctttca taggtgcacg tacttccaca tagaatcagt    3660
gtgttcctta gaaaagagtg tagatcttac ttagcatttg tctgaatagt ggttacaacc    3720
ccaaagatct atgcagtcta gtaaagaaa agatagagcc agtttgaaag gtgacaagaa    3780
ggtgttttcc atcctccctc ttactcttca tttcttatac tgtcttcgat ttttctgctg    3840
aggcccagca ttaggttcat ctgtaggtgc cattcttttt tcttttcttg ttttttcttt    3900
ttctgagaca gtcttgttct gttgcccagg ctggagtgca atggcgtgat cacagctcac    3960
tgcagcctca acctcctggg cctgagcaat cctcccatct cagcctcctg agtcctgggc    4020
ttgagcaatc ctcccatctc agcctcctga gtcttgggct tgagcagtcc tcccacctca    4080
gcctcctgag cagttggaac tgcaggcatg tgtcaccacc cctggttaat gaaaagtttt    4140
```

```
ttttttttttt cttctggtag cgacagggtc tggctagaac cattctttag gagctgtttc    4200
cttcagcaaa taggttctac caagcaggag tgaaaactgt cttgttcatc tggatcttaa    4260
gtatgtgggt caggagatgt aaccaatact ctcatcccct tactatctct gggaaccagc    4320
acagtggaca tccaaacccc aaatataggg ctaagaataa agtattccac agccggggct    4380
gtttctaggt aacattcact gaactctaac cttcacagag tattaaagtc agcatcagta    4440
aggtcattag atagtaagg gttccctcct tatacccgtg ccagccccccc ccaaattttgg    4500 taagtaactt gtacctttag ttagcattac atgtgacaga tgccctactt tgaattttgt    4560
ggtatattcc acaacagttt gtataagatt actgacatat acatattcag ggagtccaag    4620
gaattgattt ggaatgtctg gaataagacc tgtggccttc tcattttttg ttcttggata    4680
aagagataaa tccctcacc ctctgccagg actggttgag ctaaaattac taatatggtg    4740
ttttatcatc cctgaatact ttagtacatt ttacctacaa tcaagtacat tctcctatat    4800
atcaaaatac aaccatcaag atcagaaatt taacactgat acttcactac tattcagacc    4860
tcgggcttat caggtactgc cagttgccca gtgttgtcca ttatgtgtaa tgaatctgtg    4920
gcagaagcgc atattctgtt ttcttgtttt tgtaatttct tttaatttgg aacagttctc    4980
agtgttttcc tggctttcat gtccttgaca tttttgaaga ttgtaaaccg gttatttat    5040 ataatgtttc tcaatttggg atgccacagt agtgatgttg tcttttttgca ttaaatcctt    5100 tcagatggta cacaggtttg atttattcca ttggagttga tgccttcact tgatcaagat    5160
tgtgtctgcc agatatccct gacagctgtt cttttcccct agtaataagt attttgttga    5220
gagttacttt gagactacat atataaccca ttcaaatatt tatccctacc ccgccgcca    5280 ccccgggctg actttctgtc tcgggtggac tgataaattc atggatctct gttttattca    5340
gtgggttatg atcacttact ctccttatat gttttgatgc ttagattatc ccaaattttg    5400
ttcttaggag ccccttcaga ttggttctgt gtccttttga aatgcctcaa tcgttctttg    5460
atcgtttatt ttttttgtttt gttttgagat ggagtctcgc tctgtcaccc aggctgtagt    5520
gcagtggtgt gatctctgtt tcactgcaac ctccacctcc tgggttcaag caattctcgt    5580
gccagcctcc tgagtagctg agactacagg ctcatgccac cacgcctggt taacctttgt    5640
atttttagta gagatggggt ttcaccatgt tggccaggct ggtcttgaac tcctgacctc    5700
aagtaattct cctgcctcag cctcccaaag tattgggatt accggtgtga accaccatgc    5760
ccggtccttt gatcatttct ttaccttcaa gtacagtagg atatgccagg ttcatcttgt    5820 gttttttccta tcccagcccct gggtctact cttttcacag agaatcctgc tttttttttt    5880
ttttttttta aattaaacaa taatatttag aaagctagac ctgggcatta ggtgtgctta    5940
ttacttttgg cttgtcactt tcagatctca gtacagagct aggaacacaa acatatgcac    6000
ctgcttcctt tatgttata tttatttata tatttacata tgttttgaaa tccatgagtt    6060
tattaatctg atacctctaa taccagaaga ttcagcctgg tgttctccct ttccatcttt    6120
gtggtttctt tctctgatag taagagtctg ggctcttccc atcctcattg cgttgactta    6180
gttgattgat ttccctgtat ggtatgaatc accagtcacc atcactatgt ctctcccttc    6240
ccttctcacc taactcatgc tctgacatcc tttgttgatt ggccctgcct catggcttgg    6300
gatttaatgg tccaggatgg aaggggaga gagctttccc aggctggtag tgtgtgttat    6360
gtaatctgag gtatcatttt tcttctgata cttcacctct ttctcttgct tttattgact    6420
tcattcctgg agagtctctg ccctcaatta cttctcagtt tcctcaaaat acaattaaaa    6480
```

```
aaaaattaac aacaaaagac atcacatgta tttcttttta aaaataaaat ttgttcatca   6540
caggaaatgt agacacttgg gttggagggc agaagtcacc tgtgatccca ctactcagca   6600
agagctgcag caagccttca tcatttatga tcagctagat tacatcttaa cttttttacct  6660
catctttaca agtttccctt atttaaaatg tatgaaccct cagctgtttt aataagaggg   6720
tccatattta aagttctgat attgcaaaag cattgttcat tgctcttgtg tacttacttg   6780
ccttggtatt ctctctggag taggactctt catttcctga cagccatgtt cctactcgcg   6840
ttatcttaga tctccaagag gattatggca ttattgactg attcctgagc cttggttcaa   6900
aacctggctg tgttgctttg tagctccgtc ttcttggaca aattcctttc tctttaggct   6960
ttggtttttc atctatgata tgataattta tattatatta atgttaatac ctaagatttt   7020
tatgaggatt taaatgaaat atatgaagtt catgacacag tatctgatac gaggctcata   7080
agaaatatga gtttcactct tcttctgtct gttctatcat tcttctttca ttgtgttctc   7140
atctgtactt catgctgtct atacccatca gtgctggctc ccttaactcc ctgaccgtgt   7200
ctcatgttgg gtgtgtttcc ttaacctctg gagagagagc tgtcagcact gcctatcttt   7260
tttacatatc acctctggtc tgttgtctgg gcacaagctg tagcagtagg ctgtgcagtt   7320
tattcagatt ctgcttccaa gccctgggga ttaccaagat cagggcagg gtcagcctgt    7380
aaacaaacac tgtcgggagg ccttgtgtca tacatgcttg tttcatgagt ttgagcaaaa   7440
aaaacctgtg tcacagccaa acctcctttt gtgggaagat ttgtgtttca tgtggggttt   7500
tcagaggcag taggggtgc ctggtaaaca ttcctaggct gcactgtaaa ccctgaatt     7560
ggaatccttg agagtgggac ttaggaatcc aaatatttaa caaattcatc agtgattttt   7620
ctgcacattg aacactaaaa tctgctccat tctaaggtct gcatgtatca tccttctaaa   7680
actccaagga tataaccaca tgaaggcacc cttcatacta tacgtgcaat ataagcggaa   7740
tcattgcttt gaactacctt atgttcctaa cttttttccag aaccctcggt gtatacctgc   7800
tacaaggaca tactaaatgg tgactgtagg aacattgcct tgcaatatca ggctgcctgt   7860
agtagctgtc ctcagacatg agttttgttg ctctcttaaa tcattcttag ataagttggc   7920
acctttgtac agttttcatc tcttgaatta tttctggaga catcaacagc tgtggtctga   7980
cttggtatga aaacatgtca tttccttaga aatgcattta ttcgacctct aatcagaccc   8040
tttcctttat tacccacggt attgtccccc gcatcccaa cttatcatag tgtggaattg    8100
tacatttatt tctgtgttca tgtatctccc cctctctagt ctgaaaggtt ccctttggtc   8160
aaggccctgt agtttgttaa ctccactgca tttgaaccat ccataatgca gtacgtattt   8220
tgtttggata aaggcatttt ctctagtgtt gggttgcaag tacgggatag gcagagtgct   8280
gatgttcagg tggatctggg gaaggcatgt cggcatgagc aggctggcat gctgactggc   8340
agatcagaat ataggggcctt tgtttctgcc tcacgttttc ttaaaatcat ccatagttct   8400
ccggaatact taacctgtca cacacatttg agtgacatat atttcttacc tgtaaaaact   8460
tagggacatt attttcttca aaatagagca taaaatatta taagtataca cactagaagc   8520
atgtcagatg agtttcttcc tatacacaaa ttgcctttac ccatgtgtgt ctattttcca   8580
tctgtgaaaa cggtagactg gttgaatttt aataactcac aaaatttact gttggtggct   8640
atttgctgtc attggcatcc ctcctccctt tctccttccc tccctgcccc caaccctcc    8700
gagtctatga ctttgattta ttttatttta tttttttatga gatggagttt cactcttgtc   8760
acccaggctg gagtgcaatg ctgcaatctc cactcactgc ctctacctcc cgggtacaaa   8820
caattctcct gcctcagcct cccgagtagc ttggattaca ggcatgcacc accatgccca   8880
```

-continued

```
gctgattttt gtattttag tagagatgag gtttcaccat gttggccatg ctggtctcga    8940
actcctgacc tcaagtgatc cgcctgtctc agcctcccaa agtgcaggga ttacaggtgt    9000
gagccactgt gcccaatctg tgttgttttt taaggaaaaa aaagcaaaga accttaaagc    9060
tgctttagaa ttgatatttg tacagtaaaa agaataacaa acaaaagaaa tatttgtaca    9120
gccaagtaat gttggctgtg ttacatcaga ggttcttcgc tgggtgcggt tttgaccct     9180
gggagtccat ttgtgaatgt ttggagacat ttgcttgccg tgacgggctg ctactggcat    9240
ctcttgggca gagccaggga tgctgctaaa ggttccacg cgcacaggac agttaccat      9300
aacagaaatt actcagctcc taatgtcagc agtgcccaga tggaaaatct ctgccataga    9360
aatgcctgtt tttgtctatt aaatggtgt tgtgtggctg aagtatttta tagacgtgtg     9420
gtctttactt tctgttcctt ttgatagaaa gataaccttt ctttattcac agttcttta    9480
cttaaaatca ttaatgctgc acagatactt aattcactat gcttttcatt tattagttgg    9540
cttaatttgg cttaattcaa gccttaaaaa gaaaccctgc ctatctatgt gaacaaagca    9600
atagatgctc ttgaacctat tacataaggc ctcattacat ttcttttatg gagaccaagg    9660
agattctgac tcctgatctg ttggtgcttt aaattgacaa ggatattat gatacaagct     9720
ttaaatagca tgacaggtga gttcatggtt tattcattga gcttgatga tgtgcaaaac     9780
gttgtacttt actacagggc acatagaggt aaatgagaaa cagccctact ttctagatta    9840
tggcctctta gactttgcca ctagaatgcc agctacttaa gggcagagcc ttgacctgtc    9900
tagcttccct ggcaccccag tagaacaatc tgtggcctgc tgaatagtga ctgaatgaat    9960
agactgctca aatatctttt ttttcatcta agtgtggttc gttaataata agtgagaaaa   10020
gggaagatat gtgagggcta aaggaagaa tgttatattt gaatagagga ctcagaaaag   10080
atgttataaa aaactgaaag ggactttgtc agtaaagaat atttggatga tgttgagagt   10140
atggggcact actcagacta atcctggag gcagaacaag gtgtaagaag ccctaactgc    10200
ttgtgtttc ctaacaaatg gggaaactaa aaattgatgg tagaagatta ggtttaaaag    10260
cagtttggga gcatcatgta gaggatagag atgagtgtga gaaatttgtg gtgaagtaac    10320
tttaaagcat cacttcaaaa tattaccaaa atccccaca gaaaaccgaa agaaagcaga    10380
gtagaaacag aatcctggtg ttataatctc tcctcttttt acaaaacata tttagcaggc    10440
cgggcatggt ggcccacgcc tgtaatccca gcactttggg aggccgaggt gggcagatca   10500
cgaggtcagg agattgaggc catcctggcc aacatatcga agccctgtct ctactaaaga   10560
tacaaaaaat tagccgggca cggtggcacg cgcctgtagt cccagctcct cgggaggcgg   10620
aggcaggaga atcacttcaa cgtgggaggc ggaggttgca atgagttgag attgcgccac   10680
tgcactccag cctgggcgat agaacgagac tctgtctcaa aaaataaaa acaaaaaata    10740
aaatatatt tagcaaaaga gcagtgccaa atgtcagca gtatgtggta ggcctgaggt    10800
gttttttga aatatacttt tatcttgttg ctgcagcacc atttatcgag aaagacttgt    10860
tcccccacct attcagttgc ttgcctttgt ccatcagtag acagaatgta tgggggtttg   10920
tttgtggact ccatctgctc catccctctt ttggtcaatg cttgctctaa aggtctggtt   10980
actatagctt tgtatagcat gccttgaatg ggtagtgtca gtcttccagc tttgtgcttc   11040
tcttccagga ttgttttgac ctgtctcgat cctttgcatt ttgtataaat tcagagtcag   11100
cttatacata taaattttag atacgcctta ataatattga atcttccaac ccattaacat    11160
ggtattgtgt ccgtttattt aggtctttat tgttctcaga aatgttttgt agttttggt    11220
```

```
gtggttttga tgggttatag aaatgtaact gattcttatg caccaaccac gtggcctgta    11280
actatgctgt ttgcttattt attagtgttt gtgcatgtgt aaatttctct aggttttctc    11340
tacacacaat catttcatca tttcagggca aatggaggtt tttcttcttc cttatgattc    11400
tttataaatt attattcttt tttgcctcat tcttttatgc atgaggttga atagaagtgg    11460
taagaataga catctcccct gtcttgtttc taatcttaca gtaatatgt agtttttttt     11520 tagataccct tatcaggttg agatggatca tatatttaaa tataaagtta aaactgtaaa    11580
gtttctagca aaaagtaaga gaatatcttc acaaccttgg gagtagggaa ggatttatta    11640
gagagcatat aagaaacatt aactataaaa taaaaaatta attagactta atcaaaatta    11700
aaaactgttc ctgattaaaa gacatttta aaaatgaaaa gaccagcttc agactgggag     11760
aagctctttg caatacattt acctgacaaa gaatgtgact gggagggaac ttcaagtgtg    11820
agattttgga aaaatgttct gtatattgat tagagtatat gtatttgtca aaaagcaggg    11880
aatcgtacac ataaaacctt tgactttcat tgcatgtaaa tatctgaatt ttaaaaaaca    11940
ttgatagtag ctagttacat ctggattgta gggttttggt ttttgtcttc tttacctctt    12000
tgtattggtt ttctttgttt tctgcattga gcatatattt ctttgtaaat acagaagaat    12060
atgtgctttt actgctgaaa gaaatcatag acgacacaaa caaatggaaa cacatcccat    12120
gctcataggt gggtagaatc agtattgcga aaatgaccat actgccgaaa gcagtctaca    12180
aattcggtgc aattcccatc aaagtactac cgtcattctt cacagaacta gaaaaaacca    12240
tcctaaaatt cacatggaac cgaaaaagag tctgcatagt caaagcaaga ctaagcaaaa    12300
agagaaaatt tgaaggcatc acattacctg atttcaaact gtactgtaag agcacagtca    12360
ccaaaacagc atggtactgg tataaaaata ggcacataga ccagtggaac agaatagaga    12420
actgagaaat aaacccaaat acttacagcc aactgatctt tgacaaagca acaaaaaag    12480 ggaacagaca ccctattcaa caaatggtgc tgggaaaact ggcaagccat ctgtaagaga    12540
atgaaactgg atcctcattt catacctta acaaaaatca actcaagatg gatcaaggac      12600
ttaaatctaa gacctgaaac tataaacatt attaggaagg taacatcgga aaatccttc      12660 tagacattgg cttaggcaag gatttcatga tcaagaacct aaatgcaaat gtgatcaaaa     12720
caaagttaaa tacctggaac ttaattaaac taaaagagctt ttacacagca aaggaagag    12780 tcagcagagt aaacagacaa ccgaaagcgt aggagaaaat cttcacaatc tatacatccg    12840
acaaggacta atatccagaa actacaatga actcaaatta gcaaggaaaa aaaaatccca    12900
tgaaaaagtg ggctaaggac atgaatagac agttctccaa agaagatata cagatggcca    12960
atagactatg aaaaaatgct caacatcact aatgatcagg gaaatgcaaa tcaaaatcac    13020
aatgcaatac cactttactc ctgcaagaat gtccataatc aaaaaatcaa aaataatag     13080 atgttagcat ggatgcagtg aaaagggaac acttctacac tgctggtggg aatgtacagt    13140
agtacagcca ctatggaaac cagtgtggag attccgtaaa gaactaaaag tagaactacc    13200
attgatccag caatcccact aactgagtat ctacctagag gaaataagt cgttatataa      13260 aaaagttact tgctcatgca tgtttatagc agcacaattc acaattgcaa aaatgtggaa    13320
ccaacccaaa tgtccctcaa taatgagtg ataaagaaa ctgtggtgtg tgtggagtac        13380
ttctcaacca taaaaagtaa tgaattttgg agcaacctgg ataggattgg agactctatt    13440
attctaattg aagtaactca ggaatggaag accagacatc ctatgttctc tcactcataa    13500
gtgggagcta agctatgagg atgcaaaggc ataagaatga cactgtagac tttggggact    13560 caggggggaaa gggtaggaaa gggatgaggg acaaaagact acagactggg ttcagtgtat   13620
```

-continued

```
actctatcgg tgatgggtgc accaaaatct cacaaatcac cactaaagaa cttactcatg    13680
taaccaaaca ccacctgttc ccccaaaact tatggaaatt aaaaaaaaaa aaaaaagcag    13740
aagcagaagt ggagctttta aaaggaataa gtggaccagg catggtggct tacacctgta    13800
atcctagcac tctgggaggc caaggcagaa gatcatttga gctcaggagt tcaagacagc    13860
ctgggcaaca tattaagact ttgtctctat ttaaaaaaaa aaagttttt tttgtttttt     13920 tttacaaaag gataaaaaga accagtgtag gttttaaaga gggaagtgct ataattaagg    13980
aagcttaatt tgaaatctta gttgattgac attaaagaga gagaagatac aaggagaaga    14040
caaaagcaaa caatgttatg gaggtaccgt ctttattatt caacaatctg ttgagtatgg    14100
agggcagtga ccagaaaacc ccacacactt ctaagtcctg gaataatcag aagaatagta    14160
ccttctgggc atcatttatt ttagtgtact ctgaattatg aaactgcttt tcttcccctt    14220
ccccatagag atagagtgtc tcattctatt gcgtaggctg gaaggcagtg gtgtgatcac    14280
agctcactac tactacaacc tcccaggctc aagctatcct cctgagtagc tgggactaca    14340
ggtctgcatc accatgcctg gctgatgttt aaattttttt gtagagacag gattcgctat    14400
gttacccagg ctgttcttga actcctgagc tcaaggaatc tcctcctgtt tctgcctccc    14460
aaagtgctag gattgtgggc atgagtcacc atgcctggcg gattttaaaa atgttgatag    14520
agacggggtc tccctatgtg tctcaggg tg gttgtcattt cttttttgca ttggatatcg    14580
tttggctatg aaaagctct gagccaaatg tgcagcccac ctctaacaag tgaacagtaa    14640
tttatagcat gcattctgta tcctaacttc actgtagcat tattctgttt tactttttct    14700
gggctatttt ttctgtgccc caatttcttt ctaattttgt atcttatatt gtggttttat    14760
aagctgcctc aattccttat agaaaaaaat agtgtaacat atattaaaac atcacatcat    14820
accccataca tacaattatg gcttactaat taaaaatagc ttttttaaaca aggtgaaata    14880 atgttggcat tattagtaga aacagtgaag tcgcagttgg attggggaag atgttgatga    14940
gtttgactgt tgatggaaat atcaagaagg tggttagaaa tatgaatcgg agaatcagaa    15000
gtatcagcaa gcaggtggtt tagtaaagaa tttaaccttg cctaaagaga tatctagcct    15060
ttgtccttgg agccttccaa gggcatagag atctgggtgc cttgggccac acctgatagt    15120
ctaacagtgt ggcacattat tgaacgtgag gatggtcttt gggaccccca aactctgtga    15180
ttcatgtcag aagggaaggc agttggtgga ctgttcccaa accttacaca gatattatag    15240
atttgatagg taaaacagat catataatgg taagtggttt aaaaaaacaa acaaaaaaag    15300
gatgcagaga ggctgttcaa tgacaagcct ttgagaaatt taatggaatg caagaggaaa    15360
aggaacacgt acaagaaaca gacatagcag tcaaggaggt aggagagcaa ccaagatatg    15420
tgttcatttt gacctagagt ggactgagat ggcagccgtg gtgttattct gaatgacaca    15480
ttcctgaaca cattcagttg tgtaacccaa agtttatatt gtttgaatat agatgggcag    15540
tcatacttgc agtcattcca gatgtcagtg gctcttgtcc tcacttgtca gccctgcat    15600 aatctgccct tttggatctg gaagtcgcca gagggagcgc aggatccaga ccggagtccc    15660
catgtgtgat ctgttgtgat cctccttcct gctcctggcc tgctcctgct ggtgctgcca    15720
ttacccacta agagaatgct gtggcgttct gccacaaggc tgtcccccact gtactcagtg    15780 ccagagcaca gttgtgtggc atggcagtgg tgagagacca gttcatatgt ctgcaacagc    15840
cccatgccat cacgccacag cgtgcccacc acccctatag ccagtggcct cacccactgg    15900
tccctggagt ccagtttaat ttttaaaaa tttgtaaaaa gagttataaa agaacttcta    15960
```

```
gtcaaaaaga ccaaagccca tgccatcatc acactcctca gattcttctt tgttttcct     16020 tttctttatc tttttctttt cggagaccga gtctggctct gtcacccagt cactgcaacc    16080
tccgcctccc aggttcaagt gattcttgtg cctcagcctc ctgagcagct gggattacag    16140
gcatccgcca gcccacccat ctaattttg tattttggt ggagactgtg ctttgccatt     16200
ttggccaggc tggtctagaa ctcctggctt caagtgatct gcccacctca gcctcccaaa   16260
gtgctgggat tacaggtgtg agccactgca tccggccgag attctttttt ctttgcttac   16320
acttccttct cctcagctgg agcagctgct ctggacaggg caggacctac tgttgatgca   16380
gcagcagctg ctggagcagg tccaccaacc cctacattag gatgagtctc tcgatgtcac   16440
cataggccag ggccttgcc aacaaaccag gccgaaaagg ttcaacattt acaccaccta    16500
ctttaattag ggccttgatt tatcctctgt gacggtcacc tcgttcatag tgaagaatga   16560
gggtggagta gatgcaggcg aattcagggg ctgtggtgcg ggcgagtggc ggggctggtg   16620
ctgctgttgg atgcagtgca agttgctgga tgaagtgagg gcctctcccc agtgtgactg   16680
tagctttccc agaagtactg agcccctgg cagcagctga ggaaagggct ggagtctggg    16740
tttagaaagt gtcgacaatt aacatggtgg cttcttctta gctcattctc tgtcccttcc   16800
tccctccacc cccttaggc tcactgtagc ataagggttt ttttcctttt atgctcccag    16860
ctaaaagctg gaacactctt gcaagtcttt ttgttagttg gggctatcca ccaattctct   16920
ttaagggccc aggcatgttt gattcttatt tgggatctaa ggtagtattc taaaaacatt   16980
tacaaacaga acctgttacg agtaatatct tttctcttt atttcccatt tggtgctaat    17040
ttaaaaatgg actgtattct tagagttctt tattcagatt tcactcctta acattgatgt   17100
tctggattca gtagaattgt taaaatttt tcctctttgt tttggatcct gttttaacct    17160
ggaattgaaa agagtgaaat gaagtaatgg agttccagat tttgttgggg attttttgtc   17220
tggtttatgt tgactaggaa gcagtaattg aaaacatgct atttttccc tcatacattt    17280 taaaaaattg agatataatt tgcaaacata acattctctg ctttaaaggg tacaattgtg   17340
tggttttcag tatattcaca taatttgca actcaccact ttaaaattcc agaacatttt    17400
catcattctc cagaagaaat gactgtccat tgacagccag tccctattct cctcccctct   17460 acaacccta gcaatcacta agctactttt tgtctctatt ctggacattt tcatataaac    17520
aaacacaata catcactttt tgtgtttggc ttcttttact tataatgttt taaagattca   17580
ttcttgttat accatgtatt ttattcattc atttcatgat taatatttca ttttctggat   17640
gtatcacagc agttcatata catttgggtt gttatcactt ttggctattg agaatatgct   17700
gctgtgaaca tttgtatatg agttaaagtg tacatttgtt ttcatttctt tggtatgtat   17760
ctaggagtgg aagtgctggg tcatatggta atcacttaag gagctgtcag attatttccc   17820
cagatggctg tgtcactgta tattcccacc agcaatccta tcttggttat aatttactca   17880
cctttgtccc tttatgttt attttcttg tgacttactt gcttctgtaa ttctattata     17940
atgaatgagt tttacctatt tttttaaaaa acctttgatt gatcctgtca atggcctctt   18000
cagctctgct tactacacca cgcatattca ccatgagact ttaaacctga acgtctggtc   18060
agacacccac accaaaatcc ttcccttgga caatagtaat tttgcctgtg ttggtaacac   18120
actgagatgg tggtggtctt tccaaggcta tatggtctga ggtataaaaa aagagttttc   18180
aagacggaag gatttaataa tagcatttag tttaagctaa atttcagttt caggaaggta   18240
aaagctgaca ggaacagtga actacctgtg gggaattctc tagagactca tgtgtggggc   18300
cagtgatgag tcaggcagat gtcaaggtga ggatatatta gcaaagcata gcagattatt   18360
```

```
cggtgaaatt tagcaatgaa atgattgtag cttctaggga gtggggtcag atttgtgcaa    18420
gaaaaagcat ttattttagt gtgacatatc tgggcatatt tctaggcaga agagataagg    18480
tttgagtaga gttgaaaggc cagcaacaaa ggaattaaat gagtgatttt tggagctagt    18540
tgatcagtct tttaaagatt gaaggcacat cttacctgca gaaccgagga ggaggttttg    18600
catagctgtt gtggtgagca gaataaagac cgttgtgatt attgttgtat aataaattat    18660
cctcaaactt agccttaaac ccctttttaa ttttgttcat gattttatgt atcaagaatt    18720
tagaaaagac aaagctggga tggcttgccc attgcttcac ggtatctggg gcctcaactg    18780
agacatctca agggcttgat gtggcttcat ggctggggac tagaattaac tgaaagctta    18840
catctggccc ctgggctaga aagataaaca actaggacag ccttatggag cacctatcca    18900
tgccctttgc atatggcttg gctttctcag agcatggtgg cctcagagca gtcatacttc    18960
ctacctggca acttagagtt cccaaaggta acacacacct tccagagtgg aagctgtgtt    19020 cctttttatga cctagcctca aaagtcacac agtctcatcc actatattct ttttggttag    19080
aagcacatca gacgctcatt cagtttcatg attagagtcc atttcttgat agtagaacat    19140
cagagtagaa gggatagtag aagagcaggt agttggggag atactgtttc ggcctttgtt    19200
gaagaacaca gtccgtcaga atacagcaac aagaaatcaa taaagcagcc atagagaatg    19260
aaatgatttc ctttgcagca acatggatga agctggaggc cattatttta agtgaaaaaa    19320
cttagaaact gaaaatcagc tactgcatgt tctttcttgt aagtgggaac taaacaatgg    19380
gcacacatgg acttaaagat ggaaacaata gacactgagg actccaaaag gggcaaagtt    19440
gggagggtgg tgtggcttga taattaccta ttgggtataa tggtcactat ttggttgatg    19500
ggtataccgg aagcccaaac cccaccattg tgtaatatat acacataaca aacctgcaca    19560
tgtactccct gaatctaaaa taaaatttaa aaagtaaaaa cctataagca agggcattct    19620
tcctactgtc aaatgataca acattcatag aaatagagat ttgtgtagtt tgaaaatacc    19680
ttatataaat caagatgaaa cctttatttt gcagacatta aacctaaagt tgactgataa    19740
agacatattc gtcccatagc ccagaacatt ctaggggaat aaaatctata aaagatgca     19800 gacttccaaa tatatgtagt tatagttatg taggtacagt aaaactaaccc ccttttttag   19860 gacatgtatt tatctaattc tcttttttgtc tggcatggat tataagcctt ctaagcctag   19920
agtctactaa gtatgtctaa attgctatgt tgggtgccta acaaaggagt atgtacaagt   19980
tggtgcatga gttagacttt ttgatggtga ttaaactgga aagcatgaat tattcttgga   20040
ttataaaact aggtggggct ttcgagtgag gctcaaaaat cagttttgtt ttccacatag   20100
agacctttta cttattcttt ttgtagtcag tttgtctcta agcctttttt tctctttctc   20160
attttttaga ataattaaga atttcattag agtagtttag aatttagatt atttacagtg   20220
tattattatt attatttttt gacaagagaa cgtaacatac acctgggaac atgtcttcag   20280
ttatgagtca gacatggata tgtgctataa tatataccct tgcactccat gaacagcagg   20340
agcctgaaat aggtcctaac ctttggaagg aacttaattt tttagttata ttttgaggtt   20400
ggaatgtgga taatgagggc ttttagtttt aaacagccag agagctgttt tctgagttat   20460
tttaattgtt aaatttttt agttactaag aattttttct tttagatata atcttattt    20520 ctttttctct tttttttaatt ttttctttta aagaaatct catgtcttaa gtggattctg   20580
atttctgaat tctactttga ctcagctaag actttctcat tctaagatca gttatgtttc   20640
ttcagttcat aattcaatat attatacatt tatttatctg aaacataatt aagaaccgag   20700
```

-continued

```
aaatgagccc aaagtttttg aacagataca aacaatgtcc aagttcacgt actaaagttc   20760
atgtactcaa gctcatgttc tttattctgg aggaaagtcc ttttaatgat ctcatagaat   20820
gtctactcct cctttgccca tgaaacaagg agaaggttaa gaataagaag gaattagaaa   20880
taatatataa aaactatcat aaagtcccaa taaacattgc agcctagata agtggtaaa    20940 attcttagat ggaaagacca catgacttat taggggataa ccagattgtt attaagtatt   21000
tttgcagcaa aatgttaggc cagaagacac tagagaagta catttaacat actcaaggaa   21060
agaaaatgtc agtcaaatat tttacatcca gccaaactga ccttcattat acaaatctca   21120
tacaaactgt tatatacatt taagcactga gggaatattg ttcttttgaa cactgaagtt   21180
aaaagcttct agcaacctaa atcaaggaag aggcctgtat agacatacag actgctttca   21240
ttaaaataca aagtatacct gaaaaatcaa atctgtagca ttcctctggg acacttagct   21300
tatagaatac tattaagcgt cttaactaga cagttaaatg gacttgaaag atcgtgtatt   21360
tggtttccat agaaatttaa gggtaaattt tataacaaca tatattttgt aacagtggtt   21420
tggattattc tgtcaaggta tcctaagaga gaaatagctg tgtctggcat tatgtatgta   21480
agaaataaag gaaaaatatt agtaatagac caggtgtggt ggctcactcc tataatccca   21540
gcactttgag aggccaaggt gggcagatca tttgaggtca ggagttcgag accagcctga   21600
ccaacatagt aaaaccccgt ctctactaaa aatacaaaaa aaattagcca ggtgtggtgg   21660
cacattcctg tactcccagc tactccggag gctgaggcag gagaatggct tgaacctggg   21720
aggcggaggt tgcagtgagc tgggatcatg ccactacact ccagcctgca acagagag    21780 actccatctc aaaaaaaaaa aaaaaaaaa aattggtaat agtgtacgtt aactcttttt    21840
agttatggaa tctgagattt acagggtatc agtatactta aaatacattc agcgaagttg   21900
aacacttagt tgtatttgtg tgtatgagaa aaaacagctt gtttcccaaa ttacagagtc   21960
aagtaaatct ctagacatgg cctcttaaaa acagccacgc agggcgtggt ggctcacacc   22020
tgtaacccta gcagtttggg aggccaaggt gggcagatca tttgaggtca ggaattgtag   22080
accagcctga ctaacatggt gaaaccccca tctttactaa aaatacaaaa aaattagcca   22140
ggtgtggtgg cacatgcctg tactcctagc tactctggag gctgaggcag gataatggct   22200
tgaacctagg aggtggagat tgcagtgatc tgggatcatg ccactgcact ccagcctggg   22260
caacagagtg agactctgtc tcaaaaaaac aaaatagac aaacaaacaa acaaaaaaa    22320 cccgctagcc atttacgatc tgatatgtta accattgtgc agttgtagga ttcctgctga   22380
tccccaagtg catttaaaat tgtgttctaa agtactcttg gtattgagac atggttctgg   22440
agtgttctag actagaatgt agattaggat tttagttatt ggcttgtata gtaatgtgac   22500
tttgcattgt gagctcttat tctctagggt ttttctgaa aaatcagtat cagtatattg    22560
aagaaaattt tttacacagc tacaaactta tagcactaaa atgacaaaaa aagatgatta   22620
gtcataaaaa cataagagat ccttatttgt atttaaataa ttttctttgt ctagaatttg   22680
attccagctt tgtaaatgta tggagctttt agtgaacttt aacttcataa atgtttgtgg   22740
atcccgtgat agcttggctc aggatcttgt aaatactatc acagctcagt ctttcttact   22800
agtttgcctt gagtactaca catttttaatt ttacattgta atagaaatat gattttttt    22860 tcccctatac agttgtcttc gtagtgtttt atatgatact acttgggata tatttagatt   22920
agtagtttac tttccctcct tctggtcata agagataagg ggaaatcttc taataaatac   22980
tttgttaatt ttttccttac aagtaacaaa gtcaaaactt gccaggcact gtggctcacg   23040
cctgtaatcc cagcactttg ggaggccaag gcaggtggat tgcttgaggc taggagtttg   23100
```

```
agaccagcct ggccaacatg gccaaatccc atctctactt aaaataaat aaataaaaaa   23160 cacaaaaatt agccgggcat gttggtgcac atctgtaatt ccagctactt gggagactga   23220
gacacaagag ttgcttgaac ccaggaggtg gaggttgcag tgagctgaga ttgtgccgct   23280
gcacttcagt ctgggcagca gggtgagact ccatctcaaa aaaaaaaaaa aaaggcgggg   23340
ggggaaacaa agtcacaagt tttgcacaaa tctcaaggct cttcaaagtc tgattcaatg   23400
taccattctt gttttctttc tcagcctcaa acatagttaa tttatttcac cttaaactgc   23460
tgtgcttgtc gtcatgctat cctttttac gtcagggctt cctctttttt tgctgttaga   23520
gtatacggtt gaattttttt ttttttttt tttttgagac agagtcttgc acttgttgcc   23580
caggctggag tgcagtggtg tgatcttggc tcactgcaac ctccacctcc tgggttcaag   23640
cgattctcct gcctcagcct cctgaatagc tgggattaca ggtgcctgcc accacgcttg   23700
gctaattttt ttgtattttt agtagagttg gggtttcatc atgctggcca ggctggtctt   23760
gaactcctga cctcaagtga tccacccgcc ttggcccccg aaagtgctgg gattacaggc   23820
gtgagccccc gcgcctggcc atctcagttg aattttagcc tacatttggt ttttgtgtgt   23880
gtgttttctg tttttttttt tttttacttt tatcttaggt tcagggtac atgtatgtgc   23940 acatgtgtta tgtaggtaaa ctgtgtgtca cggggatttg gtgtatagat tatttcatca   24000
cccaggtaat aagcatagtg ccctatagat gtttttttcta attctctctg ttcttccacc   24060
ctccatcctc aagtatgccc cagtgtctgt tgttccctc tttgtgtctt tgtgttctca   24120
ttgtttactt cccacttata catgggaaca tgaggtattt ggtttctgct cctgtgttag   24180
tttgccaagg gtaatgaatg gcctccagct ccatccatgt tcctgcagcg gacatgatct   24240 tgttctttt ttatagctac atagtattcc atggtatatg tgtaccacgg tttctttatc   24300
cagtctactg ttgatgagca ttgcttccat gcctttgtca ttgggaatag tgtcgcagtg   24360
aacatacacg tgcgtgcgtg tgtctttaca gtagaacagt ttatattcct ttcggtgtat   24420
acacaataag gaattgctgg gtcgaatgat aactctgttt aaatttcctt gaggaattgc   24480
catactgatt tccacaatgg ctgaactaat ttacactccc acctgcagag tataagcatt   24540 ccctttctc cacaaccttg acaacatctg ttaattttgt gacttttag tagccattct   24600 gactggtgtg agatggtgtt tcatcgtggt ttcaatttgc atttctctaa tgattagtga   24660
tgttgagcag gttttatat gcttattggc cgcatgtacg tcttcttttg aaaatgtcta   24720
ttcatgtcct ttgcacactc tttaatgggg tggttttttg cttgtatatg tgtttaagtt   24780
ctgtgtagat tctggatatt ataccttgt cagatgcttt gtttgtaaat atttctgcca   24840
tcctgtaggt tgtttactct gttgatagtt tattttgctg ttcaggaagt tcttaggttc   24900
cctttgtcag ttttttggttt tgttgcaatt gctttgaca ttttcatcat gaaatctttg   24960
ccaggtccta tgtccagaat ggtatttcct agattatctt ccaggctttt attttttctt   25020
gttgttgttg agacaaagtc ttgctgtgtc acccaggctg gagtgcagtg gcaccatctc   25080
ggctcactgc aaccttcatc tcccgggtta agtgattct cctgcctcag cctcccagt   25140 agctgggatt aaaggcatgc gccaccacac ctggctaatt tttgtatttt tttagtagag   25200
acagggtttc accatgttgg ccagactggt ctcgaactcc caacctcaag tgatctgcct   25260
gccttggtcc cccaaagtgt taggattaga gacgtgagcc actgcaccca gcctttccag   25320 ggttttata gttttaggtt gtacatttaa ctcttaatcc atcttgattt ttgtatatgg   25380
tgtaaggaag gggtgcggtt tcagtcttct gcatatggct agcaagtaat tctagcacca   25440
```

```
cttatggact aggaagtcca ttccccattg cttgtttctg tcagctttgt caaagatcag   25500
cggttgtagg tgtgtggcat tattttttggg ctctctactc tgttccattg gtctttgtgt   25560 ttgttttttgc atcagtgcca tgctgttttg gttactgtca ccttttagta tactttgaca   25620
tcaggtaacg tgattcttcc tgctttgttc ttttttgctta ggattgcctt ggctatttgg   25680
gcttttttgg ttccttatgg actttaagat cttttctaatt ctgtgaagaa tgccattttat  25740 agtttgatag gaatagcatt gaatctgtaa attgtttcag gcagtatagc tgttttaaca   25800
atattgattt ttcctgtcca tgggcatgga ctgttttttcc atttgtatca tctctgattt   25860
ctttgagagt gttttgtaat tcttattgta ggatctttca cttccctggt tagctgtact   25920
ccaagatatt ttattctttt tttttttttt tttttttttt gagatggact cttactgtgt   25980
tgcccaggct ggagtgcaat ggcgcaatct cagctcactg caacctctgc ctcctgggtt    26040
caagtgattc tcctgcctca gcctccccag tagctaggat taaaggcatg cgccaccaca   26100
cccggctaat ctttgtattt ttagtggaga tgcggtttca ccatgatggc caggctggtc   26160
tcaaactcct gacctcaagg gatccgcctg cctcagcctc ccaaagtgct cggattacag   26220
acattagcca ccatccctgg tcttttaatt ttttaagtga catttaccag ctgtaaatta   26280
tcatacctga attgctattt gggctactgt agtgaatcgg attatgcttt gggccagtta   26340
gttttacagt tttaaatagc catagacaat actcttaact ctgacctgct catttgttaa   26400
tctgtcatta gtcacagtgg ttagagtac tggcagaaca gtaaacacta acgtggcaca    26460
taatatatac ccaggtatag ttttgagtga ggtagctggg gcaagtgctg acacaggtta   26520
agtaactggc ttaatgttat agtagtaaat gccaatgctg atattcaaat cgacatccct   26580
gaattcaagc ataaatatct gttaagtaat tggtagtagg caggggttta gaattatgtg   26640
ttggccttga catgaacatt ttaggtattc agggttgctc aatcaacgga ctgaccttta   26700
atctgtgtga tttcactgca aaaatggttt ctgaatccat ttatatttt atatttttata   26760 aaagaaaac actatttcc ttattagtaa tttaaagcac aatttacatt caccacagca    26820 taattttttga tagtattatt attattagtg tttcttctgt ggtgaatgta atttaaattg   26880
tggtttaaat tactaatgag gaaaatagtg ttttcattta tatttatctt acccttaagt   26940 aattttttgtt gttacttgtt tttttgttt tgttttgaga gagggcctta ctttgtctcc    27000
caggttggag tgcagtggtg tcatcactac tcattgcagc ttcgacctcc tggacccaag   27060
tgatccttcg gagtagctgg gatcatacgc atgcgccacc atgcccagca aaattttta    27120 aattttggaa tgatggggga ctctcactct tttgcccagg ctagtctcga actcctggct   27180
tcaagtgatc ctcctgcctc atgtgtgatt atcagcggcg tgagccacca tgcccagcct   27240
gttgttactt ttttaggttg tagataagta ggaatcctcc cgtgtctttt ggaatattag   27300
cctttgctct ggttttttcct ctagagcagt ctcccattca ttactgttat aggaaatatt   27360
tgactgtaat aacagagatt gacttgtatt caagagttct taaataacaa tggcttctct   27420
gattgactgc ttttgaattt cttccagttt caagggagtt taatggttgt gccagaggct   27480
tcattattgt ttatattttt ggttgctact aagtgctttt aaaaacgtcc ttagtcttga   27540 tgctttttt atatttagta ttattattat tagtgttttt gctgtggtga atgtaattta    27600
aattgtgctt taaattactg atgaggaaag tagtgttttc ttagattgaa acattttat    27660 tgatatcacc tacaggcatt tcttcacag ctcagggaat gtgactgtca aatcttagga    27720
agaatgtgtt gtgaattttt tttttttttt tttttgaga cggagtctcg ctcagtcgcc   27780
caggctggag tgcagtggtg cgatctcagc tcactgcaag ctccaccttc cgggttcacg   27840
```

-continued

```
ccgttctcct gcctcagcct cccgagtagc tgggactaca ggcgcccgcc actatgccca   27900
cctggctaat ttttttttgt attttttagta gagatgaggt ttcaccgtgt tagccagggt   27960
ggtctcgatc tcctgatctt gtgatccgcc cgtctcggcc tcccaaagtg ctaggattac   28020
aggcgtgagc cacccgtgcc tagcctgttt tttctgtttt tgttttttgtt tttttaagag   28080 cagttttagg ttcactgcaa aaattgaaag cacagtgata acctatgaac tccctgccct   28140
gacgcatgca tagccgcccc caggatgagc atcctccttc agagtagtac atttgttaga   28200
attggtaaac ctccattgac acatcatttg tactgttttt aaaaacttac attttaactc   28260
ttttatgttg aaaatcttgg tttttaaatg acatttacct atttgtttta tcttgtaaat   28320
gagatatttc aataatattc ataagaacat cattgacaac aaatatgcta aggttttaag   28380
attttcttgc agtcctttgt gtccttacat tgtatcacac atcttaataa tctaaagata   28440
tcctttcatt gaagtaaaaa gattggttgc atatgttcta ataatttttt ttttcagtga   28500
agaaaagtgg tggttagtgc atacataata gcaagtcatg ccgtctattc tcagtgcttt   28560
taaaaaaagc aagtcatcaa aaggtttcat tgatatctct gcatatcatg ttttttatttt   28620 cactttacca gctctttttt atgtgttttt ttttcctgat ttaatcactt tcctgacaat   28680
taccaggtac tttttggaag tggttaatat tagcggaatt gcagcatgta taaccaagaa   28740
ggtattaaca tgtatacgga atatctacag tgataagaaa atgacagtcc attagaaaag   28800
tgatcaaaat cattgaacag attcttactt cactcaagaa aatatatgac taggcagggc   28860
atgatggctt gcgcctgtaa tcccagcact ttgggaggcc ggggcaggcg gatcacctga   28920
ggtcaagagt tcaagaacag cctggccaac atggtgaaac cctgtctcta ctaaaaatac   28980
aaaaattagc caggcgtggt atatatatat atacacacac acacacacac acacatatac   29040
acacatacat acatacatac acacacacac acatacacat acatatatat gtacacacac   29100
acatgcatac atctatatat atgtatgtaa aaccatatgc cactgtgcat atatatatat   29160
atatacacac acgtatatac acacacacac acacacacat atacatacac acacacacac   29220
acacacacat atatgcaaaa ccacatacat ctctgtggct tgtctgtgaa taaagataaa   29280
ttttatttct tttttttcca gcagtgatgc ctttttattt attttgcatg actgtactag   29340
ttagagcttc caaaacagca gactagaaat ggggagagca gacatcctta tcttgtttct   29400
gatattaggg ggaaagcatt tggtcttttaa tagttaaatc tgatgttatc tgtgggcttt   29460
tcattgatgt tcctctattc ctgcttcatt gagaattgtg atcaagaatg aatgtttcat   29520
attgtcagat gattttctgt gtctgatgtg ctcatcatat agatttttctt ttttagcata   29580 ttaattatga tgaattacat cagttggatt ttgaatactg acccaagttt gtgttcctgg   29640
aataaacccc atttgatcat gatgttttat ccttttgata tattatttga tttgatttgt   29700
tgaacgtttg tctggaacgt tgtatccac attatgagga aaattggtct gcagttttct   29760
tataatgtct ttgcctggct ttggaataaa aaatgctggc ttcataggat caaaactgga   29820
agtatttcct ctttttttac ttttttaggag gaatttgtag tatttttttc ataatatcaa   29880
gataaaatat accaatgcat tttttatggg aagattttga acaataaatt cattttttaa   29940
aatagataca tggttttttca gattttttttt tctgtttgga ccttgagtgg tttgtgactt   30000
ttcaggtatt tgtccatttt atctaagtttt tcacatgtat aggtataaca tgataatatt   30060
cccttctatc tttttaatac ctcaaaaata catagtgaca ttacctcact cattgctcat   30120
gatggtaatt tgtgttttct ctcactgccc aatctgcctg gcccgaaatt tgttaattgc   30180
```

```
ttttattttc ttaaagaacc agcttttgtt ttcactgatt ttctcgactg ttcttatgct    30240
tttttgtttt acttatttat agttcatatt attattatat tttcattctt ccgtttgctt    30300
tgggttaagt ttgctatttt tttagttttc taaggtggaa actaagatta ctttttttgag   30360 atcttttctg gtataggcat ttagtgctat aaatttccct ctgagtttgc tttaacagca    30420
tttcatagat tctgatatat taagttttca ttttcactta atgtaagaaa tacttgctat    30480 tttcttttg atttcttctt tatcccatgg gttattttg aattgtgtta cttagtttcc      30540
aaatttctga gtatttctc ttcttggttt gtaatttaat tctgttatgg tctgaggaca     30600
tactttgtgt gatttgaatc ctcttctttc tttctttttt ttttttgaa acggagttta     30660 actctgtggc ccaggctgca gtgcagtggt gtgatctcga ctccgcaacc tctgcctcct    30720
gggttcaaga gattctgcct catcatccca aatagctggg actacaggcg tgcaccacca    30780
cgcccagcta ttttttgtat ttttagtaag agaggcgttt ttgtcacatt agccaggctg    30840
gtcttgaatt cctgacttca ggtgatccac ctgcctcggc ctcccaaatt gttgtgatta    30900
caggcatgag ccaccatgcc cagccgaatc ctcttatttc tattgagact tgttttatgg    30960
tctagtacat tatatatctt ggtaaatgtt ttgtgtgccc ttgaaaagag tatttgttgt    31020
tgagtgtagt gatctataaa tggtaattag gtcaagctgg ttgatagtgt gttcaaatct    31080
tccatatcct tactgatttt atgtctgctt gcttttatca gttttggggg aaggaaatat    31140
taaaatcttc agtgacacag aatgtgtctt tatgttatgt tactgtgaac aaatttcttt    31200
tttccacccc ttcctttttt taatcattgt gtgtgttggg ggtgattctc agcttttccct  31260 agtcctttga aagttttcag tggttatgta gagaaacccc acaatcagag ggctgagaaa    31320
gcattctcag cggaactcag gtaatactta atattatctt tattaagaaa ataaagagac    31380
tttgttgaaa atacttccag aacattgtca tggagttctg aacttctggt taactccata    31440
aatagaatct attttttgcta ggcaaggaaa agggaacctt tatctttggc cagtaagtct   31500
cccaaatagg taaaaaggag agttttaaaa ttttcttctt tggagtcttc ttattagcat    31560
aggtagagtt ttagttacag aaatcttggc tgtgctagag gcatggaagt agaagaaacc    31620
agagcaatga atttaatggt tacttaacag tttgttcttg ttctctttgt gtttgtaatc    31680
cgataagagt ttttttttt ttttattaga gacagggtct cactgtactg cccaggctgg     31740
tgtcgaactc ttgggctcaa acaatccacc tgcctcagcc ttccaaagtg ctaggattac    31800
aggtgtgagc cactgcaccc ggctaagatt tgttttttta agcagccaaa aaaaaaaaa     31860 aaaacaccaa cacacaacta tttgataaat gcatggtttt tatattaaat agtacaaata    31920
gtgaagtgta caggtgttat caaccaaact cttaagtcat ggtgatcttc aagtgcctga    31980
ggctttctgg caccctgcct aatgctatta gcagggtcca tagcagtgtt attgtcccat    32040
actccttttc tgttctctgg tgaagcagca aactgaataa agtttgagtc tttgtctagt    32100
gactgtactt gttttcttgt gtgctgggca atgtggtaga ccatggggtt ccattgctaa    32160
tagccattat ggtgcacata gttaactaag cccagggaat tggggtcatt tctggtggag    32220
ttactggagt gttcatttt tcagattccc tgggtattag gttagtgtgg tctggtgcac      32280
ggggacagag accactcttc tggcagcatg ggtgttagag gagatgccct gtgagcaagg    32340
ctgccattct gtgagaaggg aatgaaaaat gaatggtcag aagatacttg attgtgtagg    32400
aaaccaggag ttacaatatg agaatataca tagacttgaa attgtgtata tcacgttttc    32460
aaaatagaag taagttaagt gcgttatact ttcagttgtt ttaaaaatac tattactagc    32520
caggcatggt ggcatgtact tcttggaggc tgagttgaga agattgcttg aacccaggag    32580
```

-continued

```
ttcaaggatg tagtaagccc tgttcgtgct gctctactgc actccagcct gggtgacaga   32640
gctagcccgc atctctttaa aaaaaaaatg cccctcttgt gtaatttgcc tttttataga   32700
gataatattt ttagctagac tgagggcttc agggatactt tactccagta gtaattttgt   32760
tgttgttagc tttcaaagcc cttgagaaaa ggagctgcta tgcttacact gtgattacat   32820
tggaaatagt gctcttctgt ttttgctcac atgtatacac ttcggctaat tgagaatttg   32880
aatctgaaac atatactagt gatacaggtt tcttttatg cataaattat ttttaaattt    32940
agtgacaaat attagcaata atgtacgttt aagtagtata tagattttaa ttaagacatc   33000
ccatgttttc tgtgtactaa gaccaggaag cagtcctcta gttattaaaa ttggagtgta   33060
tttcttacta gttgataaaa catgggtttt ggagtcatac ctagtttcca gccgtgaacc   33120
tagtacttca taatctatga tacttggtgt tctctgtagc attgtagaaa taataccatc   33180
tactttgtat ggtggtttca agaattatgg tagatcagtc tttcctaaat acttgtgtta   33240
taaaatgtaa ctaggtctct gaagaaataa ttccatgaac acgtatgtca ggaatatgca   33300
gcattttctg ttctcttaaa ggttctcact ctgtattaaa acattaggcc tatggtcaag   33360
aaatctgctt tcttttgttc aacactgcgt ttctcaaaca gaacttctcc cttcttcctt   33420
cctactcccc tgctcctcta ttgaacacct gcagtatatt atagtttatt tttgtttcat   33480
ggaacatagt tttgaaaata aagtgcctcg cacagtgttc ctaattatac tggataaact   33540
gtttcatttc ctgcttttgaa tgttaatttt aatggtttga aaactgtatt gtaggctggg   33600
cgcagtggct catgcctgta atcccagcat tttgggaggc caaggtgggt ggatcacctg   33660
aggtcaagag ttagagacca gcctgaccaa catggcaaaa ccctgtctct actaaaaacg   33720
caaaaattag ccaggtgtgg tggtgcaagc ctgtaatccc agctacatgg gaggctgagg   33780
caggagaatg gcttgaaccc aggaggtgga ggttgcagtg agccgagatg gccagtgcac   33840
tctagcctgg gtaacagcga aactcggtct caaaaaatat aaataaataa ataaataaat   33900
aactgtatta taaactcaga gctcatttct tttaattaat tttagtttaa tcttctaagt   33960
agtaagccat ttaataattt gctacatttt attcctaatt cactatcatt tagttcatat   34020
atttagccca aaatgttgtc atacaccttg agattcaaat ccaggacaag caagtgcaga   34080
ggcagtagaa gggtaagaat ctcacgaact cagtatctgg tcagattcct gcttcactaa   34140
tccaacacaa tttaaatgtt cagaaatata ttcttgaagt attattgaga gccctctggg   34200
aatatattga aggatctggt tagatacttc ctataactgc tctagagctc ttaagactag   34260
gcacaagcca tccacatctt tattgagtaa tttgtaagaa ttctgcagat taaaaagaa    34320 ataacatctt tacaataaaa aagcaaatgt taaaagaatg aaaaatctgt ttccaaagta   34380
aaaaagtagt aaaatattgt tttagaaaaa ttgaagaaat tgaaaagca tagataaaaa    34440 gaataaaatg tagataaaga gacttaagag taattttata cccaggaatg tccattccta   34500
acatcttatc ctccgtattt cacaaaaagt gtaccatatt atccatgcta gtttgtagct   34560
tgcttattct gctaaaaat gcgaagtgaa gaacttctca tgccagatat cagtgaggca   34620
ccctacttgc cctcaagaat ctaccttaat agggtgccct ctatagctga tttcttcctc   34680
tcccttcccg tccctcccc tccctcccc tttcttcttt ttcttttttc tttccttgc     34740 ctgcctttcc ttccttcctt ccttccttcc tctctttctt tctttctttc tcttctttc   34800 tttcttctc tttcttttctt tcttttcttc tttcttcttt tctttcttc tttcttcct    34860 ttttcttttt ctttctcctt tctttctttc tttcttcttt tcttctttc tttcttcttt   34920
```

-continued

```
tctttctttc tttctttctt cctttctttc tctttctctc cctctttctc tttctctccc   34980
tctctctctc cctccctccc tccctccctc ccgtccttcc ttccttcctt ccttccttcc   35040
ttccttcctc cctttcttcc ctttctttcc ttttctttct ttcttgtctt tcttgtcttt   35100
cttggtggag tctcactctg taacccaggc tggagtgcag tggcttgatc ttggctcact   35160
gtaacctctg cttcctgggt tcaagcaatt cttcttcatc agcctcccga gtagctggga   35220
ttacaggagt tcgccagcac acctgactaa ttttttgtat ttttagtaga gatggggttt   35280
caccgtgttg gccaggctgg tcttgaactc cagacctcag gtgatctgtc cgccttggcc   35340
tcccaaagtg ctgggattac aggtgtgagc caccgtgccc ggcctcattt cttcatttgt   35400
gaggaatgtt tccgggcagg agttaggagt tggcagaaga gtgatgagag gaacaagccc   35460
tgttagaggg taaattaaga catcattgta cagtttctag ttattaataa accattaatg   35520
tatgcagaat tatacagagt aaacattgtt tattttggtc agttttcttg cacatatcca   35580
aaagatttg aatttaactt gtttaggaga aaaaagtct ttaaatacca agagctggta    35640
tgtgcataac gtacacacct agattgaaat acagaacctt ggccaggtgt ggtggctcat   35700
gcctataatc ccagcacttt gggaggggag atgtgcggat tgtttgagcc taggagttca   35760
agaccaacct gggtaatgtg gtgaaaccct gtccctacaa aaaatacaaa aattagctgg   35820
gcatgggtgg tgtgtgcctg tagttccagc tacctggag gctgaggtgg gaggacctct    35880
tcagcctggg aatcagaggt tgcattgagc tgagatcatg ccattgcact ccagtctaga   35940
caacagagtg agaccctgtc ttaaaaataa ataagtaaat agagaacctc aagttatcat   36000
tacggtgtgc tagatggttc attgcctctt taaattaaat taaaacaaga agtctaatag   36060
gaattcatag aacacttttt ggtcaggctg tctggattgc agtcgcacac ttttcactca   36120
ggctcattgc agcctccacc tcccagtttc aagtgattct ctcccctcag cctcctaagt   36180
agctgggatt acaggtgctc gccaccatgc cctgctgatt tttgtatttt tcgtagagac   36240
tggatttcac catgttggcc aggctggtct cgtactcctg atctgaaatg atccacctgc   36300
cttggcctcc caaagtgctg agattacagg tgtaagccac cacatccagc caacactttt   36360
tcttgttgaa agatattcct gaaaaaatg ttgtattatt aaacatgttt tagtctgcat    36420
gtattatgta gagctttctt taatgacatc aagaatgaca aaagagatga aatgtttatt   36480
actactttc gaatattttg aatttttttc tttctttctt gtttttttaag gtggatatca    36540
tccagtgaaa attggagacc tcttcaatgg ccggtatcat gttattagaa agcttggatg   36600
ggggcacttc tctactgtct ggctgtgctg ggatatgcag taagtgttct ttgtcatttg   36660
tgcatttgtt tcctggagta gttcaacatc tgtgttctaa gaaggtatgg ctgagggtca   36720
ccactgcttt gttgaggtat gtgaagtgct tagcacaggc ctgcctcagc tggctagatt   36780
ccttcctgcc ccctgcctta gtttgaagtt catttgaaat cttaaaatat tacttgcttc   36840
cagctttatt tcaaagttaa ttcattgaaa ttgttttaca ctgggattat attatttttc   36900
tagtaattca tccatatcag acaaacataa tgtatagtat aggcgtttca aatcagtcat   36960
ttttaacttt tcaaagccat gacccatagt aagaaacttc attgctactc catacacaca   37020
cacacacaca cacacacaca cacacacaca cacacacaca tttggtgcgt gtgtgtgtgt   37080
gtgtgtactg aaacaaagtg ttaaaagaga atggttttca ctattaggtt ggtgtgtaat   37140
attcgtgata actctgatgt ttatctagtc ttattttaat tagggaaaaa acaaaacaaa   37200
acataaaaga gattgtcttg acccatacta ctatttaatg tggccccacc atttgaaaag   37260
tactatttta aggaaagct tatgtttctg tgtattggat agatctcatt acaagttgaa    37320
```

```
tatcccttat ctgaaatgct ttgagaccag aagtgttttg gattttggaa tatttgtgta    37380
tatacacaat gacctatctt ggagatgtga cccagatcta aacacaaaat tcattatatt    37440
tcatatacac catatacaca taccctgaag gcaattttat acgatatttt aaataatctt    37500
gtgcaacatg caaatctttt actgagtttt gattgcagtc agaggtggaa ttttacactg    37560
tggcatcgtg ttgacacact cataatgttt taggttttgg cgcattttgg attttacatt    37620
ttccaattag ggatgctcaa cctggatacc agtgattctt tctactgata atatagataa    37680
atagactctt tttttgtttt ttcttttagg gggaaaagat ttgttgcaat gaaagttgta    37740
aaaagtgccc agcattatac ggagacagcc ttggatgaaa taaaattgct caaatgtgta    37800
agtactttaa aaatgtgaat gatataagaa aacttaatga cttaaaattt tacagaaaga    37860
tttttctggg taatactaaa ttaaagtcaa gtttggctgg gcacggtggc tcatgcctat    37920
aatctcagca ctttgggagg ccaaagcgag cagatcactt gaggtcaaga gttcgagacc    37980
agcctggcaa acacggtgaa accccatctc tgctaaaaat ataaaaaata gccaggcatg    38040
gtggtgggca cctgtaatct cagctccttg ggaggctgag gcatgagtat cacttgaacc    38100
tgggaggcag aggttgcagt gagccgagat cgtaccactg cactccagac tgggcgatag    38160
agcaagactc tgtctcaaaa aataaataaa taaataaata aataaagttt atttttata    38220 actttgtgat gaattttta ttttaaaata tactttattt aaacagtatt ggtgttataa    38280
tgggaaaaca tgctttgtct caaactcctg tgttcttgca ttcattttc ttggcatagg    38340 ttcgagaaag tgatcccagt gacccaaaca aagacatggt ggtccagctc attgacgact    38400
tcaagatttc aggcatgaat gggatacgta tcctttactt cctgatttat ttgtattttt    38460 acctttaaa aaatgaaaat atttcaagct cctataatct ctgtttactg ctgtatcacc    38520
ttcaacataa acactctagg aacattgtca agtattatga agtggtccac ctagaatagt    38580
tttcatggct ttttgggtg tttggtagag tagcatctta gaaacttatt tttaacacaa    38640
caacttgact taatttggt gtggaattaa ttattgatct cttcccatta atagtggtaa    38700
agtttttttt gtggtggtag ataaaagcat acatcagcac cacttctttg tgttttaaac    38760
tttctaaaac cagtgcataa ggacaatctg tgtgtgcccc agtggctgca aagcaccatg    38820
tgaaaatgga gcattggtta agataaaagg aaaaatgctc tgtaaatgtc cacatcccaa    38880
ggtggcgctt gactgctctt agttctgaat agtactaata attgccaaat tcttttcca    38940 aaatgataca actgagcctt tcaaataatt gtcctgcaga ggctcatctt tctgtcaggt    39000
gagtatggaa acattttggt tttcttgatt ttattcctgg ttatctatat tgcaaaagtt    39060
aaggaaaagt aaaatgatgc attttctata ctctgcattt tctatactcc ttgataaatc    39120
tgacataagc cagtgcttga tcgaaaatac ctttattgtt tttctttaca aacttattgg    39180
gagaaatttc aaacatataa gaaagagatc atactacagt aaattgttgt aaattcgtca    39240
ctcaagttta ataattgtca tggtctggcc ataattgatc catctatctt ttcttgctga    39300
attattatag agcaaatcct agaagtcatg tcctttact tctgtgtcat tgtgaatctt    39360
tgaaaaaaat atgaactttt aaacataacc ttaaaactca ccaaagacat taacgggttc    39420
ttgatatctc gtcagatatc gttggtattg gagacttctt aatacagatt tccttggtat    39480
tgcaaaaatg aacttttaaa gacatatttg aatcattttt aacaatattg tttactccta    39540
agtctgtatt cacttacttt agttgttcag tttcagatta atttgctcaa tttacatttt    39600
tctgtttctt gttagactat gatccacaga gtatttaaat tatcctgaca gaaagttagt    39660
```

```
gattcttaac agaggaaagt gtttcttggt cagctataag tgtaggtgtt tctcatgttt   39720
tttaaaagga tggatggcct tagtcgtaat gtgtccgttt ccttctggtg ggttcttggt   39780
ctcactgact tcaagaatga agctgcggac cttgcagtga gtgttacagc tcttaaaggt   39840
ggcgcatcca gagttgtttg ttcctcccgg tgggttcgtg gtctcgctga cttcaggaat   39900
gaagccacag accctcatgg tgagtgttac agctcttaaa gttggtgtgg acccaaaaag   39960
tgagcagcaa caagatttat tttgaagagt gaaagaacaa agcttccaca gcatggaagg   40020
ggacccaagc aggttgctgc tgctggttcg ggtggccagc tttattccc tcatttgtcc    40080 gtgcccacgt tggagaaatg gacctgccga ttggtccatt ttacagagtg ctgattggtg   40140
catttacaat cctttaggta gacacagtgc tgattagtgt gttttttacag attgctgatt   40200 ggtgcattta caatccttta gacacagacc actggtcagt gcgttttac agagtgctga    40260 ttggtgcatt tacaatcctt tagctagaca cagagcactg attggtgcat ttacaatctt   40320
tagatagaca cagagcactg attggtgcat ttacagtcct ctagctagac agaaaagttt   40380
tcaaagtccc cactcgaccc aggaagtcca gctggcttca cctctcacta atactagtta   40440
tctttggaag tgtgtctagg aagaagacaa gcaaaggtgt cccttgactt tccttctttt   40500
tttgagaata tcagttttga ccatgctact aagttatgtg gatgcttgtt ggttttgatg   40560
gggactcagg aggaagtgaa ttaggattgt agaaagggtt ggcatgttat ccttatcctt   40620
cctctacctg aggagttggc aaagggtagc tccagggaga agtgacagag agcaaagtat   40680
cccaaaacct gtagctcaga gaagaaagca aaaatgaaga gaagagatga tgccttcagt   40740
gtcatgagta cttttttcttt atgtgggtgt tggatcctct gagatagccc tttgtgtgcc   40800
tggagtaggc agtactttca ttttccaagg ttcaagaaaa tcggaccact ttactcagag   40860
gcacatgact gatgggtgct aggttgtgtc agtagctgtg gtcttctggc ttctttcaga   40920
ttttttgctc tttatatcat gtttggaaca gatccaccat tttgatattt tactttcaca   40980
aatgtcagaa gcctaaggat aaggcttttt cccagattta aactccaaaa tgacatccag   41040
tttatgcatc tactaagtca tgatcaacta gggaagcatt tccttcactc tatatatttg   41100
agaaggtttt tatacaaggg aatgtcacca tgttcataga aaaactagat taaaagacaa   41160
aaataaagaa tataaacttt atttctcaca taagtttcat caagttcaag acactttgt    41220 aaacaatcat atcagccatt tagttgctcc ccaaagaacc aggggtctta ggaatttaac   41280
catgtcagtg aaatctttt tacattatta actgaagaaa aatgggtgcc ctttttaaga    41340
ttaagaaaca aaaattagga gtagccaaat aaggataata aggtggatgt ctaatgagtt   41400
tccactgaaa ctcttcacaa aattgccctc gtttgatgag aggaatgaac aggaacattt   41460
acatggtgga gaaggactcc ttggtgaagt tttctgaggt attttcctgc taaagcattc   41520
actgactttc tcaaaattag ctctcataat aagcaggtgt tatcattctt tggttctcca   41580
taaagtcaac aagcaaaatg cctcagcatc ccaaaaaacg gttgcagtga cctttcctct   41640
tcactagttc actagtgctt tgactggacc actgccacct cttggtagtt attgctttga   41700
ttgtgctttg tcttcaggat catactgtag aaccatgttt tatgtcctgt tacagtcctt   41760
tgaagaaatg cctcaggatc tcgatcgtac ctgtttaaaa tttccgttga agctctgct    41820 cttgtcttga tctgggaaca atggttttgg cacccattga gtggaaagtt tgctcaactt   41880
cagttttcaa ttggaattgc ataagttgaa ccagtcgtga agtctgtggt gttggctgtt   41940
gtttgtgctg tcatctgtcc tcttcaatta gggtgcaaac tttttttttc tttgagatgg   42000
aattttgctc ttgttgcgca ggctggagtg caatggtgca gtcacggctc agcacaacct   42060
```

```
ccgcctcccg ggttcaagag attctcctgc ctcagcctcc tgagtagctg ggattacagg   42120
catgtgccac cacgcccagc taattttgta tttatttttt attttttatt tttttagaga   42180
cgggatttct ccatgtgggt caggctggtc tcgaattccc gacctcaggt gatctgcccg   42240
cctcagcttc ccaaagtgct gggattacag gtgtgagcca ccatgcccgg ccgcaaactt   42300
tttttccaca caaattgatg caaatggtct gccgctgcag gcttcatctt caacattatc   42360
tcatcccttc ttaaaaccgg ttattcattt gtaaactgcc gatttatttg cggtattgtc   42420
cccttaaact taccataaag catcagtgat ttcaccattt tttcacccaa gcttcatcat   42480
aaatttgatg tttgttattg ctttgatttt agaattcatg ttgctctgtt agaggctttt   42540
ttcaaactga tgtcttatct tgcgagtgcc tcaaactaga tcctgttcag atactttaac   42600
aaactagtat gagtttattt tggtgcaaaa aaattttttga aatctatgca tagtgttttc   42660
aaaatacaca ttttccatag acttttttgaa aatccctcat atttcttttta gaaattcatc   42720 ttgagtatac taggaagtac cagtggctgc taatgttacc tcgtcctttt tctccagtta   42780
atttctgcta actgctgagt atattttttcc ctttggatag ataaatcagt aagcagatag   42840
cggcagagca ctcacttctt ctgtgtccga cttgcaaggt ccttcttggg acagctaata   42900
gaacatttct ttggagaaac tacttaatcc gtgggtaaat agaggttttt gaaatatacg   42960
ttctagtggg tattttttact gttaagcaaa atgcgaagta atcatcatat ccagatatgc   43020
cagtgctttg agaagactta ggttatgttt gggatatcct gggcctcgcc ctatgcctgc   43080
tgctaaatgt agtccttaaa taatctgccg ttttttgtaat gagcctggga aatagtaaga   43140
aacttctggc tttagattat ctgcgcataa atctgtagtg cttacattct taaacagtat   43200
agaaagattt ttcttttttt cactaaaaat atttaaaata atattgtttt aatatagcat   43260
attcagttat tatagttgat taaatcaact actttttttg attctaaagt caaatgtaag   43320
cctccaggga tgaataaaat gttctcaaag ggtttcagag ccatttgtaa tcttcctgta   43380
tgaatgacat gaatatataa tgaaattgga ggtatcatag ttgtgaaggc tgaaatacct   43440 atttttaaaaa aaaattaagt tggggccagg tgtggtggct catgcctgta atcccagcac   43500
tttgggagac caaggtgtgt ggatcacttg agattaggag tttgagacca gcctggccaa   43560
catggtgaaa ccctgtctct actaaaactg gaaaaatcaa ctgggcatag tggcacacgc   43620
ctgtaatccc agctatttgg gaggccgagg taggagaatc gcttgaaccc aggaggtgga   43680
ggttgcagtg agctgagatc gtgccactgc actccagcct gggtgacaga acaagactgt   43740
gtctcaaaaa aaaattaagc tgggcatggt ggttttcacc tgtagtactg actacttggg   43800
aatctaaggc aagagagtat ctttagccca ggagttctag tccacctggc acagcgtagt   43860
gagaccctgt cttttttaag aaaagaaaat ccagattcct gagatgttgt tactatagat   43920
taagtcttaa taccatgtct taaatggtga tcatacattc ttaacacctg cctatagtat   43980
taaaattgat ctagttgtat aatgtaagat attattcaag gaaaagatta ataggtctt    44040 aactgtgttt actaaatttt tattttataa tgtgttttat gtagcttatc aagtagaaat   44100
ttaggcaggc agttaggaca cttgagatac tggagctctg tatttgtttc atgtcagttc   44160
ctaggaggtt tcagtcttgc ctgtttcatc aggctgattt ccagggagtg tgctgagatg   44220
ggtgagagtg cagctcagtg taggcttgag tagtggctca gccacctggc actttctaag   44280
tgcactctac acctagaaag tgccatgtcc tcatgcctac agtgggggtta attacattat   44340 tgcctaaggt tgtttggagt acacgtgaaa taatatatgg cacagagtaa gtacacttag   44400
```

```
cccttttta tctgctggtt ccccattcat agatttaata aacgttggat gaaaatatt   44460 tgggaaacac cagtaaaaag tagtagaaat taagaaatag agtataacaa ctatttacat   44520
agcatataca ttgtattagg tattataagt aatctagaca tgatttaaat aaagtatatg   44580
ggctgggcac ggtggctcat gcctgtaatc ccagcacttt gggagcccaa ggcgggtgga   44640
tcatgaggtc aggagatcga gaccatcctg gctaacatgg tgaaaccctg tctctactaa   44700
aattacaaaa aattagccga gcgtggtggc gggcacctgt agtttcagct gctcgggagg   44760
ctgaggcagg agaatggtgt gaacccagaa agcagagctt gcagtgagcc aagatcacac   44820
cactgcactc ctgggcgaca gagcaagact ccgtctcaaa aaaaaataaa aataaagtat   44880
atggaaggat gtgaataggt tatgtatata ctacaccagt ttactgaaga ggcgagcata   44940
tgtacatttt ggtatctgag agcggtcctg gaaccaatct cctgagatac tgggaaacac   45000
ctgtatttag taatgtcagt tcttgttatt taagtgagat acaacatttt ctcacttttg   45060
gtattactga tagggttgat gttgtatttt ataaagtaat aagtgctttg caagtgacac   45120
aatggtgctg ctttcaataa ctgcctcact ccaggcagtg catccacaaa cgatccttaa   45180
ctgtgtccca gatgtctgca tggtcttcga agtacttggc caccatctcc tcaagtggat   45240
catcaaatcc aactatcaag gcctcccagt acgttgtgtg aagagtatca ttcgacaggt   45300
gagacttttg acagcagccc ctaggcccta gtacctaatt ggttaggctt tcaacatgaa   45360
tgctgtttac aaatatgtat atgtattaca tatgtatcag tgcataatgt atatatgtta   45420
tgtatgttac atatgtatca gtgcataaca ttttgaactc ttattaagtc agtatttaat   45480
gatattttgt gttgtgaagg gaacaacatg taattgtcag gcatacgttt tttgcctgtc   45540
gttttttttt ttaaggtatg tgacatggta caattacatt gtttttgttc agtatctact   45600
ataaaacatc cacttagttc attaggaagt aatttagaag aaataactta ctgggtttat   45660
ttactaagta tccttggatg gagattaaat aatagataat tgaagagttg tgtacaaagt   45720
ttcagttata acgtggttaa attctgcaga tctaatagac agcatgatga ctatagttaa   45780
cattattgtg tacttggaat ttgttaacag agtagacttg aatgttctca tcatgtacac   45840
acacacagag tctatatgtc atactgggtt aggttaatta gctgttttgt gctaatcatt   45900
tcacagtgta cacatatttc aagacatgta cactactaat atattcagtt tttattgtca   45960
gttgtacctc agtaaagctg gggaaaaaaa tggaaatgtt taactcatat agaaattact   46020
gtattagatg tgtgttttgt tcagttgccc tgccagaaga aaaccctcag ctagggtcag   46080
gcttagagat gatgctctag taaacatctg tagaatgaaa gtatgcgtag atggaagaac   46140
tcctcctaat tagcagtgtt tgcccattcc agtgttctgc atggaatcag tatgtattct   46200
actcattgcc tgtaaaaagt ttgaagttta aatttgtgta gtaaaagcat cttttgatatt   46260 tctgttgaat ttgtgtgcag ataacttttgt ttagcctgcc tgtgtgttca tctcttcttc   46320
cttttgtacg ggttttttttt tttttttttt tttttttgga gacggagtct cgctctgtca   46380
cccaggctgg agtgaagtgg tgcaatctca gctcattgca gcctcctgag cagctgggac   46440
tataggtgct tggtaccaca cccagctaat tttttgtattt ttagtagaga cagggtttca   46500
ccgtgttgcc caggtggtc tcaaactcct aagctcaggc agtctgcctg cctctgcctt   46560
ccaaagtgct gggattacag gtgtgaacca ctgcacccag ccttgtatgg aaaattggca   46620
gcttattctg taacatgaca gatgttactt gagaagaggg gctggagagg gaaaagttca   46680
ctacattgtc ttctatatca gttgaattga ggtgtttcta tgtagtatta tgctaggtat   46740
acatgtgggc ctagatttat ggctaacttt tgttcagtac tgtatctgtt tgcccttagc   46800
```

```
tttcaaatag tagcattttt attcattatt tcgacaggct gatatctcaa atgaacaact    46860
ttaatgtaga agaggttatg tggtgagggc agaaattagt atgttaagtg gaattatttg    46920
atccccaaat aagactagtg tattatttgt aacatttagc agcaactcta aagtctttaa    46980
aaaaaaaaaa aaacacaaaa aaacacaaaa aaataaagcc atattgttaa aacttgggaa    47040
gaatctccta attattttg ataaatcttg aaaatattaa aggaattaca cattctaaca     47100
aatactgaat aatttcagaa atagctgcct gcatgtattt cccgcaggct ccatcatttc    47160
ccagaacctc atgctttcag aggggcttgc tgttgcctta agtgactgac cacaccacca    47220 cccttaggc ttagtgtgta agaaggtgaa tttggccagg cgcagtggct cacgcttgta    47280
atcccagcac tttgggcggc caaggcgggt ggatcacgag gtcaggagat tgagaccagc    47340
ctggccagca tggtgaaacc ccatctctac taaaaacaca aaaattagcc aggcgtggtg    47400
gcacacgcct gtaatcccag ctactctgcc agctgaggca ggagaattac ttgaacccgg    47460
gaggtggagg ttgcagtgag ctgagatcat gccactgcac tccagcctgg gcaacagaac    47520
aagactccat ctcagggaaa aaaaaaaaa ggtgaattca cagatgagcc attgacattt     47580
attttatctt ctagagaaga aaatatagcc ttagcaagtt gaaggagtct gtaagttgaa    47640
agatgaaaat ctgaggttca gtggaacctc agtgcatcct tgttgaatga accgaagatt    47700
aaataagtta acctgtgttc ttcattttgt ttttgttttt tgagacaggg tcttcctctg    47760
ttacccaggc tggagtgcac tggtcagtca cagctcactg cagccttggc ctcctgggct    47820
ctagtgatcc tcccacctca gcctccctag tagctgggac tgcaggcatg caccaccgtg    47880
ctagctaatt tttattttt tgtagagacg gggtctcact gtgttgctca ggctggtctc    47940
tttgtctcct ggactcaagc agtcttccca tctcagcctc ccaaagttgc taggattata    48000
ccacacctgg ccaatgcgtg tgttatcctc actgtaattc atgtaccctg ttttggtgg    48060 aaacttagaa agagctctta tattatttct ttagttcaga gaaattcaag ctgaaaattt    48120
gattgtgtca tgtggtctgc actttgttct tatatgcagt gttaatgaaa ttttggtttg    48180
gttttggttt tgtgtgtgtg aacccatctt tctttaagaa aaatattatc atggaatctg    48240 gatttttcc ccctaagctt acgcagaact ttcagtgtag taagttgttc aagaaattac     48300
atactccagt taataatcta cttacctgag gtttcccttc aacccctttg attcagccta    48360
tgttttcagt atttctttct cccgggtagt actaggaaga tttttattg cagactgaca     48420 cagttatatc atttcccaga acaagccaga gcagaccaat ttcttagta ttttcttagt     48480 atcctttcac tgtagacctt cttcttaaga gtcatggata accgaccatg ttccagtcat    48540
tctccttact ctatcacttg ctgtgcttcc ccaggaaccc gcctgttgaa ctctcctttg    48600
ccatgtcttt tactcttgat gttctttgta tttctgttgc tgtcctcttt agttcaggcc    48660
cttatcacct ccagctagta ccttttcaca ggcttttctt ggctctctgt gcatacagcc    48720
catccaattc ccggtccctt ttccagttta ttctcctttc tattgcaagt aaaaccttgc    48780
tttaatgact catattccca ttgagaattc tttagtggct tcccattgcc tgtttgctga    48840
agctttatgt tcttggcctt catgaagcaa tatatggagt tgttaagagc ttgggtttgg    48900
catcaaatat accctacttt caccaaaggg ctttggccaa gttacctaac ttctgcaaac    48960
cacaatttca tcatcaataa aagtggggaa aataatgata ccagccaggc gtggtggctc    49020
atgcctgtaa tcccagcact ttggaaggtt gaggtgggag gatttcttga gaccaggagt    49080
tcaagaccaa cctgggcaac atcgcaagac cgtgtctcta ccaaacaaaa tttaaaaatt    49140
```

-continued

```
agccaggtat gatggcatgc acctgtggtc ccagctacct gggaggctga ggtcggagga    49200
tcacttgagc ccaagggggtc aaggctgcag tgagccatga tggtgccact gcactctagc   49260
ctgtgtgaca gaacaagact gtctctttaa aaacaaaaaa caaacaaaaa tgataccttc    49320
ctcattagtt tattgtaaag atgtaatgag agatagtaat gctaatagta gcaaatagtt    49380
aattcagtgc ttactatgtg ccaggtataa tttgagtact ttgcatagtt gagttcctca    49440
caataaccct gtgaaatggg tattattact ttcctgattt catcaagagg aaacagaagc    49500
ccagagaggt taagtaactt gcccctagtt aggaagtcgc ttaaaaagtg ctaagtggtg    49560
aagcaggaat tcaaacccag atagtctggc ttcagagctc atgggtttac cattttggcc    49620
gttatataat gggttttata taataaactt attatgagcc tgtaataagt ttggaattgt    49680
actgggccta tgtccagtag aagttaagtc actttctggg aacctgttta agattttcta    49740
tcatctggtg tcagcctgta tttccccttg cagacaaaaa gtgatgtccc tcaggtaccc    49800
tatttccctc tggaatctac cagcttacgt tttttatgaa tgttcaaaga tgtcccaaac    49860
atttataatg tgcagattta ccagaatttt cattcatgaa tgtttactgg ttttattttg    49920
taggtagttt agagaaagta ctcactggta atcatcttga cccctaaggg cacctttccg    49980
tttttttatct ccacatcttt gatcatctct tttgttctag gctgccagaa atgccatcct   50040
tgtctaccca catttttaag actcaacgaa atcccacca ttgtgacaaa ggcttctcac    50100
agtacccaat taagaggatg ccttcccttc ttgaaatgcc ttcagctcac atttggtccc    50160
ataactacgt gtaggcccca tctcaaccct agggctgctg gcacttcaga ccagatagga    50220
tgtttagcag cgtccctggc atctaccct cagagccagt atcagctgtc accatccctg    50280
attgtggcaa ttagaaatat ctctgaactt tgccagtttt cctctcactg agaaccactg    50340
ggataagaga aagtgtaagg tgtattgtgc tttggtgaca gacttgattt aacatcatag    50400
ctttggcact tctatcttgt actcctgatc agttacttag cctctgtgag tctgtttcct    50460
catttgtaaa ctcgaaatag taatgcataa tttgtagttt gattgtggag attaagaata    50520
aggggggctgg gtgcagtggc tcacgcctgt aatcccctgca cttttgggagg ttgaggtggg    50580
tgtatcacct gaagtcagga gttcaagacc agcctggcca acatagtgaa accttgtctc    50640
tactaaaaat ataaaaaatt agctgggagt ggtggcacat acatatagtt ccagctactt    50700
gggaggctgc ggcaagagaa tcacttggac ttgggaggcg gaggctgcag tgagccgaga    50760
tcgtgccatt gcactccagc ctgggtgaca atagcgaaat tctgactcaa acagacaaac    50820
aagaataagg gtgggccagg tgcggtggct cacacctgta atcccagcac tttgggaggc    50880
caaggcgggc agatcatgag gtcaggagtt ctagaccagc ctgaccaata tggtgaaacc    50940
ccatctctac taaaaataca aaaattagct gggtgtggtg gcacgtgctt gtagtcccag    51000
ctactcggga ggctgaggca ggaattgctt gaacccagga tacggaggtt gcagtgagcc    51060
gagattgtgt cactgctgct cttcagcctg ggtgacagac tctgtctcca aacaaacaaa    51120
aaaagtatag ccattagatt ttatgaagta gatattataa tatgtaacca gatgagacct    51180
ttaaaaccca atgttttttcc agacttctcc ctttggggtg caaccctcta gtatgccgag    51240
agccacggtg gtgccccgca ggtcctctca cctgtatcat tggctgattt tgtctctcta    51300
cacttagtat ttatttacca ttgtaattct ttcagtggcc ctgtttatca gtaaattttg    51360
ttatgactga accagtattg ttcaagttca gaccagaagc tttcatgtca atttggtaaa    51420
cattttgata ttactgggtt tgttcagcat ggtagtgcac acgatgctgt attgacttgg    51480
aattctcctc aggatgttga gcccttgact caggaaatgt ggtgaggtgg ctctgtttca    51540
```

-continued

```
agggactaag ctgctttcct gagccattgc tttgtgcagt cccagtgctg ggcacagcag    51600
ctttaacttt cttcctgatg acattcagaa gtacagctgc tggcttttct cattaattct    51660
caccagttag agatgaaaga aaaggagca gaggctattt caggacaatg tgggtaagga     51720
cgccgtcccc tggattttg gtttgagcgt gtctctggct cttgtcctct tttattgtta    51780
acaggtattt ccaagctcct ccattgagtt taacatcttg gttttcacag gcagttggtg    51840
ggacctgcct tgtgtgtttc actgtggaag ggaaatctag tggaaccctc agtgtttcca    51900
gcaggaaact tctaggcttg cggagaaccc ctctggtgtc ccgcacgccc acaagtaatt    51960
aatattctca atgaagaact cctgcttggg gtcgcctcct tcctctgcca gcccatctgg    52020
ctgcccacgt gggtttctct gggtgcttca ttaggttctg ttacccacag agtaggagga    52080
gacagagtct ccctgctctg tgtcctttgt tcaggtgtgg gaggaagaaa gtccaccgct    52140
tatcaccagt agcagagcat aatttggaaa gttgctctca ttctatttct ttttacagtt    52200
cagaattttg ggggaagctt tgcactctgg gctgtgagca aggccaggga gacagtcttt    52260
agaggagtct ccacattatg cttgactgtt ccccgactta tctacaagat tacaggacct    52320
atttcaatca agttgtggtg gagaggagca gatttgtgtt gcgaagacca gtaatagatg    52380
gtatctgaca caaatgttga tgtacagaaa gaaagctttg agaccatttt aaccaagccc    52440
cttattttga agatgaattt gaggttcaag gaaagaagg aactttctct gaacctgtag     52500
ctagttaatt tggaatggga ctcggggctt ctagctccca gccctagact tagccttctt    52560
ttccgcactg ctgctgaact caaagtctga ctttacccag agaaacctgg cacttgttcc    52620
tcatgtgtgt gaaatggctc cctgagtggg atgattgaga gtcacgtccc tggctcgtct    52680
gggcttaggt tgatctcagc ttccctggca gccaaaggat ctctgctgcc tcctgctgct    52740
agcaccaagt attaaggttt tttgttttgtt tttgagacgg aatcttgctc tgtcaccagg    52800
ctggagtgca gtggcgcgat ctcggctcac tgcaacctcc gcctcctgag ttcaagcaat    52860
tcttgtgcct cagactcctg aatagctggg attacaggca tgcaccacca cacccagcta    52920
atttttgtat ttttagtaga gatggggttt caccatgttg gccaggatgg tctggatctc    52980
ctgaccttgt gatccgccca tttcggcctc ccaaagtgct gggattacag gcgtgagtca    53040
ccgcgcccag ccgtattaag gtttttaggc aagaaagatg aacatactgt gatttgacaa    53100
gtaaaagcaa cagaggaaag aattagtaaa gacttaactc tgtcagattt tgcaagggga    53160
gatctatccc atgggatga aacatgattc cttttggttt gtgttttgt ttttcccatt     53220 gtcacagtta tcctgtataa ataattgtag gagttctcgt caatgttggt tgattctggg    53280
gtgcattatt acttaaaact tcactggaaa gacaaatgtt attttttgaaa ataaaaccat   53340 ttaaaaatag tagttctggc caggcatggt ggctcacgcc tgtaatccta gcactttggg    53400
aggccgaaat gtgtagatca cctgaggtca ggagtttgag accagcctgg ccaacatggc    53460
gaaaaccccg tctctactaa aatacaaaaa gtagctgggc atggtgacat gtgcctgtaa    53520
tcccagctac tagggaggct gaggcaggag aattgcttga acccagtagg tggaggttgc    53580
agtgagccaa gatcgtgcca ctgcactcca gcctgggtga tagagtgaga ctccatctca    53640
aaaaaagaaa aaagtagttc aaaattaaat tatggaatca aagttttgtt gctgggatgt    53700
accatacggg ttatcaagta tagtcctttt atattagaaa tggaaacaac tgagacccag    53760
ataatttttt ttttttttt tttgagacag aacctcactc tgttgcccat actggagtgt    53820
ggtgacacga tctcagctca ctgcaaccac cgctttctgg gttcaagtga ttctcctgcc    53880
```

```
tcaacctcct gatagcagcg attacaggca tgcaccacca tgcctggctt attttgtat    53940
ttttagtaga gagggggttt caccgtgttg gccaggctgg tcttgaactc cagacctcag    54000
gtgatccacc tgccttgacc tcccaaagtg ctgggattac aggtgtgagc catcgtgcca    54060
gccaacccag agaactttaa taagtgactt aggaagctgg atgtggtggc tcacacctgt    54120
aatcccagcc acttgggagg ctgaagcaag aggatcactt gaggccagaa gcttgaggct    54180
tcagtgtgct ttacttacac ctctgaatag ccactgcact ccagcctggg aacatagcgg    54240
gatcccatct ctaaaaagaa attaattttt aaaaagtgat gaaaaatcat aattcaataa    54300
gtcaatatca gtacaagtct tctgacttag atacgtttta ccatttaagt ttcttgtgtg    54360
ctagactttg tttttgtgag ttttccgtag attatttcta aagcttattg ctacatttgt    54420
gtgtaacagg tgtttccccc tcccatagat gagaatgaaa gctcaaacag cttaaacagc    54480
ttgcccaggg gtaacacaat gagtaaatgg ttgagcagta atttaagagc agtctgaatc    54540
caaggtcatg ttttaacgc tgccctgttg ccatttcctt taatggtttc aattatctta     54600
actaacttta tttgtcccag tggcaaagta tttttcttgt gtttattgcc cattgctgtt    54660
ttaggaaagt tagcctagtt gagtgcaata gccaattttt tttaaaaaaa atctggaact    54720
ttaagttttt actgagatca cttcttgctt gtcatgaggt gcatcattgt cattgggacc    54780
tcatgtgaac acatttgcac actgaggcac attaactctt aactgtgcag cctcccgcac    54840
agtgaatcaa cctttgaact gtgaaagaag ccaaggtgga aagataggac aactctcgtg    54900
catgagaaaa tggtcaaata tattttagga aagaaagata ctgacatttt taccttgaga    54960
tagtatttga taccgaaata caatttagt tggaaaacga ttttcaaaa atcgtattcc      55020
tttgacctct atgggctgga catcatcaat gtgcctatcc attaatttct tgtacttttc    55080
agaatctctt ttgttgttca gatatagaac tccacatatt attcagtttg caccaggaag    55140
atgcatgaat gtcgttgaat aacatgagcc cattggattg tgtttccttc aaaagtataa    55200
ccatgttctc catggaaata ttttacatca tgttatcttt cttactattg gtcctttgac    55260
attttatttg cttttttttct tttttccttt tagacagagt tttattctgt cgcctaggtt    55320
ggagtgcagt gccatgatct cagctcactg tgacctccgc cttgtgcctc agcctcttga    55380
gtagctggga ttacaggcgt gtgctacctt gcctgtgcca ctatgcctgt gcagtttttt    55440
tgtgttttta gtagagacag ggtttcgcca tgttggccag gctggtctcg cactcctggc    55500
ctcaagtgat ctgcctgcct cggcttcccg aagggctggg attacaaggc aaggctgagc    55560
ccggccttga cattttaaat gtaatttaaa catatcctaa ttgcagtatt atccaaaaca    55620
gtaaatattc taaggcaaaa aatgtcttaa aatcttatcc tagttttatc tacttcactg    55680
gtacttacta ggaacttgtc agtatcttat taaatcatat ttgccatgcc catgattcat    55740
cttggttttt ttttggcca attacccac ccgtcatact catttcctgt cctgaattgg      55800
taacctctgt gaggatatga ggactgtaag caacatgaag cctgggagct tttatatatc    55860
aaacacctgg aataatggca tgtgatagga gctcaggcga tgcacattca gtgaatttat    55920
gtaaaaatac tctgtaaggt aaagttgttt taaatgtttg tagggatttt gatcgttttt    55980
aagaggtatt cctgttttca ttttccttgt aaaatctttg ttccctctca cttcataatg    56040
ctactttaac ttctactaac agtaggctaa ctactaatag cttactgttg atcagatgcc    56100
ttccactgtc gattaaactg ggaatatttc agtgttggat tgaaggagtg gcctgcccct    56160
ccacacctgt gggtatttct agtcgggtgg gacgagagac tgagaaaaga aataagcac     56220
agagacaaag tatagagaaa caacagtggg cccaggggac tggcgcccag cataccaagg    56280
```

-continued

```
acctgcaccg gcaccggtct ctgagttccc tcagttttta ttgattatta tcttcattat    56340
ttcagcaaaa aggaatgtag taggagggca gggtgataat aaggagaagg tcagcaacaa    56400
acacgtgagc aatagaatct atgtcataat taagttcaag ggaaggtact atgactggac    56460
gtgcacgtac accagattta tgtttctctc cacccaaaca tcttagtgga gtaaagaata    56520
acaaggcagc attactgcaa acatgtctca cctcccacca tagggcggtt tttctctcat    56580
ctgagaattg aacaaatgta taatcgggtt ttataccgag acattcagtt cccaggggca    56640
ggcaggagac agtggccttc ctctatctca actgcaagag gctttcctct tttactaatc    56700
catctcagca cagacccttt atgggtgttg ggctggggga cggtcaggtc tttctcatcc    56760
cacgaggcca tatttcagac tatcacatgg ggagaaacct tggacaatac ccagctttca    56820
agggcagagg tccctgcagc tttccacagt gcattgtgcc cctggtttat tgagactaga    56880
gaatggcgat gacttttacc aagtatactg cttgtaaaca ttttgttaac aaggcatgtc    56940
ctgcagagcc ctggatccct taaaccttga tttcatataa cacatgtttt tgtgagctcc    57000
aggttgggtc aaagtggctg gagcaaagtg gctgggcaa agctacaaat taacaacatc    57060
tcagcaaagc agttgtttaa agtacaggtc ttttcaaaa tggagtctct tatgtctttc    57120
ctttctacat agacacagta acagtcggat ctctcttttc cctacattgg atgatgtgaa    57180
acatataaca cttcctgtct cttgtgaaca aaatgcctat tcaattcatt gtttgaatgg    57240
tcattgatgt aatatttgct taacatttgg aatttctaat gcttatatga gaacatgatc    57300
tgttttgtaa aaataaattt tgtttatgga ataattgaa aaaattattc tccagtggaa    57360
ataattatag aaaaacactg accttgtatt taggtcactg acactgtaag ttttttgattg    57420 ttttaatatg agaaatatga atatcttggt tcatcacttt cttttagtat aatgctgtag    57480
ggttgtctag ataccaaggc tattttctat ttaaatcaag ccccccttct cttgcagtgt    57540
taaaaatgta tggacatcat tagccatcag ggaaatgtag atcaaaacta caacaagata    57600
cttcatatcc acttgggtgg ataaagtaaa aaacgatagt aagtgttgtt cagggcgaag    57660
aattggaacc ctcatacatt ggtgatagga atgtaaaatg gtgcagccac tgtggaagac    57720
actttggcag ttcatcaaaa agctaaatat agaggcacca tatgacctaa gtacggtaac    57780
tcctaggtat atacctcccc tcaaaaaaag tatgttcaca caaaaatgta tacacggagt    57840
gtgaatagca gtattatttt tatagcccct aaagtgaaaa taacccaaat gttcatgagg    57900
tgaagggata aacacaatgt tgtatctcca tacagtggaa tactgtttgc caataagaat    57960
aagcgaagta ctaatacatg ctgcacaaga gtcaaacttg aaaacattat gccagttaca    58020
aaaaaatact ttatatgatt ccatttatag gaaatgtcca gaatcagcaa gtagattagt    58080
ggttgctaag ggttagaagg ggtaggagag agatgggaag tgaatgctga tgaatatgtt    58140 gtttctttt ggagcaatga aaatgttgtc atttaaatag tggtggtagt tgccgtgtgt    58200
ggtggctcac gcctgtaatc ccagtacttt gggaggtcga gacaggtgga tcacaaggtc    58260
aggagttcga gaccactggc caatatggta aaacccgtc tctactaaaa atacaaaaaa    58320
aattagccag gcgtggtggc atacgcctgt aatcccagct gcttgggagg ctgaggcagg    58380
agaattgctt gaacctggga ggcggaggtt gcagtgagcc aagattgtgc cactgcactc    58440
cagcctgggt gacagagcga gactctgtct caaaaaataa atacataaaa aatttaaaaa    58500
ataaatagta atgatagtcg cacatctaaa atccattgaa ttgtataccct aaaggggtca    58560 attgtatgat acatgaatta ctagcctact gttgatcaga atccttaatg atcacatgac    58620
```

```
caattaacat gtattttgta tgtgtgttat atagcatatt tttacaacaa agtaagctag    58680
agaaaagaat gttaagacaa tcataaagaa gagaaaatat acttactatt cattaagtgg    58740
atagatcata tgaagtagat gatcataaag gtcttcatcc tcattatctt cgcgttgagt    58800
aggctgaggg gttggtcttg ctgtctcagg agtggcagag gtggaagaca atctgtgtat    58860
aagggaaccc atgcagttca aacctgtgtt gttcaaggtt caactgtatg tagatgcatt    58920
tgcttccatg agcataaata atctctgaaa ttatacacac tggttgctta tggaaaggag    58980
agctggattc caatgtgggt aggcatggga gggagatttt tactaaatat ccttttgtgt    59040
ttatcaaact ttgtaccctg gcattgtatt acatgttttt caaataaata aaagttatat    59100
aatgagatat taatagctta tcttctctct tgattttact atatccaggt ccttcaaggg    59160
ttagattact tacacagtaa gtgcaagatc attcatactg acataaagcc ggaaaatatc    59220
ttgatgtgtg tggatgatgc atatgtgaga agaatggcag ctgaggccac tgagtggcag    59280
aaagcaggtg ctcctcctcc ttcagggtct gcaggtgagg gagctgagcc agcttcattt    59340
cagtgtgggg gcattgggag cttgcaaagt tgcagttgtt gaaggtatct gaatcaaacg    59400
ttacacataa ggaagatttt ggaaaagttt aattgctgga ataactgca cccttgaaat     59460 ggaaaatgcc ccagctacat tatattttaa tattggaagt atttactttt gtcccccttt    59520
aaaaggccat ttaaatttgt agttgctgct tcatctatat ttgaacagtt ttttctgttg    59580
ccagcttctc tgcagaggag aacatagtaa cagctttcct gtagctgacc tttagtcatc    59640
agaatatttt tctggcttca atttgtgta cataaattct tgttgtccat ttagcatagc     59700
tatgtcaatc tgagttgtat caacagattt ggagttagtt agaaaaggcc tgatggtggg    59760
ggaagaagat caagtgacct gagtattggg atatctttat ttctggggcg gggtcgggga    59820
ggtggtgcag tgaagtgtgg actgtgcttc tcactcttcg acaccatgat ctgtgccttt    59880
gtgtgttgtc aggcaagcat ggatactaaa gggctgaggc tcctgggact gcctgggcct   59940
ctcttcacat ctcctttact gccatcaggg tgttgtttag atcatggacc cagcctgtta   60000
agcttttgac cctggtgtag gggtttaatc atgtgattcc tagactattt gctgcatacc    60060
aactgcagta tttgatttaa attatagaaa gcttgcaaaa tagattccaa atatcgatgt    60120
acatctacat tgttcatttc attatatttt aaacaaattt ggtttaatga ctgtgatatg    60180
tattcttttc cattttctta agtgatctgt tggtgcttga gcttgactgt gtttgagatg    60240
tattagtatt tcattttaga taaataagag aaatggctca gtatgagtaa cttctgctgt    60300
gacttcagga gtcactcatt tgtttcagtg gcataaactt actctagatc cttgtgatta    60360
agaagctctg attaatagtt tttgaagttg gatagccatt aaaagacaat aattatttca    60420
ctttgcaatt cgaatgacct acatgaaggc atgtgtctgt tttctgctaa atacagattt    60480
tgtttgattt tattttagtg agtacggctc cacagcagaa acctgtaagt acttacgcat    60540
attactttat atgcaccatg ttaaaagaga ccgtttatta ttgagttgtt caaattataa    60600
aaaagttgtg tatttaaagg gtagacacat ttataaaagc tgtgtatcct caaataggta    60660
agacttaatg tcttgttaat tttttttttt tttttttga aaactgagtt tcactctgtt    60720
gctcaggctg gagtgcaagt ggtgcgatct cggctcactg caacctcccc ctccctggtt    60780
caaacgattc ttgtgcctca gcctcccgag tagctgggat tacaggcacc tgccaccgca    60840
cccaactaat ttttgtattt ttagtagaga ggggtttcac catgttggcc agactggtct    60900
cgaactctta acctcaagtt atctgcctgc ctcggcctcc caaatttctg ggattacagg    60960
tgtgaaccac cacgcccagc ctgtcttgtt aagttttaat gatctgtgca gagttgggat    61020
```

```
agttagagcc tttcaaaaat tgtcttcttt atgcattttc tggactatgg tggccaagtt    61080
tagtgaaatg tgaggtgatg gagttgaagt atttttattt caaaaccact ttacattatt    61140
tctgattggc tgctaagtta cctgtttttc tgaagctgtt gttctaattt tttccatgcg    61200
gatgttaaat aagaaagaga ctgatctatt ttgtggtcct gtcaaaacac tatgtcctta    61260
ttagatactg ggtgtggtga ctcacgcctg taatccctgc actttgggag gctgaggcca    61320
ctagatcact tgaagtcagg aattcaagac cagcctggcc aacatggtga atcctgtct    61380 ctaccaaaaa tgcaaaaact agctgagtgt gctggtggca gtctgtaatc ccggctactc    61440
aggaggctaa ggcagtagaa tcacttgagc ccaggaggta acggttgcag tgagctgaga    61500
tcacgccact gcactccagc ctgggcgaca gagtgagact ccatctcaaa aaaaaaaaa    61560 aaaattagcc gggtgtgatg gtgtgcacct gtagtcctag ctacatggga ggctgaggca    61620
tgagaatcac ttgaactcaa gaagtggagg ttgcagtcag ctgagatcac gccactgcac    61680
tccagcctgg gcaacagaga ctctgtctca agaaaacaa caacaacaac aacaaaacac    61740 tattttact gagacagctc ttgatttgga atgtaagttc tggaacaaga gggagcttta    61800
ataattaagc ttcctggcct gctgagaagc tcaagttgtt tcccatagtt cttccctggc    61860
ttgagctgct tgaatttact gattgattga aaggttggag gctgtcattg ccagtgctttt    61920 gcaagtcagg taaccatgac gggaggcaga caaaagctgt agcttttttct tttttcccttt    61980 tgcagcatag gcttatctct tacagttcat gttgtcttgg ctgctaagag cttcatatgt    62040
gagacccaaa cacacagtga catacacctg ctcgggcacc tgtttcatttt ttggcattga    62100 ggagctggga tgttgttact ttgtatatag acagcagcaa ataaaacttg caagaggagc    62160
ttctccttta aggccaagag aatttcgaac ttcagttctc ttagagtttg aatggtgaag    62220
acttactgga tttaagctat atccctctga gggcaggacc tggtagtaga cctagtacgt    62280
gatatcagtc agcactgctt tccctttgat tttatcgtaa gccttaccac aaagtggatc    62340
tgtctgggtt tgggatttta atagaatatg gcatgagaaa gcagagttta ttgctatttg    62400
ccatgctgct agtcgttata ctatcgtggt gctttaaaaa aagaatact gacctgtggt    62460 ctttccttaa catagatagg aaaaatatct aaaacaaaa agaaaaaact gaaaagaaa    62520 cagaagaggc aggctgagtt attggagaag cgcctgcagg agatagaaga attggagcga    62580
gaagctgaaa ggaaaataat agaagaaaac atcacctcag ctgcaccttc caatgaccag    62640
gatggcgaat actgcccaga ggtgaaacta aaaacaacag gattagagga ggcggctgag    62700
gcagagactg caaaggacaa tggtcagtgg ggcctggaac ctgggctgca tggggttctc    62760
agagctccat tagtagggtt ctgccaggtc aacatggggg ctgatttgtg ctgctgctgc    62820
agatgacaag gatgattctc tccaactccc tattgggaaa tatgggaaat agcctcgtac    62880
ttcatttgtg aactgtatgc cagaaatatg ttaacatttc aaaatagttt ttaaaaatgt    62940
aaaataattg agaaattcca tgtttctatc atgctaatga tggtgcttta ttttgtcatt    63000 aacttttac ctaactgtaa tgcaccacaa gtctgtttct gaagattata gagggtagaa    63060
atggaagtgc aactttattt agaaagagtt attttcccttt aaagctaact ttttcttata    63120
agagcaggcc aattactaaa tgaatgaaaa atgagattta gaaaacctga aggttttacc    63180
ccaaaagcca agaggtgttt accaggtggt acataagcat attcaaaatg tatttttattg    63240 atggagataa gtacttaatg aggctgtatt aaggagagta acaagttcta attcttgacc    63300
catcaaattc ttaaggtgaa gctgaggacc aggaagagaa agaagatgct gagaaagaaa    63360
```

-continued

```
acattgaaaa agatgaagat gatgtagatc aggaacttgc gaacatagac cctacgtgga    63420
tagaatcacc taaaaccaat ggccatattg agaatggccc attctcactg gagcagcaac    63480
tggacgatga agatgatgat gaagaagact gcccaaatcc tgaggaatat aatcttgatg    63540
agccaaatgc agaaagtgat tacacatata gcagctccta tgaacaattc aatggtgaat    63600
tgccaaatgg acgacataaa attcccgagt cacagttccc agagttttcc acctcgttgt    63660
tctctggatc cttagaacct gtggcctgcg gctctgtgct ttctgaggga tcaccactta    63720
ctgagcaaga ggagagcagt ccatcccatg acagaagcag aacggtttca gcctccagta    63780
ctggggattt gccaaaaggt aagtgtttct tcccatcaac tgtctgccat cgctgactcc    63840
agggacgtgc ctttaacaaa tgctgtgaag gaattggctg gaagtggcca agccctgtgt    63900
gtgtgtactg atcagtttta ttacttttat actcctgaag aagtaatgtg atttaaataa    63960
attttctatg ccattaggct atttcttgct ctctgcatac caaatcttat ttctgaccag    64020
ttttcatttt taatatattt agtcagcagc atcatttgca aaaccttcc agttttagca     64080
acttacacct ttctagaatg tgtagtttag tttaaaattc gtatcttctt ccatctaatg    64140
tcattatatt tagtttagtt tagttttgtt ttgtttctat tcaagaaaat tatgcctcct    64200
ctttgactct attgagaaag aagtgtcata ttgtcttttg atagttgttc ctgattatag    64260
gaccctacta ttggtaactg gcccaggatt gtaattttca aggaattggc atggatttaa    64320
atgtgatgac agattataga ttggctcttg tgttcttgtc tacctaagaa ggcttgactt    64380
attcaaagcc ttattttggg agtgaatgcc aagtgactct agtaagtgaa aactgggtaa    64440
cacagctggt ttccatactg gcttatgggg gaaaagctct gaaacctccc tctgctccct    64500
ctactgacaa gactgtttaa cacacagcga gtaaaattga tgagcagcc ctgcaaacag      64560
cccgacattc tgcagcccct ttggttccag cagtctggaa ttgcacgccg agtaagctgg    64620
ctttgttacg cactggctat gatgaatcct cctaaggatt tgctttcttt acttggctgg    64680
acgtggtcag ctcctgttcc cctttccagg gagtgtttga aggtgcttac atagaatgta    64740
ggttaatttc tgggaaaggg cagtagtgag aggtaccttca tccagactta ttgttgctgt    64800
tgcagttcaa ttttctctct acttgaagtt tcttttttt tttatgagat tgagtcttgc     64860
tctgtcaccc aggctgtagt gcagtggcgc gatctcggct cactgcaacc tctgcctccc    64920
gggttcaagc gattctcccg ccccagcctc ctgagtagct gggattatag gcgcgtgcca    64980
ccatgcccgc taatttttg tatttttagt agagacaggg tttcaccatg ttggtcaggc     65040
tggtctcaaa ttcctgacct cgtgatccac ccgcctcagc ttcccaaagt gctgggatta    65100
caggcgtgag ccaccgcgcc cggctgaagt ttcatataga aagtaattta caaagtacct    65160
ttttaattat ttctatttta ttcattcatt tatttattta tttttgaga cagtctcact     65220
ctagttgccc aggctggagt gcagtggtgc aatctcagct cactgcaacc tccgcctcct    65280
gaactcaagc aattctcctg cctcagtctc ccgagcagct gggattacag gcgcccgtca    65340
ccatgcccgg ctaattttta tattttagt atagacagag cttcaccatg ttggccaggc     65400
tggtctccag tgcctgacct caggtgatct gccctcccca gcctcccaaa gtgctgggat    65460
tacgagcctg agccaccatg accagctcaa agtaccttt ttattcatac ttattttgca     65520
agtattagct tgggctgcag tggcttcaag tacagtcagc cctccatatc catgggtttt    65580
acatctttgg atttcccatc catgtgttca gctaacttca ggtgggaaat agttggaggg    65640
gaaaaaaaac tgtgtcttta ttgaacatgt acagattttt ccccccttgt cattactccc    65700
taaacaatac agtataacaa ctatttacat accatttaca ttgtagcagg tattataaat    65760
```

-continued

```
aactagagat caactaaagt gtataggaag atatatgtag gttatatgca aacactacac    65820
cgttttatat cagagacttg agcatctgtg gattttggta tcctcaggat gtcctggaac    65880
cagttcccct gcagacaccg agaggcacct gcatatcaga ttaaacccca gctcaaaact    65940
taataactgt ggaactttgg tttcttaccc tgtctgagcc ttggttcatt cctctatcaa    66000
aagaaagaaa tggctacctc taaggttgtt agtagcactg aattaaataa aacaggtcaa    66060
tggcaaaggt acataaataa catataataa taatatattg aaaaatttcc cattgaatgt    66120
aagttgcctt ggtcatcaca atccatgtaa aggagcagaa ttgctgcttg ttaccacatg    66180
gtcatcattg gaggcccagg caagtcataa gacttatcct attgtttaca tgacagctcc    66240
atctctgtgt cacaggaaac ttcaaacctt acatgtccaa aaccagaata caactttccc    66300
tgccaacctg ctacacatac tgtatttcct acacttgttg ccaccatttc ttgttgctcc    66360
agtgagaaac ttgatcatca ggatgtcttc ttttttctc tcatgtccag taaatcatct    66420
cattttgcca gtcataacctc ctaagtaggg gtcccccttg ccttgtccct aaagtgggca    66480
gtgtcattgc ttgcctctcc tattatggag gttccttact ggtgtcttgg ctttgtgttc    66540
tctccagctt ttctccccac ctgcctttca gcatgccctt ccatggtgct gctagagtgt    66600
ctttgcagta tgctcacccg atcagtgtat tcccctgctc acagtttcca cagctcccca    66660
tcatctacag cagtggtctc cacagtggag agtgtacatc cctgcataac cagcaccatc    66720
caggaaggtg caggaaggaa ttattagagc atctgtgtat ttttttattt tgaaagaata    66780
gtacaataaa caactgtata tcctccacat agattgagca attcacattt gccgcattg    66840 catatacttt gtgtacacag acactgcatg ctacacatat taggatactt cactcctaaa    66900
tacttaagca ttcatcttct gagagatgaa ttagaacgtc ctccattgta acaataatac    66960
tattacaacg tgtaagaata gcactaattt tatattatta ttattttgag acaggatctt    67020
gctctatcgc ccaggctgga gtgcagtggc gtgatctcgg ttcactgcaa cctctgcttt    67080
ctggctcaag tgatcctccc acctcagccc ccaagtagct gggactacag ttggcactac    67140
catgtctggt caacttttat attttggta gagaaagtag ggttttacca tgttgcccat    67200
gccagtcctg aactcatggg ctcgagtgat ctgcctacct tggcttccca aaatgctggg    67260
attaaaggcg tgagccatca cacctggcct aatatcatct attatttatt ccatattcaa    67320
atttcctcaa taattctaaa attttctttt taaattttcc tgatctagga tatgatccaa    67380
cacagtagcc tgcctcctgg gtgagggctt cctgtatccc cagcaggctt acttctcttt    67440
cccctctgct cctgctggcc atgcttgtct tagttgtatg ggcagtgctc attgtcactg    67500
tctgtcttct cattagaatg tgaactcttg gagagtgcag tgtgtttta tctttgcatc    67560 ctcagcatct gattcagtgc taagataaat atttattgaa taacgaacaa acaaatgagt    67620 gataccttttt tacattcttc ttctctttcc tttctcccgc ttttttccat ttatagtcac    67680
aattttactg tgtccaacac acataccatc cccaatacct gttgcatcag gtagaaactg    67740
gaggtcttga agagcatttt aatattggca aattctaggg atgtaccagg acaggatct    67800 cctttgtttg gaagcactca gttttcgccc gcagcttggc catttgataa gcaagagcag    67860
cctcccccat gggaggtgtg ttttgttttc tgcatgggaa ggggtataag cctagagtct    67920
tgcacttgac cacacggtac ttcgtgaatt tgaggcaaga gaaacaatga agagtttgtg    67980
tagatcctga cttagggca gaatgtacat gttagggcat agtagaagaa agactggggc    68040
cagtttgagg aacttgaaga aacctaaatg ccaggctaaa gaaggtacac ttttttccta    68100
```

```
gagtaatttg gcagccattg aaggttgaga agaggatggt ccctcttaga tgatcagctg   68160
ccagagcctt agtgtgtatc ttggctcaac acatctgaag acaaaggcc ctggaacagg    68220 gtggttttgt tggtcttacc tgtgggctat ttctggaatc cttctgtgt cactcgatgg    68280 ggacccacac cactgtcagt ccttgctagg ctactgttaa cacagcctcc gtgctcctat   68340
cacttgagct tttgctcccc agtctgtctc tgtctggcag tccagagaga actgtttaag   68400
gcttaacttc ttccccctta cccaccctcg cctcaccaac atgatctcca ttgtgtttcc   68460
catgtagagt agtgatgccc tgagttgtcc ttcactgaag ctgacaaact ctccagtgtg   68520
ttccctggca ggtctctgtt ggtgcctgct ccagacccat tctctgtttc cctaattcat   68580
tctacaccgt tcacactggc ttctttctaa agtttctcaa agttgcaagc ctgtttctgc   68640
cttaggattt ttgtacttcc cgtgtccttt gcctcaaact tctcttactt tcatgcctgc   68700 cttgttcag acctctcctg aatgtcacct tctcagaaaa gatctcccct gaacagcctt    68760
ggcattatcc atctccttc tctgctttgt ttttcttcat agcctgttta gctacctgac    68820
aggatgtgtg gattcctcgt ttatttgcct tattgcccat attttcaacc agtacacgag   68880
tttcctaatt tagcttgtgt ttttttctta cagtgttccc agtaccaaga ccatgcttag   68940
cacacagaag gtactcagta aatatttgtt gcacgaatgg ttgaggtggc aacattaaat   69000
ctcttagttc cactacttcc ttgggcctca tagtgaacct cctccatata gagggatat    69060 tcttgtcgtc cttgtaagga cccttatga tgtaaagagt cagtgtgtgc ctagctccat    69120
gtgttatgtg cgtgtgacag cagctgtctc attatgctga ggcactgttg ctaccatct    69180 aatagttcct aggatagctt cttgtggaat gagtgaccac agtgtcaccc aaagactagc   69240
gtatcagaag gtgacttaag gggcccagtt cttcccgaag tgaaagcttt ccactcattc   69300
ccctcttagt ggaagcagag tgcaattgca agcttttcat tttggaagga agacagctcc   69360
agtttgtcct ttgtgtcacc attatctgta agaaggaaac cgtgtgacag gtcactactg   69420
tggtgactca gtcagaggag gtgtgacaaa agcattccag ttgggtttca gtggacttct   69480
tgggaatgta gcagtctggt accttagttc aggaactatc atactgagaa agaaagaaa   69540 agcaaaatct cttttacctc ctgttgtgtt tttatacaat taagttattg agatacatta   69600
cctagcatca tttggaacgc atcagaagct aagtaactgt ttacaaaccc gaaccaggag   69660
gataacagca tgtcaccaaa gagattctgt tcagtgaacc ttaatgaggg atattaagta   69720
caagaaacac ccctgaattt aggccaggtg cggtggctta tgcctgtaat cctggcactt   69780
tgggaggcca aggtgggcag atcacttgat gtcaggagtt cgagaccagc ctggccaaca   69840
tggtgaaacc ccgtctctac taaaaataca aaaattaatc gggcatggtt tcaggcgcct   69900
gtaatcccag ctactcggga ggctgaggca ggagaattgc ttgaatctag gaggtggagg   69960
ctgcagtgag ccgagatcgc gccactgcac tccagcctag cgacagagt gagactctgt    70020 ctcaaaaaaa aaaaaaaaa ttccctgcat ttaaatgtga ggtgatgggt ctttgaaagt    70080
atatttcttc tagcgtgatt gaattaagca gctcctgaga aatgttttta aaacaacat    70140 ctcagagtgg tggcagatta cagatcatct ccttccactt gagtgccctc agataacagc   70200
caactcggct actgttctca tggagaaaaa gaaatcacat cgttctgtgg ctcaggagga   70260
ccacaatatg tctaaccggg cttcgccctc ttctcattag acctatgatt tgagttgttt   70320 gtggggggcgg aacttgctct tgggcctccc cttccctctg ctgctgctct ctggtccctc  70380
actgaccagt tgggagcctc tgccccagac gatggttcag ctggtcacag cagagggaag  70440
cccctgcgtc tggccaggcg cccagatgct gtcctgactc tcctgtgttt gggtttttag  70500
```

```
tgtcttcggt ggggaagggg tggtcccttc cgattcttct tttcctgaac accaagcctc   70560
atagagttta agtcatttgc cagtcttaca acttgtagat attgaaactt agatttgaat   70620 ccaattttc aaacctcaaa ttccattttc cttcttgctg attcttcttg attaaatgac    70680
atacggggca ttcatctagt catgtctagt gttgttcatc tacccattgg gtcagcattt   70740
ttatatttat cctggacctc tgttctcagc cccaggtgaa tcagtgtata ttcattttgc   70800
cttctttttt ggtctttgtg ctgctttctt tctgaatttt tgctgagttc tggtgtttct   70860
tttcctgagc tcatacctgg cctttggtga ggctgtgcag aatccttata agaaggaaa   70920 caggcatatg gaaggtagca agcagggaat atctgtacct ggctggctca tttgattaac   70980
atgctagagg aacaggtctt gagggttaag atactggtca gaattctctt ggcgtcctct   71040 ggagccccc tagggagctg tgtgggcacc ctaggtcctg aggcccttgc ctgttcactg    71100
ccttacggca agttgcaagg ctgggcctcc ttcctcttat ggggcttgct gaagaatcag   71160
agcctcccca agcaccctgg tttcacagct cgtatgtacc ccaacagagg tttagttcat   71220
ttcagcagtg cccagcttca aggaaacaaa ggggctctcc taggtaggtg tttatattag   71280
tctgttctca cattgctgta aaaataccg gaaacccggt agtttataaa gaaaacaggt    71340
ttaattggct cacagttcca caggctgtac aggaagcatg gctggggagg ccttaggaaa   71400
ctttcaaata tggtagaagg ggaagcaggc atcttacatg gctggagcag gaggaggaga   71460 gaaggggac gtgctacaca cttttaaaca accagatctc gtgagaactc actcagtatc    71520
acgagaacag caacgtggaa atctgccccc atgatccagt cacctctcac caggcccctc   71580
ttctaacact agggattaca attcgacatg agttatgggc agggacacaa acccgaatca   71640
tatcagtgtt taatgttcta cattgaacag gcttttctgc ttggtttta aataccattt    71700 caaaatttac ttatacagta aataaaagtc ctggttttat ttcatcttta ccagaaatct   71760
gatcttgtag gtcagtctga ggtttggtga tgaagatgct gactttaagg actatttttc   71820
tgggcctcac cagattattt ttgtttgtca cttgcccctt ggttaactct gcttgataca   71880
ggcatgatct gaacttgttt gagaagatct ggccccagaa tctctgggaa gctggcccta   71940
tacctgcctt tgagattccc tggagtcatc ctggaattta gaatgactgc tcatgtacat   72000
gacaagttca tgactgacct cagaggttgc ctttatggcc caggccatct caggagacct   72060
ctgtctggga ccttccttgt ctaaaacaaa accagaatag tttagtccct gcctttaatc   72120
tgtgtttgtt aatcaacagt catctacccc ttgagatctg tgtgtgctca gcccaagcag   72180
tgggaactgt aggggatgat gtgggtgtga ggtgtcggtg ccaggaccc tgatgtcttg    72240 tggcgtccaa ggaactgtgt gtcactgaga gtgatcggcc cccacagcag tgttctttct   72300
accttcatgt tccttgtaat aatgcatcag caagctcgat ctgggccgtg aagggatgga   72360
ttgacaccat gaagagccgc cacaaagctg cagacagggg gacagcaagg ctggcttgtt   72420
ctagggctga cctggacccg aagaaactgg ggataaaaag agaaaggtca aggcagtgcc   72480
cttggcgtcc tgtgggcagc ccagtttgct cttttctgga gtattttcca gaggtggaga   72540
acaagcaatt ttagttctgt caagtttaat ttacagtatt ccaggcctaa gtgatcattc   72600
cactactctt gaggaaagga gactgaccct ggcaaacact gtgctcacac atgcaaacca   72660
cctatcccga tcactaactg tcctgctgtt tgctcatgcc agcaaaaacc cgggcagctg   72720
acttgttggt gaatccctg gatccgcgga atgcagataa aattagagta aaaattgctg    72780
acctgggaaa tgcttgttgg gtggtaagta gagttttctt tctaaaacct ttggtcttga   72840
```

```
ttctgtgtgc gaagacactt tttgaatgtc tgtgttgctc cgtggtaatg cagcctgttc    72900
ccttccagca taaacacttc acggaagaca tcccagacgc gtcagtaccg ctcccataga    72960
ggttttaata ggagcggggt acagcacccc tgcggacatc tggagcacgg cgtgtatggt    73020
aaggacggct gtgcccttty ctgccatggg aattggctcg ttcctttcac actctggatg    73080
gggctgagtc tctctgaggc atgcgacctc agtttttctg actgtaaggg tcatccaccg    73140
tgggctgggt gaggggaagg ttgctgccgc aggcatctta agaagtggaa ggatcctcct    73200
caggcgggcc ctgggtgttt ggtgtggttg tgggcttgtg agagagacat ggtctcttct    73260
taaggccctg cacagcccac agcccatga atcagactca gttgttgtga cacagtgact    73320
tcacttgtgg tccctgaaaa tgtgcagggt atagggagct tttcccttca ctcacactgt    73380
ggaggaagat gaggtagcat ctccagggga agactgccta aggcgggcag gtgggagccc    73440
ctccaggtaa gcctctgcct ggtcaaccag acatgcaggg ttcctcacct ttccagactg    73500
gaagggattt ccccagatgc caatgcataa tctctcttcc cttataaagc aagagctagc    73560
agatattctg gcttattcta ggatgtctag ccccttctga acagtggca gcaacgccca    73620
ctccctctga cagagtctgt tcccagagtg gttgagatga cggcttccac agggcggcag    73680
aagcctcttc ttctatctgt caggcctgtt ttgctgctgg ttttgtgctg cacagttgca    73740
ttgtctgtaa actcccctgg ccctgcctgg catcgtttgg tcattgaccc tgaacctgtg    73800
agttggtgaa cacaaagggc cctgcatttg cgagccagtt cctggttctc ttcctctgcc    73860
ctgtttcctg gcccattcag cagcttttc tcagtggtat ttacttaggc gttccgtgtt    73920
gggaaaggtg ggttgcttgc tgttgggttt catgcttttc ctattccata ctgctttta    73980
tccatattct tccaatattt aaaagaaaag attgtgtgca aggcttagca ttttttcttct   74040
cactgaaaaa aggaatgcag aataaatata ttaattttct gttattcaga ggttaattta    74100
acaatttct tgaatttact gtgttttacc tcctctaatg ctcaagtaaa agcattgttg    74160
agcagatagt gccagctgat aggagaaaaa gagggtgctt tctgtctttc agctttgact    74220
cagcatgatc tgagtcagca catggccaga taggtcctga acaccaggc cttctattc    74280
cctcgttgct cttaaggata ataccagaca ataacgttta aattattaaa ggtattaaag    74340
ttcttccata tcaaaaacca agtccctgcc ttagctaggt atagaaaga acggttaaaa    74400
gaaccggtgg ccaatgatgg tcactttgaa tttagagagt gctgtgtgga gaggcatttg    74460
accctctctg tgtgacccca gcaggcagac tgagacgtgg gagttagtgt aacgggagct    74520
gcggagacac tgagtgggag tcggggagca ggggccattt caggatgtgg ggaggttaga    74580
ccacaatggc cactagcagc agggctgccc cgaattaggc gctaagtact cttttgaactc    74640
tgaaatgctg tgcttctaat ttgggtatt aagtttggtg atataaccag aaaaatagga    74700
cgcagtcacg gatgtagtgg gttaatggag ctttcagcac aattttatac caggttatct    74760
gacctgcctt ccattagatg aacgtttgtc cctccataca atttccctgt cctgcttact    74820
tcttgaaatg ctattgctgt gaacagtggc ataaatatca ataacagatt cccaaggaaa    74880
agcctttctg tcttctcacc tgcccccttc ccaagaatta agcataagct ccctcagtgc    74940
tgtcaggacg gcttatgagg tttgcttttt cagttggttg tcataaggga ggttttttt    75000
ttttggaaa ggggcaggcc ctcattcact gcttgcccca ccccaaaa gtcatggctt      75060
tagaggtttc ttttgttcct cctagagaac ctagagcaa tgaggcagtt tttcttacct    75120
catcgttctg ttgtagtgta aaaataggac atttaatata ttaaatttga cctcataata    75180
ccaagctgtc ataaggccac agatggttct tggtggtaaa gcctatatat agtctttgag    75240
```

```
ggttttgttt gtttgtttgg agacaaggtc ttgctctgtt ccccaagctg aagtgcagtg    75300
gcaggactat agttcactgc agactccact tcccaagctc aagtgatcct cccacctcag    75360
cctctggtgt agctgggact acaggcacat gccaccacgc ctggctaatt tttgtatttt    75420
ttgtagagat ggagtttgtc acgttgtcta ggctggtctt gatctcctga gctcaagtga    75480
tccacccgcc ctggtctccc atagtgctgg gattacaggg atgtgacact gtgcccggct    75540
gtctttgaga tttataaata gcatcaaatc tcacagagac tctgttggga atgagagctg    75600
acgggtggta gccattggct attgtcaggg aggacagctt taggctctgc agctggagaa    75660
gcacaacaga atgagggacc acagcaaggg tatgttgggt ttggatctgt tttacttttc    75720
ttgagtttta ctttttttt gagctttaca ccttccagtg taagtacata taatctgaaa    75780
cttctttgtg gctgaagcat tggtttctct gcatttatgt attagagtct ctgataggac    75840
tttttatgaa ctccatggtg agtcctggtt agtgccatag aaacaagaaa agccattcca    75900
acaaacttca ccagacttct tcggcactgg tcacattaca gaacaaatac gtgatcttat    75960
ttgttcagaa tcgggatact tcagcatagg agaatgtttt aggagagagg tagttggtct    76020
cccaagaatc tggaaacaag taggtccagg gaagagccct ttgagggat tgagccaagt    76080 agagaagaat ccggagttcc cagtgtattaa aaataataat aaagattata cttaggccca    76140
gcgaggtgat gcacacctgt aatcccagca ctttgggagg ccaaggcagg cagatcactt    76200
gaggccagga gtttgagacc agcctggcca acatggcaaa accccatctc tactgaaaat    76260
acaaaaatta gctgggcatg gtggcacgtg cctatagtcc tagctactca ggtggctgag    76320
gcaggagaat cgcttgaacc caggaggcag aggttgtagt gagccaaaat tgtgccgctg    76380
cactcagcct gggcaataga aggttatact gggagtaact gagttgaagg cagagttttt    76440
ttcattgtaa tgtgcatttg ccctgttgta catgttgtat tgttaagaga atcttgccac    76500
tctccaaaga atcaaaaatg ggtagcatta cagccttcat cttccttgtt cctttaaaaa    76560
aaaagaaaat tatttggccg ggcttggtgg ctcacgcctg taatcccagc actttgggag    76620
gccgaggcag gcgggtcacg aggtcaggct aacatggtga atcccgtct ctacaaaaaa    76680 ttagccgggc gtggtggcgg gcgcctgtag tcccagctac tcaggaggct gaggcaagga    76740
gaatggtgtg agcttgcagt gagctgagat tgattgtgcc actgcactcc agcctgggcg    76800
acagagcgag actccgtctc aaaaaaaaat tatttcattg gttggcttct atacatgttt    76860
tcttgggaat atgtgggtgc taatcaaaat gatgattttt ttcaaagaat acatacctga    76920
catattttgg cagtaagaaa tatgtacaaa gctgggtgca gtgtagtgcg cctgtagtcc    76980
cagcttctct ggaggctgag agaggatcac tggagcccaa gaggttgagt ccagcctgga    77040
caacatagcg aggtcccttc tctaaaaaat atgaaagaaa aagaaatata tgcaaccaga    77100
ttgaagtcat tttgaaaatt aattaaaaga gttagttagc atagggctca aggcagggt    77160 tgaaaagcag cttggaactt gatccaggct tttcaagtcc tcgttgtccc attagagttt    77220 tcagatttt ctcttagctt gtaagatact gaattgattg tttcccaggc tagaaggact    77280
ctcctggcca ttgagtgtgt aatctagttg ttccacttgg atttggggcc agttatgagg    77340
ttttcctgcc ctcatctggg attggcccaa ctgtcttctt tgtttattgg gtggaaagga    77400
gaggccctac ataagggctt tcctgggttt tctgctggtg ccttcgtgca tccacagtgc    77460
tgggaccacc agctccaccat gctgagatgt gacatgtccg tgtcttgctc agacctatgc    77520
caggttcagg gcagggatcc tgagttcata aattaatgct tatcgctcgg tcagctggaa    77580
```

```
gccatcttgt caccatcctt ccttccttca agtgattgac aggcagtctt ttttttttaaa   77640 aaaggtgaaa agatgtggtc ctgggctgac tgcactcact cttggtttgt taaagacagt   77700
gccaggagag gtggcccctc acccaggcag gtgagccttc ccttaaaggt gccttttccag  77760 cactgtgtgg tcattgaaag aaaaagaagg taggttgatg cagtgaagtt tccccagtat   77820
tggctccttg gggcgggaat ggggagggca gtcacagatc cacaggcatc agtgattggg   77880
cctctgagca cctttttggga cagcaagatc cgttcagaat agaagcagct atgagaaaaa  77940
ccagaaatgg gatttagctt attctttttt tctcttttaa aacattctct ttgatcagca   78000
gagcagtagc agttgccatt tttgtatatt gttactagct taaactcatg tttttgaggg   78060
tttttttgtg agcaagggaa atgggaacaa atggtgttcc ctacatgctg gcatgctgag   78120
ggacagccag tggccaccca ggaagccagt gctccgtgac atccacaaaa gggtctgcaa   78180
gaccatctgc ttcctctggc cctggggaca agagggtct ttttttgttc caggttttcc    78240
tttggttgaa tcagaaatga atgaaatgat gatgaaaatg gttgatgaga tactgaaaat   78300
agtccttggt tactaaaaca tgaaggtctt cgcctaaaag acgcagcagt gtctgctata   78360
cagaggccaa ggctattata gtggttgagg caggtgctgg agtcagacgg gccttgttga   78420
gtcctgggtt gaactctcgt tctaccattt atagagtgca taccgcgctc tggccaggcc   78480
tgcatgcagg tgcggctgac tcactgacgt ttttggtttt gcttcctgca aaatgaagag   78540
aatacatagc tcttatatct ttccttagaa atgtaaaaat acttctgaaa cttctttgaa   78600
tgtggaagaa agaaaaaaat tagtattgag cactttcagg aggctatttt gtttgattca   78660
gatcttcata aagtgcggt ctcttctata aggagaaaaa gctgttgact tggggggccag  78720 tctctgaagt gcttagcatg tcgtctgttg tatcctaggc atttgagctg gcaacgggag   78780
attatttgtt tgaaccacat tctggggaag actattccag agacgaaggt gagtattggt   78840
gcctgctgaa tacctcggtc taggtcttct gccagccctg aacttctgta gagtactgta   78900
tttttgtact gaaatagagc catgtgtttg gttttcaaac accaaattca gatgcttttc   78960
ctttgagttt gatgcccct cagtctcagt gaatgggcag agcctgccta gcacaggcag    79020
cactccagcg agccctcagg ggccctacac cagcggctct tcctggcctt gcacagggca   79080
ggaacccagc tggctgagag aagacagatg atacagacct gaagcctcta tgtggtcctt   79140
ttgaccattg atgtgctgcc catttctctg tcctgtttgg gagctgagtt gaaaacccag   79200
gaattctggc ttgaatgcca tctgtaaacc tgaccatctc catgcttatt tgcttgcgat   79260
gctggggtgg cctggggtga gctggcctca gtcactgtta ctgctccagg tggtgcctga   79320
ggcctgccat tcccacaagc ctctgcatgg atgtgctgca gacactgttg atttgaatct   79380
atttctgatt ttttactaat ttcaatttt ccctcttctt ttatcccatc cttcccttg     79440 ccctccccat tccatatcc ttttttttctc tcctccatag accacatagc ccacatcata    79500
gagctgctag gcagtattcc aaggcacttt gctctatctg gaaaatattc tcgggaattc   79560
ttcaatcgca gaggtagtac ctcttctttt tgaaaagcgc cacgatgcag acagaaactg   79620
aagagcagct gctgattta gcattaatgg tgacaaaggc atttctccta aattcgaaac    79680
gcaacccagc agaattccta tgctgataga aaaattgtca gggaagacca catttagccc   79740
tgtgctgcgg tcaccctgtt caccagcccc tctcctgtgc cctccagctc tggatcctga   79800
atccagcaac gcgaggaagg cctgtacttt tggtcattca agttgcgctc tgtttctgtc   79860
tgcgcgggcg gtggtagtgt ctgcatgcag tgtactgatt aaactgtcgt gtgtttctgt   79920
tttgctggca atgtttccca atgcagatca catagcattg atcattgaac tgctggggaa   79980
```

```
agtccctcga aaatacgcta tgttggggaa atactccaag gagtttttca ccagaaaagg    80040
taacggtatt tatgcaacac taattttcag catagtcttc tcccaaaagg agaaattgtg    80100
cattcgtgat tgggcagtgg agaaagatct ggagtttcac aactgggaa ttcttccgaa     80160 gaaagctctc aagaaataaa cctgacccat ctgatacctg gagtaagaat tttgtaagag    80220
aacagccttc ctaacagcat ttttcctcc tccgcttctc tcttttactc caagttacca    80280
atctgtatat tatttataaa aaggagttta ggtgattgtt aaaagccagc tagacttatc    80340
tttccatttc atggactctc tgtagtagaa cagaggtggc ctagagactg gacttaggga    80400
acgtccaggg acattgcttt tggtctgcct gggttatttc tgtagtgggt gtaggcctgt    80460
gaaatgctgc gtacctcaca ttcttaaaaa tgacatccta cattcccatt gtgttatgcc    80520
acactgtatt aaggtgatta ttttcatgtt gtagttctta ctgatcttcc aactgtttat    80580
ttgcccagta tagtccccag ttagtaattt ataaaaacac ccaagagccc taggagtatt    80640
tttaaaagaa ctccttctaa gtgctatatt cttttttttt tttttttttt tgagatggag    80700
tcttgctctg ttgcccaggc tggagtgcag tggcgcaatc ttagctcact gcaacctgtg    80760
cctcccaggt tcaagcaatt ctcctgccgc agcctcccat gtagctggga ttacaggcac    80820
accaccacgc ccagctaatt tttgtatttt tagtagagac agggtttcac tgtgttggcc    80880
aggctggtct caaactcctg acctcaagtg atccacccgc cttagccttc caaagtgctg    80940
ggattacagg catgagccac tgcgcccagc ctgctgtact tttttgtgat gagtgtagtt    81000
ggtccttcat atttttcagg ttagattttt tttttggatg tgacagccct taataaagaa    81060
cttttaaagt tgatgtgagt aggacatgga cttttagaaa tttctgaaag tcccagatgc    81120
tctgtctacc ttacttagct aaatttggag aaccacattg attttttttt tttttttttt    81180
tttttttttt agatggagtt tgctcttgt tgtccaggct ggagtgcagt ggcgcaatct    81240
tggctcactg caacttccgc ctccaggctt caagtgattc tcctgcctca acttcacaag    81300
aagccgggat tacaggcacc tgccaccacg cccggctaat ttttgtattt ttagtagaga    81360
gaggttttca ccatgttggc caggctggtc tcgaactcct gacctaaggt gatccaccca    81420
cctcggcctc ccaattgctg ggattacagg tgtgagccac tgcgcctggc tgtgcattta    81480
tttgtctttg ttaatcgtct gtctgttgag gggatcgagg actccatact gtgcacagcg    81540
ggaaggaagg aaagagggac agaaagagag gccttgaatg atcaagtgaa gtcactgagt    81600
tgttggaagg cagggcctgt cagcggcctg caggcatgga gctggttgca ggcatctgct    81660
cttgggctgt cactcctgtg atggttcctt tcagtgagag cggcctgcgt gtggccataa    81720
atggctggaa ggcagcttcc acgtgggcct gtcagcaacc ttgctccctg agacagcttg    81780
tggatgtgta tctccaggtt actgccatca tcaccacgta tacttaggac ttacgtgatc    81840
gagttctttt tgagcagctt atttgaaggt aacctgcaga gttaaaatgc atttggcatc    81900
cttcctaatg agagaccaaa aatattttca cttggtgttc ctgtggtacc tcgagttctt    81960
ttttcctgtt tttggatata agagaccgtt tgtgactagg tgagaaatcc cctgaaatga    82020
ctgggaattg ggacttcagt tctttcctga ttattatttc taatggcagt agagatcaga    82080
agggatttag ggttttaca gaagtcacag gataacatta tgaggaatga gggccggtca    82140
tggaaataga tttcaccgtt gtctcttagg atgagggaa tggcttgctg cgtgaaacat    82200
gtgttttggc atgttcccat aagtaatata ggggaaattc cataatttcc ataatttgg     82260 aaataatgga atcttaaaaa tatccattta aattttttt cctaaaatag ctaaaatact     82320
```

-continued

```
ttgtgctaga actgataaca aaatttaaaa cagctgttga tatgccgtat cacttttgaa    82380
agcagttact gatggagagt gccttcccag gaggttttcc cgctctttct cctctgggtc    82440
agaggcagat tttcatcctt gccacgcagc cagagaagag tggggtctgt gtgttaaggt    82500
tgaacatcaa atgcagctca tttgtctcct ctccttgcgt ataatttaag aagtcatgat    82560
cattactagt ttgaatcatt ccttggccag aaagttaaaa attgagctgt attttggtc     82620 agggaatgta attacagctc tcaccctctt aaggttaatt tgctggacat gagccaccaa    82680
aaagcattaa gaaactactg tgttgatagg tggtccaata gaaatcagca cgtccatgaa    82740 tttttttccct gtcctgtctt caagaagtgg gtggtcccca gaagctttcc agccctcaga   82800
tcatggtagg aaaaacggtg cagccaggag cagacctcac tgggctggtc accaggaatt    82860
tttctgacca ttcagcaggc atattttagt aaaaattgct gcgtggataa tgggattatc    82920
aaatgagaca gtttacttaa aaaaaaaaaa ctggtctcta gatgacagca tcgagtgtgt    82980
tgggataaaa gagagtgatt gtgtgcatgt gtgcgcgcgc gtgtgtgtat gtgtgtgtgt    83040
cagactacag accttaaata caattgaaaa tttcaaaagc aagaagcttc tgtgcagcag    83100
cataaaatcc acgtttccct gagtcaggga caacatcaag agaaatgtga gaactgaggg    83160
ctaaaaccca ggagctgagt tttaaaaaga gatactgtat tctgtatttt taatatttag    83220
tgtctgagct gaacttgtca cagtgtttta aaattatctc ctgaatacct aaaaagcaac    83280
agattctttt gatgctgtaa agagcaaaga aagctctttc gtgggcattt gacagctaca    83340
caggctgggc gttgtcactg ccactcctct tgtttatccc tccatcagat gatgggcgtt    83400
tggttttccc ccacttttttg gctattatga atgatgctac tatgatcatt aatgtacaag   83460
tttgtgtggg cagatgtttc cgtttctctt gaatacacat gtgaaagttt aagtataaat    83520
ttttaaattt tgatgaagtc caatttatat acattttaca atttgtgctt ttgatgtcac    83580
atctaataaa tcattgccta cttcaaggtc atgaagattt acttttctag gaattgttta    83640
gttttagctc tgaggcatat gacctatttt gagttgattt ttgtatggga tgtgaggtag    83700
ggtttataca cattttaaac tccaatattt acctacattt ggttgtctac ttgtgtaaga    83760
attcattcag atctcttcat tgtctcttgc tttgtattgg tatttcttgg taggtttact    83820
ttctacgtgt acacaattga tgctcatcag ttttatatca tggtttgctt tgtaattacc    83880
agtgttcatg taaatatagt ccaggatttg cctttagagt cctcccacat gtagtgtgga    83940
acctcatggg cttctttatt taattctgga atatgacaat ttcatggata aaataatgta    84000
ttttccttca caaaccactt taagattcaa gagaagtata atagaacttc cctgtttcct    84060
tagaaggact ctgcaagtcc aggactggcc agtacagttg ctgtcacaaa gcctttactc    84120
tgcaggagga acccttcctc agagcctgct tcctgttggt tttccttggc tctttcaagc    84180
tgtttctcag agcaaattca gaagcctaag gggctcttgg ggaccacaca attggctgcc    84240
aggctcatgt ttgcttgtgt gtgtgtgagt tgatactgag attgacagct gatagtcaca    84300
ggaagggtga agtgatattc cacattcttt aaggaggaca ggctagaaat ggaactttaa    84360
gaaactaaaa ttgtcacagt tgtctagtta tttgcaaaac ttgtttcagt gaaacacatc    84420
ttcatatatt ttcttttctc tctctttttt tttttttacg tcttcatata ttttcttttt    84480
tccttttttt gagacagagt ctcactctgt tgcctaggct ggagtgtagt gatgctatct    84540
cggctcattg caacctctgc ctcctgggtt caaacgattt tgtgcctca gcctcccaag     84600 tagctgggat tacaggtgtg caccaccacg cctggccaat tttgtattta ttagagatcg    84660
ggtttcacca tgttggccag gttggtctcg aactcctgac ctcaggtgat cttcctgcct    84720
```

```
tggcctccca gagtgctgga attacagtca tgagccaccg tgcccggccg atgacatttc    84780
tttaacttgt tagggtgcta ctttttatagt aagagcaaat ggtgaaaatg tgttttttaaa    84840 atatgctttc ccctcttatt cttaattatc attctaagtg atggaggtgg ctacatttct    84900
tgggcatcat ctgcagggct ggagctggct catggactcg agaccctcac tcattcagtg    84960
agcccactct tgttgtgtct cctagcaata gatacagagt tgggggcttg ggctttgtgt    85020
ttaagtaacc ttatcaacta tttccagggc aaggttactt cttatactga gcttaagggt    85080
ttgcacacat aatcattata gcatctgggt gagttgattt ccttttgcat tatattataa    85140 acttttttcca caaaaaaagt ccacacattt tttttttttt tagaggcggt tcagtgtttt    85200
gttatattgc agtgctgctc tgtgctcagg accataggtg tttaggactc tcctgcatat    85260
actgttgttt atagactgct tctttgcaca gtctttacct tgttaaaagt agttagatat    85320
tttactgctc cttgcgaata ttttttaccag tttatagtat gcctagttat ggatgaatag    85380
tttctcatgg ccttttcacta ttatattgtt ttgctcactg ttactatgca gctgttaagc    85440
atttatagtg gtaaaacttc tcttttcatg gaagattgta cttaaaagat gccttgttga    85500
tggatcttag tttaacacct ggcgcctcag aaataggttc ctttactatt ctcagcacac    85560
agtgcttctc tgtagttacc tatatttgca aacctggaga gtatttttttc tgagataaa    85620 tagattcatg tcataaaagt tcgctccctt tcccagagaa cttggtttag tcacatgtga    85680
gctttcttag tttgcttttaa ctgttgctgt ggtgagatca acagtctaaa tcaatatagt    85740
catattacag aaaatgtgga aattgaaata acctactaac aaaagctgat gttttgattc    85800
agttgatttc catcttaatg agcattttttaa taatcttgtg attatctgta ggacatagtt    85860
tgactgttct tttactgcct aatgttgtac catgatcttc tcccatgttg ttaagtaata    85920
ttaaatacta ttaagtgaat ctaccttggt tttcttttaa ccaccatttt actattactg    85980
gctcttcgta attttgcgag tacatataat tttgtgccag catatattag gcatgaattt    86040
ggggtggtgc aaccagggtt tatctccttg ggctggattc ctagagccgg aatttcaggc    86100
ttagagggat aaacctgcag tctctgttca gactttgttt ttatggagac tgtgtttcct    86160
tcaacaggag atcctttccc gcctctaata ttacaggttc atttcttcat caacacagac    86220
ctgatgtcta gtctggatgc gatgctttac tctagctcca gtcctcatat tggaaacaga    86280
agcttatttt acatctcagc cccctttagca agcagccctc ttaaagattc ttatacgga    86340 accctgtgca cagcatgatt gcaactttgt agacatacta gtgtgtaaga acactcttca    86400
caatagacac aaaagaagag cagttgtggg taggattgta ggctacttcc ccttttgttc    86460
ttatactttt ctgtaatgct cttttccttt cattgtgttt ttaaacggga gggcttttcc    86520
aagttgactc gaataaatgg gtgaaacaga acaagcctcc tgagaacacc tttgtgagca    86580
gagcactgat tatctattga tgcatctcat gaaaaaaatg taccttgttt aaattaaagc    86640
agttgaaagg ggagagaagt cagtccttgc atgaagtgtg ccctgcaggt gcttgaatgc    86700
ctctctcccc ccaccgagac ctggctgctc tgaggtgtgg gcacagggg gtgtttcctc    86760 tgcagaagct gctcaggatg cactgagggg cacctaagga ggtctgtggg cagggtggg    86820 atgtcctatg aaaacttcaa acaggcagag aaaacgagtt attcacagtg aaattatctg    86880
gagcttttga cagtttattg cctttttgaa aaggttatgg ggagacaggg tttcgcttgc    86940
tctgtcccag gatggagtgc agtggcatga ccttgactca ctgcagcctt gacctcctgg    87000
actcaagcaa tgctcctgcc tcagcctcct gagtagctgg gatgtaccac cgtgcccagc    87060
```

-continued

```
tactttttttt cttttttaagt agagacaggg tctggtctat gttacccagg ctggtctgaa     87120
actcatgggc tcaagggatc ctcctgcctc agcctcccaa acggctagga ttgcaggagt      87180
gagccactgc cctcagccct ttattgcagt tttgacttaa aaataacctt ttttttctct      87240
tatgaaatga ccattacagc tcgtaggcca tttactagct tgttagtcat tctgttatgt      87300
caaccaaagc tgcctgtaac cgacactttt catactgcag ctagcacagt ttgtgaagta     87360
taacttcaag gtttacaaat taatgtccta ggatcttaga tcttacaaca aatgcgtaga     87420
catgaatggt gtttgatttg ggttggcctc aagtttgcaa attttacgga agatcccagg     87480
ttgaaatgag agtggcttgc ttcaaccttt ggaaaagaaa acactctggg caaactgagc     87540
ccactccact tacttaaaga agcttagaac taatgtgaat gaactattaa ttaacctcta     87600
tttagatcca ccaggcttac ttgaaatatg ccttggtcat atgtacatgt aatgattatt     87660
gcttagtggg gaaaagctgg tgttctttgt tgttgctgta caagtgttga gcaggtggtt      87720
gtccgcttca ctgaaaagaa cctgactgga ccaacaatgg ggaatgcaga tttggagctt     87780
tcttgacatt ggcctgtttt tcccctgta ggagaactgc gacacatcac caagctgaag      87840
ccctggagcc tctttgatgt acttgtggaa aagtatggct ggccccatga agatgctgca     87900
cagtttacag atttcctgat cccgatgtta gaaatggttc cagaaaaacg agcctcagct      87960
ggcgaatgcc ttcggcatcc ttggttgaat tcttagcaaa ttctaccaat attgcattct     88020
gagctagcaa atgttcccag tacattggac ctaaacggtg actctcattc tttaacagga    88080
ttacaagtga gctggcttca tcctcagacc tttattttgc tttgaggtac tgttgtttga     88140
cattttgctt tttgtgcact gtgatcctgg ggaagggtag tcttttgtgt cttcagctaa     88200
gtagtttact gaccatttc ttcctggaaa caataacatg tctctaagca ttgtttcttg      88260
tgttgtgtga cattcaaatg tcattttttt gaatgaaaaa tactttcccc tttgtgtttt    88320
ggcaggtttt gtaactattt atgaagaaat attttagctg agtactatat aatttacaat    88380
cttaagaaat tatcaagttg gaaccaagaa atagcaagga aatgtacaat tttatcttct    88440
ggcaaaggga catcattcct gtattatagt gtatgtaaat gcaccctgta aatgttactt     88500
tccattaaat atgggagggg gactcaaatt tcagaaaagc taccaagtct tgagtgcttt    88560
gtagcctatg ttgcatgtag cggactttaa ctgctccaag gagttgtgca aactttcat     88620
tccataacag tcttttcaca ttggatttta acaaagtgg ctctgggtta taagatgtca    88680
ttctctatat ggcactttaa aggaagaaaa gatatgtttc tcattctaaa atatgcatta    88740
taatttagca gtcccatttg tgattttgca tatttttaaa agtacttttta aagaagagca   88800
atttcccttt aaaaatgtga tggctcagta ccatgtcatg ttgcctcctc tgggcgctgt     88860
aagttaagct ctacatagat taaattggag aaacgtgtta attgtgtgga atgaaaaaat   88920
acatatattt ttggaaaagc atgatcatgc ttgtctagaa cacaaggtat ggtatataca   88980
atttgcagtg cagtgggcag aatacttctc acagctcaaa gataacagtg atcacattca   89040
ttccataggt agctttacgt gtggctacaa caaattttac tagcttttc attgtctttc    89100
catgaaacga agttgagaaa atgattttcc ctttgcaggt tgcacacagt tttgtttatg    89160
catttcctta aaattaattg tagactccag gatacaaacc atagtaggca atacaatttt    89220
agaatgtaat atatagaggt atatttagcc tcttttagaa gtcagtggat tgaatgtctt    89280
tttattttaa attttacatt cattaaggtg cctcgttttt gactttgtcc attaacattt    89340
atccatatgc ctttgcaata actagattgt gaaaagctaa caagtgttgt aacaataatc    89400
cattgtttga ggtgcttgca gttgtcttaa aaattaaagt gttttggttt ttttttttcc     89460
```

```
agacattgcc ttggtcattg ccctataaat gatagaatca atgaacattt gctatcagag  89520
tagtgtcact aaaactaaat accagcattc ctgttgcagc agatgtagtt gtagaacatg  89580
cattgaggcg tattataagg aaatcattta ttgtttttta agggcagaag ggatttagga  89640
gaaaagctac agtatagatt gattctctag aatatcaatg atccctttc atccatggtt  89700 ucatcaaaaac atactaactg catttgtttg atcattgcaa atttaaaaca aaacagcatt  89760
tgctgttagg aaacaagaca cataatcctc ttaggaatta ccattatatc acattaccac  89820
tgtgaggtag aatggatcat tcattaattt ctttatgaaa tttgcatgct aagttttct  89880 aatgaggctg taggtttcca tgtaaattct gtgatagata gtggctgtag actggtgatg  89940
ctatccgtga tttctatgag aaacatcctt acaagaacca tagggcataa tttatatctt  90000
ccctaagtgt aaaaggattt ttatcagggt gatagtatac ttgaatgaaa tttgtctaat  90060 gcagttttg cttatgttgg aaaataaact agattatgaa tttttacagg tgtgtccctt  90120
atgataaaac agcctaacta gtttataata cagaaacggt tgttctagaa ggaatataca  90180
tttgtattag gcataatatg gctttatcag attcttggcg gcttgttgat aaagaatgca  90240
caaaaactaa atgagaacca ctggttatgc taaacattat aactagctct ctgacttcaa  90300
ttgaatgtcc tatctatctt ttcctttctg tagtccatgt gaaatcttca tggaaaatga  90360
caagcagtgg atcacatatg tgtttatagc agatacagga gctggctatc tagaagttgg  90420
cagacagaac tgcccaaagg cagagaaaag gtggatataa gatcttccga gtcataaact  90480
tcttaggtga aaaccgattt actaacttgc ttcttcccat acctggacca tacataacta  90540
g                                                                  90541
```